US012747449B2

(12) United States Patent
Mo et al.

(10) Patent No.: US 12,747,449 B2
(45) Date of Patent: Sep. 29, 2026

(54) HERBICIDE-TOLERANT GENES AND METHOD FOR USING SAME

(71) Applicant: QINGDAO KINGAGROOT CHEMICAL COMPOUND CO., LTD., Qingdao (CN)

(72) Inventors: Sudong Mo, Qingdao (CN); Junjie Zhang, Qingdao (CN); Yanmin Luo, Qingdao (CN); Huarong Li, Qingdao (CN)

(73) Assignee: QINGDAO KINGAGROOT CHEMICAL COMPOUND CO., LTD., Qingdao (CN)

( * ) Notice: Subject to any disclaimer, the term of this patent is extended or adjusted under 35 U.S.C. 154(b) by 72 days.

(21) Appl. No.: 18/838,441

(22) PCT Filed: Feb. 6, 2023

(86) PCT No.: PCT/CN2023/074624
§ 371 (c)(1),
(2) Date: Aug. 14, 2024

(87) PCT Pub. No.: WO2023/160362
PCT Pub. Date: Aug. 31, 2023

(65) Prior Publication Data
US 2025/0163449 A1 May 22, 2025

(30) Foreign Application Priority Data
Feb. 25, 2022 (CN) ........................ 202210180516.3

(51) Int. Cl.
*C12N 15/82* (2006.01)
*A01N 43/40* (2006.01)
(Continued)

(52) U.S. Cl.
CPC ......... *C12N 15/8275* (2013.01); *A01N 43/40* (2013.01); *A01P 13/02* (2021.08);
(Continued)

(58) Field of Classification Search
None
See application file for complete search history.

(56) References Cited

U.S. PATENT DOCUMENTS 10,023,874 B2 * 7/2018 Ellis .................. C12N 15/8274
2007/0300321 A1 12/2007 Leon et al.
(Continued)

FOREIGN PATENT DOCUMENTS

CN 102094032 A 6/2011
CN 102575263 A 7/2012
(Continued)

OTHER PUBLICATIONS

National Institute of Intellectual Property (NIIP); First Office Action in Kazakhstan Patent Application No. 2024/0738.1, mailed Oct. 3, 2025.
(Continued)

*Primary Examiner* — Weihua Fan
(74) *Attorney, Agent, or Firm* — Leydig, Voit & Mayer, Ltd.

(57) ABSTRACT

The present invention provides a polypeptide and recombinant DNA molecule suitable for conferring tolerance to pyridinyloxy acid herbicides, as well as a herbicide-tolerant plant, seed, cell and plant part containing the recombinant DNA molecule and the method of use thereof.

20 Claims, 11 Drawing Sheets

Specification includes a Sequence Listing.

(51) Int. Cl.
*A01P 13/02* (2006.01)
*C12N 9/02* (2006.01)

(52) U.S. Cl.
CPC ....... *C12N 9/0071* (2013.01); *C12N 15/8205* (2013.01); *C12Y 114/11* (2013.01)

(56) References Cited

U.S. PATENT DOCUMENTS

| | | | |
|---|---|---|---|
| 2014/0329676 | A1 | 11/2014 | Fischer et al. |
| 2016/0108422 | A1 | 4/2016 | Ellis et al. |
| 2017/0022515 | A1 | 1/2017 | Wright et al. |

FOREIGN PATENT DOCUMENTS

| | | | |
|---|---|---|---|
| CN | 104270946 | A | 1/2015 |
| CN | 106793761 | A | 5/2017 |
| CN | 110628733 | A | 12/2019 |
| CN | 110759978 | A | 2/2020 |
| CN | 113528473 | A | 10/2021 |
| CN | 116694654 | A | 9/2023 |
| RU | 2415566 | C2 | 4/2011 |
| WO | WO 2011/022470 | A1 | 2/2011 |
| WO | WO 2016/060843 | A1 | 4/2016 |
| WO | 2017/217794 | A1 | 12/2017 |
| WO | 2019/008001 | A1 | 1/2019 |

OTHER PUBLICATIONS

Chinese National Intellectual Property Administration, International Search Report and Written Opinion issued in International Patent Application No. PCT/CN2023/074624, mailed on Jun. 5, 2023.

"(R)-phenoxypropionate/alpha-ketoglutarate-dioxygenase [Sphingobium herbicidovorans]", *NCBI Reference Sequence: WP_031942865.1*, Aug. 17, 2020.

Wright et al., "Robust crop resistance to broadleaf and grass herbicides provided by aryloxyalkanoate dioxygenase transgenes", *PNAS*, 107(47): 20240-20245 (2010).

China National Intellectual Property Administration, Office Action issued in counterpart Chinese Patent Application No. 202310096349.9, mailed on Apr. 15, 2026.

Alvarez-Barcia et al., "Atom Tunneling in the Hydroxylation Process of Taurine/a-Ketoglutarate Dioxygenase Identified by Quantum Mechanics/Molecular Mechanics Simulations", J. Phys. Chem. B, 121(21): 5347-5354 (2017).

* cited by examiner

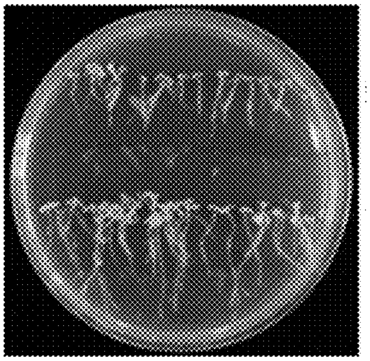

Wild-type *Arabidopsis thaliana*

Transgenic *Arabidopsis thaliana* comprising the protein-coding gene of SEQ ID NO: 46

Figure 3

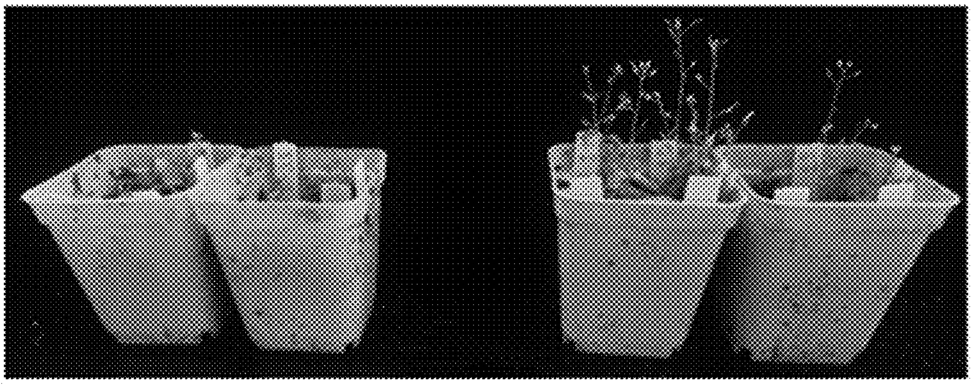

Transgenic *Arabidopsis thaliana* comprising the protein-coding gene of SEQ ID NO: 1

Transgenic *Arabidopsis thaliana* comprising the protein-coding gene of SEQ ID NO: 42

Figure 4

17DAT

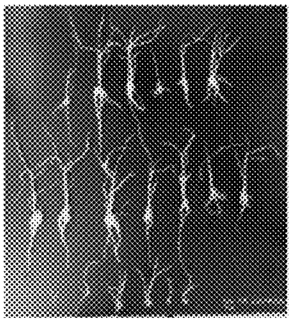

T0 generation transgenic rice comprising the protein-coding gene of SEQ ID NO: 138

T0 generation transgenic rice comprising the protein-coding gene of SEQ ID NO: 86

Wild-type Jinjing 818

Figure 5

22DAT

Wild-type Jinjing 818

T0 generation transgenic rice comprising the protein-coding gene of SEQ ID NO: 102

17DAT

T0 generation transgenic rice comprising the protein-coding gene of SEQ ID NO: 82

Wild-type Jinjing 818

22DAT

Wild-type Jinjing 818

T0 generation transgenic rice comprising the protein-coding gene of SEQ ID NO: 106

26DAT

Wild-type Jinjing 818

T0 generation transgenic rice comprising the protein-coding gene of SEQ ID NO: 126

26DAT

Wild-type Jinjing 818

T0 generation transgenic rice comprising the protein-coding gene of SEQ ID NO: 142

22DAT

Wild-type Jinjing 818

T0 generation transgenic rice comprising the protein-coding gene of SEQ ID NO: 38

Wild-type *Arabidopsis thaliana*

Transgenic *Arabidopsis thaliana* comprising the protein-coding gene of SEQ ID NO: 42

Wild-type *Arabidopsis thaliana*

Transgenic *Arabidopsis thaliana* comprising the protein-coding gene of SEQ ID NO: 78

Wild-type *Arabidopsis thaliana*

Transgenic *Arabidopsis thaliana* comprising the protein-coding gene of SEQ ID NO: 82

Wild-type *Arabidopsis thaliana*

Transgenic *Arabidopsis thaliana* comprising the protein-coding gene of SEQ ID NO: 86

Wild-type *Arabidopsis thaliana*

Transgenic *Arabidopsis thaliana* comprising the protein-coding gene of SEQ ID NO: 98

Wild-type *Arabidopsis thaliana*

Transgenic *Arabidopsis thaliana* comprising the protein-coding gene of SEQ ID NO: 102

Wild-type *Arabidopsis thaliana*

Transgenic *Arabidopsis thaliana* comprising the protein-coding gene of SEQ ID NO: 126

Wild-type *Arabidopsis thaliana*

Transgenic *Arabidopsis thaliana* comprising the protein-coding gene of SEQ ID NO: 138

Wild-type *Arabidopsis thaliana*

Transgenic *Arabidopsis thaliana* comprising the protein-coding gene of SEQ ID NO: 142

10 g Compound C

Wild-type soybean

Transgenic soybean comprising the protein-coding gene of SEQ ID NO: 46

10 g Compound C

Wild-type soybean

Transgenic soybean comprising the protein-coding gene of SEQ ID NO: 46

10 g Compound C

Wild-type soybean

Transgenic soybean comprising the protein-coding gene of SEQ ID NO: 42

SEQUENCE LISTING

```
Sequence total quantity: 181
SEQ ID NO: 1            moltype = AA  length = 295
FEATURE                 Location/Qualifiers
source                  1..295
                        mol_type = protein
                        organism = Sphingobium herbicidovorans
SEQUENCE: 1
MHAALSPLSQ RFERIAVQPL TGVLGAEITG VDLREPLDDS TWNEILDAFH TYQVIYFPGQ  60
AITNEQHIAF SRRFGPVDPV PLLKSIEGYP EVQMIRREAN ESGRVIGDDW HTDSTFLDAP  120
PAAVVMRAID VPEHGGDTGF LSMYTAWETL SPTMQATIEG LNVVHSATRV FGSLYQAQNR  180
RFSNTSVKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295
```

-continued

```
SEQ ID NO: 2            moltype = AA  length = 295
FEATURE                 Location/Qualifiers
source                  1..295
                        mol_type = protein
                        organism = synthetic construct
SEQUENCE: 2
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGRVIGDDW HTDSTFLDAP  120
PAAVVMRAID VPEHGGDTGF LSMYTAWETL SPTMQATIEG LNVVHSATRV FGSLYQAQNR  180
RFSNTSVKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 3            moltype = DNA  length = 888
FEATURE                 Location/Qualifiers
source                  1..888
                        mol_type = other DNA
                        organism = synthetic construct
CDS                     1..888
                        protein_id = 2
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGRV
                         IGDDWHTDSTFLDAPPAAVVMRAIDVPEHGGDTGFLSMYTAWETLSPTMQATIEGLNVV
                         HSATRVFGSLYQAQNRRFSNTSVKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 3
atgcatgcag cgctgtctcc gctgtctcag cgctttgaac gtattgcagt tcaaccgctg  60
accggtgttc tgggcgctga aatcaccggc gtggacctgc gtgaaccgct ggatgattcc  120
acttggaacg aaattctgga cgcctttcac acttaccagg ttatttattt tccgggtcaa  180
gcgatcacca acgaacaaca cattgcgttt agccgtcgct tcggcccagt agatccggtt  240
ccacacctga aatctatcga aggttacccg gaagttcaga tgatccgtcg tgaggctaac  300
gaaagcggcc gtgtaatcgg cgacgactgg cacaccgact ctaccttcct ggacgcaccg  360
ccggctgcag ttgttatgcg cgcaatcgat gttccggaac acggtggcga taccggcttc  420
ctgtctatgt acaccgcttg ggaaactctg tccccaacta tgcaggcaac catcgagggt  480
ctgaacgtag ttcactctgc tacccgtgtg tttggctccc tgtaccaagc gcagaaccgt  540
cgcttcagca acacctccgt gaaggtgatg gatgttgatg cgggcgatcg tgaaactgtt  600
cacccgctgg tagtaaccca tccaggctct ggccgtaaag gtctgtacgt taaccaagta  660
tactgtcagc gtatcgaagg tatgactgat gcggaatcca aaccgctgct gcagttcctg  720
tacgaacacg cgacgcgctt cgattttact tgccgtgtac gttggaaaaa agatcaggtt  780
ctggtgtggg ataacctgtg caccatgcac cgtgcagtgc cagactacgc gggtaaattc  840
cgctacctga cgcgtactac tgtgggtggt gtgcgtccgg cacgttaa              888

SEQ ID NO: 4            moltype = DNA  length = 888
FEATURE                 Location/Qualifiers
source                  1..888
                        mol_type = other DNA
                        organism = synthetic construct
CDS                     1..888
                        protein_id = 2
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGRV
                         IGDDWHTDSTFLDAPPAAVVMRAIDVPEHGGDTGFLSMYTAWETLSPTMQATIEGLNVV
                         HSATRVFGSLYQAQNRRFSNTSVKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 4
atgcatgctg ctttgtctcc gttgtcccag aggtttgagc gtatcgccgt ccagccactc  60
acaggtgtgc tcggtgcaga gatcaccggc gtcgatttgc gcgagccact ggacgactct  120
acttggaacg agattttgga tgcttttcat acctaccagg tgatctactt cccgggtcaa  180
gccattacca acgaacagca tatcgctttc tccaggaggt tcggcccggt ggatcctgtg  240
ccgcacttga agtccatcga gggttaccct gaagtccaga tgattcggag agaggccaac  300
gagagcggta gggttattgg cgatgactgg catacggaca gcaccttcct ggatgcgccg  360
ccagccgctg ttgtgatgag ggctatcgac gtccccgagc acgggggcga cactgggttc  420
ttgtctatgt atacggcctg ggagaccctt tccccaacca tgcaggcaac tatcgagggc  480
ctgaatgtcg tgcacagtgc gaccagagtg tttgggtcct tgtaccaggc tcaaaacaga  540
cgctttagca atacttcagt caaggtcatg gatgttgatg cgggtgacag ggagactgtc  600
caccctcttg tcgttaccca tccaggctca ggtaggaagg gtctgtacgt caaccaggtc  660
tactgtcagc gcattgaggg gatgacagat gcggagtcga agcctttgct gcaattcctt  720
tacgagcacg ccacccggtt cgatttcaca tgtcgggtcc gctggaagaa agaccaggtc  780
cttgtttggg ataatctctg cacaatgcac cgcgctgttc ccgactatgc cggcaaattt  840
cgttacctca ctaggactac agttggcggc gtcaggcccg cccgctga              888

SEQ ID NO: 5            moltype = DNA  length = 888
FEATURE                 Location/Qualifiers
source                  1..888
                        mol_type = other DNA
```

-continued

```
                         organism = synthetic construct
CDS                      1..888
                         protein_id = 2
                         transl_table = 1
                         translation = MHAALSPLSQRFERIAVQPLTGVLGAEITGVDLREPLDDSTWNEIL
                          DAFHTYQVIYFPGQAITNEQHIAFSRRFGPVDPVPHLKSIEGYPEVQMIRREANESGRV
                          IGDDWHTDSTFLDAPPAAVVMRAIDVPEHGGDTGFLSMYTAWETLSPTMQATIEGLNVV
                          HSATRVFGSLYQAQNRRFSNTSVKVMDVDAGDRETVHPLVVTHPGSGRKGLYVNQVYCQ
                          RIEGMTDAESKPLLQFLYEHATRFDFTCRVRWKKDQVLVWDNLCTMHRAVPDYAGKFRY
                          LTRTTVGGVRPAR
SEQUENCE: 5
atgcatgctg cactttctcc tctcagccag aggtttgaaa gaattgctgt acaacctttg  60
acaggagtct tgggagccga aattactggg gtagaccttc gagagcccct ggatgattct  120
acctggaacg aaattttaga cgcatttcat acttaccaag ttatttattt cccaggacaa  180
gctattacca acgaacagca cattgcattt agccgaagat tcggtcctgt tgaccctgtg  240
cctcatttaa aatctatcga aggttacccc gaggtacaaa tgattagaag agaggctaac  300
gagtcaggtc gtgtgatcgg ggatgattgg cacactgata gcactttttt ggacgcacca  360
cctgctgctg tcgtcatgcg tgctatcgat gtaccagaac atgggggtga tacagggttc  420
ttgagtatgt acactgcttg ggagactttg tctcctacta tgcaagctac aatcgaaggc  480
cttaacgtcg tgcatagtgc caccagggtg ttcgggtctc tttaccaggc acaaaatagg  540
agattttcta atacctcagt aaaggtgatg gatgttgacg ccggcgatag agaaactgtg  600
catccacttg tcgttactca cccaggttca gggaggaagg gtctgtatgt taatcaagtt  660
tactgccaac gaatcgaggg tatgactgac gcagagtcaa agcctttgtt gcaatttctt  720
tatgaacatg caactagatt tgatttcaca tgccgtgtga ggtggaagaa agatcaggtt  780
cttgtttggg ataatttgtg tactatgcat agagctgttc ctgactatgc tggtaagttt  840
agatacctca ccagaacaac cgttggtggt gtccgtcctg ctcgatga              888

SEQ ID NO: 6             moltype = AA  length = 295
FEATURE                  Location/Qualifiers
source                   1..295
                         mol_type = protein
                         organism = synthetic construct
SEQUENCE: 6
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGRVIGDDW HTDSTFLDAP  120
PAAVVMRAID VPEHGGDTGF LSMYTAWETL SPTMQATIEG LNVVHSATRV FGSLYQAQNR  180
RFSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 7             moltype = DNA  length = 888
FEATURE                  Location/Qualifiers
source                   1..888
                         mol_type = other DNA
                         organism = synthetic construct
CDS                      1..888
                         protein_id = 6
                         transl_table = 1
                         translation = MHAALSPLSQRFERIAVQPLTGVLGAEITGVDLREPLDDSTWNEIL
                          DAFHTYQVIYFPGQAITNEQHIAFSRRFGPVDPVPHLKSIEGYPEVQMIRREANESGRV
                          IGDDWHTDSTFLDAPPAAVVMRAIDVPEHGGDTGFLSMYTAWETLSPTMQATIEGLNVV
                          HSATRVFGSLYQAQNRRFSNTSLKVMDVDAGDRETVHPLVVTHPGSGRKGLYVNQVYCQ
                          RIEGMTDAESKPLLQFLYEHATRFDFTCRVRWKKDQVLVWDNLCTMHRAVPDYAGKFRY
                          LTRTTVGGVRPAR
SEQUENCE: 7
atgcatgcag ctctgtctcc gctgtcccag cgtttcgaac gtattgctgt acaaccgctg  60
accggcgttc tgggtgctga gattactggc gttgatctgc gtgagccgct ggatgactct  120
acctggaacg agatcctgga cgcgttccac acctaccagg tcatttactt cccgggtcag  180
gcaatcacta acgaacagca cattgctttc tctcgccgtt ttggtccggt ggatccagtt  240
ccgcacctga agtctatcga aggctatccg gaagttcaga tgattcgccg cgaagctaac  300
gaaagcggcc gtgttatcgg cgatgactgg cataccgact ctacctttct ggatgcaccg  360
ccggccgctg ttgttatgcg tgcaatcgac gtaccggaac atggtggtga caccggcttt  420
ctgtccatgt ataccgcctg ggaaaccctg tctccgacca tgcaggcaac tattgaaggt  480
ctgaacgtcg ttcacagcgc cactcgcgtt ttcggctctc tgtaccaggc tcagaaccgt  540
cgtttcagca acacctccct gaaggttatg gacgttgacg ctggcgatcg cgaaaccgtc  600
cacccgctgg ttgttactca cccgggctct ggtcgcaaag gtctgtatgt taaccaggtt  660
tactgtcagc gtatcgaagg catgaccgat gcagaatcta aaccactgct gcagttcctg  720
tatgaacacg cgacccgttt tgacttcact tgtcgtgtac gttggaagaa agaccaggta  780
ctggtttggg acaacctgtg caccatgcat cgcgcggttc cggactacgc tggtaaattt  840
cgctatctga cccgcactac tgtaggtggt gttcgccctg cccgttaa              888

SEQ ID NO: 8             moltype = DNA  length = 888
FEATURE                  Location/Qualifiers
source                   1..888
                         mol_type = other DNA
                         organism = synthetic construct
CDS                      1..888
                         protein_id = 6
                         transl_table = 1
                         translation = MHAALSPLSQRFERIAVQPLTGVLGAEITGVDLREPLDDSTWNEIL
```

-continued

```
                          DAFHTYQVIYFPGQAITNEQHIAFSRRFGPVDPVPHLKSIEGYPEVQMIRREANESGRV
                          IGDDWHTDSTFLDAPPAAVVMRAIDVPEHGGDTGFLSMYTAWETLSPTMQATIEGLNVV
                          HSATRVFGSLYQAQNRRFSNTSLKVMDVDAGDRETVHPLVVTHPGSGRKGLYVNQVYCQ
                          RIEGMTDAESKPLLQFLYEHATRFDFTCRVRWKKDQVLVWDNLCTMHRAVPDYAGKFRY
                          LTRTTVGGVRPAR
SEQUENCE: 8
atgcacgctg ccttgtcccc gttgtcgcaa aggttcgaaa gaattgcagt tcaaccactc  60
acgggcgtgc tgggagcaga gatcacgggc gtggacttgc gcgagcccct tgacgatagt  120
acctggaatg aaattctgga cgcgttccat acttaccaag tgatctactt tcctggccag  180
gctatcacga acgaacagca catagcattc tcccggaggt ttggccccgt cgaccctgtg  240
cctcatctga agtctataga gggatatccg gaggtccaga tgatccggcg tgaggcgaac  300
gagtccggga gggttatcgg agacgactgg cacaccgata gcacattcct ggacgcgccg  360
cctgcggctg tggtgatgag agcgatcgac gttcctgagc acggcggcga caccggcttc  420
ctttccatgt acacggcgtg ggagacgctt tcacctacaa tgcaagcgac tatcgaggga  480
cttaacgtgg ttcacagcgc aaccccgcgtg ttcggatcac tgtaccaggc gcagaatcgc  540
aggttttcaa acacctctct caaagtgatg gacgttgacg cgggtgacag ggaaaccgtt  600
catcctctgg tggtgactca tccaggctct ggccggaagg ggctgtacgt taatcaggtc  660
tactgtcagc gcatagaagg tatgactgac gcagaatcca agccgctgct tcaattcctc  720
tacgaacacg ccacgcgctt cgacttcact tgcagggtgc gttggaagaa ggaccaagtt  780
ctggtttggg ataacctgtg cacgatgcat cgcgccgtgc cagactacgc aggcaagttc  840
aggtacctga cccggacgac ggttggaggt gtccgcccag ccaggtga             888

SEQ ID NO: 9              moltype = DNA  length = 888
FEATURE                   Location/Qualifiers
source                    1..888
                          mol_type = other DNA
                          organism = synthetic construct
CDS                       1..888
                          protein_id = 6
                          transl_table = 1
                          translation = MHAALSPLSQRFERIAVQPLTGVLGAEITGVDLREPLDDSTWNEIL
                           DAFHTYQVIYFPGQAITNEQHIAFSRRFGPVDPVPHLKSIEGYPEVQMIRREANESGRV
                           IGDDWHTDSTFLDAPPAAVVMRAIDVPEHGGDTGFLSMYTAWETLSPTMQATIEGLNVV
                           HSATRVFGSLYQAQNRRFSNTSLKVMDVDAGDRETVHPLVVTHPGSGRKGLYVNQVYCQ
                           RIEGMTDAESKPLLQFLYEHATRFDFTCRVRWKKDQVLVWDNLCTMHRAVPDYAGKFRY
                           LTRTTVGGVRPAR
SEQUENCE: 9
atgcacgccg cactatctcc cctcagtcag aggtttgaac gaatcgcagt acaaccattg  60
accggagttc taggagccga gataaccggg gttgacctga gagaaccctt ggacgatagc  120
acctggaatg aaatcctgga cgcctttcat acctatcagg taatctattt tccaggacaa  180
gcgataacga atgagcagca tatagcattc tcgcggagat tcggacccgt cgatcccgta  240
cctcatctca aatctataga aggctaccca gaagttcaga tgattagacg tgaagcgaat  300
gagagcggcc gagttatagg ggatgattgg catacggact ctacattcct cgacgcaccg  360
ccagccgctg tagtgatgcg tgcaattgat gtcccagaac acggtggcga tactggtttc  420
ttgtcgatgt acactgcatg ggaaactctc tcgccgacga tgcaggcaac gatagaagga  480
ctcaacgtgg tacactcggc cacccgggtc tttggttccc tgtatcaagc ccaaaatagg  540
agattctcca acacgtccct gaaagtgatg gacgttgacg caggggatag agagactgtg  600
cacccgcttg tggttacaca cccgggctct ggcaggaaag gcctttacgt caaccaggta  660
tactgtcagc gtattgaagg gatgactgat gcagaaagca aacctctcct ccagtttctt  720
tacgaacatg cgacacggtt tgactttact tgtcgcgtac gttggaaaaa ggaccaagtc  780
ctcgtttggg ataatctttg taccatgcac cgagctgtgc cggactacgc tggcaaattt  840
cgctatttaa cgcggacgac tgtcggaggc gtaagaccgg cacggtga             888

SEQ ID NO: 10             moltype = AA  length = 295
FEATURE                   Location/Qualifiers
source                    1..295
                          mol_type = protein
                          organism = synthetic construct
SEQUENCE: 10
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGRVIGDDW HTDSTFLDAP  120
PAAVVMRAID VPEHGGDTGF LSMYTAWETL SPTMQATIEG LNVVHSATRV FGSLYQAQNR  180
RFSNTSMKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 11             moltype = DNA  length = 888
FEATURE                   Location/Qualifiers
source                    1..888
                          mol_type = other DNA
                          organism = synthetic construct
CDS                       1..888
                          protein_id = 10
                          transl_table = 1
                          translation = MHAALSPLSQRFERIAVQPLTGVLGAEITGVDLREPLDDSTWNEIL
                           DAFHTYQVIYFPGQAITNEQHIAFSRRFGPVDPVPHLKSIEGYPEVQMIRREANESGRV
                           IGDDWHTDSTFLDAPPAAVVMRAIDVPEHGGDTGFLSMYTAWETLSPTMQATIEGLNVV
                           HSATRVFGSLYQAQNRRFSNTSMKVMDVDAGDRETVHPLVVTHPGSGRKGLYVNQVYCQ
                           RIEGMTDAESKPLLQFLYEHATRFDFTCRVRWKKDQVLVWDNLCTMHRAVPDYAGKFRY
                           LTRTTVGGVRPAR
```

-continued

```
SEQUENCE: 11
atgcacgcag cgctgtctcc actgtctcaa cgtttcgaac gtatcgctgt tcagccgctg  60
accggtgttc tgggcgcaga aatcactggt gttgacctgc gcgagccgct ggatgactct  120
acctggaacg agatcctgga cgcttttcac acctaccagg tcatttactt tccgggtcag  180
gctattacta acgagcagca catcgcattt agccgtcgtt ttggtccagt ggatcctgtg  240
cctcatctga aaagcatcga aggttatccg gaagttcaga tgatccgtcg tgaagcaaac  300
gaatccggtc gcgtcattgg tgacgactgg cacaccgact ctaccttcct ggatgctccg  360
ccggcagctg ttgttatgcg tgccatcgac gtgccggaac acggtggtga taccggtttc  420
ctgtccatgt acactgcctg ggagacgctg tctccaacta tgcaagccac catcgaaggc  480
ctgaacgttg ttcatagcgc aacccgtgta ttcggctctc tgtaccaggc gcagaaccgt  540
cgtttctcta acacctctat gaaagtaatg gacgttgacg ctggtgatcg cgaaactgtt  600
cacccgctgg ttgtgaccca cccgggttct ggtcgtaaag gtctgtatgt gaaccaggtt  660
tactgtcagc gcatcgaggg tatgaccgac gccgaaagca aaccgctgct gcagttcctg  720
tacgaacacg ctacccgctt tgatttcacc tgccgcgtac gttggaagaa agatcaggtt  780
ctggtgtggg acaacctgtg caccatgcac cgtgcggttc ctgattacgc gggcaagttc  840
cgctatctga cccgtactac cgtgggtggt gttcgtccgg cacgctaa              888

SEQ ID NO: 12          moltype = DNA  length = 888
FEATURE                Location/Qualifiers
source                 1..888
                       mol_type = other DNA
                       organism = synthetic construct
CDS                    1..888
                       protein_id = 10
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGRV
                        IGDDWHTDSTFLDAPPAAVVMRAIDVPEHGGDTGFLSMYTAWETLSPTMQATIEGLNVV
                        HSATRVFGSLYQAQNRRFSNTSMKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 12
atgcatgctg cactgtcacc actttctcag aggttcgaga ggatagcagt ccagccgttg  60
accggtgttt tgggtgcaga gataacaggc gtcgaccttc gcgaacccct cgatgacagt  120
acgtggaacg agatcctcga cgcgttccac acctatcagg tgatctactt tccgggccaa  180
gcgatcacga acgagcagca tattgcgttc tcccgccggt ttggcccagt tgacccggtt  240
cctcatctta agtctatcga gggataccca gaggttcaga tgatccgccg tgaggcaaac  300
gagagtggac gggtgatcgg cgatgactgg cacactgaca gcactttctt ggatgcacct  360
cccgcagctg ttgttatgag agctattgat gtgcctgagc atggtggcga caccggtttt  420
cttagcatgt atacagcttg ggagacattg tcgcccacaa tgcaggcgac gatcgaaggc  480
ctgaacgtgg tccatagcgc taccagggtc tttggctccc tgtaccaggc gcaaaataga  540
cggttttcaa acacttctat gaaggtcatg gatgtcgatg ccggagacag agaaaccgtc  600
catccactcg tcgtcactca tccaggaagc ggccgcaagg gtctctatgt gaaccaagtc  660
tattgccaac gcatcgaggg catgacggac gccgaaagca agccgttgct ccagttcctt  720
tacgagcacg ctacaagatt cgactttacg tgcagagtta ggtggaagaa ggaccaggtg  780
ctcgtgtggg acaacctgtg tacgatgcat cgggcagttc cggactacgc cggaaagttc  840
cgttacttga ctaggaccac agttggtggg gtcaggcctg cgagatga              888

SEQ ID NO: 13          moltype = DNA  length = 888
FEATURE                Location/Qualifiers
source                 1..888
                       mol_type = other DNA
                       organism = synthetic construct
CDS                    1..888
                       protein_id = 10
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGRV
                        IGDDWHTDSTFLDAPPAAVVMRAIDVPEHGGDTGFLSMYTAWETLSPTMQATIEGLNVV
                        HSATRVFGSLYQAQNRRFSNTSMKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 13
atgcatgccg cgttatctcc cctgtctcag agattcgagc gaattgccgt ccagccgctc  60
actggtgttc taggcgcaga gataactggc gttgatctcc gcgaaccact agatgactcg  120
acctggaacg agatcctgga tgcatttcat acgtatcagg tcatctattt tccgggccaa  180
gcaattacaa acgagcaaca catagctttc tctcgaaggt ttggaccagt ggatcccgta  240
ccccatttga agagtatcga gggctacccg gaagtccaga tgataagacg agaagcaaat  300
gaatctggcc gtgtgatagg agatgactgg cacacggact ccactttttt agacgcccca  360
ccagcagctg tagtaatgcg cgctatagat gtacctgaac atgggggcga tactggattt  420
ctgtccatgt atactgcatg ggaaacacta tctcctacta tgcaagccac tatagagggt  480
cttaatgttg tccattctgc cactagagtt tttggttcac tctatcaggc gcaaaatcgt  540
agatttcta acacctcaat gaaggtgatg gacgtcgacg ccggcgaccg agaaacagtt  600
catcctctag tcgtaaccca ccccgggtcg gggcgtaagg gcctgtacgt caatcaggtt  660
tactgtcaaa gaatagaagg catgacagat gctgagagca aaccattgct acagtttctg  720
tatgaacatg cgacacggtt tgattttact tgcagagttc ggtggaagaa agaccaggtc  780
ctcgtctggg acaatctatg cacaatgcat cgcgcagtac ctgactatgc ggggaaattc  840
agatacctga ctagaacaac cgtagggggc gtacgaccag caaggtga              888
```

-continued

```
SEQ ID NO: 14           moltype = AA  length = 295
FEATURE                 Location/Qualifiers
source                  1..295
                        mol_type = protein
                        organism = synthetic construct
SEQUENCE: 14
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGRVIGDDW HTDSTFLDAP  120
PAAVVMRAID VPEHGGDTGF LSMYTAWETL SPTMQATIEG LNVVHSATRV FGSLYQAQNR  180
RFSNTSIKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 15           moltype = DNA  length = 888
FEATURE                 Location/Qualifiers
source                  1..888
                        mol_type = other DNA
                        organism = synthetic construct
CDS                     1..888
                        protein_id = 14
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGRV
                         IGDDWHTDSTFLDAPPAAVVMRAIDVPEHGGDTGFLSMYTAWETLSPTMQATIEGLNVV
                         HSATRVFGSLYQAQNRRFSNTSIKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 15
atgcacgcag cactgtctcc tctgtctcag cgtttcgaac gtattgctgt tcagccgctg  60
actggcgttc tgggcgctga aatcactggc gttgatctgc gcgaaccgct ggatgactcc  120
acctggaacg aaatcctgga tgcgttccac acctatcagg tcatttactt ccctggtcag  180
gcaatcacta acgaacagca tatcgctttc agccgtcgtt tcggtccggt tgatccggta  240
ccgcacctga aatctatcga aggctatccg gaagtacaga tgatccgccg tgaagcgaac  300
gagtctggtc gtgttatcgg tgatgactgg cacactgact ccaccttcct ggatgcaccg  360
ccagcggcag tcgttatgcg tgcaatcgat gtcccagaac acggcggtga taccggcttc  420
ctgagcatgt acaccgcgtg ggaaactctg tccccaacta tgcaggctac tatcgaaggc  480
ctgaacgtgg tgcatagcgc gactcgcgta ttcggctctc tgtaccaggc acagaaccgt  540
cgtttcagca acacctccat caaagtgatg gacgttgacg ctggtgaccg cgaaactgtc  600
catccgctgg tagttaccca cccgggttct ggtcgtaagg gtctgtacgt aaaccaggtt  660
tattgccaac gcatcgaggg catgaccgac gccgaatcca aaccgctgct gcaattcctg  720
tatgaacacg ccacccgttt cgacttcact tgccgtgtcc gttggaaaaa agaccaggtt  780
ctggtttggg acaacctgtg caccatgcac cgtgcggttc cggattacgc tggcaaattc  840
cgttacctga cgcgtaccac cgttggcggt gttcgtccgg cacgttaa             888

SEQ ID NO: 16           moltype = DNA  length = 888
FEATURE                 Location/Qualifiers
source                  1..888
                        mol_type = other DNA
                        organism = synthetic construct
CDS                     1..888
                        protein_id = 14
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGRV
                         IGDDWHTDSTFLDAPPAAVVMRAIDVPEHGGDTGFLSMYTAWETLSPTMQATIEGLNVV
                         HSATRVFGSLYQAQNRRFSNTSIKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 16
atgcatgctg ccctgtcccc tctgtctcag agatttgaac ggatagccgt ccagccgttg  60
acaggcgtcc tgggtgcgga gatcacgggc gtcgacttgc gcgagcctct cgacgattca  120
acctggaacg agatcctcga cgcgttccat acataccagg tgatctattt ccccggccag  180
gcaatcacca atgaacagca cattgccttc tcccgccggt tcggtccagt cgaccccgtg  240
ccacacctga agtcgattga gggctaccct gaggtgcaaa tgatcaggag ggaggcgaac  300
gaatctggcc gtgtgatagg tgatgattgg cacaccgatt ccacattcct ggatgcccct  360
cctgcagccg ttgttatgag ggcaatagac gtcccggaac acggcgggga caccggattc  420
ctctccatgt acacggcctg ggaaaccttg tccccgacca tgcaagctac aatcgaggga  480
ctgaacgtcg tgcactcggc gacaagagtt ttcggctcac tctaccaggc ccaaaacaga  540
aggttcagca acacgtctat caaggttatg gacgtggatg caggagatcg cgaaacggtt  600
caccccacttg tcgttacaca cccgggctcc gggcgcaaag gtctctacgt taatcaagtc  660
tattgccaga ggatcgaggg catgaccgac gcagagtcga aaccgctgct gcagttcctg  720
tacgagcatg caaccaggtt cgactttacc tgccgcgttc gctggaaaaa ggatcaggtc  780
ttggtgtggg acaatctttg taccatgcat agggccgtcc cggactacgc cggcaagttt  840
agatacctga cgaggaccac ggtcggcgga gtcagaccgg ccagatga             888

SEQ ID NO: 17           moltype = DNA  length = 888
FEATURE                 Location/Qualifiers
source                  1..888
                        mol_type = other DNA
                        organism = synthetic construct
```

-continued

```
CDS                     1..888
                        protein_id = 14
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGRV
                         IGDDWHTDSTFLDAPPAAVVMRAIDVPEHGGDTGFLSMYTAWETLSPTMQATIEGLNVV
                         HSATRVFGSLYQAQNRRFSNTSIKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 17
atgcatgccg cactctcgcc cctttctcaa cgttttgaaa gaattgctgt gcagccgcta  60
acaggggttt tgggagcgga aattaccggg gtggatctac gtgaacctct tgacgacagc  120
acgtggaatg agattctcga tgcgtttcac acataccaag taatctattt tcccggccag  180
gcaataacaa atgaacagca tatcgcattc tcccggagat ttggccccgt cgatcccgtg  240
ccgcacttga aatctatcga gggttacccg gaagtccaga tgattcggag agaggcgaat  300
gaatccggac gggtcattgg ggacgactgg cataccgata gtaccttctt ggacgctcca  360
cctgcagctg tagttatgag ggcaattgac gttcctgagc acggaggaga taccggtttt  420
ttgtctatgt atacagcatg ggagactctt tcccctacta tgcaagcaac gatagaaggg  480
cttaatgtgg ttcatagcgc gactagggtg ttcggatcgc tgtatcaagc gcaaaacaga  540
agatttagca atactagcat caaagtgatg gacgtagatg ccggcgatag agaaaccgtg  600
catcccttgg tagtcactca ccctggtagt ggaaggaaag gcctctacgt caaccaggta  660
tattgccaaa gaatcgaggg gatgacggat gcggagagta aaccactatt acaattcttg  720
tacgaacatg ccactcgatt tgatttcacg tgtcgagtac gctggaaaaa agaccaggta  780
ctggtatggg ataacttgtg cacgatgcat agggccgttc cagactatgc cgggaagttc  840
cgttatctaa ctagaacaac tgtgggagga gtcagacctg cccgctga              888

SEQ ID NO: 18           moltype = AA  length = 295
FEATURE                 Location/Qualifiers
source                  1..295
                        mol_type = protein
                        organism = synthetic construct
SEQUENCE: 18
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGAVIGDDW HTDSTFLDAP  120
PAAVVMRAID VPEHGGDTGF LSMYTAWETL SPTMQATIEG LNVVHSATRV FGSLYQAQNR  180
RFSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 19           moltype = DNA  length = 888
FEATURE                 Location/Qualifiers
source                  1..888
                        mol_type = other DNA
                        organism = synthetic construct
CDS                     1..888
                        protein_id = 18
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGAV
                         IGDDWHTDSTFLDAPPAAVVMRAIDVPEHGGDTGFLSMYTAWETLSPTMQATIEGLNVV
                         HSATRVFGSLYQAQNRRFSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 19
atgcacgctg cgctgtctcc tctgtctcag cgttttgaac gtatcgccgt tcagccgctg  60
accggtgttc tgggtgccga aattaccggc gtcgatctgc gcgaaccgct ggatgacagc  120
acctggaatg aaatcctgga cgcgtttcac acctaccagg ttatttactt tccaggtcag  180
gcgatcacga acgaacagca catcgctttc agccgtcgct ttggtccggt tgacccggtt  240
ccgcacctga aatctatcga aggttatccg gaagtgcaga tgatccgtcg cgaagcaaac  300
gagagcggcg cggtaattgg tgatgattgg cataccgatt ccaccttcct ggatgctccg  360
cctgcggctg tagttatgcg tgctattgat gttcctgaac acggtggtga caccggtttc  420
ctgtctatgt acaccgcctg ggaaacgctg tcccctacga tgcaagcgac catcgagggt  480
ctgaacgtgg ttcactctgc tacccgcgtt tttggctccc tgtatcaggc acagaaccgc  540
cgcttctcca acacctctct gaaagttatg gatgtggatg ccggtgatcg tgaaaccgtc  600
cacccgctgg ttgttaccca tccgggtagc ggtcgtaaag gtctgtacgt taaccaagtt  660
tactgccagc gtatcgaagg catgaccgat gcggaatcca aaccactgct gcagttcctg  720
tacgaacacg caactcgttt tgatttcact tgtcgtgttc gttggaaaaa agaccaagtg  780
ctggtgtggg acaacctgtg caccatgcat cgtgctgtgc cggattacgc tggtaaattt  840
cgttatctga ctcgtactac cgttggtggc gtgcgtccgg ctcgttaa              888

SEQ ID NO: 20           moltype = DNA  length = 888
FEATURE                 Location/Qualifiers
source                  1..888
                        mol_type = other DNA
                        organism = synthetic construct
CDS                     1..888
                        protein_id = 18
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGAV
```

-continued

```
                        IGDDWHTDSTFLDAPPAAVVMRAIDVPEHGGDTGFLSMYTAWETLSPTMQATIEGLNVV
                        HSATRVFGSLYQAQNRRFSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 20
atgcacgcag cactctcccc actgtcccaa cgcttcgaaa gaatagccgt ccaaccactg  60
acaggcgtgc ttggagccga gataactggc gttgacctcc gtgaaccgct ggacgactct  120
acctggaacg agatcctgga cgcgttccac acctaccaag tcatctactt ccccggccag  180
gcaattacta atgagcagca tatcgcgttc tcaagaaggt tcggacccgt cgacccagtc  240
ccacatctga agtccatcga ggggtaccca gaggtgcaga tgattcgcag ggaagcaaat  300
gagagtggcg ccgttatagg tgatgattgg cacaccgatt ccacgtttct tgatgcaccg  360
ccggctgcgg ttgttatgag agcaattgat gtgcctgaac acggtgggga tacgggcttc  420
ctttccatgt acacggcctg ggagaccctc tccccgacta tgcaggccac cattgagggc  480
ctgaacgtgg tccacagcgc aaccagagtg ttcggcagct tgtaccaagc ccagaatagg  540
aggttctcca acacgtccct taaggtgatg gatgtggatg ctggggaccg tgagaccgtg  600
cacccacttg tggtcacgca tccaggctca gggcggaaag ggctctacgt taaccaagtc  660
tattgtcagc gtatcgaggg gatgacggat gcagagagca aacctcttct gcagtttctc  720
tacgagcacg ctactaggtt cgattttacc tgtcgcgtcc gctggaagaa ggaccaagtt  780
cttgtttggg acaacttgtg taccatgcat agagctgtgc cagactacgc gggcaagttc  840
agatacctga cccgtactac tgtcggcggc gttagacccg caaggtga             888

SEQ ID NO: 21           moltype = DNA  length = 888
FEATURE                 Location/Qualifiers
source                  1..888
                        mol_type = other DNA
                        organism = synthetic construct
CDS                     1..888
                        protein_id = 18
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGAV
                         IGDDWHTDSTFLDAPPAAVVMRAIDVPEHGGDTGFLSMYTAWETLSPTMQATIEGLNVV
                         HSATRVFGSLYQAQNRRFSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 21
atgcacgcgg ccttgtctcc tctctcgcag agatttgaaa gaattgcagt acagccgtta  60
accggggttt tgggagctga aataacgggt gtggatttac gtgagccgct tgacgacagc  120
acctggaacg agattcttga tgcctttcat acgtatcagg tgatttattt ccccgggcag  180
gcaatcacga acgagcagca catcgcattt tcccgccgat ttggtcccgt cgacccagtt  240
ccgcatctaa agagcatcga gggatatccg gaagtccaaa tgatacgacg agaagctaat  300
gaatcgggcg cggtcatagg tgatgactgg cacactgatt ccacatttct agatgccccc  360
ccggcagccg tcgtaatgcg cgcgattgac gtgcccgagc acggaggcga cacaggtttc  420
ctctcgatgt acaccgcatg ggaaacactg tcgccgacta tgcaagcaac gattgagggg  480
ttgaacgtgg tgcattccgc aacaagagtg ttcggatcac tataccaggc acagaataga  540
cgcttttcga atacctcgct aaaagtaatg gacgtagatg ctggagaccg tgagacagta  600
catcccctgg tcgttacaca tccgggtagc ggccgcaagg ggttgtacgt aaatcaagtt  660
tattgccaac ggatcgaagg gatgaccgat gctgaatcga aaccactcct gcaattttta  720
tatgaacatg caacaaggtt cgactttact tgtcgggttc gttggaagaa ggatcaagtc  780
ttggtgtggg acaacttatg tacaatgcat cgagccgtac ccgattatgc aggaaaattt  840
cgatatctaa cgcgcacgac tgtagggggt gtgcgcccgg ctcgctga             888

SEQ ID NO: 22           moltype = AA  length = 295
FEATURE                 Location/Qualifiers
source                  1..295
                        mol_type = protein
                        organism = synthetic construct
SEQUENCE: 22
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGDVIGDDW HTDSTFLDAP  120
PAAVVMRAID VPEHGGDTGF LSMYTAWETL SPTMQATIEG LNVVHSATRV FGSLYQAQNR  180
RFSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 23           moltype = DNA  length = 888
FEATURE                 Location/Qualifiers
source                  1..888
                        mol_type = other DNA
                        organism = synthetic construct
CDS                     1..888
                        protein_id = 22
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGDV
                         IGDDWHTDSTFLDAPPAAVVMRAIDVPEHGGDTGFLSMYTAWETLSPTMQATIEGLNVV
                         HSATRVFGSLYQAQNRRFSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 23
```

-continued

```
atgcacgctg ctctgtctcc gctgtctcag cgttttgaac gtatcgctgt acaaccgctg  60
acgggcgtac tgggtgctga gatcaccggc gtcgatctgc gtgagccgct ggatgactct  120
acttggaacg agatcctgga cgccttccac acttaccagg taatctattt ccctggtcag  180
gctatcacga atgaacagca catcgctttt tcccgtcgtt tcggtccggt tgatccggtt  240
ccgcacctga aaagcattga aggctacccg gaagttcaga tgatccgccg cgaggcaaac  300
gaatctggcg acgtgatcgg tgatgattgg cacaccgatt ctacgttcct ggacgctccg  360
ccggctgctg tagttatgcg cgctattgat gtaccggaac acggtggtga caccggtttc  420
ctgtctatgt acactgcttg ggaaaccctg tctccgacca tgcaggcaac cattgaaggc  480
ctgaacgtag tgcatagcgc aactcgtgtc ttcggctctc tgtatcaggc gcagaaccgt  540
cgtttctcca acacttccct gaaagttatg gacgttgacg cgggtgatcg tgaaaccgtg  600
cacccgctgg ttgttaccca cccgggttct ggtcgtaaag gtctgtacgt caaccaggtg  660
tattgtcagc gtattgaagg tatgacggac gcggagagca aaccgctgct gcagttcctg  720
tatgaacacg ctacgcgttt tgacttcact tgccgtgttc gctggaaaaa agatcaggtt  780
ctggtatggg ataacctgtg caccatgcat cgtgcggttc cggactacgc aggtaaattc  840
cgttatctga ctcgcactac tgttggcggt gtacgcccgg cacgttaa              888

SEQ ID NO: 24          moltype = DNA  length = 888
FEATURE                Location/Qualifiers
source                 1..888
                       mol_type = other DNA
                       organism = synthetic construct
CDS                    1..888
                       protein_id = 22
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGDV
                        IGDDWHTDSTFLDAPPAAVVMRAIDVPEHGGDTGFLSMYTAWETLSPTMQATIEGLNVV
                        HSATRVFGSLYQAQNRRFSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 24
atgcatgccg cactgagtcc cctgtcacaa agatttgaga ggattgctgt tcaacccctc  60
acaggggttc tcggagcgga gatcacaggc gtcgatttgc gggagcccct cgacgattct  120
acctggaacg agatcctcga cgccttccat acgtaccagg tcatttattt cccggggcaa  180
gctatcacta acgagcagca tatcgcattt tcgcgccgct tcggccctgt ggaccctgtg  240
ccacacttga agtccataga aggttaccca gaggtccaaa tgattcggag ggaggcgaat  300
gagagcggcg acgtcattgg tgatgactgg cacactgact caaccttcct tgacgctccg  360
cctgcagcgg ttgtgatgcg cgcgatcgat gtcccggagc acggaggcga cacgggcttc  420
ctctctatgt acacagcctg ggaaacactg agccctacca tgcaggcgac aattgaaggg  480
ttgaacgttg tgcattccgc aacacgggtg ttcggatctc tgtaccaggc ccagaatcgg  540
aggtttagca acacaagttt gaaggtgatg gacgtcgacg ccggggaccg cgagacagtc  600
catcctctcg tggtgaccca cccggggtcc ggcaggaagg gactctacgt caaccaggtg  660
tattgccagc gtattgaggg catgaccgac gctgagagca agcctctgct ccagtttttg  720
tatgagcatg cgacgaggtt cgatttcact tgcagggtga ggtggaaaaa ggaccaggtg  780
ctggtctggg acaatctctg taccatgcac agggctgtcc ccgactacgc gggcaagttc  840
aggtacctca caaggaccac cgttggtggg gtccggccgg ccaggtga              888

SEQ ID NO: 25          moltype = DNA  length = 888
FEATURE                Location/Qualifiers
source                 1..888
                       mol_type = other DNA
                       organism = synthetic construct
CDS                    1..888
                       protein_id = 22
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGDV
                        IGDDWHTDSTFLDAPPAAVVMRAIDVPEHGGDTGFLSMYTAWETLSPTMQATIEGLNVV
                        HSATRVFGSLYQAQNRRFSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 25
atgcacgcgg cactaagccc tctatctcag cggtttgaaa gaattgccgt ccagccactg  60
actggagtcc tgggagccga aatcactggt gttgacttgc gagaaccctt agacgattca  120
acctggaatg aaattttgga cgcttttcat acctatcaag tgatttattt tccggggcag  180
gctatcacga atgaacagca tatcgctttt tctcgcagat ttgggccggt agaccctgtg  240
ccacatttaa aaagtatcga gggataccct gaagtacaaa tgattcgacg cgaagccaat  300
gagtctggcg acgttattgg ggatgattgg cacaccgact caaccttcct cgatgcgcct  360
cctgcggcag ttgttatgag agcaattgat gtgccggagc acggagggga tacgggattc  420
ctgagtatgt atacagcttg ggaaacgctg tcgccaacga tgcaagctac catcgaaggg  480
ctgaatgtcg tccattccgc caccagagtc tttgggtctc tttaccaagc acaaaatcgg  540
cgcttctcta acacctcttt gaaggttatg gacgtcgatg cgggagacag agagaccgtt  600
catccacttg ttgtaactca cccgggatcc ggaagaaaag gattgtacgt aaaccaggtc  660
tattgccaaa ggatcgaagg aatgacagat gccgaaagca agcctttgct gcaattttta  720
tatgagcacg ctacacggtt cgattttacc tgtcgtgtcc gctggaaaaa agaccaagtc  780
ttggtctggg acaacctttg caccatgcat agagcagtac cagattatgc tggtaaattc  840
cggtatctaa ctagaacaac tgttggaggg gtgcgccctg caaggtga              888

SEQ ID NO: 26          moltype = AA  length = 295
```

-continued

```
FEATURE                 Location/Qualifiers
source                  1..295
                        mol_type = protein
                        organism = synthetic construct
SEQUENCE: 26
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGLVIGDDW HTDSTFLDAP  120
PAAVVMRAID VPEHGGDTGF LSMYTAWETL SPTMQATIEG LNVVHSATRV FGSLYQAQNR  180
RFSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 27           moltype = DNA  length = 888
FEATURE                 Location/Qualifiers
source                  1..888
                        mol_type = other DNA
                        organism = synthetic construct
CDS                     1..888
                        protein_id = 26
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGLV
                         IGDDWHTDSTFLDAPPAAVVMRAIDVPEHGGDTGFLSMYTAWETLSPTMQATIEGLNVV
                         HSATRVFGSLYQAQNRRFSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 27
atgcacgcgg cactgtctcc gctgtcccaa cgttttgaac gtattgctgt ccagccgctg  60
actggtgttc tgggcgctga gatcactggt gttgacctgc gtgaaccgct ggacgattct  120
acttggaacg agatcctgga tgccttccac acctatcagg tcatttactt tccgggccag  180
gcgatcacga acgaacagca cattgcgttc agccgtcgct ttggcccggt tgatccggtt  240
ccgcacctga aaagcatcga aggctatccg gaagttcaga tgatccgtcg cgaggcgaac  300
gaatctggtc tggttattgg tgacgactgg cacaccgact ccactttcct ggatgctcct  360
ccggcagccg ttgttatgcg tgcaatcgat gttccggaac atggcggtga taccggcttc  420
ctgtccatgt acaccgcttg ggaaactctg tccccgacca tgcaggctac cattgaaggt  480
ctgaacgtcg tccactccgc tacccgtgtt ttcggttctc tgtatcaggc acagaaccgt  540
cgtttctcca acacctctct gaaagttatg gacgttgacg ccggtgaccg tgaaaccgtg  600
catccgctgg ttgttaccca cccgggttct ggccgtaaag gtctgtacgt aaatcaggtc  660
tattgtcagc gcatcgaagg tatgaccgac gctgagtcca aaccgctgct gcaattcctg  720
tacgaacacg ccactcgttt tgacttcacc tgtcgtgtcc gctggaaaaa agaccaggta  780
ctggtttggg ataacctgtg caccatgcac cgtgcggttc cggactatgc gggtaaattc  840
cgttacctga ctcgtactac tgtgggtggc gtacgtccgg ctcgttaa              888

SEQ ID NO: 28           moltype = DNA  length = 888
FEATURE                 Location/Qualifiers
source                  1..888
                        mol_type = other DNA
                        organism = synthetic construct
CDS                     1..888
                        protein_id = 26
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGLV
                         IGDDWHTDSTFLDAPPAAVVMRAIDVPEHGGDTGFLSMYTAWETLSPTMQATIEGLNVV
                         HSATRVFGSLYQAQNRRFSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 28
atgcatgccg cgcttagtcc gctctctcaa agattcgaga ggatagcggt ccagccattg  60
accggcgtcc ttggtgcaga aataacaggc gtcgatctga gggagccact ggacgattcc  120
acatggaatg agatcctcga cgcttttcat acgtaccagg tcatctactt cccgggacag  180
gcaatcacca acgagcagca cattgccttc tcccgcaggt tcggtcctgt tgaccctgtg  240
ccccatctca agagtatcga gggctaccct gaggtgcaga tgatccggcg cgaagctaac  300
gagagcggtt tggttatcgg cgacgactgg cacaccgact cgacttttct ggatgcgcct  360
cctgccgcag ttgtgatgag agctattgat gttcccgaac acggaggcga taccgggttt  420
ttgtcgatgt atactgcgtg ggagacgctg tccccaacca tgcaggccac catcgagggc  480
ttgaacgtgg tccatagcgc tacgagggtc ttcggcagtc tctaccaggc acagaacagg  540
cggttcagta acacctcatt gaaggtgatg gacgtggacg ctggcgatcg cgagactgtg  600
catcccctgg tcgttactca ccctggcagt ggtagaaagg gactctacgt gaatcaggtg  660
tattgccaac ggatagaggg catgacggac gccgagtcaa aacccccttct tcagtttttg  720
tacgagcacg ctacgcgctt cgatttcaca tgtagagtga gatggaagaa ggaccaagtg  780
ctcgtttggg acaatctttg tacgatgcac agggctgtgc ctgattacgc ggggaagttc  840
cggtacctga ccaggacaac agttggcggc gttagaccgg cccggtga              888

SEQ ID NO: 29           moltype = DNA  length = 888
FEATURE                 Location/Qualifiers
source                  1..888
                        mol_type = other DNA
                        organism = synthetic construct
CDS                     1..888
```

```
                        protein_id = 26
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGLV
                         IGDDWHTDSTFLDAPPAAVVMRAIDVPEHGGDTGFLSMYTAWETLSPTMQATIEGLNVV
                         HSATRVFGSLYQAQNRRFSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 29
atgcatgcag ctctatctcc cttaagccag cgctttgaac gcatcgctgt acaacctcta  60
actggagtcc ttggcgcgga gataaccggc gtagatctga gagaaccgtt ggacgactcc  120
acctggaatg aaatcctaga cgccttccat acataccaag tgatctattt tcctggccaa  180
gccatcacaa atgaacaaca tattgcgttt agccgcaggt tcggaccggt agatcccgtt  240
ccgcacttaa aaagcataga aggttatccc gaggtccaaa tgatacgaag agaagccaac  300
gaatcgggac tcgtaattgg ggacgactgg cataccgatt ccactttcct agatgctccc  360
cccgcagccg ttgtgatgag agctatagat gtgcctgaac atggaggtga tacagggttt  420
cttagcatgt atacagcctg ggagactctg tcgccgacta tgcaggccac catcgagggg  480
ttgaatgttg ttcactctgc cactagagta tttgggagcc tataccaagc tcagaatcgc  540
cgattctcta atacgtcgct taaggtcatg gacgtagacg cgggagatcg ggaaaccgtg  600
cacccccctgg ttgtaacgca tcctggctcc gggcgcaaag gcctttacgt taaccaagtc  660
tactgtcagc gaattgaggg aatgacagat gccgaatcta agccgctgtt acaatttttg  720
tatgaacatg cgactcgctt tgatttcacg tgtcgcgtaa ggtggaaaaa ggaccaagta  780
ctagtctggg ataatctgtg tactatgcat cgggccgtac ccgattatgc gggaaagttt  840
cgctatttga cacgtacgac agtcgggggt gttaggccag cccgctga              888

SEQ ID NO: 30           moltype = AA  length = 295
FEATURE                 Location/Qualifiers
source                  1..295
                        mol_type = protein
                        organism = synthetic construct
SEQUENCE: 30
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGRVIGDDW HTDSTFLDAP  120
PAAVVMRAID VPEHGGDTGF LSMYTAWETL SPTMQATIEG LNVVHSATRV FGSLYQAQNR  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 31           moltype = DNA  length = 888
FEATURE                 Location/Qualifiers
source                  1..888
                        mol_type = other DNA
                        organism = synthetic construct
CDS                     1..888
                        protein_id = 30
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGRV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 31
atgcatgctg cactgtctcc actgtctcag cgtttcgaac gtattgcggt acagcctctg  60
accggtgtac tgggtgccga aatcaccggc gtcgatctgc gcgaaccgct ggatgatagc  120
acctggaacg agatcctgga cgctttccac acttatcagg taatctattt cccaggtcag  180
gcgattacca acgaacagca catcgccttt tcccgccgtt tcggtccggt agatccagtg  240
ccgcatctga aaagcattga gggctacccg gaagttcaga tgattcgtcg cgaagcaaac  300
gaatccggtc gtgttatcgg tgacgattgg cacaccgatt ctactttcct ggacgcacct  360
ccggctgctg ttgttatgcg tgctatcgac gtaccagaac acggcggcga cactggtttc  420
ctgtccatgt acaccgcatg ggaaaccctg agcccgacca tgcaagcgac catcgaaggc  480
ctgaacgttg ttcactctgc tacgcgtgtg tttggttctc tgtaccaggc acagaatcgt  540
cgctggtcta acacttccct gaaagttatg gacgtggatg cgggtgatcg tgaaaccgtg  600
catccgctgg ttgttactca tccaggtagc ggccgtaaag gcctgtatgt taaccaggtt  660
tactgccagc gtatcgaagg catgaccgac gcggagtcca aaccgctgct gcagttcctg  720
tatgaacacg caacccgttt tgattttacc tgccgcgttc gttggaaaaa agaccaggtt  780
ctggtatggg ataacctgtg cactatgcac cgtgctgttc cggattatgc tggtaagttc  840
cgctacctga ctcgtaccac tgttggtggt gttcgcccgg ctcgctaa              888

SEQ ID NO: 32           moltype = DNA  length = 888
FEATURE                 Location/Qualifiers
source                  1..888
                        mol_type = other DNA
                        organism = synthetic construct
CDS                     1..888
                        protein_id = 30
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGRV
                         IGDDWHTDSTFLDAPPAAVVMRAIDVPEHGGDTGFLSMYTAWETLSPTMQATIEGLNVV
```

-continued

HSATRVFGSLYQAQNRRWSNTSLKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR

SEQUENCE: 32
atgcatgcag ccctctcccc acttagccaa aggttcgaga ggattgctgt tcaaccgctg 60
accggagtgc tgggggcgga gatcactggt gtcgacctcc gggaaccact cgacgacagt 120
acgtggaacg aaatccttga cgcgtttcac acttaccaag tgatctattt ccctggacag 180
gcgatcacaa acgagcaaca catcgccttc tcccgccgct ttggaccagt ggacccagtt 240
ccgcacctta aatccatcga agggtacccc gaggtccaga tgatccggcg cgaggcgaac 300
gagtcggggc gggttatagg cgatgactgg cacactgata gtacattcct ggacgccccc 360
cccgccgcgg tggttatgcg cgcgatcgac gttccggagc acggtggcga caccggattc 420
ttgagcatgt acactgcctg ggagactctg agcccgacga tgcaagctac gatcgaggga 480
ttgaatgtgg tccactcagc gacgcgcgtg ttcggatcac tctaccaagc acaaaacaga 540
agatggtcta acactagcct caaggtgatg gacgtggatg caggcgatag ggagacggtc 600
cacccactcg tggttacaca tccgggctca ggccgtaagg gactttacgt caaccaggtg 660
tattgccagc gcatcgaggg aatgaccgat gcagagagca aaccgctgct gcaattcctt 720
tacgagcacg ccacccggtt cgatttcaca tgccgcgttc gttggaagaa ggaccaggtg 780
ctcgtctggg acaacctttg cactatgcac cgtgctgttc cagactacgc tggtaagttc 840
aggtacctca ccaggactac ggtcggcggc gtccgcccgg cgaggtga 888

SEQ ID NO: 33 moltype = DNA length = 888
FEATURE Location/Qualifiers
source 1..888
mol_type = other DNA
organism = synthetic construct
CDS 1..888
protein_id = 30
transl_table = 1
translation = MHAALSPLSQRFERIAVQPLTGVLGAEITGVDLREPLDDSTWNEIL
DAFHTYQVIYFPGQAITNEQHIAFSRRFGPVDPVPHLKSIEGYPEVQMIRREANESGRV
IGDDWHTDSTFLDAPPAAVVMRAIDVPEHGGDTGFLSMYTAWETLSPTMQATIEGLNVV
HSATRVFGSLYQAQNRRWSNTSLKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR SEQUENCE: 33
atgcacgccg ccctaagccc attatctcag agatttgaaa gaattgctgt tcaacctcta 60
accggcgtgt taggcgctga aataaccgga gttgacttgc gtgagcccct tgatgactcg 120
acctggaatg aaattctaga cgccttccac acatatcagg taatttattt tccaggtcag 180
gcaattacga atgaacagca catagccttc agtaggaggt tcggtcccgt agaccccgtg 240
ccacacctaa aaagcattga aggttatccc gaagtccaga tgattcgaag agaggcaaat 300
gaatcgggta gggtcatcgg agacgactgg catacggact caacttttct tgatgcgcca 360
ccggcagctg tagtgatgag agcaattgat gtgcccgagc acggtggaga tactgggttt 420
ctaagtatgt acaccgcttg ggagacgctt tcgccgacta tgcaggcgac catcgaagga 480
ttaaatgtcg ttcactcggc tacgcgggta ttcgggagtc tataccaagc tcagaatcgt 540
agatggtcca atacatcttt aaaagtaatg gacgtcgatg ccggcgatcg tgaaactgta 600
catccgttgg ttgtaaccca tcctggaagc gggcgtaaag gactatacgt caaccaagtg 660
tactgccaac gcattgaagg tatgacggac gctgaatcga agccgttgct ccaattcttg 720
tacgagcatg caacccgatt cgactttacc tgtcgggtac gctggaagaa agatcaggtc 780
ctggtgtggg ataatctatg tactatgcat agagcagttc ctgactacgc gggcaaattt 840
agatacttga cccgtacgac agtcggggga gtgagacctg cgagatga 888

SEQ ID NO: 34 moltype = AA length = 295
FEATURE Location/Qualifiers
source 1..295
mol_type = protein
organism = synthetic construct SEQUENCE: 34
MHAALSPLSQ RFERIAVQPL TGVLGAEITG VDLREPLDDS TWNEILDAFH TYQVIYFPGQ 60
AITNEQHIAF SRRFGPVDPV PHLKSIEGYP EVQMIRREAN ESLRVIGDDW HTDSTFLDAP 120
PAAVVMRAID VPEHGGDTGF LSMYTAWETL SPTMQATIEG LNVVHSATRV FGSLYQAQNR 180
RFSNTSLKVM DVDAGDRETV HPLVVTHPGS GRKGLYVNQV YCQRIEGMTD AESKPLLQFL 240
YEHATRFDFT CRVRWKKDQV LVWDNLCTMH RAVPDYAGKF RYLTRTTVGG VRPAR 295

SEQ ID NO: 35 moltype = DNA length = 888
FEATURE Location/Qualifiers
source 1..888
mol_type = other DNA
organism = synthetic construct
CDS 1..888
protein_id = 34
transl_table = 1
translation = MHAALSPLSQRFERIAVQPLTGVLGAEITGVDLREPLDDSTWNEIL
DAFHTYQVIYFPGQAITNEQHIAFSRRFGPVDPVPHLKSIEGYPEVQMIRREANESLRV
IGDDWHTDSTFLDAPPAAVVMRAIDVPEHGGDTGFLSMYTAWETLSPTMQATIEGLNVV
HSATRVFGSLYQAQNRRFSNTSLKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR SEQUENCE: 35
atgcacgctg cactgagccc gctgtctcaa cgttttgaac gtattgcagt tcagcctctg 60

-continued

```
acgggcgttc tgggtgcaga aattactggc gtggatctgc gtgaaccact ggacgactct  120
acctggaatg aaatcctgga tgcgttccac acttaccagg ttatttactt tccgggccag  180
gctatcacca acgagcagca cattgctttc tcccgtcgtt tcggtccggt ggacccggtt  240
cctcatctga aatccattga aggctatccg gaagtacaga tgatccgtcg tgaagccaac  300
gagtctctgc gcgtaattgg cgacgactgg cacaccgact ccacttttct ggacgctccg  360
ccggcagctg tagttatgcg tgctattgat gttccggagc acggtggtga caccggtttc  420
ctgtccatgt acaccgcttg ggaaaccctg tccccgacca tgcaggcaac catcgagggc  480
ctgaacgtag tccactccgc aacccgtgta ttcggctctc tgtaccaggc tcagaatcgc  540
cgtttcagca acacctccct gaaagttatg gatgttgatg cgggcgatcg tgaaaccgtt  600
cacccgctgg ttgtgaccca cccgggttct ggtcgcaaag gtctgtacgt taaccaggtt  660
tattgccagc gcattgaagg tatgaccgat gcagaatcca aaccactgct gcagttcctg  720
tatgaacacg cgacccgttt cgatttcacc tgccgcgtgc gttggaaaaa agatcaggta  780
ctggtgtggg acaacctgtg cactatgcat cgcgcagtgc cggactatgc aggtaaattc  840
cgttacctga cccgtaccac cgttggtggt gttcgtccgg cacgttaa              888

SEQ ID NO: 36          moltype = DNA  length = 888
FEATURE                Location/Qualifiers
source                 1..888
                       mol_type = other DNA
                       organism = synthetic construct
CDS                    1..888
                       protein_id = 34
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESLRV
                        IGDDWHTDSTFLDAPPAAVVMRAIDVPEHGGDTGFLSMYTAWETLSPTMQATIEGLNVV
                        HSATRVFGSLYQAQNRRFSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 36
atgcatgccg ctctctcacc gctcagccaa aggtttgaga gaattgctgt tcagccgctc  60
accggtgtgt tgggagccga aattacggga gtcgatctca gagagcctct tgacgattcc  120
acctggaacg agatcttgga tgcattccac acgtatcagg tcatttactt tccaggacag  180
gccatcacga acgagcagca tattgcattc agccgtcggt tcggaccagt ggacccggtt  240
cctcatctga agtctataga aggttaccca gaggtgcaga tgattaggcg cgaggccaac  300
gaaagcctca gagtcatcgg cgatgactgg cacactgact ccaccttcct cgacgcccct  360
cctgctgctg tcgtcatgag agctattgat gtccccgagc atggcggaga tacgggcttc  420
cttagcatgt acacggcctg ggaaaccctg tcccccacta tgcaggctac cattgagggc  480
cttaacgtgg tgcattctgc cactcgggtg tttggctcgt tgtaccaggc tcagaacagg  540
aggttctcca acacatctct taaagttatg gatgttgatg ccggtgatag ggagactgtg  600
catcctctcg tcgttaccca cccaggctca ggacgtaaag gactgtacgt gaaccaggtg  660
tactgtcaaa ggatcgaagg catgacggat gccgaaagca agcccctctt gcaattcctc  720
tacgagcatg cgacgcggtt tgatttcacc tgcagggtgc ggtggaagaa ggaccaggtc  780
ctcgtgtggg ataacctgtg cactatgcac agggccgttc cggattatgc gggcaagttt  840
agatacctta caagaaccac agtcggtggc gtcagacctg ccaggtga              888

SEQ ID NO: 37          moltype = DNA  length = 888
FEATURE                Location/Qualifiers
source                 1..888
                       mol_type = other DNA
                       organism = synthetic construct
CDS                    1..888
                       protein_id = 34
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESLRV
                        IGDDWHTDSTFLDAPPAAVVMRAIDVPEHGGDTGFLSMYTAWETLSPTMQATIEGLNVV
                        HSATRVFGSLYQAQNRRFSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 37
atgcatgccg ctctttcgcc ccttagtcag agattcgaaa ggatagcggt ccaacctctc  60
accggtgtcc tgggagcgga gataaccggc gtagacttgc gcgaacctct tgacgattcc  120
acatggaatg agattctcga tgcttttcat acgtaccaag tcatttattt ccctggccaa  180
gccatcacca acgaacaaca cattgcattc agtcgccgtt ttgggccggt cgatccggta  240
ccacatttga aaagcataga aggatacccc gaggtgcaga tgattcggag ggaggcaaat  300
gagtctctgc gtgtaatagg cgacgattgg catacggatt caacctttct cgatgcacca  360
ccggcagcag ttgtaatgag agccattgat gtaccggagc acggaggaga tacgggcttc  420
ttgtctatgt atacggcatg ggagacttta tcgccaacta tgcaggcaac tatagagggg  480
ttaaatgtcg ttcactcggc tactcgagtt tttgggagcc tttatcaggc ccagaaccga  540
cgcttctcca atacatcgtt gaaggtcatg gatgtggatg ccggagatcg cgaaacggta  600
cacccacttg tggtaacaca ccctgggtca gggcgcaaag gcctttatgt taaccaagtc  660
tattgccagc ggatagaagg aatgaccgac gcggagtcta aaccactgtt gcagtttctc  720
tatgagcatg cgaccagatt cgattttacg tgccgtgtaa gatggaagaa agatcaagtc  780
ttagtatggg ataacctgtg cacgatgcac agagccgttc ccgattatgc cgggaaattc  840
agatacttga cgagaacaac agtaggaggt gttcgacctg cgcggtga              888

SEQ ID NO: 38          moltype = AA  length = 295
FEATURE                Location/Qualifiers
```

-continued

```
source                  1..295
                        mol_type = protein
                        organism = synthetic construct
SEQUENCE: 38
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGGVIGDDW HTDSTFLDAP  120
PAAVVMRAID VPEHGGDTGF LSMYTAWETL SPTMQATIEG LNVVHSATRV FGSLYQAQNR  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 39           moltype = DNA  length = 888
FEATURE                 Location/Qualifiers
source                  1..888
                        mol_type = other DNA
                        organism = synthetic construct
CDS                     1..888
                        protein_id = 38
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 39
atgcatgctg cgctgtctcc tctgtctcag cgtttcgaac gtatcgctgt tcagccgctg  60
accggtgttc tgggcgcaga aattaccggc gtagatctgc gtgagccgct ggacgactct  120
acctggaacg aaatcctgga cgccttccac acttaccagg tgatctattt cccgggtcag  180
gcaatcacca acgaacaaca cattgctttc tctcgccgct tcggcccggt agatccggta  240
cctcacctga aatctattga gggttacccg gaggtccaga tgatccgccg tgaggcgaac  300
gagtccggcg gtgttatcgg tgatgactgg catacggatt ctacctttct ggacgcacct  360
ccggcagcag tggtgatgcg tgcaatcgac gtgccggaac atggcggcga tactggcttc  420
ctgtctatgt ataccgcgtg ggagaccctg tctccgacca tgcaggccac catcgaaggc  480
ctgaacgtag ttcactccgc tactcgtgtt ttcggcagcc tgtaccaggc gcaaaaccgt  540
cgttggagca acacctccct gaaagttatg gacgtcgatg ccggtgatcg tgaaaccgtt  600
cacccgctgg ttgtgaccca cccgggctct ggccgtaaag gtctgtacgt caatcaggtg  660
tattgtcaac gcattgaagg catgaccgac gcagaatcta agccactgct gcagtttctg  720
tacgaacacg ctactcgctt cgacttcacc tgtcgtgttc gttggaaaaa agatcaggtt  780
ctggtttggg acaacctgtg taccatgcac cgtgcagttc cggactatgc tggtaaattc  840
cgttatctga ctcgcaccac cgtgggtggt gtacgtccgg cgcgttaa              888

SEQ ID NO: 40           moltype = DNA  length = 888
FEATURE                 Location/Qualifiers
source                  1..888
                        mol_type = other DNA
                        organism = synthetic construct
CDS                     1..888
                        protein_id = 38
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 40
atgcacgctg cattgagccc gctttctcag cgtttcgaga gaatcgcagt gcagcccctg  60
acgggcgtgc tcggcgctga aatcacgggc gtggatctcc gggaaccact ggatgatagc  120
acatggaacg agatccttga tgcgttccac acttaccaag tcatttattt ccccggccag  180
gctatcacaa acgagcagca tatcgctttc tcgaggaggt tcggcccggt ggaccccgtt  240
ccgcacctca agtccattga aggctatcca gaggtccaaa tgatccggag agaggctaac  300
gaaagcggtg gcgtcatcgg ggatgactgg cataccgatt ccacgttttt ggacgccccc  360
ccagcagcgg tggtgatgcg cgcaatcgat gttccagagc atggcggtga tactggcttc  420
ctctcgatgt atacagcatg ggagacactc tcgccaacca tgcaggcgac gatagagggg  480
ctcaatgtcg ttcacagcgc cacccgcgtc ttcgggagct tgtatcaggc ccagaataga  540
cggtggagca acactagcct caaggtgatg gacgtcgacg ctggcgatag agagaccgtg  600
catccgctgg tcgtgactca cccgggatca ggtaggaagg gcttgtatgt taaccaggtt  660
tactgtcaga ggatcgaggg catgaccgac gccgaatcta agcccttgct gcagttcctc  720
tacgagcatg ctaccagatt cgacttcact tgcagggtta ggtggaagaa ggatcaggtc  780
cttgtctggg acaatctctg cacaatgcat agggctgtgc cggactacgc tgggaagttc  840
cggtatctca cgaggactac ggttggcggc gtgcgcccag cgcggtga              888

SEQ ID NO: 41           moltype = DNA  length = 888
FEATURE                 Location/Qualifiers
source                  1..888
                        mol_type = other DNA
                        organism = synthetic construct
CDS                     1..888
                        protein_id = 38
```

-continued

```
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 41
atgcacgctg ctttaagccc acttagccag aggtttgaac gtattgctgt ccaaccactc  60
actggcgttt tgggagctga aataacaggt gttgatctca gagaaccact cgatgattca  120
acctggaacg aaatcttgga cgcatttcat acataccaag tgatttattt cccaggccaa  180
gctattacca atgaacaaca tatcgctttc agcagaagat tcggtccagt tgaccctgta  240
cctcatttga agagtatcga gggataccca gaagtgcaaa tgattagacg tgaagctaac  300
gagtccgggg gagttatcgg agatgattgg cataccgatt caacttttct cgatgcaccg  360
cctgcagctg tggtgatgag ggctatagat gtcccagagc acggaggtga tactggcttt  420
ttgtctatgt acactgcctg ggaaacctta agccctacaa tgcaagctac aattgagggt  480
ttgaatgttg tgcatagtgc cactagggtg ttcggatctc tttaccaggc tcaaaataga  540
agatggtcaa atacaagtct taaggtaatg gacgttgatg ctggtgatcg tgagactgtg  600
cacccgcttg tagtgaccca ccctggtagt ggtaggaagg gtttatatgt caaccaagta  660
tattgccagc gtattgaagg tatgactgat gcagagtcaa agccccttct tcaatttttg  720
tacgaacacg caactcgttt cgattttact tgcagagtga ggtggaagaa agatcaggtt  780
cttgtctggg acaacttatg tacaatgcat cgtgcagtgc ccgactatgc tggaaaattt  840
agatacttga ctcgaaccac tgtaggaggc gtgcgtccgg cacgatga              888

SEQ ID NO: 42           moltype = AA  length = 295
FEATURE                 Location/Qualifiers
source                  1..295
                        mol_type = protein
                        organism = synthetic construct
SEQUENCE: 42
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESLRVIGDDW HTDSTFLDAP  120
PAAVVMRAID VPEHGGDTGF LSMYTAWETL SPTMQATIEG LNVVHSATRV FGSLYQAQNR  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 43           moltype = DNA  length = 888
FEATURE                 Location/Qualifiers
source                  1..888
                        mol_type = other DNA
                        organism = synthetic construct
CDS                     1..888
                        protein_id = 42
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 43
atgcatgcag cactgtctcc gctgtctcag cgcttcgaac gtattgctgt gcagccgctg  60
accggcgttc tgggtgctga aatcactggc gtagacctgc gtgaaccgct ggatgattcc  120
acctggaacg agattctgga tgcgttccac acctatcagg ttatctattt cccgggtcag  180
gctatcacta acgaacaaca cattgctttc tcccgccgct ttggtccggt cgacccggtt  240
ccgcacctga aatctatcga aggctacccg gaagtgcaga tgattcgtcg cgaagccaac  300
gaaagcctgc gtgttatcgg cgatgattgg cacaccgaca gcaccttcct ggacgctccg  360
ccagcagcgg tggttatgcg tgccatcgac gttccggaac acggcggtga tactggtttc  420
ctgtctatgt ataccgcgtg ggaaactctg tctccgacta tgcaggctac cattgaaggt  480
ctgaacgtgg tgcactctgc gacccgtgtg ttcggcagcc tgtaccaggc gcagaaccgt  540
cgctggagca acacctctct gaaagttatg gacgttgacg caggcgatcg tgaaaccgtg  600
cacccgctgg ttgtgaccca cccgggttct ggtcgcaaag gcctgtacgt gaaccaggta  660
tactgccaac gtatcgaagg tatgactgat gcagaatcta aaccgctgct gcagtttctg  720
tacgaacacg cgactcgttt cgactttact tgtcgtgtgc gttggaagaa ggatcaggtg  780
ctggtttggg acaacctgtg taccatgcac cgtgccgttc cagattacgc gggtaaattc  840
cgttacctga cccgcaccac cgtcggtggc gtccgcccag ctcgttaa              888

SEQ ID NO: 44           moltype = DNA  length = 888
FEATURE                 Location/Qualifiers
source                  1..888
                        mol_type = other DNA
                        organism = synthetic construct
CDS                     1..888
                        protein_id = 42
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
```

-continued

RIEGMTDAESKPLLQFLYEHATRFDFTCRVRWKKDQVLVWDNLCTMHRAVPDYAGKFRY
LTRTTVGGVRPAR

SEQUENCE: 44
```
atgcatgctg cgctttcccc cctgagccaa cggtttgaga ggatcgccgt ccaaccactc  60
acgggcgtgc tgggcgcgga gatcactggt gtagatctcc gtgaacctct tgatgattca  120
acgtggaatg aaatacttga cgcgttccac acatatcagg tcatctactt cccggggcaa  180
gcaataacga atgagcagca catagctttt agtcgacgct tcggccccgt ggatcctgtg  240
ccgcacctca aatctattga aggataccg gaggtacaga tgatccggag agaggccaac  300
gaatcgttgc gagtgattgg tgacgactgg cacaccgaca gcacctttct ggacgcccca  360
ccagcagcag tcgtgatgcg tgccattgat gtgccagagc acggcggcga cactggtttt  420
ctctccatgt acacggcgtg ggagacgctc tcacctacaa tgcaggccac aattgagggg  480
ctgaacgtgg tgcattctgc tactagagtt tttggttcat tgtaccaggc gcagaaccgc  540
cgctggtcca atacctcgct aaaggtcatg gacgtcgatg ctggagacag agaaactgtt  600
catccgctgg tagttacaca tcctggatct gggaggaagg gactatatgt caaccaagtt  660
tactgccaga ggatcgaggg catgactgat gccgagagca aaccacttct gcagttcctc  720
tatgaacatg caacgaggtt cgacttcacc tgccgggtga ggtggaagaa ggatcaagtt  780
cttgtgtggg ataatttgtg taccatgcac cgcgctgtcc ccgactacgc cggcaagttc  840
cgctatttaa ccaggacaac agttggtggg gttcggcctg ctcgttga               888
```

```
SEQ ID NO: 45          moltype = DNA  length = 888
FEATURE                Location/Qualifiers
source                 1..888
                       mol_type = other DNA
                       organism = synthetic construct
CDS                    1..888
                       protein_id = 42
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESLRV
                        IGDDWHTDSTFLDAPPAAVVMRAIDVPEHGGDTGFLSMYTAWETLSPTMQATIEGLNVV
                        HSATRVFGSLYQAQNRRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
```

SEQUENCE: 45
```
atgcatgctg ctttgagtcc tcttagccaa cgatttgaaa ggatcgctgt ccaacctttg  60
actggtgtat tgggtgctga gattaccggc gttgatcttc gtgagccact cgacgactct  120
acatggaatg aaattctgga tgcttttcat acatatcagg tgatttattt tccagggcaa  180
gctattacca atgagcagca tattgctttt tctcgtaggt tcggtcccgt ggatccggta  240
cctcatctga aatcaattga ggggtacccg gaggttcaga tgatacgtag ggaggctaat  300
gagtcccttc gagtcattgg tgatgattgg catacagata gtacatttct cgatgcccca  360
cctgctgctg tggttatgag ggccattgat gttcccgagc atggtggaga cacagggttc  420
ctttcaatgt atacagcctg ggagactctc tccccaacaa tgcaggccac tatcgagggt  480
cttaatgtag tgcattcagc tacaagggtt ttcgggagcc tttaccaggc acaaaatagg  540
aggtggtcaa atacaagctt gaaagttatg gacgtcgatg ctggcgacag agaaacagtg  600
catccacttg tggtgaccca tccaggatcc ggaagaaagg gattgtacgt aaaccaggtg  660
tactgtcaac gtattgaggg aatgactgat gcagaaagta aaccactcct ccagttcttg  720
tatgagcatg caactaggtt cgattttacc tgtagggtta gatggaagaa ggatcaagtt  780
ctcgtttggg ataacctctg taccatgcat cgtgcagttc ctgattatgc agggaaattt  840
cgttacttga ctagaacaac cgtgggagga gttaggccag ccagatga               888
```

```
SEQ ID NO: 46          moltype = AA  length = 295
FEATURE                Location/Qualifiers
source                 1..295
                       mol_type = protein
                       organism = synthetic construct
```

SEQUENCE: 46
```
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGGVIGDDW HSDSTFLDAP  120
PAAVVMRAID VPEHGGDTGF LSMYTAWETL SPTMQATIEG LNVVHSATRV FGSLYQAQNR  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295
```

```
SEQ ID NO: 47          moltype = DNA  length = 888
FEATURE                Location/Qualifiers
source                 1..888
                       mol_type = other DNA
                       organism = synthetic construct
CDS                    1..888
                       protein_id = 46
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHSDSTFLDAPPAAVVMRAIDVPEHGGDTGFLSMYTAWETLSPTMQATIEGLNVV
                        HSATRVFGSLYQAQNRRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
```

SEQUENCE: 47
```
atgcacgcag ctctgtctcc gctgtctcag cgttttgaac gtatcgcggt tcagccgctg  60
accggtgttc tgggtgctga aatcaccggc gtagacctgc gtgaaccgct ggacgattct  120
```

-continued

```
acctggaacg aaatcctgga tgctttccac acctaccagg tgatctactt tccgggccag  180
gctattacta acgagcaaca cattgcgttt agccgtcgct tcggcccggt ggacccagtt  240
ccgcacctga aatctatcga aggctatccg gaggttcaga tgatccgtcg tgaggccaac  300
gaaagcggtg gtgtgatcgg tgacgactgg cactccgact ccaccttcct ggacgcgccg  360
ccggcggcag ttgttatgcg tgctattgac gttccagaac atggtggtga tacgggtttc  420
ctgtccatgt ataccgcatg ggaaaccctg agcccaacta tgcaagcaac tatcgaaggc  480
ctgaacgttg tccacagcgc cacccgcgta ttcggtagcc tgtatcaggc ccagaaccgc  540
cgctggagca atacctctct gaaagtgatg gacgtggatg ctggcgaccg tgaaaccgtt  600
caccctctgg ttgtaaccca tccgggttct ggccgtaaag gtctgtacgt taaccaggtg  660
tactgtcagc gtattgaagg tatgaccgac gcagaatcca aacctctgct gcagttcctg  720
tatgaacacg caacccgttt tgatttcacc tgtcgcgttc gttggaaaaa agaccaggtt  780
ctggtatggg ataacctgtg caccatgcac cgcgctgttc cggactacgc gggtaaattc  840
cgctacctga ctcgcaccac cgttggtggc gttcgtccgg cacgttaa              888

SEQ ID NO: 48          moltype = DNA  length = 888
FEATURE                Location/Qualifiers
source                 1..888
                       mol_type = other DNA
                       organism = synthetic construct
CDS                    1..888
                       protein_id = 46
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHSDSTFLDAPPAAVVMRAIDVPEHGGDTGFLSMYTAWETLSPTMQATIEGLNVV
                        HSATRVFGSLYQAQNRRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 48
atgcacgctg cattgagtcc attgtcgcag cggtttgagc ggattgcggt ccagcccctg  60
acaggcgtgt tgggagctga gattaccggc gtggacctcc gcgagccgct tgacgactca  120
acctggaatg agatcctgga tgcctttcat acctatcaag tgatttactt tcccgggcag  180
gctattacga acgagcagca tatagcgttc tccaggaggt tcggcccagt ggatccggtc  240
ccacatctga agtccattga aggatatcca gaggtgcaga tgatccggag ggaggctaac  300
gagagtggcg gtgtgattgg cgacgactgg cactcggact cgactttcct cgacgccccg  360
ccagcggccg tcgtgatgag ggctatcgac gtgccagaac acgggggaga cacggggttc  420
ttgagcatgt acaccgcttg ggaaaccctc agtcctacca tgcaggccac gatcgaaggc  480
ctgaacgttg tgcactcagc cacccgggtg ttcgggtcgc tgtaccaggc tcaaaatcgg  540
agatggtcca acacctccct gaaggtgatg gacgttgatg ccggggatcg cgagaccgtc  600
catcccttgg tggtgaccca cccgggaagc gggaggaagg gcctctacgt taaccaagtc  660
tattgccaac gcatcgaagg aatgaccgat gcagagtcga agccgctcct gcagttcctc  720
tatgaacacg caacgcgttt tgacttcacg tgcagggtca ggtggaagaa ggaccaagtt  780
ctcgtgtggg acaacctctg cacaatgcac agagcagttc ccgactacgc tggcaagttt  840
aggtatctca cccggaccac ggttggcggg gtgcgcccgg cgcgttga              888

SEQ ID NO: 49          moltype = DNA  length = 888
FEATURE                Location/Qualifiers
source                 1..888
                       mol_type = other DNA
                       organism = synthetic construct
CDS                    1..888
                       protein_id = 46
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHSDSTFLDAPPAAVVMRAIDVPEHGGDTGFLSMYTAWETLSPTMQATIEGLNVV
                        HSATRVFGSLYQAQNRRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 49
atgcatgcag cactgagtcc gctgtctcag cgttttgaga gaatcgcagt ccaacccttg  60
actggcgtcc tcggagctga gatcactggc gtggatcttc gtgaacccct cgatgattca  120
acatggaatg agatcctcga tgcttttcat acctatcagg tgatttattt tccaggacaa  180
gcaatcacca atgaacaaca tattgccttc agcagaagat ttggtcctgt ggatccagtg  240
ccccacttga aaagcatcga aggttacccg gaagtccaaa tgatcagacg agaagctaac  300
gaatcagggg gagttatagg cgacgattgg catagcgact caactttctt ggacgcacct  360
ccagcagctg ttgttatgcg tgccattgat gtgccagaac acggtgggga taccggcttc  420
ctctcaatgt acactgcttg ggagacactt tctccaacta tgcaggctac tattgaaggt  480
ctcaacgtag tgcatagcgc aactcgagtt tttggctcct tgtaccaggc tcaaaacaga  540
cgttggagca atacatctct taaagttatg gacgttgacg ctggtgatcg agaaaccgtt  600
catcctttgg ttgttacaca tccaggttcc ggtagaaaag gtctttatgt gaaccaagtg  660
tactgtcaaa gaatagaagg tatgacagat gccgagtcca aacccttatt gcaattcttg  720
tatgaacatg caaccagatt cgactttaca tgcagagtta ggtggaagaa ggatcaagtt  780
ctcgtatggg acaatttgtg caccatgcac cgtgcagttc cagattatgc tggaaagttc  840
agatatctga caagaaccac tgttggtgga gtgcgtccag ccaggtga              888

SEQ ID NO: 50          moltype = AA  length = 295
FEATURE                Location/Qualifiers
source                 1..295
```

```
                         mol_type = protein
                         organism = synthetic construct
SEQUENCE: 50
MHAALSPLSQ RFERIAVQPL TGVLGAEITG VDLREPLDDS TWNEILDAFH TYQVIYFPGQ  60
AITNEQHIAF SRRFGPVDPT PHLKSIEGYP EVQMIRREAN ESGGVIGDDW HTDSTFLDAP  120
PAAVVMRAID VPEHGGDTGF LSMYTAWETL SPTMQATIEG LNVVHSATRV FGSLYQAQNR  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 51            moltype = DNA  length = 888
FEATURE                  Location/Qualifiers
source                   1..888
                         mol_type = other DNA
                         organism = synthetic construct
CDS                      1..888
                         protein_id = 50
                         transl_table = 1
                         translation = MHAALSPLSQRFERIAVQPLTGVLGAEITGVDLREPLDDSTWNEIL
                          DAFHTYQVIYFPGQAITNEQHIAFSRRFGPVDPTPHLKSIEGYPEVQMIRREANESGGV
                          IGDDWHTDSTFLDAPPAAVVMRAIDVPEHGGDTGFLSMYTAWETLSPTMQATIEGLNVV
                          HSATRVFGSLYQAQNRRWSNTSLKVMDVDAGDRETVHPLVVTHPGSGRKGLYVNQVYCQ
                          RIEGMTDAESKPLLQFLYEHATRFDFTCRVRWKKDQVLVWDNLCTMHRAVPDYAGKFRY
                          LTRTTVGGVRPAR
SEQUENCE: 51
atgcacgctg cactgtctcc gctgtctcag cgttttgaac gtatcgctgt acaaccgctg  60
actggcgtac tgggtgctga aatcactggc gtagacctgc gtgaaccgct ggacgattct  120
acctggaacg aaattctgga tgcgttccac acctaccagg ttatctactt cccgggtcag  180
gcaattacca acgagcaaca tattgctttc tctcgtcgtt ttggtccggt ggacccgacc  240
ccacacctga aaagcatcga gggctacccg gaagttcaga tgattcgtcg tgaagccaac  300
gaatctggtg gtgtcattgg tgacgactgg cacaccgaca gcaccttcct ggacgcacct  360
ccagcagcgg ttgtcatgcg tgccatcgat gtaccggaac acggtggtga taccggcttt  420
ctgtctatgt ataccgcttg ggaaaccctg tctccgacta tgcaggctac catcgaaggt  480
ctgaacgttg ttcacagcgc tacccgcgtt ttcggttctc tgtaccaagc acagaaccgt  540
cgttggtcta acacttctct gaaagtgatg gatgtagatg caggtgatcg tgaaactgtg  600
cacccactgg ttgttacgca cccgggtagc ggtcgcaaag gtctgtacgt aaaccaggtt  660
tactgtcaac gtattgaggg tatgaccgat gcagaaagca aaccgctgct gcagttcctg  720
tatgaacacg ctacccgttt cgatttcacc tgtcgcgtcc gttggaagaa agatcaggtt  780
ctggtgtggg acaacctgtg caccatgcac cgtgctgttc cggactacgc tggcaaattc  840
cgttacctga cgcgtacgac cgttggtggt gttcgtccgg cgcgttaa              888

SEQ ID NO: 52            moltype = DNA  length = 888
FEATURE                  Location/Qualifiers
source                   1..888
                         mol_type = other DNA
                         organism = synthetic construct
CDS                      1..888
                         protein_id = 50
                         transl_table = 1
                         translation = MHAALSPLSQRFERIAVQPLTGVLGAEITGVDLREPLDDSTWNEIL
                          DAFHTYQVIYFPGQAITNEQHIAFSRRFGPVDPTPHLKSIEGYPEVQMIRREANESGGV
                          IGDDWHTDSTFLDAPPAAVVMRAIDVPEHGGDTGFLSMYTAWETLSPTMQATIEGLNVV
                          HSATRVFGSLYQAQNRRWSNTSLKVMDVDAGDRETVHPLVVTHPGSGRKGLYVNQVYCQ
                          RIEGMTDAESKPLLQFLYEHATRFDFTCRVRWKKDQVLVWDNLCTMHRAVPDYAGKFRY
                          LTRTTVGGVRPAR
SEQUENCE: 52
atgcatgcgg ctctctcccc tctctcccaa cgcttcgaaa gaattgcggt gcagccactt  60
actggtgttc tcggggccga gatcaccggt gtcgatctga gagaaccgct cgacgactct  120
acctggaacg agatcctgga tgcgttccac acgtaccagg tcatctactt tcccggccaa  180
gccatcacca acgagcagca cattgccttc agccggcgtt ttggaccagt cgatcccact  240
ccacatctga agtccattga ggggtatcca gaggtgcaga tgataaggag ggaggcgaac  300
gagtcaggag gggtgatagg cgacgactgg cacacagact cgaccttcct tgacgctcct  360
cctgccgccg tcgtcatgag agctatcgat gtgcctgagc acggtggcga cacgggtttt  420
cttagcatgt acacggcctg ggagaccctc tctcctacaa tgcaggccac tatcgaaggc  480
ttgaacgtgg ttcattccgc aacgagagtc tttgggtcac tctaccaggc gcagaaccgc  540
aggtggagca atacgagctt gaaggtgatg gacgtcgacg ccggtgatag agagaccgtg  600
cacccgctcg tggttactca ccccggcagc ggacgcaaag ggttgtacgt gaaccaggtt  660
tactgccagc gtatagaggg catgacagac gccgagagca agcctctttt gcagttcctc  720
tatgaacacg caacgcgctt cgactttact tgccgcgtgc gttggaagaa ggatcaggtg  780
cttgtctggg acaacctttg cactatgcat agagcagttc cagactacgc cggtaaattc  840
cgctacttga ctaggaccac cgtcggcggt gttaggcctg caaggtga              888

SEQ ID NO: 53            moltype = DNA  length = 888
FEATURE                  Location/Qualifiers
source                   1..888
                         mol_type = other DNA
                         organism = synthetic construct
CDS                      1..888
                         protein_id = 50
                         transl_table = 1
```

-continued

```
                        translation = MHAALSPLSQRFERIAVQPLTGVLGAEITGVDLREPLDDSTWNEIL
                         DAFHTYQVIYFPGQAITNEQHIAFSRRFGPVDPTPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 53
atgcatgcag cactgtctcc cttgtctcaa cgtttcgagc ggattgctgt acaacctttg  60
acaggggtgt tgggagcaga aatcaccgga gtagacctaa gggaacctct tgatgattca  120
acgtggaacg agattctaga tgcctttcac acctaccagg taatctattt tccaggacag  180
gctattacta acgagcaaca tattgctttc agtcgtcgct ttggacccgt ggacccaaca  240
cctcacttaa aaagtattga gggatatccg gaagttcaga tgatccgacg cgaagccaat  300
gagagtggcg gtgtgatcgg agatgactgg catacggaca gtacgtttct tgatgcccct  360
cctgcagctg tggttatgcg ggctattgat gtacctgaac atggagggga cacgggattc  420
ctctcgatgt ataccgcgtg ggagacgtta agccctacga tgcaagctac cattgaaggc  480
ctgaacgtcg tgcattctgc cacccgcgtg ttcggcagtc tctatcaagc gcagaatcgg  540
cgttggtcca atacgagctt gaaagttatg gatgtagatg ccggagaccg cgagacggtc  600
catccactgg tggttactca tcctggctca ggacgaaaag gactatacgt gaatcaggta  660
tactgtcaga gaatcgaagg gatgacagat gccgaaagca aacccttact ccagtttttg  720
tacgaacatg ccacccgttt tgatttcaca tgtcgtgtac gttggaagaa agatcaagtc  780
ttagtctggg ataatctctg cactatgcat cgcgcggtcc ccgactatgc gggcaaattc  840
cggtacttga cgcgtacgac ggtcgggggc gtccgacctg cgagatga             888

SEQ ID NO: 54           moltype = AA  length = 295
FEATURE                 Location/Qualifiers
source                  1..295
                        mol_type = protein
                        organism = synthetic construct
SEQUENCE: 54
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGGVIGDDW HTDSTFLDAP  120
PAAVVMRAID VPEHGGDTGF LSMYTAWETL SPTMQATIEG LNVVHSATRV FGSLYQAQNW  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 55           moltype = DNA  length = 888
FEATURE                 Location/Qualifiers
source                  1..888
                        mol_type = other DNA
                        organism = synthetic construct
CDS                     1..888
                        protein_id = 54
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNWRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 55
atgcatgcag cgctgtctcc actgtctcag cgcttcgaac gtattgctgt tcagccgctg  60
accggtgttc tgggtgcaga gatcaccggc gttgatctgc gtgaaccgct ggatgactct  120
acctggaacg aaattctgga cgcgttccac acctatcaag taatctattt tccgggtcag  180
gccatcacca acgaacagca cattgctttc tcccgtcgtt tcggtccagt tgatccggtt  240
ccacatctga aatccatcga aggttaccca gaagtacaga tgattcgtcg cgaagcaaac  300
gagtctggcg gtgtgatcgg tgatgactgg cacaccgatt ccactttcct ggacgctccg  360
ccggcagcgg ttgttatgcg tgcaatcgac gttccggaac acggcggcga cactggtttc  420
ctgtccatgt acaccgcttg ggagaccctg tctccgacga tgcaggcgac tatcgaaggt  480
ctgaacgttg tccactccgc tacccgcgtt ttcggctctc tgtatcaggc tcagaactgg  540
cgttggagca acacctccct gaaagttatg gacgtggatg ctggcgaccg tgaaaccgta  600
catccgctgg tggtgactca tccgggttct ggtcgtaaag gcctgtacgt gaaccaggtt  660
tactgccagc gcatcgaagg tatgaccgac gcggagtcta aaccgctgct gcagttcctg  720
tacgaacacg ctacgcgttt cgacttcacc tgccgtgtgc gttggaaaaa agaccaggtt  780
ctggtctggg ataacctgtg taccatgcac cgcgcagttc cggattacgc aggtaaattc  840
cgttacctga ctcgtactac tgtaggtggt gtccgcccgg cgcgttaa             888

SEQ ID NO: 56           moltype = DNA  length = 888
FEATURE                 Location/Qualifiers
source                  1..888
                        mol_type = other DNA
                        organism = synthetic construct
CDS                     1..888
                        protein_id = 54
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNWRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
```

```
                          LTRTTVGGVRPAR
SEQUENCE: 56
atgcacgctg cactgtctcc tttgtcgcag agattcgaaa gaattgcagt ccagcccctc  60
actggagtcc tcggagcgga aatcacaggc gttgacctcc gcgagcctct ggacgactcc  120
acctggaacg aaattctcga tgccttccac acataccagg ttatctactt ccctggccaa  180
gcgatcacta acgagcagca cattgccttt agccgccgct ttggtcctgt ggatcctgtc  240
ccccatctta agagcatcga gggctaccca gaagtccaga tgatccggcg cgaggcgaat  300
gagagcggcg gcgtgatcgg ggacgactgg cacactgact ctaccttctt ggacgctccg  360
cccgcggctg tcgtcatgcg tgccatcgac gtccccgagc acggtggtga caccggcttt  420
ttgtcaatgt acaccgcctg ggaaactctc agtcctacga tgcaggctac catcgagggt  480
ctgaatgttg tccatagcgc gacccgggtg ttcggctctc tgtaccaggc ccagaactgg  540
cggtggtcta acacctccct gaaagtcatg gacgtggatg ccggcgacag ggaaaccgtc  600
cacccgctgg tcgtgaccca tcccggttca ggccgtaagg gtttgtacgt taaccaggtt  660
tactgtcagc ggatcgaggg gatgacagac gctgagtcca agcccttgct tcaattcctg  720
tatgaacacg ccacgagatt cgatttcacg tgcagggtgc gctggaagaa ggatcaagtc  780
cttgtgtggg acaacttgtg cacaatgcac agggcggtcc cggactatgc tggtaagttc  840
aggtacctga ctcgtacaac cgtgggcgga gtgcgtcctg ccagatga              888

SEQ ID NO: 57            moltype = DNA  length = 888
FEATURE                  Location/Qualifiers
source                   1..888
                         mol_type = other DNA
                         organism = synthetic construct
CDS                      1..888
                         protein_id = 54
                         transl_table = 1
                         translation = MHAALSPLSQRFERIAVQPLTGVLGAEITGVDLREPLDDSTWNEIL
                          DAFHTYQVIYFPGQAITNEQHIAFSRRFGPVDPVPHLKSIEGYPEVQMIRREANESGGV
                          IGDDWHTDSTFLDAPPAAVVMRAIDVPEHGGDTGFLSMYTAWETLSPTMQATIEGLNVV
                          HSATRVFGSLYQAQNWRWSNTSLKVMDVDAGDRETVHPLVVTHPGSGRKGLYVNQVYCQ
                          RIEGMTDAESKPLLQFLYEHATRFDFTCRVRWKKDQVLVWDNLCTMHRAVPDYAGKFRY
                          LTRTTVGGVRPAR
SEQUENCE: 57
atgcatgctg ctttgagccc tctctcacaa agatttgaaa gaatcgcggt ccaaccgctt  60
accggcgtct taggagccga aataacagga gtagatttaa gagaacctct agatgattct  120
acctggaatg agattttaga tgcgttccac acatatcaag ttatctactt cccgggccaa  180
gcgattacca atgagcagca catcgcgttt tctagacgtt tcggaccagt ggatcccgtg  240
ccgcatctaa aatccatcga gggatatcca gaggtccaga tgattagacg tgaggcgaac  300
gagtccggag gggtaattgg agacgactgg cacaccgata gcacctttct tgacgccccc  360
cccgcagcgg ttgttatgcg tgcgatcgat gtcccagaac atggcggaga cacggggttt  420
ctctccatgt acacggcgtg ggagacgctg agcccgacga tgcaagcgac gatagaagga  480
ttgaacgtgg ttcactccgc cacacgtgtg ttcggttctt tgtaccaagc tcaaaattgg  540
cggtggtcga acacgagcct gaaagtaatg gacgtagatg caggcgatcg ggagacagtt  600
cacccccttag tggtcaccca cccaggatcg ggcaggaagg ggctctatgt gaaccaggta  660
tactgtcaaa gaattgaagg tatgaccgat gccgaatcca aacctctcct gcagttcctg  720
tatgagcatg cgacccgatt tgatttcacc tgccgtgtgc gttggaaaaa agatcaagtg  780
ctggtttggg acaatctttg cacaatgcat cgcgcagtgc ccgattatgc gggaaagttc  840
agatatttga cccgtacaac cgttggaggc gtccgccccg ccaggtga              888

SEQ ID NO: 58            moltype = AA  length = 295
FEATURE                  Location/Qualifiers
source                   1..295
                         mol_type = protein
                         organism = synthetic construct
SEQUENCE: 58
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGGVIGDDW HTDSTFLDAP  120
PAAVVMRAID VPEHGGDTGF LSMYTAWETL SPTMQATIEG LNVVHSATRV FGSLYQAQNM  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 59            moltype = DNA  length = 888
FEATURE                  Location/Qualifiers
source                   1..888
                         mol_type = other DNA
                         organism = synthetic construct
CDS                      1..888
                         protein_id = 58
                         transl_table = 1
                         translation = MHAALSPLSQRFERIAVQPLTGVLGAEITGVDLREPLDDSTWNEIL
                          DAFHTYQVIYFPGQAITNEQHIAFSRRFGPVDPVPHLKSIEGYPEVQMIRREANESGGV
                          IGDDWHTDSTFLDAPPAAVVMRAIDVPEHGGDTGFLSMYTAWETLSPTMQATIEGLNVV
                          HSATRVFGSLYQAQNMRWSNTSLKVMDVDAGDRETVHPLVVTHPGSGRKGLYVNQVYCQ
                          RIEGMTDAESKPLLQFLYEHATRFDFTCRVRWKKDQVLVWDNLCTMHRAVPDYAGKFRY
                          LTRTTVGGVRPAR
SEQUENCE: 59
atgcacgctg cactgtcccc tctgtcccaa cgttttgaac gtatcgcagt tcagccgctg  60
accggtgtgc tgggtgcaga aatcacgggc gtggatctgc gtgaaccact ggatgactct  120
acctggaacg aaatcctgga cgcgttccac acttatcagg tgatctactt tccgggtcag  180
```

-continued

```
gcaatcacca acgagcagca tatcgcgttc agccgtcgtt tcggtccggt tgaccctgtt  240
ccgcacctga aatctatcga aggttacccg gaagttcaga tgatccgtcg tgaagcgaac  300
gaaagcggtg gcgtcatcgg tgatgactgg cacaccgata gcactttcct ggacgcacct  360
ccagcagcag tggttatgcg tgcaattgat gttcctgaac acggtggcga caccggtttc  420
ctgtctatgt ataccgcctg ggaaaccctg tctccgacca tgcaggctac cattgagggt  480
ctgaacgtcg ttcacagcgc aacccgcgtg ttcggctctc tgtaccaggc gcagaacatg  540
cgttggagca acaccagcct gaaagttatg gacgtagatg ctggtgatcg tgaaaccgtt  600
catccgctgg ttgttactca ccctggttcc ggccgtaagg gtctgtatgt gaaccaagtg  660
tattgccagc gtatcgaagg tatgaccgat gcagaaagca aaccgctgct gcaatttctg  720
tatgaacacg caacccgttt cgacttcact tgccgcgttc gctggaaaaa agaccaggta  780
ctggtatggg ataacctgtg taccatgcac cgtgccgtac cggattacgc aggtaaattc  840
cgttatctga cgcgtaccac cgttggtggt gtgcgtccag cgcgttaa              888

SEQ ID NO: 60          moltype = DNA  length = 888
FEATURE                Location/Qualifiers
source                 1..888
                       mol_type = other DNA
                       organism = synthetic construct
CDS                    1..888
                       protein_id = 58
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHTDSTFLDAPPAAVVMRAIDVPEHGGDTGFLSMYTAWETLSPTMQATIEGLNVV
                        HSATRVFGSLYQAQNMRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 60
atgcacgctg cccttagtcc tttgagtcag agattcgaga ggatcgccgt gcaacccctc  60
accggcgtgc tcggagcgga aattacgggg gtggacctga gagaaccttt ggatgactcc  120
acatggaacg aaatcctcga cgcgttccac acctatcaag tcatctactt cccgggtcaa  180
gcaattacta acgagcagca tattgctttc agcagacgct tcggacccgt cgaccccgtg  240
ccccatctca agtcaatcga ggggtacccc gaggtccaaa tgatcaggag ggaggctaac  300
gagtccgggg gtgttatcgg cgacgattgg cacaccgatt ccacgttcct cgatgcgcca  360
ccggcagctg ttgttatgcg ggccatcgat gtccctgagc atggcggcga cacgggcttt  420
ctttctatgt acaccgcttg ggaaaccctt tctccaacca tgcaagccac aatcgaaggt  480
ctcaacgtcg ttcattctgc cacgcgggtc ttcgggagcc tctatcaagc acagaacatg  540
cgctggtcaa atacgtctct caaggttatg gacgttgacg ccggtgatcg cgaaacggtc  600
catccattgg tggttacgca ccctggttcc ggaagaaaag gcttgtacgt gaatcaagtt  660
tattgccagc gcatagaggg gatgaccgat gccgagtcta agccactgct ccaatttctc  720
tacgagcatg cgaccagatt cgatttcacg tgccgcgtga ggtggaagaa ggaccaggtc  780
ctcgtgtggg acaatctctg cactatgcat agggcagtcc cggactatgc tggtaagttc  840
cgctacctca cccgcaccac agtcggcggc gttcgccctg cacggtga              888

SEQ ID NO: 61          moltype = DNA  length = 888
FEATURE                Location/Qualifiers
source                 1..888
                       mol_type = other DNA
                       organism = synthetic construct
CDS                    1..888
                       protein_id = 58
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHTDSTFLDAPPAAVVMRAIDVPEHGGDTGFLSMYTAWETLSPTMQATIEGLNVV
                        HSATRVFGSLYQAQNMRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 61
atgcacgcag ccctttctcc tctgtctcaa cggttcgaac gaatcgccgt gcaacccctg  60
actggggttt tgggggcaga aataacgggt gtggatttac gtgaacctct cgacgattcg  120
acgtggaatg agatactgga tgcttttcac acgtatcaag tgatctattt cccagggcaa  180
gccataacca acgaacagca catcgccttt tctagacgct ttggcccggt agaccccgtt  240
cctcacttaa aatcaataga aggttatccc gaagtacaga tgattcgtag agaagccaat  300
gaatcgggcg gagtaatagg ggacgattgg cacacggaca gcacatttct tgatgctccg  360
cccgccgccg tggtaatgcg cgctattgat gtacctgagc atggcggtga tacaggcttt  420
ttaagcatgt acaccgcgtg ggagactctg agtccaacta tgcaagctac aatcgaaggg  480
ctcaatgtcg ttcactctgc gacacgggtg tttggctcct tatatcaggc ccagaatatg  540
cgctggtcaa atacgtcact taaagtaatg gacgtcgatg cgggggatcg cgagactgtc  600
caccctctgg tagttacgca cccggggtca ggaaggaaag gcttgtacgt gaatcaagtc  660
tattgccaga ggatcgaggg tatgactgat gctgaatcaa aacccctcct acaatttttg  720
tacgagcatg cgacgcgatt cgatttcact tgcagggtta ggtggaaaaa agaccaggtc  780
ctagtatggg ataatctgtg tacaatgcat cgcgcagtcc ctgactatgc ggggaagttt  840
cgatatctga ctagaaccac ggtaggggga gtgcgaccgg cgcgatga              888

SEQ ID NO: 62          moltype = AA  length = 295
FEATURE                Location/Qualifiers
source                 1..295
                       mol_type = protein
```

```
                          organism = synthetic construct
SEQUENCE: 62
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGGVIGCDW HTDSTFLDAP  120
PAAVVMRAID VPEHGGDTGF LSMYTAWETL SPTMQATIEG LNVVHSATRV FGSLYQAQNR  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 63             moltype = DNA  length = 888
FEATURE                   Location/Qualifiers
source                    1..888
                          mol_type = other DNA
                          organism = synthetic construct
CDS                       1..888
                          protein_id = 62
                          transl_table = 1
                          translation = MHAALSPLSQRFERIAVQPLTGVLGAEITGVDLREPLDDSTWNEIL
                           DAFHTYQVIYFPGQAITNEQHIAFSRRFGPVDPVPHLKSIEGYPEVQMIRREANESGGV
                           IGCDWHTDSTFLDAPPAAVVMRAIDVPEHGGDTGFLSMYTAWETLSPTMQATIEGLNVV
                           HSATRVFGSLYQAQNRRWSNTSLKVMDVDAGDRETVHPLVVTHPGSGRKGLYVNQVYCQ
                           RIEGMTDAESKPLLQFLYEHATRFDFTCRVRWKKDQVLVWDNLCTMHRAVPDYAGKFRY
                           LTRTTVGGVRPAR
SEQUENCE: 63
atgcatgctg cactgtctcc tctgtctcag cgtttcgaac gtatcgcagt tcagccgctg  60
accggcgttc tgggtgctga aatcactggc gttgacctgc gtgagccgct ggacgattct  120
acctggaacg aaattctgga tgctttccac acgtatcagg taatctactt tccgggccag  180
gctatcacta acgaacagca catcgcgttc tcccgtcgtt ttggcccggt tgacccggtt  240
ccgcatctga aatccatcga gggttacccg gaagtccaga tgatccgtcg tgaagcgaac  300
gaatctggtg gtgtgatcgg ttgcgactgg cacactgata gcactttcct ggatgcgccg  360
ccggcagctg ttgttatgcg tgctattgac gttccagaac acggtggcga tactggcttt  420
ctgtccatgt ataccgcatg ggagaccctg tctccgacta tgcaggcgac gattgagggt  480
ctgaacgtcg ttcactctgc aacgcgtgta ttcggttccc tgtaccaggc gcagaaccgt  540
cgttggagca acacctctct gaaagttatg gatgtggatg caggtgaccg tgagaccgtg  600
catccgctgg tagttactca cccgggttct ggccgcaaag gcctgtatgt taaccaggtg  660
tattgccagc gcatcgaagg tatgaccgac gctgagtcta aaccgctgct gcagttcctg  720
tatgaacacg cgactcgttt cgacttcacc tgtcgcgttc gctggaaaaa agaccaggtg  780
ctggtctggg ataacctgtg caccatgcat cgtgctgtgc cggactacgc aggtaaattc  840
cgttatctga cccgcactac cgtgggcggt gttcgtccag ctcgttaa             888

SEQ ID NO: 64             moltype = DNA  length = 888
FEATURE                   Location/Qualifiers
source                    1..888
                          mol_type = other DNA
                          organism = synthetic construct
CDS                       1..888
                          protein_id = 62
                          transl_table = 1
                          translation = MHAALSPLSQRFERIAVQPLTGVLGAEITGVDLREPLDDSTWNEIL
                           DAFHTYQVIYFPGQAITNEQHIAFSRRFGPVDPVPHLKSIEGYPEVQMIRREANESGGV
                           IGCDWHTDSTFLDAPPAAVVMRAIDVPEHGGDTGFLSMYTAWETLSPTMQATIEGLNVV
                           HSATRVFGSLYQAQNRRWSNTSLKVMDVDAGDRETVHPLVVTHPGSGRKGLYVNQVYCQ
                           RIEGMTDAESKPLLQFLYEHATRFDFTCRVRWKKDQVLVWDNLCTMHRAVPDYAGKFRY
                           LTRTTVGGVRPAR
SEQUENCE: 64
atgcatgccg ctctttcccc actcagccaa cgttttgagc ggattgctgt tcagcctctt  60
accggcgtcc tgggtgccga aatcactggt gtggacctca gggagccatt ggacgactcg  120
acctggaatg agattctgga cgcgtttcat acctaccaag tgatctattt cccaggccag  180
gccattacca acgagcagca catcgccttt agcaggaggt ttggtccggt ggacccggtc  240
ccacatctca aatcaattga aggctatccc gaggtgcaga tgatccggag ggaagcaaac  300
gagagcggcg gtgtgatcgg ctgcgattgg catactgaca gcaccttctt ggatgcacct  360
cccgccgcag tggtcatgag agctatcgac gtccccgagc atggtggcga taccggattc  420
ctgtccatgt acaccgcatg ggaaacgctc tcacctacga tgcaggctac catcgaaggg  480
ctcaacgtgg tgcatagcgc caccagggtg tttggctcac tgtaccaggc gcaaaaccgc  540
cgctggtcta acacttctct caaagtgatg gatgtcgacg ccggtgatcg tgaaacggtc  600
catcctctcg tggttaccca ccctggctcg ggtagaaagg ggctttacgt gaaccaggtc  660
tactgtcaga ggatcgaggg aatgaccgac gctgagtcca agccgctgtt gcaattcttg  720
tacgagcatg ctacgagatt cgacttcact tgtcgcgtga ggtggaagaa ggatcaggtc  780
ctggtgtggg acaatctgtg tactatgcat cgcgcggttc cagactatgc cggcaagttc  840
agatatctga ctagaactac ggtcggcgga gttaggcctg ctaggtga             888

SEQ ID NO: 65             moltype = DNA  length = 888
FEATURE                   Location/Qualifiers
source                    1..888
                          mol_type = other DNA
                          organism = synthetic construct
CDS                       1..888
                          protein_id = 62
                          transl_table = 1
                          translation = MHAALSPLSQRFERIAVQPLTGVLGAEITGVDLREPLDDSTWNEIL
```

-continued

```
                        DAFHTYQVIYFPGQAITNEQHIAFSRRFGPVDPVPHLKSIEGYPEVQMIRREANESGGV
                        IGCDWHTDSTFLDAPPAAVVMRAIDVPEHGGDTGFLSMYTAWETLSPTMQATIEGLNVV
                        HSATRVFGSLYQAQNRRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 65
atgcatgccg ccctatctcc cctaagtcag cgctttgaac gtattgccgt acagcccctt  60
actggagtgc ttggcgctga aatcacgggg gtggacctga gggaaccgtt ggatgattct  120
acatggaacg agattttgga tgcttttcac acataccagg tcatatactt tcctggacaa  180
gcaatcacca atgagcagca catagctttc tcccgtcgtt ttggacccgt cgatcctgtg  240
ccgcatttga aatctatcga gggatatcct gaggttcaaa tgatccggag ggaagccaat  300
gaaagtgggg gagtaatcgg atgtgactgg catacagatt cgactttctt agacgcaccc  360
ccggctgcag tagtaatgag agcaatagat gtacctgagc acgggggga cacagggttt  420
ctgagcatgt ataccgcctg ggagacactg agtcctacca tgcaggcaac catagaggga  480
cttaacgtag tgcactccgc tacgcgtgtt tttggctctt tgtaccaggc tcagaatagg  540
cgatggagca atacgtccct caaagttatg gatgtcgatg cgggtgacag agaaacagtg  600
cacccgctcg tcgtaactca tccgggctcc ggtcgaaagg gactgtatgt gaaccaagta  660
tactgtcagc gcattgaggg aatgacagat gcggaaagca aacccctttt gcaattcctt  720
tacgaacacg ctacgcgttt tgacttcacc tgtagagtgc gctggaagaa agatcaggtg  780
ttggtatggg ataatttgtg cactatgcat agagctgtac ccgactacgc cggcaagttt  840
cgttacctaa cccgcacgac ggttggtgga gtacgtcctg cgcggtga             888

SEQ ID NO: 66           moltype = AA  length = 295
FEATURE                 Location/Qualifiers
source                  1..295
                        mol_type = protein
                        organism = synthetic construct
SEQUENCE: 66
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGGVIGDEW HTDSTFLDAP  120
PAAVVMRAID VPEHGGDTGF LSMYTAWETL SPTMQATIEG LNVVHSATRV FGSLYQAQNR  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 67           moltype = DNA  length = 888
FEATURE                 Location/Qualifiers
source                  1..888
                        mol_type = other DNA
                        organism = synthetic construct
CDS                     1..888
                        protein_id = 66
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDEWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 67
atgcatgcag cgctgtctcc gctgtctcag cgttttgaac gtattgctgt ccagccactg  60
accggtgttc tgggtgcgga aatcacgggt gttgatctgc gcgaaccgct ggatgattcc  120
acctggaacg aaatcctgga tgcattccat acctaccagg tgatctactt cccgggccag  180
gcaattacca acgaacagca tattgctttt tcccgtcgtt tcggtccggt agatccggtg  240
ccgcatctga aatctatcga gggctacccg gaagttcaga tgattcgtcg cgaggctaac  300
gaatccggtg gtgtcatcgg tgatgaatgg cacactgact ctacctttct ggatgcacca  360
ccggctgcgg ttgttatgcg tgcgattgat gtaccggaac atggtggtga cactggcttc  420
ctgtctatgt atacggcttg ggaaactctg tccccgacca tgcaagccac cattgaaggc  480
ctgaacgtgg ttcactccgc gactcgtgtg tttggctctc tgtaccaggc tcagaaccgt  540
cgttggtcta acacttctct gaaagttatg gacgtagatg caggcgatcg tgagacggta  600
cacccactgg tagttactca cccgggtagc ggtcgtaaag gcctgtacgt taatcaggta  660
tactgccagc gtatcgaggg tatgaccgat gcagaatcta aaccgctgct gcagtttctg  720
tacgaacatg ccacccgttt tgatttcact tgtcgtgttc gctggaagaa agaccaggtt  780
ctggtttggg acaacctgtg taccatgcat cgtgcggtgc cggactatgc gggtaaattc  840
cgctacctga ctcgcaccac tgtgggtggt gtacgtccgg ctcgttaa             888

SEQ ID NO: 68           moltype = DNA  length = 888
FEATURE                 Location/Qualifiers
source                  1..888
                        mol_type = other DNA
                        organism = synthetic construct
CDS                     1..888
                        protein_id = 66
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDEWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
```

-continued

SEQUENCE: 68
atgcatgcgg cattgtcccc actctcacag agatttgagc gcatcgccgt tcaaccgctc 60
acaggtgtgt tgggagccga gattacaggg gtggatttga gggagcccct cgacgacagc 120
acatggaatg agatcttgga tgcattccat acgtaccagg tgatctactt ccccgggcaa 180
gctatcacca atgagcagca catcgcgttc agtcgtcgtt tcggacctgt cgatcctgtt 240
ccacacctga aaagcatcga gggctacccc gaggtgcaaa tgattcggcg cgaagccaat 300
gagtccggcg gagttatcgg agacgagtgg cacactgaca gtactttcct ggatgctcca 360
ccagcagctg tcgttatgag agctatcgac gttccagagc atggtggcga taccggcttc 420
ctgtcaatgt acactgcctg ggaaaccctt agcccaacta tgcaagctac catagagggg 480
ctgaacgtcg tccattcagc gacacgcgtt ttcggatctc tgtatcaggc tcagaaccgc 540
cgctggagta acactagcct gaaggttatg gatgttgatg ccggggatcg ggagactgtt 600
caccctctcg tggttaccca cccgggttca ggaaggaagg ggctttacgt gaaccaggtc 660
tattgccagc ggatcgaggg aatgactgac gctgagtcta agccgctcct ccaattcctc 720
tatgagcacg cgacgcgctt cgacttcacg tgtcgcgtgc gctggaagaa ggaccaagtt 780
ctcgtgtggg acaacttgtg tacgatgcac agagcggtcc ccgactacgc tggcaaattt 840
aggtatctca ccagaacaac ggtgggcggg gtgagacctg caaggtga 888

SEQ ID NO: 69 moltype = DNA length = 888
FEATURE Location/Qualifiers
source 1..888
mol_type = other DNA
organism = synthetic construct
CDS 1..888
protein_id = 66
transl_table = 1
translation = MHAALSPLSQRFERIAVQPLTGVLGAEITGVDLREPLDDSTWNEIL
DAFHTYQVIYFPGQAITNEQHIAFSRRFGPVDPVPHLKSIEGYPEVQMIRREANESGGV
IGDEWHTDSTFLDAPPAAVVMRAIDVPEHGGDTGFLSMYTAWETLSPTMQATIEGLNVV
HSATRVFGSLYQAQNRRWSNTSLKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR
SEQUENCE: 69
atgcacgcgg cattatctcc gttatcacag cgctttgaaa ggatagcagt ccaaccacta 60
acaggcgtcc ttggtgctga aataacaggg gttgatctca gggaacccct ggacgactcg 120
acctggaacg agattctgga cgcgttccat acttatcaag taatctattt tccagggcag 180
gcaatcacga atgagcagca catagcattt tcacgcagat ttgggcccgt agatccagtt 240
ccgcatttaa agtctatcga gggatatcct gaggtccaga tgatcagacg ggaagctaac 300
gagtctgggg gggtcattgg agacgaatgg cacaccgata gcaccttcct cgatgcgcca 360
cccgcagctg tggtcatgcg agcaatcgat gtgcccgaac atgggggcga tacagggttc 420
ctaagtatgt ataccgcctg ggaaacttta tctcctacga tgcaagcaac tatcgaagga 480
cttaacgtcg ttcactcagc gactcgtgtg ttcggaagct tgtatcaagc gcaaaaccgc 540
cgatggagta atacatctct taaagtcatg gatgttgacg ctggggacag agaaactgtg 600
catcctttag tggtgactca tcctggaagc ggacgtaaag gtttatacgt aaaccaggta 660
tactgccaga gaatcgaagg catgaccgat gccgaaagca aaccccttact acaattcctc 720
tatgaacatg caaccaggtt cgatttcaca tgccgagttc ggtggaaaaa agaccaagtc 780
cttgtatggg ataatctatg tactatgcat agagccgttc cagattacgc cggtaagttt 840
aggtacctga cgcggactac agtaggagga gtacgcccag ccagatga 888

SEQ ID NO: 70 moltype = AA length = 295
FEATURE Location/Qualifiers
source 1..295
mol_type = protein
organism = synthetic construct
SEQUENCE: 70
MHAALSPLSQ RFERIAVQPL TGVLGAEITG VDLREPLDDS TWNEILDAFH TYQVIYFPGQ 60
AITNEQHIAF SRRFGPVDPV PHLKSIEGYP EVQMIRREAN ESGGVIGDDW HTDSTFLDAP 120
PAAVVMRAID VPEHGGDTGF LSMYTAWETL SPTMQATIEG LNVVHSATRV FGSLYQAQNR 180
RWSNTSLKVM DVDAGDRETV HPLVVTHPGS GRKGLYVNCV YCQRIEGMTD AESKPLLQFL 240
YEHATRFDFT CRVRWKKDQV LVWDNLCTMH RAVPDYAGKF RYLTRTTVGG VRPAR 295

SEQ ID NO: 71 moltype = DNA length = 888
FEATURE Location/Qualifiers
source 1..888
mol_type = other DNA
organism = synthetic construct
CDS 1..888
protein_id = 70
transl_table = 1
translation = MHAALSPLSQRFERIAVQPLTGVLGAEITGVDLREPLDDSTWNEIL
DAFHTYQVIYFPGQAITNEQHIAFSRRFGPVDPVPHLKSIEGYPEVQMIRREANESGGV
IGDDWHTDSTFLDAPPAAVVMRAIDVPEHGGDTGFLSMYTAWETLSPTMQATIEGLNVV
HSATRVFGSLYQAQNRRWSNTSLKVMDVDAGDRETVHPLVVTHPGSGRKGLYVNCVYCQ
RIEGMTDAESKPLLQFLYEHATRFDFTCRVRWKKDQVLVWDNLCTMHRAVPDYAGKFRY
LTRTTVGGVRPAR
SEQUENCE: 71
atgcatgctg cgctgtctcc actgtcccaa cgttttgaac gtatcgcagt tcaaccgctg 60
accggcgtgc tgggtgctga aattaccggc gtagatctgc gtgaaccgct ggacgattct 120
acttggaacg agatcctgga tgcgtttcac acttaccagg ttatctattt cccgggccag 180
gccatcacga acgaacagca tatcgcattc tctcgtcgct ttggcccggt ggatccggtt 240

-continued

```
cctcacctga aaagcattga aggctacccg gaggttcaga tgatccgtcg tgaagcaaat  300
gaatccggcg gtgttatcgg tgatgactgg cacactgact ccactttcct ggacgctccg  360
ccggcagctg tagttatgcg tgcgatcgac gttccggaac acggtggtga caccggcttc  420
ctgtctatgt acactgcatg ggaaaccctg agcccgacca tgcaggcaac catcgaaggt  480
ctgaacgttg ttcactccgc tacccgtgta tttggttccc tgtaccaggc acagaatcgt  540
cgttggtcca acacttctct gaaagtgatg gacgtggacg cgggcgatcg tgaaaccgtt  600
catccgctgg tagttaccca tcctggttct ggccgtaaag gcctgtacgt aaactgtgta  660
tactgccagc gcattgaagg catgaccgac gcggaatcta agccgctgct gcagttcctg  720
tatgaacacg cgactcgttt cgattttacc tgccgtgtgc gttggaaaaa agatcaggtt  780
ctggtatggg ataacctgtg caccatgcat cgtgcggttc cggattacgc gggcaaattt  840
cgttatctga ctcgtactac ggttggtggc gttcgtccgg cacgttaa              888

SEQ ID NO: 72           moltype = DNA  length = 888
FEATURE                 Location/Qualifiers
source                  1..888
                        mol_type = other DNA
                        organism = synthetic construct
CDS                     1..888
                        protein_id = 70
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNCVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 72
atgcatgccg ctttgtcgcc tctctctcag cgttttgaaa ggatcgccgt tcaacctttg  60
accggcgtgc ttggggctga gataacaggt gtcgacttgc gcgaaccgct tgatgactca  120
acttggaacg agatcctcga tgcttttcat acttatcagg tcatttactt ccccggacaa  180
gcgatcacaa atgaacaaca catcgcgttc tcccgccgct tcggccctgt ggaccctgtt  240
ccccatttga agtccattga gggttaccct gaagtgcaga tgattcgcag ggaggccaac  300
gagtctggcg gcgtgattgg agatgattgg cacacggata gcacgtttct tgacgcgcca  360
ccagctgccg tggtgatgag agccatcgac gtgccggagc atggtggaga cactggattc  420
ctctcgatgt acacggcgtg ggagactctc tcaccaacaa tgcaggcgac cattgagggc  480
ttgaatgtgg tgcacagcgc cacgcgcgtc ttcggttccc tgtaccaagc gcaaaatcgc  540
cgctggtcaa atacctcgtt gaaggtgatg gatgtggatg ccggagatag ggagaccgtc  600
cacccccctcg ttgtgactca ccctggctcc gggaggaagg gtctctacgt gaactgcgtg  660
tattgccaga ggatagaggg gatgaccgat gcggagtcta agccactctt gcaattcctt  720
tacgagcatg ctacgcggtt cgacttcacc tgccgggtta ggtggaagaa ggaccaggtc  780
ctcgtctggg ataatctctg taccatgcac agagctgtgc cagactacgc gggaaagttc  840
aggtacttga cacgtaccac cgtgggcggg gtcagaccgg ctcgctga              888

SEQ ID NO: 73           moltype = DNA  length = 888
FEATURE                 Location/Qualifiers
source                  1..888
                        mol_type = other DNA
                        organism = synthetic construct
CDS                     1..888
                        protein_id = 70
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNCVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 73
atgcatgcag cattgagtcc cctaagccag cgctttgaga ggattgcagt tcaaccgctc  60
acaggggtat taggtgcaga aatcacagga gtcgatttac gggagcccct agatgatagc  120
acgtggaacg aaattcttga cgccttccac acttatcagg ttatttattt tccaggacaa  180
gcgataacga acgagcagca tatagcattt tccagaaggt ttgggcccgt agacccggtg  240
ccccacctga agagcattga gggataccccc gaagtccaga tgatacgcag agaggcgaac  300
gagagcggag gtgttatagg tgacgattgg catacagact caacgttttt agacgccccc  360
cctgcggccg tggtgatgcg ggcaatcgac gttccggaac atggtgggga cactggcttc  420
ctttccatgt acaccgcgtg ggaaacgctc tcccccacca tgcaggctac cattgaaggg  480
cttaatgtgg tacattccgc gacacgtgtc ttcggaagtt tgtaccaggc ccaaaatcga  540
cgatggagca atactagcct taaggtaatg gacgttgatg cgggcgatag agaaacagtc  600
caccctcttg tcgtcacaca tccaggttcc gggcgtaagg gcctttacgt caactgcgtt  660
tattgccaaa ggattgaagg catgaccgat gcggagtcaa aaccgctgct tcagttcctt  720
tatgaacacg ctacgaggtt tgactttact tgccgtgtgc gctggaaaaa agatcaagta  780
ctggtctggg acaatctgtg tactatgcac cgagcagttc cggactatgc cgggaaattc  840
agatatttga ctagaacgac agtcggcggc gtgcgcccag ccagatga              888

SEQ ID NO: 74           moltype = AA  length = 295
FEATURE                 Location/Qualifiers
source                  1..295
                        mol_type = protein
                        organism = synthetic construct
```

-continued

```
SEQUENCE: 74
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGGVIGDDW HTDSTFLDAP  120
PAAVVMRAID VPEHGGDTGF LSMYTAWETL SPTMQATIEG LNVVHSATRV FGSLYQAQNR  180
RWSNTSLKVM DVDAGDRETV HPLVVTHPGS GRKGLYVNPV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 75          moltype = DNA  length = 888
FEATURE                Location/Qualifiers
source                 1..888
                       mol_type = other DNA
                       organism = synthetic construct
CDS                    1..888
                       protein_id = 74
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHTDSTFLDAPPAAVVMRAIDVPEHGGDTGFLSMYTAWETLSPTMQATIEGLNVV
                        HSATRVFGSLYQAQNRRWSNTSLKVMDVDAGDRETVHPLVVTHPGSGRKGLYVNPVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 75
atgcacgctg ctctgtcccc actgtctcag cgttttgaac gcattgcagt tcagccgctg  60
actggcgtac tgggtgcaga aatcaccggt gttgatctgc gtgaaccgct ggacgacagc  120
acttggaacg aaatcctgga tgcatttcat acttaccagg ttatctactt cccgggccag  180
gccatcacga acgaacaaca tatcgccttc agccgtcgtt tcggtccggt tgacccggta  240
ccgcacctga agtccattga gggctatccg gaagttcaga tgattcgccg cgaagcgaac  300
gagtctggtg gcgttatcgg tgatgactgg cacaccgact ctacgttcct ggacgccccg  360
ccagcagcag ttgttatgcg tgcgattgat gtgccggaac acggtggtga cactggtttc  420
ctgagcatgt ataccgcttg ggaaaccctg agcccaacca tgcaggcaac catcgaaggc  480
ctgaacgttg tgcacagcgc tacccgcgtt ttcggcagcc tgtatcaggc acagaaccgt  540
cgttggagca acacttctct gaaagttatg gacgttgacg ctggcgatcg tgaaaccgta  600
caccctctgg ttgttaccca cccgggctct ggccgtaaag gtctgtatgt gaacccggtg  660
tattgccagc gtatcgaagg tatgaccgat gcagaatcca aaccgctgct gcagttcctg  720
tatgaacacg cgacccgctt cgacttcacg tgtcgtgtac gttggaaaaa agaccaggtt  780
ctggtctggg acaacctgtg tactatgcat cgtgcagttc cagattacgc aggcaagttt  840
cgttatctga ctcgtaccac tgtaggtggt gtgcgtcctg cacgttaa               888

SEQ ID NO: 76          moltype = DNA  length = 888
FEATURE                Location/Qualifiers
source                 1..888
                       mol_type = other DNA
                       organism = synthetic construct
CDS                    1..888
                       protein_id = 74
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHTDSTFLDAPPAAVVMRAIDVPEHGGDTGFLSMYTAWETLSPTMQATIEGLNVV
                        HSATRVFGSLYQAQNRRWSNTSLKVMDVDAGDRETVHPLVVTHPGSGRKGLYVNPVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 76
atgcacgctg cgctctctcc cctttcccaa agattcgaga ggattgctgt gcaacctctt  60
acgggggttc ttggtgcaga gatcacaggc gttgatctcc gcgagcccct tgacgactca  120
acctggaatg agatacttga cgcgtttcac acataccagg tgatttactt cccgggccaa  180
gctatcacca acgaacagca cattgctttc agtcgtcgtt ttggcccagt cgacccagtc  240
ccgcacctca agagcattga agggtaccca gaggtccaga tgattcgccg cgaggcgaat  300
gagtcaggcg gcgtgatcgg cgacgactgg catactgact ctacttttct ggacgcgccc  360
cctgccgctg ttgttatgag ggcaatcgat gtgccggagc acggaggcga tactggcttc  420
ctctccatgt acacggcatg ggagaccctg tcccctacca tgcaggccac catcgaaggt  480
ctgaacgttg tccatagcgc gacccgcgtg ttcggctctc tctaccaggc ccagaataga  540
cgttggagca ataccagcct caaggtcatg gacgtcgacg caggggaccg ggagaccgtc  600
cacccactcg ttgttacgca cccaggaagc ggacgcaaag ggctctacgt gaacccggtg  660
tattgtcaga ggatcgaggg catgacagat gccgaaagca agcctctcct ccagttcctc  720
tatgaacatg ccaccaggtt cgatttcaca tgcagggtcc gctggaagaa ggaccaagtc  780
cttgtttggg ataatttgtg tacgatgcac agggccgttc ccgactacgc tggtaagttc  840
cggtacttga cccgcaccac cgtgggcggc gtcaggccag cacgctga               888

SEQ ID NO: 77          moltype = DNA  length = 888
FEATURE                Location/Qualifiers
source                 1..888
                       mol_type = other DNA
                       organism = synthetic construct
CDS                    1..888
                       protein_id = 74
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
```

-continued

IGDDWHTDSTFLDAPPAAVVMRAIDVPEHGGDTGFLSMYTAWETLSPTMQATIEGLNVV
HSATRVFGSLYQAQNRRWSNTSLKVMDVDAGDRETVHPLVVTHPGSGRKGLYVNPVYCQ
RIEGMTDAESKPLLQFLYEHATRFDFTCRVRWKKDQVLVWDNLCTMHRAVPDYAGKFRY
LTRTTVGGVRPAR

SEQUENCE: 77
atgcatgccg ccctttctcc gctatctcag cgttttgaga ggatagccgt gcaacccctg 60
actggagtat taggcgctga aatcaccggc gtggacctaa gagaaccatt agatgattcg 120
acttggaatg agatactgga tgcgtttcat acttaccagg taatttattt tcccggacaa 180
gccatcacga acgagcaaca cattgcattc tctcgacgtt ttggcccagt tgatcccgtg 240
ccccatttga aatcaataga aggttacccc gaagtgcaaa tgattcgtag ggaggcaaac 300
gaaagtggag gagtcatcgg cgacgactgg cacactgatt caacatttct tgacgcacca 360
ccagccgcag ttgtaatgag ggccattgat gttccggaac atgggggaga tacggggttt 420
ttgtcaatgt ataccgcgtg ggaaacgtta tctccgacaa tgcaggcaac cattgaaggc 480
ttgaatgtgg tccattctgc taccagggtg ttcggatctt tgtatcaagc tcaaaacaga 540
aggtggtcca acacttcgct gaaagtaatg gatgtagatg ctggagaccg agaaacggtt 600
cacccattgg tggtaacgca tccaggatcg gggaggaagg gattgtatgt aaaccctgtg 660
tactgccaga gaatcgaggg aatgactgac gccgaatcga aaccgttgtt gcagtttcta 720
tacgagcatg caacaaggtt cgatttcacc tgccgagtgc gctggaagaa agaccaggtt 780
ttagtgtggg ataatctatg cactatgcat cgggctgtgc ctgactatgc cggaaaattc 840
agatacttga cacgcacaac cgtcggtgga gtacgaccag caaggtga 888

SEQ ID NO: 78 moltype = AA length = 295
FEATURE Location/Qualifiers
source 1..295
mol_type = protein
organism = synthetic construct SEQUENCE: 78
MHAALSPLSQ RFERIAVQPL TGVLGAEITG VDLREPLDDS TWNEILDAFH TYQVIYFPGQ 60
AITNEQHIAF SRRFGPVDPV PHLKSIEGYP EVQMIRREAN ESLRVIGDDW HTDSTFLDAP 120
PAAVVMRAID VPEHGGDTGF LSMYTAWETL SPTMQATIEG LNVVHSATRV FGSLYQAQND 180
RWSNTSLKVM DVDAGDRETV HPLVVTHPGS GRKGLYVNQV YCQRIEGMTD AESKPLLQFL 240
YEHATRFDFT CRVRWKKDQV LVWDNLCTMH RAVPDYAGKF RYLTRTTVGG VRPAR 295

SEQ ID NO: 79 moltype = DNA length = 888
FEATURE Location/Qualifiers
source 1..888
mol_type = other DNA
organism = synthetic construct
CDS 1..888
protein_id = 78
transl_table = 1
translation = MHAALSPLSQRFERIAVQPLTGVLGAEITGVDLREPLDDSTWNEIL
DAFHTYQVIYFPGQAITNEQHIAFSRRFGPVDPVPHLKSIEGYPEVQMIRREANESLRV
IGDDWHTDSTFLDAPPAAVVMRAIDVPEHGGDTGFLSMYTAWETLSPTMQATIEGLNVV
HSATRVFGSLYQAQNDRWSNTSLKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR SEQUENCE: 79
atgcacgctg ctctgtctcc gctgtctcag cgttttgaac gtatcgcggt acagcctctg 60
actggcgttc tgggcgcaga gatcaccggc gtagatctgc gcgaaccgct ggacgattct 120
acctggaacg aaattctgga tgctttccac acctaccagg ttatttactt tccgggtcag 180
gcaattacca acgagcaaca tatcgctttc tcccgccgtt ttggtccagt tgatccggtt 240
ccgcacctga aatccatcga aggttacccg gaggttcaaa tgattcgtcg tgaagcgaac 300
gaaagcctgc gcgtgatcgg tgatgactgg cacaccgata gcacctttct ggacgcgccg 360
ccagcagctg ttgttatgcg tgctatcgac gttccagaac acggtggtga caccggtttc 420
ctgtctatgt acaccgcgtg ggaaaccctg tccccgacca tgcaggcgac tattgaaggc 480
ctgaacgttg tacactctgc aacccgcgtg ttcggttctc tgtaccaggc gcagaacgac 540
cgttggagca acacctctct gaaagtgatg gatgttgacg caggcgaccg tgaaacggtg 600
catccgctgg tagtaaccca tcctggctct ggtcgtaaag gtctgtacgt caaccaagtt 660
tactgccagc gtatcgaagg tatgaccgat gctgaatcca aaccgctgct gcaatttctg 720
tatgaacacg ctacccgctt cgacttcacc tgtcgcgttc gttggaaaaa agatcaggtt 780
ctggtatggg acaacctgtg caccatgcac cgtgccgtgc cggattacgc aggtaaattc 840
cgctacctga cccgtactac cgttggcggc gttcgtcctg cacgttaa 888

SEQ ID NO: 80 moltype = DNA length = 888
FEATURE Location/Qualifiers
source 1..888
mol_type = other DNA
organism = synthetic construct
CDS 1..888
protein_id = 78
transl_table = 1
translation = MHAALSPLSQRFERIAVQPLTGVLGAEITGVDLREPLDDSTWNEIL
DAFHTYQVIYFPGQAITNEQHIAFSRRFGPVDPVPHLKSIEGYPEVQMIRREANESLRV
IGDDWHTDSTFLDAPPAAVVMRAIDVPEHGGDTGFLSMYTAWETLSPTMQATIEGLNVV
HSATRVFGSLYQAQNDRWSNTSLKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR

SEQUENCE: 80

```
atgcacgctg ccctcagccc attgagccag cgtttcgaaa gaatagccgt tcagcctttg  60
accggcgtgc tcggcgctga aattactggt gtggacctgc gcgagccact ggacgactcc  120
acctggaatg agatcttgga tgctttccat acctaccaag tcatttactt tccagggcag  180
gccatcacca atgagcaaca catcgcgttc agcaggcgct tcggacccgt cgacccggtc  240
ccccatctta agtccatcga aggctacccg gaggtccaaa tgatacgcag agaagctaat  300
gagtctttga gagtcatagg cgatgattgg cacaccgatt ctacgttcct tgacgccccg  360
ccggccgccg tggtcatgcg ggccattgat gtgcctgagc acggtggcga cacaggcttc  420
ttgtcaatgt acacagcctg ggaaacattg agcccaacca tgcaggcgac aatcgaaggg  480
ttgaatgtgg tgcattctgc gaccagagtg ttcgggtcgc tgtaccaggc tcagaatgat  540
cgctggtcta acacatccct gaaggtcatg gatgtcgatg ccggggaccg tgagacagtc  600
catccgcttg tcgtcacgca ccccgggagc ggccgcaagg ggctgtatgt caatcaggtg  660
tactgccagc gcatcgaagg gatgaccgac gccgaatcca agcccctcct gcaattcttg  720
tatgagcatg caacaaggtt tgacttcacg tgccgggtta gatggaaaaa agatcaagtg  780
ctcgtgtggg acaacctctg cacaatgcat agggccgttc ctgactacgc gggcaagttt  840
cggtacttga cgagaacaac cgttgggggg gtgcgtcctg cccgctga              888

SEQ ID NO: 81          moltype = DNA  length = 888
FEATURE                Location/Qualifiers
source                 1..888
                       mol_type = other DNA
                       organism = synthetic construct
CDS                    1..888
                       protein_id = 78
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESLRV
                        IGDDWHTDSTFLDAPPAAVVMRAIDVPEHGGDTGFLSMYTAWETLSPTMQATIEGLNVV
                        HSATRVFGSLYQAQNDRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 81
atgcatgccg ccttgtctcc cttatcacaa cgttttgaaa ggatagcagt tcaacctctt  60
acgggagttt taggtgccga gataacgggg gtcgatttgc gcgagccgct cgacgatagc  120
acttggaatg aaattctgga tgcctttcac acataccaag tcatctattt ccccggtcag  180
gctattacaa atgaacaaca tatcgctttt agccggcgct ttggccctgt agatcccgtc  240
ccccacttga agagtatcga gggctacccg gaggtacaga tgatccgacg tgaagccaac  300
gaatccctaa gagtgattgg agacgattgg cacacggatt caacctttct tgatgccccg  360
ccggcagcag ttgtaatgag ggcaattgat gttccagagc acggaggaga tacaggtttc  420
ttgtcgatgt ataccgcctg ggaaacctta tcacctacga tgcaagcaac aatagaaggg  480
ctcaatgtcg ttcactcagc gacgcgggtt ttcgggtctc tctaccaggc ccagaatgat  540
cgctggagca atacaagcct gaaagtgatg gatgtagatg caggagaccg tgaaacggta  600
catcctttgg tagtgacaca cccgggcagc ggtcgtaaag ggctatatgt taaccaagtg  660
tattgccaga gaatagaagg gatgaccgat gcagaatcaa aaccactctt acaattcctg  720
tatgaacacg cgacgagatt tgattttaca tgcagggtca ggtggaaaaa ggatcaggtg  780
ttggtgtggg ataatctttg cactatgcat agagccgtcc ccgattatgc cgggaaattt  840
cgttatctta cacgaaccac tgtaggcgga gtccgcccgg cccgatga              888

SEQ ID NO: 82          moltype = AA  length = 295
FEATURE                Location/Qualifiers
source                 1..295
                       mol_type = protein
                       organism = synthetic construct
SEQUENCE: 82
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESLRVIGDDW HTDSTFLDAP  120
PAAVVMRAID VPEHGGDTGF LSMYTAWETL SPTMQATIEG LNVVHSATRV FGSLYQAQNE  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 83          moltype = DNA  length = 888
FEATURE                Location/Qualifiers
source                 1..888
                       mol_type = other DNA
                       organism = synthetic construct
CDS                    1..888
                       protein_id = 82
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESLRV
                        IGDDWHTDSTFLDAPPAAVVMRAIDVPEHGGDTGFLSMYTAWETLSPTMQATIEGLNVV
                        HSATRVFGSLYQAQNERWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 83
atgcacgctg cactgtctcc actgtcccag cgtttcgaac gtattgctgt tcagccgctg  60
actggtgtac tgggtgcgga aatcaccggc gttgacctgc gtgaaccact ggacgacagc  120
acgtggaacg aaatcctgga cgcgttccac acctaccagg tgatttattt tccgggtcag  180
gcaatcacca acgaacagca catcgccttc agccgccgtt ttggtccagt tgatccggtt  240
ccgcatctga aatccatcga aggctacccg gaagttcaga tgattcgtcg tgaagcgaat  300
```

-continued

```
gaatctctgc gtgtgatcgg cgacgattgg cacactgatt ctacctttct ggacgctcca  360
ccggctgcag ttgtaatgcg cgcaatcgat gttccggagc acggtggtga cactggtttt  420
ctgtctatgt ataccgcatg ggaaaccctg tccccgacca tgcaggcaac cattgaaggc  480
ctgaacgtgg ttcactctgc tacccgtgtc tttggctccc tgtaccaggc gcagaacgag  540
cgttggtcta acacgagcct gaaagtgatg gatgttgatg cgggcgaccg tgaaaccgtt  600
catccgctgg tcgttactca cccgggctct ggtcgcaaag gcctgtatgt taaccaggtt  660
tattgccagc gtatcgaagg catgaccgat gcggaatcta aaccgctgct gcagttcctg  720
tacgaacacg ctacccgttt tgacttcacc tgccgtgttc gctggaaaaa ggatcaggtg  780
ctggtttggg ataacctgtg caccatgcac cgcgctgttc cggactatgc aggtaaattc  840
cgctacctga cccgtactac tgttggtggc gttcgcccag cccgttaa             888

SEQ ID NO: 84          moltype = DNA  length = 888
FEATURE                Location/Qualifiers
source                 1..888
                       mol_type = other DNA
                       organism = synthetic construct
CDS                    1..888
                       protein_id = 82
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESLRV
                        IGDDWHTDSTFLDAPPAAVVMRAIDVPEHGGDTGFLSMYTAWETLSPTMQATIEGLNVV
                        HSATRVFGSLYQAQNERWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 84
atgcacgcag ctctttctcc gctgtctcag agattcgaga ggatagccgt gcagccactg  60
accggggttc ttggagccga gattacaggc gtcgatttga gggagccact tgacgactcc  120
acatggaacg aaatcctgga cgcctttcat acgtaccagg ttatctactt ccccggccag  180
gctatcacga acgagcagca catcgcgttt tctcggcgtt tcggcccagt ggacccggtc  240
ccacatttga aatcgatcga gggctacccc gaggtgcaaa tgattagaag agaagcgaac  300
gagtctctcc gcgttatagg cgatgattgg catacagatt cgaccttctt ggatgcacca  360
ccggcagccg tcgtgatgcg cgccattgac gttccggagc acggaggcga taccgggttc  420
ctctcaatgt acacagcctg ggaaacgctt tctccaacaa tgcaagcgac gattgaagga  480
ctgaatgtcg tgcattcagc tactagggtc ttcgggtccc tctaccaggc ccagaatgag  540
agatggtcga atacgtcgtt gaaggttatg gatgtggatg ctggcgaccg cgagaccgtg  600
caccctctgg ttgtgaccca tccgggtagt ggtcgcaagg gcctctacgt gaaccaggtt  660
tactgccaga gaatcgaggg aatgactgat gccgagtcga agccactcct ccagttcctc  720
tacgagcacg cccacaaggtt cgacttcacc tgtcgtgtgc ggtggaagaa agaccaggtc  780
ctcgtgtggg ataatctctg tactatgcac agagccgtgc ccgactacgc cggcaagttc  840
cggtatctca cgaggacgac agtcggtggc gtgcggcctg ccagatga             888

SEQ ID NO: 85          moltype = DNA  length = 888
FEATURE                Location/Qualifiers
source                 1..888
                       mol_type = other DNA
                       organism = synthetic construct
CDS                    1..888
                       protein_id = 82
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESLRV
                        IGDDWHTDSTFLDAPPAAVVMRAIDVPEHGGDTGFLSMYTAWETLSPTMQATIEGLNVV
                        HSATRVFGSLYQAQNERWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 85
atgcatgctg cgctcagccc cctatcccag cgctttgaaa gaatagcagt ccaaccactg  60
acgggggtat taggcgccga aattaccggt gtggatttaa gagaaccgtt ggatgatagc  120
acctggaatg aaattctcga tgcttttcac acctaccagg taatttactt tccaggccaa  180
gctataacta acgaacagca catcgcattc agtagacgtt tcgggccagt tgatccggtg  240
ccacacctta agtccatcga aggctaccct gaggtccaga tgatacgccg agaggccaac  300
gaaagcttac gtgtgatcgg ggacgactgg catacagata gcaccttcct tgacgcaccc  360
cccgcagccg tcgttatgcg tgccatcgac gtcccagagc atggcggaga cactggattt  420
ttatctatgt ataccgcatg ggaaacgtta agccccacca tgcaagcgac catagaggga  480
ttaaacgtgg tccattcggc tacacgggtg tttggatcct tgtatcaggc acagaatgaa  540
cgttggagta atacctcact taaagtcatg gatgtggatg ctggggacag ggagacagtt  600
cacccgttgg ttgtcacgca tcctggatct gggcgcaaag gactttacgt aaaccaagta  660
tattgtcaac gtatagaagg gatgacggac gccgagagca aacctttact ccaattcctg  720
tatgagcacg cgacgagatt tgactttact tgtcgtgtca gatggaaaaa agatcaggtc  780
ttagtttggg acaatctttg cacgatgcac agagccgtgc cagattatgc tggtaaattt  840
agatacctga cgcgaaccac cgtcggcggc gttcggccag cgaggtga             888

SEQ ID NO: 86          moltype = AA  length = 295
FEATURE                Location/Qualifiers
source                 1..295
                       mol_type = protein
                       organism = synthetic construct
SEQUENCE: 86
```

-continued

```
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESLRVIGDDW HTDSTFLDAP  120
PAAVVMRAID VPEHGGDTGF LSMYTAWETL SPTMQATIEG LNVVHSATRV FGSLYQAQNS  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 87          moltype = DNA  length = 888
FEATURE                Location/Qualifiers
source                 1..888
                       mol_type = other DNA
                       organism = synthetic construct
CDS                    1..888
                       protein_id = 86
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESLRV
                        IGDDWHTDSTFLDAPPAAVVMRAIDVPEHGGDTGFLSMYTAWETLSPTMQATIEGLNVV
                        HSATRVFGSLYQAQNSRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 87
atgcacgcag ctctgtctcc gctgtctcag cgtttcgaac gtattgctgt tcagcctctg  60
accggtgttc tgggcgcaga aatcactggc gttgacctgc gtgaaccgct ggacgattct  120
acctggaacg agattctgga tgctttccac acttaccaag ttatttactt cccaggtcaa  180
gcgattacta acgaacaaca cattgccttc tctcgtcgtt tcggtccagt tgatccggtc  240
ccacacctga aatctatcga aggttacccg gaagtacaaa tgatccgtcg cgaagcaaac  300
gaatccctgc gtgtaatcgg tgatgattgg cacaccgaca gcaccttcct ggatgcaccg  360
ccggcggctg ttgttatgcg tgctatcgat gttccggaac atggcggtga tactggcttc  420
ctgagcatgt acaccgcatg ggaaacgctg tctccgacca tgcaggcaac catcgaaggc  480
ctgaacgtgg tacattctgc gactcgcgta ttcggctccc tgtatcaggc acaaaactct  540
cgttggtcca acaccagcct gaaagtaatg gacgttgatg ctggtgaccg cgaaaccgta  600
cacccactgg tggttaccca cccaggtagc ggtcgtaaag gtctgtacgt taaccaggtt  660
tattgtcaac gtattgaagg tatgactgat gcagaatcca aaccgctgct gcagttcctg  720
tacgaacacg cgacccgttt cgattttact tgccgcgttc gttggaaaaa agaccaggtt  780
ctggtgtggg ataacctgtg cactatgcac cgcgcagttc cggactacgc aggtaaattc  840
cgttatctga ctcgtaccac tgttggtggt gttcgtccgg cacgttaa             888

SEQ ID NO: 88          moltype = DNA  length = 888
FEATURE                Location/Qualifiers
source                 1..888
                       mol_type = other DNA
                       organism = synthetic construct
CDS                    1..888
                       protein_id = 86
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESLRV
                        IGDDWHTDSTFLDAPPAAVVMRAIDVPEHGGDTGFLSMYTAWETLSPTMQATIEGLNVV
                        HSATRVFGSLYQAQNSRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 88
atgcatgctg ctctcagccc tctttcccaa aggttcgaac ggatcgccgt gcagcccctg  60
actggtgttc tcggagcgga gattaccggc gtcgatctcc gcgagccctt ggatgacagc  120
acatggaatg agattctcga cgcgttccac acttaccaag ttatctattt cccgggccag  180
gctatcacca acgagcagca catcgccttc tctaggagat ttggcccagt ggacccagtc  240
ccacatctga agtcgatcga aggctaccca gaggtccaga tgattaggag ggaagcaaac  300
gaatctcttc gcgtcatcgg cgacgactgg catactgatt cgacgtttct cgacgctcct  360
ccagcggctg ttgtgatgcg tgctatcgat gttcctgagc atggcggcga cactggcttc  420
ctgtccatgt acacggcctg ggagaccctc tccccaacaa tgcaggctac cattgaggga  480
ctcaatgtcg ttcactcggc gacacgtgtg ttcggcagcc tttatcaggc tcagaactcc  540
aggtggagca acacaagtct gaaggtcatg gacgtcgacg cgggtgacag agagacagtg  600
caccctcttg tggtgacaca tcctggctcc ggtcgtaaag ggctgtacgt gaaccaggtt  660
tactgtcaaa gaattgaagg gatgaccgat gcggagtcca agccccttt gcagtttctg  720
tatgagcatg cgaccagatt cgatttcact tgtagggtga gatggaagaa ggaccaggtg  780
ctggtgtggg ataatttgtg tacgatgcat agggcagtgc ccgactatgc tggtaagttt  840
aggtacctca cccggactac agtcggagga gtcagaccag cgcggtga             888

SEQ ID NO: 89          moltype = DNA  length = 888
FEATURE                Location/Qualifiers
source                 1..888
                       mol_type = other DNA
                       organism = synthetic construct
CDS                    1..888
                       protein_id = 86
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESLRV
                        IGDDWHTDSTFLDAPPAAVVMRAIDVPEHGGDTGFLSMYTAWETLSPTMQATIEGLNVV
```

```
                         HSATRVFGSLYQAQNSRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 89
atgcatgccg cgctgagccc cctcagtcaa cgatttgaga gaattgctgt acagccatta  60
acaggcgttc tgggagcaga aataacagga gttgatcttc gtgaacccct agacgattcc  120
acatggaacg aaattctgga tgcgttccac acgtaccaag tcatctactt cccgggccaa  180
gcgatcacaa atgaacagca tatagcgttt tcgaggcgat tcggaccagt agatcctgtg  240
ccccatttaa agtcgatcga agggtatcca gaagtccaaa tgatacgcag ggaggctaac  300
gaatcattac gggtcattgg agatgactgg catacggatt cgacgtttct tgatgcgccg  360
ccggcggcgg tagtcatgcg agcgatcgat gttcctgaac acggaggcga tacgggcttc  420
ctgtccatgt acaccgcatg ggaaacgttg tctcccacaa tgcaagcgac catcgaagga  480
cttaatgttg tacattctgc gacaagggta ttcggatctc tgtaccaggc tcaaaattcg  540
cgttggtcta acactagcct caaagtgatg gatgtcgacg caggtgaccg cgagaccgtt  600
caccctctag tcgtaaccca tccggggagt ggtcgtaaag gactctatgt gaaccaagtg  660
tactgccaga gaatagaggg aatgacggac gctgagtcta aacctctcct ccagttcctg  720
tacgagcacg ctacccgctt tgacttcaca tgccgcgtcc gatggaaaaa agatcaagtg  780
ttagtatggg ataacctctg cactatgcat agagcagtac ctgattatgc cggcaagttc  840
cggtacctaa cccgcacaac tgtaggcgga gtgagacctg cccggtga              888

SEQ ID NO: 90            moltype = AA  length = 295
FEATURE                  Location/Qualifiers
source                   1..295
                         mol_type = protein
                         organism = synthetic construct
SEQUENCE: 90
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESLRVIGDDW HTDSTFLDAP  120
PAAVVMRAID VPEHGGDTGF LSMYTAWETL SPTMQATIEG LNVVHSATRV FGSLYQAQNL  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 91            moltype = DNA  length = 888
FEATURE                  Location/Qualifiers
source                   1..888
                         mol_type = other DNA
                         organism = synthetic construct
CDS                      1..888
                         protein_id = 90
                         transl_table = 1
                         translation = MHAALSPLSQRFERIAVQPLTGVLGAEITGVDLREPLDDSTWNEIL
                          DAFHTYQVIYFPGQAITNEQHIAFSRRFGPVDPVPHLKSIEGYPEVQMIRREANESLRV
                          IGDDWHTDSTFLDAPPAAVVMRAIDVPEHGGDTGFLSMYTAWETLSPTMQATIEGLNVV
                          HSATRVFGSLYQAQNLRWSNTSLKVMDVDAGDRETVHPLVVTHPGSGRKGLYVNQVYCQ
                          RIEGMTDAESKPLLQFLYEHATRFDFTCRVRWKKDQVLVWDNLCTMHRAVPDYAGKFRY
                          LTRTTVGGVRPAR
SEQUENCE: 91
atgcacgcag ctctgtctcc gctgtctcag cgtttcgaac gtattgcagt acagccactg  60
accggtgtgc tgggcgcaga aattaccggc gtagatctgc gtgaaccgct ggacgacagc  120
acctggaacg aaattctgga tgcgttccat acttaccagg ttatctactt cccaggtcag  180
gccatcacga acgagcagca tatcgcgttc tcccgtcgtt tcggtcctgt tgacccggtc  240
ccgcacctga aatctatcga aggctatccg gaagtgcaga tgatccgtcg tgaagcaaac  300
gaatctctgc gtgtaattgg tgacgattgg cacaccgact ctacttttct ggatgcaccg  360
ccggccgctg ttgtaatgcg tgctattgac gttccggaac atggcggtga taccggtttc  420
ctgtctatgt atacggcgtg ggaaaccctg agcccgacca tgcaggccac tatcgaaggc  480
ctgaacgtgg ttcactctgc tacccgtgtt tttggctccc tgtatcaggc gcagaacctg  540
cgctggtcca acacctctct gaaagtcatg gacgttgatg ctggtgatcg cgaaactgtg  600
caccctctgg ttgttactca cccgggttct ggccgtaaag gcctgtacgt gaaccaggtt  660
tattgccagc gtatcgaggg catgaccgac gctgaatcta aaccgctgct gcagtttctg  720
tatgaacacg caacccgctt tgactttacc tgccgtgttc gttggaaaaa agatcaggtt  780
ctggtatggg ataacctgtg cactatgcat cgtgccgtgc cagattacgc cggtaaattc  840
cgttatctga ctcgtaccac cgttggtggc gttcgtccgg ctcgttaa              888

SEQ ID NO: 92            moltype = DNA  length = 888
FEATURE                  Location/Qualifiers
source                   1..888
                         mol_type = other DNA
                         organism = synthetic construct
CDS                      1..888
                         protein_id = 90
                         transl_table = 1
                         translation = MHAALSPLSQRFERIAVQPLTGVLGAEITGVDLREPLDDSTWNEIL
                          DAFHTYQVIYFPGQAITNEQHIAFSRRFGPVDPVPHLKSIEGYPEVQMIRREANESLRV
                          IGDDWHTDSTFLDAPPAAVVMRAIDVPEHGGDTGFLSMYTAWETLSPTMQATIEGLNVV
                          HSATRVFGSLYQAQNLRWSNTSLKVMDVDAGDRETVHPLVVTHPGSGRKGLYVNQVYCQ
                          RIEGMTDAESKPLLQFLYEHATRFDFTCRVRWKKDQVLVWDNLCTMHRAVPDYAGKFRY
                          LTRTTVGGVRPAR
SEQUENCE: 92
atgcatgcgg ccttgtctcc actctctcaa cggtttgaac gcattgcggt ccaacccctc  60
```

```
accggcgttt tgggggccga aatcaccggc gtggacctca gagaaccact tgacgattca  120
acttggaacg aaatcttgga cgcatttcac acttaccagg tcatttactt tccggggcag  180
gcgattacaa acgaacaaca catcgccttc tcaagaaggt tcggtcctgt cgacccagtt  240
ccacacctca agtccatcga gggctacccg gaggtccaga tgattcgtcg cgaggctaac  300
gagtcgttgc gcgtcattgg agacgattgg cacactgact ctacctttct ggacgcacct  360
ccggctgccg tcgtgatgcg ggctatcgac gtgccggagc acggcgggga tacaggcttt  420
ctcagcatgt acaccgcatg ggaaacactc tcacctacga tgcaggccac catagagggc  480
ctcaacgtcg ttcacagcgc tacgcgggtg tttggttctt tgtaccaggc gcagaacctt  540
cgctggtcta atacgtctct caaagtgatg gacgtcgatg ccggagaccg cgagactgtg  600
cacccccctgg tggtgaccca tcccgggtcg ggacgcaagg gactgtacgt taaccaagtg  660
tactgccaga ggatagaggg catgactgat gccgagagca agccgctgct ccaattcctc  720
tacgagcacg cgacaaggtt cgatttcact tgccgggtgc gctggaaaaa ggaccaggtg  780
ctcgtgtggg acaacctgtg caccatgcat agggctgtcc cggactatgc cggcaagttc  840
cggtatttga ctaggacaac ggtcggagga gttaggcctg cgcgctga              888
```

```
SEQ ID NO: 93           moltype = DNA  length = 888
FEATURE                 Location/Qualifiers
source                  1..888
                        mol_type = other DNA
                        organism = synthetic construct
CDS                     1..888
                        protein_id = 90
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHTDSTFLDAPPAAVVMRAIDVPEHGGDTGFLSMYTAWETLSPTMQATIEGLNVV
                         HSATRVFGSLYQAQNLRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 93
atgcacgccg ccctgtctcc attaagtcaa cgattcgaac gcatagcggt acagcccttg  60
accggtgtcc taggcgcaga aatcactggc gtagatttgc gcgaaccact ggacgattca  120
acatggaacg agatactaga cgccttccac acatatcaag tcatctattt ccctggtcaa  180
gcaataacga atgagcagca cattgcattc tctaggagat tcggaccggt cgatccggta  240
ccgcacttaa aaagtattga agggtatcct gaagttcaga tgataaggag agaagccaat  300
gaatcattgc gagtgatcgg cgatgactgg cacactgact ccaccttcct agatgctccc  360
cctgccgctg ttgtaatgag agcaattgat gtacccgaac acggagggga tacagggttt  420
ttgtcgatgt atacagcgtg ggaaaccttg tcccccacga tgcaagcaac catcgagggg  480
ttaaatgtag ttcattccgc aactcgtgta ttcggttcct tgtatcaagc tcaaaacctt  540
cggtggtcta acacttcgct gaaagtcatg gatgtcgatg cgggagacag agaaactgta  600
caccccttag ttgtaacgca tccaggatct ggacggaaag gcctgtatgt caatcaagtg  660
tattgtcaga ggatagaggg catgactgat gctgaatcca aacccctctt gcaattttta  720
tatgaacatg cgacccgttt cgattttaca tgcagggtgc gctggaagaa ggaccaagtg  780
ctggtgtggg ataatttatg cacaatgcac agagcggtcc cagattatgc aggcaagttt  840
cggtacttaa ctagaactac cgttggaggg gtgaggccag cgaggtga              888
```

```
SEQ ID NO: 94           moltype = AA  length = 295
FEATURE                 Location/Qualifiers
source                  1..295
                        mol_type = protein
                        organism = synthetic construct
SEQUENCE: 94
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESLRVIGDDW HTDSTFLDAP  120
PAAVVMRAID VPEHGGDTGF LSMYTAWETL SPTMQATIEG LNVVHSATRV FGSLYQAQNW  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295
```

```
SEQ ID NO: 95           moltype = DNA  length = 888
FEATURE                 Location/Qualifiers
source                  1..888
                        mol_type = other DNA
                        organism = synthetic construct
CDS                     1..888
                        protein_id = 94
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHTDSTFLDAPPAAVVMRAIDVPEHGGDTGFLSMYTAWETLSPTMQATIEGLNVV
                         HSATRVFGSLYQAQNWRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 95
atgcatgctg ctctgtctcc gctgtctcag cgttttgaac gtattgctgt tcagccgctg  60
accggtgttc tgggtgctga aattactggc gtagatctgc gtgaaccgct ggatgacagc  120
acctggaacg aaatcctgga tgcctttcat acctaccagg taatttactt tccgggtcag  180
gctattacca acgaacagca tattgcgttc agccgccgct ttggtccggt ggatccagta  240
ccgcacctga aatccatcga gggctaccct gaagtccaga tgatccgtcg tgaagctaac  300
gaaagcctgc gtgttatcgg tgatgactgg cataccgact ctactttcct ggatgcaccg  360
```

```
ccggcagctg tagttatgcg cgctatcgac gttccggagc acggtggtga tacgggcttt  420
ctgtctatgt ataccgcttg ggaaaccctg agcccgacta tgcaggcgac catcgaaggc  480
ctgaacgttg ttcacagcgc aacccgtgta ttcggttccc tgtatcaggc acagaactgg  540
cgttggagca acacttctct gaaagttatg gatgttgacg cgggcgatcg tgaaaccgta  600
cacccactgg tagttaccca cccgggctct ggtcgtaaag gtctgtacgt caaccaggtt  660
tattgccagc gtatcgaagg tatgacggat gccgaatcca aaccgctgct gcaatttctg  720
tacgagcacg caacccgttt cgatttcact tgccgcgttc gttggaaaaa agatcaggtc  780
ctggtttggg ataacctgtg cacgatgcat cgtgcggttc cagattacgc tggcaaattc  840
cgttatctga ctcgtacgac cgtgggtggt gttcgtccgg cacgttaa              888
```

```
SEQ ID NO: 96          moltype = DNA  length = 888
FEATURE                Location/Qualifiers
source                 1..888
                       mol_type = other DNA
                       organism = synthetic construct
CDS                    1..888
                       protein_id = 94
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESLRV
                        IGDDWHTDSTFLDAPPAAVVMRAIDVPEHGGDTGFLSMYTAWETLSPTMQATIEGLNVV
                        HSATRVFGSLYQAQNWRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 96
atgcatgccg ctcttagtcc actctcgcag agatttgaaa gaattgctgt tcaaccactc  60
accggggttc tcggagcgga gattaccggc gttgatttgc gggaaccact cgatgactcc  120
acctggaacg agatcctcga cgcgttccac acctaccaag tcatttactt ccccggacag  180
gcgattacca acgagcaaca tatcgcgttc tcacgccgtt tcggcccagt cgaccccgtt  240
ccgcacttga agtcaataga ggggtatcct gaagtgcaga tgatcaggag ggaggctaac  300
gagtcacttc gggtgatcgg ggatgattgg cacacagata gtaccttcct cgatgcccca  360
cctgccgccg ttgttatgcg cgcgatagat gtcccggagc acggcgggga caccggcttc  420
ctgtcaatgt atactgcttg ggagacattg tcaccgacga tgcaagccac aattgaagga  480
cttaacgttg tgcactccgc tacacgtgtg ttcggctcgt tgtaccaggc tcagaactgg  540
agatggtcca acacctccct caaggttatg gacgttgatg ctggcgaccg tgagacggtc  600
cacccgctcg tcgttaccca cccaggctcg ggtaggaagg ggttgtacgt taatcaggtg  660
tattgccaaa ggattgaggg catgaccgat gccgaaagca agcccctcct gcaattcctg  720
tatgaacatg ctactcgctt cgatttcacc tgccgcgtgc gttggaagaa ggaccaggtt  780
ctcgtttggg acaatttgtg cacaatgcac agagccgtcc ccgattacgc tgggaaattc  840
aggtacctta cgcggacaac tgtcggtggt gttcggcctg cccgctga              888
```

```
SEQ ID NO: 97          moltype = DNA  length = 888
FEATURE                Location/Qualifiers
source                 1..888
                       mol_type = other DNA
                       organism = synthetic construct
CDS                    1..888
                       protein_id = 94
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESLRV
                        IGDDWHTDSTFLDAPPAAVVMRAIDVPEHGGDTGFLSMYTAWETLSPTMQATIEGLNVV
                        HSATRVFGSLYQAQNWRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 97
atgcacgcag cattgtctcc actctcgcaa cggttcgaaa gaatagctgt gcagccgctc  60
acaggcgttt tgggcgccga aattactggt gtcgatttaa gggaacccct tgatgactca  120
acttggaatg aaatcctgga cgcattccat acataccaag tcatatattt tcctggccag  180
gcaataacaa acgagcaaca tatcgctttt tcacgacgct ttgggccagt tgacccggtc  240
ccacacctaa aatctattga gggatatccg gaagtgcaga tgattagacg cgaggcaaac  300
gagtccctac gggtgatagg cgatgattgg cacaccgaca gcacctttct tgacgcccct  360
cccgccgcgg tggtgatgcg cgcgatagac gtgcccgaac atggaggaga tacagggttt  420
ttaagtatgt atacagcgtg ggagactctt tcgcctacta tgcaagccac gatagaagga  480
ctcaacgtgg tacattccgc gactcgggtg ttcggaagtt tatatcaggc gcagaattgg  540
cgctggagta acacatcctt aaaggtgatg gatgtcgacg caggggaccg agaaacagtt  600
catccccttg tggtgactca ccccggctcg ggccggaaag gcctttatgt caaccaagtg  660
tattgccaac gcatcgaagg catgaccgac gcggaaagca aaccattatt acaatttttg  720
tatgagcacg caactaggtt tgacttcact tgccgggtca gatggaaaaa agatcaggtt  780
ctggtatggg ataacttatg tacaatgcac agagccgtcc cagattatgc aggtaagttc  840
cgatatttga ctagaacgac tgtgggagga gttagacctg ctcgctga              888
```

```
SEQ ID NO: 98          moltype = AA  length = 295
FEATURE                Location/Qualifiers
source                 1..295
                       mol_type = protein
                       organism = synthetic construct
SEQUENCE: 98
MHAALSPLSQ RFERIAVQPL TGVLGAEITG VDLREPLDDS TWNEILDAFH TYQVIYFPGQ  60
```

-continued

```
AITNEQHIAF SRRFGPVDPT PHLKSIEGYP EVQMIRREAN ESLRVIGDDW HTDSTFLDAP  120
PAAVVMRAID VPEHGGDTGF LSMYTAWETL SPTMQATIEG LNVVHSATRV FGSLYQAQNR  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 99          moltype = DNA  length = 888
FEATURE                Location/Qualifiers
source                 1..888
                       mol_type = other DNA
                       organism = synthetic construct
CDS                    1..888
                       protein_id = 98
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPTPHLKSIEGYPEVQMIRREANESLRV
                        IGDDWHTDSTFLDAPPAAVVMRAIDVPEHGGDTGFLSMYTAWETLSPTMQATIEGLNVV
                        HSATRVFGSLYQAQNRRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 99
atgcacgctg cgctgtctcc gctgtctcag cgttttgaac gtattgcggt ccagcctctg  60
actggtgtac tgggcgcgga aatcactggt gttgatctgc gtgaaccgct ggatgattct  120
acttggaacg aaatcctgga tgctttccat acctaccagg tgatctattt cccgggtcaa  180
gcaatcacca acgaacagca catcgcattc tctcgtcgtt tcggtccggt agatccaact  240
ccgcacctga aatccatcga aggttatccg gaagtgcaaa tgatccgtcg tgaggcgaac  300
gaatctctgc gtgtaatcgg tgacgattgg cacaccgatt ccaccttcct ggatgcacca  360
cctgctgccg tggttatgcg tgctattgac gtaccggaac atggtggtga caccggtttc  420
ctgtctatgt acacggcctg ggaaaccctg tctccgacca tgcaagccac catcgaaggt  480
ctgaacgtcg tgcactccgc aacccgtgta ttcggtagcc tgtaccaggc gcagaatcgt  540
cgctggtcta acacttctct gaaagtcatg gacgttgatg ctggcgatcg tgaaaccgta  600
cacccgctgg tagtaactca tccgggttcc ggtcgtaaag gtctgtacgt caaccaggta  660
tactgtcagc gcatcgaagg catgactgat gcagaatcca aacctctgct gcagttcctg  720
tacgaacacg ctactcgctt tgacttcacg tgccgtgttc gttggaaaaa agaccaggtg  780
ctggtctggg ataacctgtg taccatgcac cgtgcggtac cggattatgc gggtaaattc  840
cgttatctga ctcgtactac tgttggcggc gtgcgtcctg cgcgttaa              888

SEQ ID NO: 100         moltype = DNA  length = 888
FEATURE                Location/Qualifiers
source                 1..888
                       mol_type = other DNA
                       organism = synthetic construct
CDS                    1..888
                       protein_id = 98
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPTPHLKSIEGYPEVQMIRREANESLRV
                        IGDDWHTDSTFLDAPPAAVVMRAIDVPEHGGDTGFLSMYTAWETLSPTMQATIEGLNVV
                        HSATRVFGSLYQAQNRRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 100
atgcacgcag cactctctcc cctgtcacaa cgttttgaac gcatcgccgt ccaaccgttg  60
actggtgtcc tcggggcaga gatcaccggc gtcgaccttc gcgagcctct cgatgattcc  120
acatggaacg agattctcga tgctttccat acatatcagg tcatctactt cccgggccag  180
gcgatcacca acgaacaaca catcgcgttc tccaggaggt tcggccccgt cgatccaacg  240
cctcacctga agagtatcga ggggtaccca gaagttcaaa tgattcggcg tgaagccaac  300
gagagcttgc gcgtgatcgg cgacgactgg cacacagact ccacctttct ggacgccccg  360
ccggcagccg ttgttatgag ggcgattgac gttcctgaac acggaggaga caccggtttt  420
ctgtcaatgt acaccgcctg ggagacgctt tcgcctacta tgcaggccac catcgagggc  480
ctgaatgttg tccattcagc cacccgtgtg ttcggctcgc tttatcaggc tcagaatagg  540
cggtggtcga acacctcctt gaaggtcatg gatgtggacg ccggcgatag agagactgtc  600
catcccctcg tcgttactca ccccggcagc ggtaggaagg gtttgtatgt caatcaggtt  660
tactgccaga ggattgaggg aatgactgat gcagagtcca agccgttgct gcagttcttg  720
tacgaacacg caacccgttt cgattttacc tgtcgcgtca ggtggaagaa ggaccaggtt  780
ttggtgtggg acaacctctg cactatgcac cgggccgtgc ctgattatgc cggaaagttt  840
cggtacctga ctagaacgac cgtgggtggg gttaggccag cgaggtga              888

SEQ ID NO: 101         moltype = DNA  length = 888
FEATURE                Location/Qualifiers
source                 1..888
                       mol_type = other DNA
                       organism = synthetic construct
CDS                    1..888
                       protein_id = 98
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPTPHLKSIEGYPEVQMIRREANESLRV
                        IGDDWHTDSTFLDAPPAAVVMRAIDVPEHGGDTGFLSMYTAWETLSPTMQATIEGLNVV
                        HSATRVFGSLYQAQNRRWSNTSLKVMDVDAGDRETVHPLVVTHPGSGRKGLYVNQVYCQ
```

-continued

RIEGMTDAESKPLLQFLYEHATRFDFTCRVRWKKDQVLVWDNLCTMHRAVPDYAGKFRY
LTRTTVGGVRPAR

SEQUENCE: 101

```
atgcatgctg cacttagccc actatctcaa cgcttcgaac gaatcgcagt ccaaccctta  60
acgggtgtgt tgggcgcaga gatcacgggt gtggatctga gagaaccact tgacgattcc  120
acctggaatg aaatccttga tgcgttccat acatatcaag ttatatactt tcccgggcag  180
gcgattacca acgagcagca catcgcgttt tcgcgacgct ttggaccagt cgatcctacg  240
ccccatttaa aatcaataga agggtatccc gaagtacaaa tgattaggcg cgaagcgaac  300
gagtcattaa gggtaatcgg cgacgactgg catactgata gtacgttttt ggatgcaccc  360
cctgccgcgg ttgtcatgag agctatagac gttccggagc atggcggtga taccggattt  420
ctctctatgt acacagcctg ggaaacactg tctcctacca tgcaagctac tatagaaggt  480
ctaaacgtcg ttcactcagc gacaagagta tttggttcac tatatcaagc acaaaatagg  540
cgttggagca atacctcttt gaaggtcatg gacgtggacg cgggcgatcg ggagactgtt  600
cacccttttgg tcgtaacgca cccaggatca ggtcgtaagg gtctgtacgt caatcaagtt  660
tactgccagc gcattgaggg catgacggat gctgaatcta aacctttact gcaattcttg  720
tatgagcacg cgacgcgatt tgacttcacc tgtcgcgtta ggtggaaaaa agatcaggta  780
ttagtctggg ataacctgtg tacgatgcat agagctgtac cggactacgc aggaaagttc  840
agatacctaa ctaggacaac tgtcggcggg gtgaggcctg cccgatga  888
```

SEQ ID NO: 102 moltype = AA length = 295
FEATURE Location/Qualifiers
source 1..295
mol_type = protein
organism = synthetic construct

SEQUENCE: 102

```
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESLRVIGDDW HADSTFLDAP  120
PAAVVMRAID VPEHGGDTGF LSMYTAWETL SPTMQATIEG LNVVHSATRV FGSLYQAQNR  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR  295
```

SEQ ID NO: 103 moltype = DNA length = 888
FEATURE Location/Qualifiers
source 1..888
mol_type = other DNA
organism = synthetic construct
CDS 1..888
protein_id = 102
transl_table = 1
translation = MHAALSPLSQRFERIAVQPLTGVLGAEITGVDLREPLDDSTWNEIL
DAFHTYQVIYFPGQAITNEQHIAFSRRFGPVDPVPHLKSIEGYPEVQMIRREANESLRV
IGDDWHADSTFLDAPPAAVVMRAIDVPEHGGDTGFLSMYTAWETLSPTMQATIEGLNVV
HSATRVFGSLYQAQNRRWSNTSLKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR

SEQUENCE: 103

```
atgcatgctg cactgagccc actgtctcag cgtttcgaac gtatcgctgt gcagccgctg  60
accggtgtac tgggcgcgga aatcaccggt gttgacctgc gtgaaccgct ggacgatagc  120
acctggaacg agatcctgga cgcctttcac acctaccagg ttatctattt tccaggccag  180
gcgatcacca atgaacagca catcgcattc tctcgccgtt ttggcccagt tgatccagtg  240
ccgcacctga aatctatcga aggctatccg gaggttcaaa tgattcgtcg tgaagcgaat  300
gaaagcctgc gtgtcatcgg cgatgattgg catgccgact ccaccttcct ggacgctccg  360
ccagcggcgg tggttatgcg cgcaatcgac gttccggaac atggcggcga cactggtttc  420
ctgagcatgt acaccgcgtg ggaaaccctg tctccgacta tgcaggccac tatcgaaggt  480
ctgaacgtgg tgcactctgc gacccgtgta ttcggctccc tgtaccaggc tcagaaccgt  540
cgctggagca ataccagcct gaaagtgatg gacgttgatg cgggcgaccg tgaaactgtt  600
catccgctgg ttgtgaccca cccgggctct ggtcgcaaag gtctgtacgt gaaccaggtt  660
tattgccagc gcatcgaagg catgactgat gcggagagca aaccgctgct gcagttcctg  720
tatgaacacg cgactcgttt cgactttacc tgtcgtgtgc gctggaagaa agaccaagtt  780
ctggtatggg acaacctgtg caccatgcac cgcgctgttc cggactatgc aggtaagttc  840
cgttatctga ctcgtactac cgtgggtggt gtccgcccgg cgcgttaa  888
```

SEQ ID NO: 104 moltype = DNA length = 888
FEATURE Location/Qualifiers
source 1..888
mol_type = other DNA
organism = synthetic construct
CDS 1..888
protein_id = 102
transl_table = 1
translation = MHAALSPLSQRFERIAVQPLTGVLGAEITGVDLREPLDDSTWNEIL
DAFHTYQVIYFPGQAITNEQHIAFSRRFGPVDPVPHLKSIEGYPEVQMIRREANESLRV
IGDDWHADSTFLDAPPAAVVMRAIDVPEHGGDTGFLSMYTAWETLSPTMQATIEGLNVV
HSATRVFGSLYQAQNRRWSNTSLKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR

SEQUENCE: 104

```
atgcacgcgg ctctgtctcc actttctcaa agattcgaga ggatcgcagt ccagccactt  60
accggtgtgt tgggggctga gattaccggc gtggatctca gggaaccact ggatgactcc  120
```

-continued

```
acctggaatg agatcctcga tgccttccat acctaccagg tgatttattt tcctggccag  180
gcgatcacta acgagcagca catagcattt agccgtaggt tcggcccagt ggacccagtc  240
ccacatctca agagcataga gggttatcca gaagtccaga tgatcaggcg cgaagcgaac  300
gagtccttgc gcgtgattgg agatgactgg cacgccgact ccacatttct ggatgcgcca  360
ccagctgccg ttgtcatgag agccatcgac gtgcctgaac acggagggga caccggattc  420
ctcagcatgt acactgcttg ggaaaccttg tctccgacca tgcaggcgac tattgagggc  480
ttgaacgttg ttcattcagc tacccgggtt tttgggagcc tgtaccaggc tcaaaaccgg  540
aggtggtcaa atacgtcttt gaaggtcatg gatgtggatg ctggagatag agagaccgtc  600
catccccttg tcgtcacaca tcccggtagc ggtcggaagg gcttgtacgt gaaccaggtg  660
tactgtcagc ggattgaggg gatgaccgac gctgagtcca agccactcct gcaattcctg  720
tatgagcatg cgacccgctt cgactttacc tgccgggtgc ggtggaaaaa ggaccaggtg  780
ctggtctggg acaatttgtg cactatgcat cgcgctgtcc ccgattatgc aggtaagttc  840
aggtacttga ccaggacaac ggtcggtggc gtgagacctg ctaggtga              888

SEQ ID NO: 105          moltype = DNA  length = 888
FEATURE                 Location/Qualifiers
source                  1..888
                        mol_type = other DNA
                        organism = synthetic construct
CDS                     1..888
                        protein_id = 102
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHADSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 105
atgcacgctg cactatcgcc cctcagtcag aggttcgaaa gaatagcagt ccaaccacta  60
actggagtgc ttggagcgga gattacggga gtagacttgc gtgaaccact tgatgacagt  120
acttggaacg aaatcttaga tgcgtttcac acataccaag taatatattt tcccggccag  180
gcgattacca atgaacagca catagctttt tcgcgccgtt ttggcccagt agaccccgtt  240
ccgcatctta agtcgatcga gggttacccg gaggttcaaa tgattcgccg ggaagcgaat  300
gaatctttac gtgtaattgg tgacgactgg catgcagatt ctacctttct agacgcgccc  360
ccagcggccg tggtcatgcg ggccattgac gtgccagaac atggcggcga tacaggcttt  420
ctttctatgt acaccgcctg ggaaactttg tcccccacca tgcaggctac tatagagggt  480
cttaacgttg tacattctgc cacgagagtg tttgggtctc tgtatcaagc tcaaaatcgc  540
cgttggtcta atacgagtct taaagtgatg gacgtcgacg ctggggatcg tgaaacggta  600
catccgctcg tggttacaca tcctggatca ggcagaaaag ggttatatgt taaccaagtg  660
tattgtcagc ggatagaggg aatgacggac gccgaaagca agcccctgct acaattttta  720
tatgagcacg cgacaagatt tgattttact tgtcgtgtca ggtggaagaa ggatcaggtg  780
cttgtatggg ataatctctg tacaatgcac cgggctgtgc ctgattatgc gggaaagttc  840
aggtatctga cgaggactac tgtaggggga gtacgccccg cacgttga              888

SEQ ID NO: 106          moltype = AA  length = 295
FEATURE                 Location/Qualifiers
source                  1..295
                        mol_type = protein
                        organism = synthetic construct
SEQUENCE: 106
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESLRVIGDDW HSDSTFLDAP  120
PAAVVMRAID VPEHGGDTGF LSMYTAWETL SPTMQATIEG LNVVHSATRV FGSLYQAQNR  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 107          moltype = DNA  length = 888
FEATURE                 Location/Qualifiers
source                  1..888
                        mol_type = other DNA
                        organism = synthetic construct
CDS                     1..888
                        protein_id = 106
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHSDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 107
atgcacgctg ctctgtcccc gctgtcccaa cgttttgaac gtattgcagt ccaaccactg  60
accggtgttc tgggtgctga aatcactggc gtagatctgc gtgaaccact ggatgactct  120
acttggaacg aaattctgga cgcgttccac acgtaccagg ttatctactt cccgggccag  180
gcaatcacta acgagcagca tatcgcattc tctcgtcgtt tcggtccggt tgatccggta  240
ccgcacctga aatctatcga aggctacccg gaagtacaga tgatccgtcg tgaggctaac  300
gaatccctgc gcgtcatcgg cgatgattgg cacagcgatt ctaccttcct ggacgctccg  360
ccggctgcag ttgttatgcg tgccattgac gttccggaac acggcggtga caccggtttc  420
```

-continued

```
ctgtctatgt ataccgcatg ggaaaccctg agcccgacta tgcaggcgac cattgaaggc  480
ctgaacgtgg ttcacagcgc gacccgtgtg tttggtagcc tgtaccaggc tcagaaccgt  540
cgttggagca atacctctct gaaggtgatg gatgtggacg cgggcgaccg tgaaaccgtc  600
catccgctgg tggttactca tccgggttcc ggccgtaaag gcctgtacgt aaaccaggtt  660
tactgccagc gcattgaggg catgaccgac gcggaatcta agccgctgct gcagttcctg  720
tatgaacatg caactcgttt cgatttcacc tgccgtgtac gttggaaaaa agaccaagta  780
ctggtatggg ataatctgtg cactatgcac cgcgctgttc cagactacgc tggcaaattc  840
cgttacctga cccgtactac tgttggtggt gtgcgtccgg ctcgttaa              888

SEQ ID NO: 108         moltype = DNA  length = 888
FEATURE                Location/Qualifiers
source                 1..888
                       mol_type = other DNA
                       organism = synthetic construct
CDS                    1..888
                       protein_id = 106
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESLRV
                        IGDDWHSDSTFLDAPPAAVVMRAIDVPEHGGDTGFLSMYTAWETLSPTMQATIEGLNVV
                        HSATRVFGSLYQAQNRRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 108
atgcacgcag cgctttcacc gctctcccaa agatttgaaa ggatagctgt gcaacccctc  60
accggtgtcc ttggagctga gattaccggt gtggacctga gggaaccact cgatgactct  120
acttggaacg aaatcttgga tgcgttccac acttaccagg tgatttactt ccctggtcag  180
gcaatcacca acgaacagca tattgccttc agcaggcgtt ttggccctgt tgacccagtg  240
ccccatttga agtccatcga gggttacccc gaagtgcaaa tgatacgtcg cgaggcgaac  300
gaatcattgc gggtcatcgg cgatgactgg cactcggact caacttttct ggatgccccc  360
ccagcggcgg tcgtgatgag agccatcgat gttccagagc atgggggaga caccgggttc  420
ctcagcatgt atacagcctg ggagactctc agccccacca tgcaggccac aatcgagggg  480
ctcaatgttg tgcactcagc cacaagagtc tttggctccc tctaccaggc ccagaaccgc  540
cgctggagca acacctctct gaaggtgatg gatgttgacg ctggcgaccg ggagaccgtc  600
caccctcttg ttgttaccca tcctggaagt ggaaggaaag ggctgtatgt gaatcaggtc  660
tattgccagc gcattgaggg catgactgac gctgagtcca aaccgctttt gcaattcctc  720
tacgagcacg caaccagatt tgacttcacc tgcagggtga ggtggaagaa agaccaggtt  780
ctcgtttggg acaacctgtg caccatgcat agggccgtgc cagattacgc aggcaagttc  840
cgctacctga caaggacgac cgtgggaggc gtccgtccgg cgaggtga              888

SEQ ID NO: 109         moltype = DNA  length = 888
FEATURE                Location/Qualifiers
source                 1..888
                       mol_type = other DNA
                       organism = synthetic construct
CDS                    1..888
                       protein_id = 106
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESLRV
                        IGDDWHSDSTFLDAPPAAVVMRAIDVPEHGGDTGFLSMYTAWETLSPTMQATIEGLNVV
                        HSATRVFGSLYQAQNRRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 109
atgcatgcag cgttatctcc tctgagccaa agattcgaaa gaattgcagt tcaacccttg  60
acgggtgtct tagggggccga gatcacgggc gtagatctcc gcgagcctct tgacgatagc  120
acctggaatg aaatattgga tgctttccat acatatcagg ttatatattt cccagggcaa  180
gctattacga atgaacaaca tatcgctttt agccgtcgct tcgggccagt ggatcctgta  240
ccacacttga aatcaattga aggatatccg gaagttcaga tgattaggcg tgaagctaac  300
gagtcgttaa gagttattgg tgacgattgg cactctgaca gcacattctt agatgcaccc  360
cccgccgccg ttgtaatgcg cgccatcgat gtccctgaac atgggggaga cacgggtttc  420
ttatcaatgt acacagcgtg ggagaccttg tcgcccacta tgcaagccac tatcgaaggt  480
ctcaatgtag ttcatagcgc tactagggtc ttcggaagcc tctatcaagc gcagaatcgg  540
agatggagta atacatcact taaagtaatg gacgtagacg caggggacag agaaaccgta  600
catcccctcg tagtcaccca cccgggaagc ggcaggaagg gattatacgt taatcaagtc  660
tactgtcaga ggattgaggg catgacagac gccgaatcta aaccgctcct tcaatttctg  720
tacgaacacg caacgagatt tgactttaca tgtcgtgtaa gatggaagaa agaccaagtt  780
ctggtatggg acaatctctg tacgatgcac cgcgccgttc cggactatgc cggaaaattc  840
cgttatctga caaggacgac ggtggggggc gtgagacccg cacgttga              888

SEQ ID NO: 110         moltype = AA  length = 295
FEATURE                Location/Qualifiers
source                 1..295
                       mol_type = protein
                       organism = synthetic construct
SEQUENCE: 110
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESLRVIGDDW HMDSTFLDAP  120
```

-continued

```
PAAVVMRAID VPEHGGDTGF LSMYTAWETL SPTMQATIEG LNVVHSATRV FGSLYQAQNR  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 111          moltype = DNA  length = 888
FEATURE                 Location/Qualifiers
source                  1..888
                        mol_type = other DNA
                        organism = synthetic construct
CDS                     1..888
                        protein_id = 110
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHMDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 111
atgcacgctg cgctgtctcc actgtctcag cgttttgaac gtattgcagt tcagccgctg  60
actggcgtac tgggtgctga aattaccggc gttgacctgc gtgaacctct ggacgactct  120
acttggaacg aaattctgga cgcgttccac acctaccagg ttatctattt tccgggtcag  180
gctatcacca acgagcagca cattgctttt agccgtcgtt tcggccctgt cgatccggtt  240
ccgcacctga aaagcattga aggctatcca gaagttcaga tgatccgtcg tgaagctaat  300
gaaagcctgc gcgtcattgg tgacgactgg cacatggata gcacgttcct ggatgcgcca  360
cctgcggcag ttgttatgcg tgcgattgac gttccggagc acggtggcga cactggtttc  420
ctgagcatgt acactgcctg ggaaacgctg tctccgacca tgcaggctac catcgaaggc  480
ctgaatgtcg ttcactccgc cacccgtgtt ttcggttccc tgtatcaggc gcagaaccgt  540
cgttggtcta acacttctct gaaagttatg gatgttgacg ccggtgaccg tgaaaccgta  600
cacccgctgg tggttaccca tccgggttct ggtcgtaaag gtctgtacgt gaaccaggtt  660
tactgccagc gtatcgaagg tatgactgac gcggaatcca agccgctgct gcagttcctg  720
tatgaacacg caacgcgttt cgacttcact tgtcgtgtgc gctggaaaaa agatcaggtt  780
ctggtgtggg acaacctgtg taccatgcac cgtgcagtgc cggactatgc tggtaaattc  840
cgttacctga ctcgtaccac cgttggtggt gttcgcccag ctcgttaa              888

SEQ ID NO: 112          moltype = DNA  length = 888
FEATURE                 Location/Qualifiers
source                  1..888
                        mol_type = other DNA
                        organism = synthetic construct
CDS                     1..888
                        protein_id = 110
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHMDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 112
atgcatgccg ccttgtcgcc tttgtcccag agatttgaaa gaattgcagt ccagcccctg  60
actggcgttc tgggcgctga gatcactggg gtggatctgc gcgagccact ggatgactct  120
acgtggaacg aaattttgga tgccttccat acctaccagg tcatctactt ccccggccaa  180
gccatcacga atgagcagca catcgcgttt tcacgtagat tcgggccggt ggatcctgtg  240
cctcacctga agtccattga ggggtacccc gaggtgcaaa tgattagaag agaggccaac  300
gaatcccttc gcgtcatcgg tgatgactgg cacatggact ccacattcct tgatgcaccc  360
ccagccgcgg tggtcatgag ggccattgac gtgccggagc atgggggaga caccggtttt  420
ctgtctatgt ataccgcctg ggagaccctg tctcccacca tgcaggctac catagagggc  480
cttaatgtgg tccactcagc caccagggtc tttgggagtt tgtatcaggc ccagaacagg  540
cggtggtcta acactagtct caaagtcatg gatgtggacg cgggagaccg cgaaacagtt  600
cacccactgg tggttacaca cccgggcagt ggaagaaagg gcctgtatgt gaatcaagtt  660
tactgccagc gcattgaagg gatgaccgac gcggagtcga agccattgct gcaattcttg  720
tatgagcacg cgacacggtt cgactttact tgcagggtga gatggaagaa ggaccaggtg  780
ctggtctggg ataatctgtg caccatgcac cgtgctgtcc cagactatgc cggcaagttc  840
cggtacctta ccaggactac cgttggagga gtgaggcctg ctaggtga              888

SEQ ID NO: 113          moltype = DNA  length = 888
FEATURE                 Location/Qualifiers
source                  1..888
                        mol_type = other DNA
                        organism = synthetic construct
CDS                     1..888
                        protein_id = 110
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHMDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
```

LTRTTVGGVRPAR
SEQUENCE: 113
atgcatgctg ctctaagtcc actgtcacaa cgctttgaac gcatcgcggt gcagcccctc 60
actggtgtat taggagcgga aataaccgga gtagacttac gagaaccctt ggatgattct 120
acatggaatg agatcctcga tgcattccat acttaccagg tgatatactt ccccggacag 180
gccataacaa acgaacagca tatcgccttc tccaggcgct ttggacccgt cgatccagtc 240
ccgcatctta agagcatcga aggataccct gaagtgcaaa tgattcgccg cgaggcaaac 300
gaatccctga gagtaattgg agacgattgg catactgact ctaccttcct tgacgctccc 360
cccgcagctg ttgtaatgag agcgatagac gtccccgaac atgggggcga cactggcttt 420
ttgtcaatgt acacagcgtg ggaaacttta tcacctacta tgcaagcaac tattgaaggt 480
ctcaacgtag tccactctgc cacaagggta tttggatcac tataccaagc acaaaatcgc 540
cgctggagca acacctcgct taaggtgatg gatgttgatg ccggagatcg tgaaacggta 600
catcccctgg ttgtgactca cccagggtcg ggcaggaaag gcctttacgt caatcaggtt 660
tactgtcaac ggatagaagg aatgacggac gcagagtcga aaccactttt gcaattctta 720
tatgagcatg ccaccaggta tgatttcaca tgccgcgttc gctggaagaa agatcaggtg 780
ttggtttggg acaacctctg cacaatgcat agggccgtac cggattatgc gggaaaattt 840
cgttacctaa cgcgaacaac ggtgggggga gtacgccctg cgagatga 888

SEQ ID NO: 114 moltype = AA length = 295
FEATURE Location/Qualifiers
source 1..295
mol_type = protein
organism = synthetic construct
SEQUENCE: 114
MHAALSPLSQ RFERIAVQPL TGVLGAEITG VDLREPLDDS TWNEILDAFH TYQVIYFPGQ 60
AITNEQHIAF SRRFGPVDPV PHLKSIEGYP EVQMIRREAN ESLRVIGDDW HTDSTFLDAP 120
PAAVVMRAID VPEHGGDTGF LSMYTAWETL SPTMQATIEG LNVVHSATRV FGSLYQAQNR 180
RWSNTSLKVM DVDAGDRETV HPLVVTHPGS GRKGLYVNQV YCQRIEGMTD AESKPLLQFL 240
YEHATRYDFT CRVRWKKDQV LVWDNLCTMH RAVPDYAGKF RYLTRTTVGG VRPAR 295

SEQ ID NO: 115 moltype = DNA length = 888
FEATURE Location/Qualifiers
source 1..888
mol_type = other DNA
organism = synthetic construct
CDS 1..888
protein_id = 114
transl_table = 1
translation = MHAALSPLSQRFERIAVQPLTGVLGAEITGVDLREPLDDSTWNEIL
DAFHTYQVIYFPGQAITNEQHIAFSRRFGPVDPVPHLKSIEGYPEVQMIRREANESLRV
IGDDWHTDSTFLDAPPAAVVMRAIDVPEHGGDTGFLSMYTAWETLSPTMQATIEGLNVV
HSATRVFGSLYQAQNRRWSNTSLKVMDVDAGDRETVHPLVVTHPGSGRKGLYVNQVYCQ
RIEGMTDAESKPLLQFLYEHATRYDFTCRVRWKKDQVLVWDNLCTMHRAVPDYAGKFRY
LTRTTVGGVRPAR
SEQUENCE: 115
atgcacgcag ctctgtcccc gctgtctcag cgttttgaac gtattgctgt tcaaccgctg 60
accggcgttc tgggcgcaga aattaccggc gtagacctgc gtgaaccgct ggatgatagc 120
acttggaacg agatcctgga tgcttttcac acctaccagg tgatctattt cccgggccag 180
gctattacca acgagcagca catcgcgttc tcccgtcgtt tcggtccggt agacccggtc 240
cctcacctga aatctatcga gggttatccg gaagttcaga tgatccgtcg tgaagcaaac 300
gaaagcctgc gcgtcatcgg cgatgactgg cataccgatt ctacttttct ggatgcaccg 360
ccagcagcgg tagttatgcg tgcgatcgat gtcccagaac acggtggtga taccggcttc 420
ctgtctatgt acaccgcttg ggagactctg tctcctacta tgcaggccac cattgaaggc 480
ctgaacgtgg tgcactccgc tactcgcgtt tttggctccc tgtaccaggc acagaaccgt 540
cgttggagca acacctccct gaaagtgatg gacgttgacg cgggtgatcg tgaaaccgtt 600
catccgctgg tcgtaactca cccaggttct ggtcgtaaag gcctgtacgt gaaccaggtg 660
tattgccagc gtatcgaagg catgaccgat gcagaatcta agccgctgct gcagttcctg 720
tacgaacacg cgacccgtta cgacttcact tgtcgtgtgc gttggaagaa agatcaggtc 780
ctggtttggg acaacctgtg caccatgcac cgtgcggtac cggactatgc gggtaaattc 840
cgttacctga cccgtactac cgtcggtggt gttcgtccgg cacgctaa 888

SEQ ID NO: 116 moltype = DNA length = 888
FEATURE Location/Qualifiers
source 1..888
mol_type = other DNA
organism = synthetic construct
CDS 1..888
protein_id = 114
transl_table = 1
translation = MHAALSPLSQRFERIAVQPLTGVLGAEITGVDLREPLDDSTWNEIL
DAFHTYQVIYFPGQAITNEQHIAFSRRFGPVDPVPHLKSIEGYPEVQMIRREANESLRV
IGDDWHTDSTFLDAPPAAVVMRAIDVPEHGGDTGFLSMYTAWETLSPTMQATIEGLNVV
HSATRVFGSLYQAQNRRWSNTSLKVMDVDAGDRETVHPLVVTHPGSGRKGLYVNQVYCQ
RIEGMTDAESKPLLQFLYEHATRYDFTCRVRWKKDQVLVWDNLCTMHRAVPDYAGKFRY
LTRTTVGGVRPAR
SEQUENCE: 116
atgcatgccg ctctcagtcc tttgagccaa cgcttcgaaa ggattgcggt ccaaccgctg 60
actggggttc tgggcgctga gatcacggga gttgatctcc gtgagcccct cgatgactcc 120
acatggaatg aaattcttga cgcgtttcac acgtaccaag tgatttattt ccccggccaa 180

-continued

```
gcgatcacaa atgaacagca catcgctttc tcaaggcggt tcgggcctgt tgacccagtg  240
ccccacttga agtcgattga gggctaccca gaagttcaga tgatcaggcg ggaagcgaac  300
gagtccctcc gcgtgatcgg cgatgattgg cataccgaca gcacattcct cgatgcgccc  360
ccagcagctg tcgtgatgcg ggccatcgac gtgccagaac atggcggtga caccgggttt  420
ctgtctatgt acacagcatg ggagactctt agccctacca tgcaggcgac tatcgagggc  480
ctgaacgtgg ttcactctgc cactagggtc ttcggcagcc tgtatcaggc gcaaaaccgt  540
cggtggagca acacgagtct taaggtcatg gacgtcgacg ccggggaccg cgagacggtt  600
cacccccttg ttgtgacaca tccaggctca ggcaggaagg gcttgtatgt gaaccaggtc  660
tactgccaaa ggatcgaagg aatgacagat gcggagtcga agccactcct ccaatttctg  720
tacgaacatg ccaccaggta cgatttcacc tgcagggtcc gctggaagaa ggaccaggtc  780
ctggtctggg ataacctctg caccatgcat cgggccgttc ccgactatgc aggcaaattt  840
cgctatctca cccgcactac tgtcggcggc gtccgcccgg ctagatga              888
```

```
SEQ ID NO: 117          moltype = DNA  length = 888
FEATURE                 Location/Qualifiers
source                  1..888
                        mol_type = other DNA
                        organism = synthetic construct
CDS                     1..888
                        protein_id = 114
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRYDFTCRVRWKKDQVLVWDNLCTMHRAVPDYAGKFRY
                         LTRTTVGGVRPAR
SEQUENCE: 117
atgcatgcgg ccctgtcacc gctttcacaa agattcgaaa gaatcgcagt ccagccgtta  60
actggagtcc taggcgcgga aattactggc gtggacttgc gtgagccctt ggacgactcg  120
acctggaatg aaattttaga cgcgtttcac acatatcagg taatctactt ccctggtcaa  180
gcaattacga atgagcaaca cattgctttt tctcgccggt ttggtcctgt tgatcctgta  240
ccccatctaa aatcaattga ggggtacccg gaagtgcaga tgatccggag agaagcgaac  300
gaatcgttgc gagtaattgg agatgactgg cacacggact ccacgttcct agatgcccca  360
ccagctgcgg tagttatgcg agcaattgat gtaccagagc acggcgggga cacgggtttc  420
ctttcgatgt atacagcttg ggaaacgttg agtcctacga tgcaagcaac gatcgaagga  480
ttaaacgtcg tgcattcagc cacacgcgtc ttcggatcgc tgtaccaggc ccaaaacaga  540
cgttggtcaa acacttccct gaaggttatg gacgtagatg cgggtgacag ggagactgtg  600
cacccattag tagtaaccca cccagggtcg ggcgcaaag gactgtatgt taatcaagtt  660
tattgccaga gaattgaagg gatgaccgac gccgaatcga aacctctctt gcagttcttg  720
tacgagcacg ctacccgcta cgacttcacg tgccgtgttc gctggaagaa ggatcaggta  780
ttggtttggg acaatttgtg tactatgcat cgggcagtcc cggattacgc gggcaaattt  840
cgatacctaa ctagaacgac agttggtggg gttcggccag cgagatga              888
```

```
SEQ ID NO: 118          moltype = AA  length = 295
FEATURE                 Location/Qualifiers
source                  1..295
                        mol_type = protein
                        organism = synthetic construct
SEQUENCE: 118
MHAALSPLSQ RFERIAVQPL TGVLGAEITG VDLREPLDDS TWNEILDAFH TYQVIYFPGQ  60
AITNEQHIAF SRRFGPIDPV PHLKSIEGYP EVQMIRREAN ESGGVIGDDW HTDSTFLDAP  120
PAAVVMRAID VPEHGGDTGF LSMYTAWETL SPTMQATIEG LNVVHSATRV FGSLYQAQNR  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295
```

```
SEQ ID NO: 119          moltype = DNA  length = 888
FEATURE                 Location/Qualifiers
source                  1..888
                        mol_type = other DNA
                        organism = synthetic construct
CDS                     1..888
                        protein_id = 118
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPIDPVPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 119
atgcatgctg cactgtcccc gctgagccaa cgtttcgaac gtattgcggt acagccgctg  60
accggtgttc tgggtgctga aatcactggt gtggacctgc gtgaaccgct ggacgactct  120
acttggaacg aaatcctgga tgccttccac acttatcagg tgatctactt tccgggtcag  180
gctatcacca acgaacagca tatcgctttt tctcgtcgtt tcggtccgat cgatccggtg  240
ccgcacctga aatctattga gggttatcct gaagtacaga tgattcgtcg tgaagctaac  300
gaatccggcg gcgttattgg tgatgattgg cacacggaca gcaccttcct ggatgctccg  360
ccggccgctg ttgttatgcg tgcaatcgat gtaccagaac acggcggtga cacgggcttc  420
ctgtccatgt acactgcgtg ggaaacgctg agcccgacca tgcaggcaac cattgaaggc  480
```

-continued

```
ctgaacgttg tccactccgc tacccgtgta ttcggttctc tgtaccaggc gcaaaaccgt  540
cgttggtcta acacctccct gaaagtgatg gacgtagatg cgggcgatcg tgaaactgtc  600
cacccgctgg tagtaaccca ccctggctct ggtcgtaaag gtctgtacgt caaccaggtt  660
tattgccaac gtattgaagg catgaccgat gcggaatcca aaccgctgct gcagttcctg  720
tacgaacacg cgactcgttt tgactttacc tgccgcgtcc gttggaaaaa agatcaggtt  780
ctggtttggg ataacctgtg cactatgcat cgtgccgttc cggattacgc tggtaaattt  840
cgctacctga ctcgtaccac tgtgggtggc gtacgtccgg ctcgttaa              888

SEQ ID NO: 120          moltype = DNA  length = 888
FEATURE                 Location/Qualifiers
source                  1..888
                        mol_type = other DNA
                        organism = synthetic construct
CDS                     1..888
                        protein_id = 118
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPIDPVPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 120
atgcatgctg cgttgtcccc ccttagccag cggtttgaga gaatagccgt tcagcctttg  60
actggggtgc tcggagccga gatcaccggc gtcgacctcc gcgagcctct ggacgacagc  120
acgtggaacg agatcctcga cgccttccac acataccaag ttatctactt tccggggcag  180
gctattacaa acgagcaaca catcgctttt tcgaggaggt ttggccccat agatccagtc  240
ccacacctca agagcatcga gggataccca gaggtgcaga tgatccgtag ggaagccaac  300
gagtcgggtg gagtcatcgg cgacgactgg cataccgatt cgacgtttct cgatgcgcct  360
cctgccgcag ttgtcatgcg ggcaatcgac gtcccggagc acggcggcga tacaggtttc  420
ttgagcatgt acaccgcctg ggagactctg tcccctacga tgcaggccac tatcgaaggc  480
ctgaacgtgg tgcatagcgc caccagggtt tttggcagct tgtaccaagc acagaacaga  540
agatggtcta acacttcgct caaggtcatg gacgtggatg ccggcgatag ggagactgtg  600
cacccgctcg tcgtcactca cccgggctca ggtaggaagg gtctgtacgt taaccaggtg  660
tactgccagc gcatcgaagg catgacggac gctgagtcaa aaccccttct gcaattcctc  720
tacgaacatg ccacaaggtt tgacttcaca tgtcgggttc gctggaagaa ggatcaggtt  780
cttgtctggg acaatctgtg tacgatgcat agggccgtgc cggattacgc cggcaagttt  840
cgctatctca caaggactac cgtcggcggc gttaggcctg cccgctga              888

SEQ ID NO: 121          moltype = DNA  length = 888
FEATURE                 Location/Qualifiers
source                  1..888
                        mol_type = other DNA
                        organism = synthetic construct
CDS                     1..888
                        protein_id = 118
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPIDPVPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 121
atgcacgctg cactctcacc tctctcccaa cgttttgaga ggattgctgt gcaaccgctt  60
accggcgtac tcggtgctga aattaccggc gttgatctca gggagcctct tgacgattct  120
acatggaacg aaattctcga tgccttccat acttatcagg tcatctattt cccaggccaa  180
gctataacca atgaacagca tattgctttc agccgtaggt tcggtcctat tgaccctgtt  240
cctcatctca aatcaataga ggggtatcct gaagtccaaa tgattagaag ggaagccaac  300
gaaagcggtg gtgtgatcgg tgatgattgg cataccgata gcaccttctt ggatgcccct  360
cctgcagctg ttgtaatgcg agcaatcgac gttcccgaac atggcggaga caccggcttc  420
ctttctatgt acacagcttg ggaaactctt tcaccaacta tgcaagcaac tatagaagga  480
cttaacgttg ttcattcagc tactagggtt ttcggatcac tctatcaagc tcagaatcgt  540
agatggagta acactagcct taaagtcatg gatgtagacg ctggagacag ggagactgtt  600
catcctctcg ttgttactca ccctgggagc ggtagaaaag ggctctatgt taaccaagtt  660
tattgccaga gaattgaggg aatgactgat gctgagtcaa aacctctctt acagtttttg  720
tatgagcatg ctacaaggtt tgacttcacc tgcagggttc gttggaagaa ggatcaagtt  780
cttgtatggg acaacttgtg caccatgcat cgagctgttc ccgattacgc aggcaagttt  840
cgttatttga cacgaacaac tgtcggcggt gttaggcctg caaggtga              888

SEQ ID NO: 122          moltype = AA  length = 295
FEATURE                 Location/Qualifiers
source                  1..295
                        mol_type = protein
                        organism = synthetic construct
SEQUENCE: 122
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESLGYIGDDW HTDSTFLDAP  120
PAAVVMRAID VPEHGGDTGF LSMYTAWETL SPTMQATIEG LNVVHSATRV FGSLYQAQNR  180
```

-continued

```
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 123          moltype = DNA  length = 888
FEATURE                 Location/Qualifiers
source                  1..888
                        mol_type = other DNA
                        organism = synthetic construct
CDS                     1..888
                        protein_id = 122
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLGY
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 123
atgcatgcag ctctgtcccc gctgagccag cgttttgaac gtattgctgt gcaaccgctg  60
accggcgtac tgggtgctga aattactggt gttgatctgc gtgaaccgct ggatgactct  120
acctggaacg agatcctgga cgcgttccac acctatcagg ttatctattt cccgggccag  180
gcaattacca acgaacagca catcgcattt tctcgtcgtt tcggtccggt tgatccggtt  240
ccacacctga aatctatcga gggctacccg gaggtccaga tgatccgccg tgaagctaac  300
gagagcctgg gctacatcgg tgatgactgg catacggatt ctacctttct ggatgcaccg  360
ccggctgctg ttgttatgcg tgccatcgat gtccctgagc acggtggcga cactggtttc  420
ctgtctatgt acaccgcgtg ggaaactctg agcccgacga tgcaggctac tattgaaggt  480
ctgaacgtag tacacagcgc tacccgtgtg ttcggttctc tgtatcaggc tcagaaccgt  540
cgttggtcca acacctccct gaaagtcatg gacgttgacg ccggtgaccg tgaaaccgtt  600
catccgctgg tagtcaccca cccgggttct ggtcgtaaag gcctgtatgt taaccaggtg  660
tactgccagc gtatcgaggg catgaccgac gctgaaagca agccgctgct gcagttcctg  720
tatgagcacg caacccgttt tgactttacc tgccgtgttc gctggaaaaa ggatcaggta  780
ctggtgtggg ataacctgtg taccatgcac cgtgctgttc ctgactacgc gggcaaattc  840
cgttacctga cccgtactac cgttggtggt gttcgtccag ctcgttaa              888

SEQ ID NO: 124          moltype = DNA  length = 888
FEATURE                 Location/Qualifiers
source                  1..888
                        mol_type = other DNA
                        organism = synthetic construct
CDS                     1..888
                        protein_id = 122
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLGY
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 124
atgcatgcag ccctgagccc tctttcccag cgctttgaaa gaattgccgt gcagccgctg  60
accggcgtcc tgggggccga gatcacaggc gttgacctcc gcgagccctt ggatgacagc  120
acgtggaacg aaattcttga tgcattccat acctatcagg tcatctactt tccagggcaa  180
gctattacca acgagcagca catcgcattc tccagacgct tcggcccagt cgatccagtc  240
cctcacctta agagcataga agggtaccct gaggtccaaa tgattaggag agaggccaac  300
gaaagtcttg gctacatagg cgatgactgg cacacggaca gtacgttcct tgacgctcca  360
ccagctgcgg tcgtcatgag ggcgatcgac gttcccgagc acgggggtga taccgggttc  420
ctgtccatgt acactgcatg ggagacactt tctcccacca tgcaggcgac gatcgagggg  480
ctgaacgttg tccattccgc tactcgcgtt ttcggctctc tctaccaggc acaaaaccgg  540
cgctggtcca acacaagcct caaggtgatg gacgtggatg ctggcgaccg ggaaacggtt  600
cacccccttgg ttgttactca cccggggtct ggcagaaagg gtctctacgt gaaccaggtg  660
tactgccaaa gaattgaggg tatgactgat gcagagtcga agcccttgct gcaattcctg  720
tacgaacacg ccaccagatt cgatttcacc tgtcgggtga gatggaagaa agaccaagtg  780
ctggtgtggg acaacctctg cacgatgcat cgcgcggttc cagactacgc aggcaagttc  840
cgctacctta ccagaactac cgtcgggggt gtgaggccgg cccgctga              888

SEQ ID NO: 125          moltype = DNA  length = 888
FEATURE                 Location/Qualifiers
source                  1..888
                        mol_type = other DNA
                        organism = synthetic construct
CDS                     1..888
                        protein_id = 122
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLGY
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
```

-continued

```
SEQUENCE: 125
atgcatgcgg cattatcccc gcttagccag aggtttgaaa gaatcgcagt gcagccctta  60
actggggttt taggcgcgga gataaccgga gtggacctgc gtgaaccact tgacgattcc  120
acatggaatg agattcttga tgcattccac acataccaag taatttattt cccaggacag  180
gccataacga atgagcaaca tatcgcgttt tcacgcagat ttgggcccgt tgaccctgtc  240
cctcacttaa aatctattga ggggtaccct gaggtacaaa tgattcgtcg tgaagctaac  300
gaatcgctcg gctatatagg tgatgattgg cacacggatt ctacttttct ggatgctccg  360
ccggcggctg tagttatgag ggcaatcgac gtcccagaac acggaggcga cacagggttt  420
ttatccatgt atacggcatg ggaaacgtta tctcctacta tgcaggccac aatcgaaggg  480
ttgaacgttg tccattcagc gactcgtgtt tttggatcac tgtatcaagc tcagaatcgc  540
cgttggtcaa atacttcctt aaaagtcatg gacgttgatg ccggagatcg ggagaccgtt  600
cacccactag ttgtaaccca tccagggagc ggcaggaaag gattgtatgt aaatcaggta  660
tattgtcaac gcatagaggg tatgacagac gcggaatcca agcctctgct tcaatttttg  720
tatgaacatg ccacacgttt tgactttacg tgcagagtgc gctggaaaaa ggatcaggtc  780
ttagtgtggg ataatctctg cactatgcac cgtgcagtcc cagactatgc agggaaattt  840
agatatttga ccaggacaac tgtcggggga gtgcggccgg ctaggtga              888

SEQ ID NO: 126          moltype = AA  length = 295
FEATURE                 Location/Qualifiers
source                  1..295
                        mol_type = protein
                        organism = synthetic construct
SEQUENCE: 126
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGGVIGDDW HSDSTFLDAP  120
PAAVVMRAID VPEHGGDTGF LSMYTAWETL SPTMQATIEG LNVVHSATRV FGSLYQAQNK  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 127          moltype = DNA  length = 888
FEATURE                 Location/Qualifiers
source                  1..888
                        mol_type = other DNA
                        organism = synthetic construct
CDS                     1..888
                        protein_id = 126
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHSDSTFLDAPPAAVVMRAIDVPEHGGDTGFLSMYTAWETLSPTMQATIEGLNVV
                         HSATRVFGSLYQAQNKRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 127
atgcacgcag ctctgtctcc gctgtctcaa cgttttgaac gtatcgcagt tcagccgctg  60
accggtgttc tgggcgctga aattactggt gtggatctgc gcgaacctct ggacgattct  120
acctggaacg aaatcctgga cgcttttcat acctatcagg ttatctactt cccgggtcag  180
gcaatcacca acgaacagca catcgctttc tctcgtcgtt tcggtccggt tgacccggtg  240
ccacacctga aatccatcga aggttaccca gaagtacaga tgatccgtcg tgaagctaac  300
gaatctggtg gtgtaattgg cgacgattgg cattctgata gcactttcct ggatgctccg  360
ccggcggcag ttgttatgcg tgctatcgat gttccggaac atggcggcga cactggcttc  420
ctgtccatgt acactgcatg ggaaaccctg tctcctacta tgcaggcgac catcgaaggt  480
ctgaacgtgg tccactctgc cacccgtgtt ttcggttctc tgtatcaggc tcagaacaaa  540
cgttggagca acacttccct gaaagtgatg gacgttgacg cgggcgatcg tgaaactgtg  600
cacccgctgg ttgttaccca ccctggttct ggtcgcaaag gtctgtacgt taaccaggtt  660
tactgccagc gtatcgaagg tatgaccgac gcagagtcta aaccgctgct gcaattcctg  720
tacgaacacg cgacgcgttt cgactttacc tgccgcgtac gttggaaaaa agatcaggtt  780
ctggtatggg acaacctgtg caccatgcac cgtgcggttc cggattacgc aggtaaattc  840
cgttacctga cccgcactac tgtaggcggt gttcgcccgg cacgttaa              888

SEQ ID NO: 128          moltype = DNA  length = 888
FEATURE                 Location/Qualifiers
source                  1..888
                        mol_type = other DNA
                        organism = synthetic construct
CDS                     1..888
                        protein_id = 126
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHSDSTFLDAPPAAVVMRAIDVPEHGGDTGFLSMYTAWETLSPTMQATIEGLNVV
                         HSATRVFGSLYQAQNKRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 128
atgcacgccg ctttgtcacc gctgtcccaa agatttgaga ggattgcggt ccagcccctc  60
actggcgtgc tcggtgctga gatcacaggt gtggacctga gagagccgtt ggacgattcc  120
acttggaacg agatcctgga tgccttccat acctaccaag tcatatattt tcctggacaa  180
gccataacca acgagcagca catcgccttc agccgcaggt tcggccccgt ggatcccgtc  240
```

-continued

```
cctcatctca agtcgatcga aggataccca gaggttcaaa tgatcaggag ggaggcaaac  300
gagagtggcg gtgtcatcgg ggacgattgg catagcgact ctacgtttct ggacgctccc  360
cctgcagctg tggtcatgcg cgcaatagac gttccagaac acggcggcga cactggcttc  420
ctctcgatgt atacggcctg ggagactctc tcaccgacta tgcaggccac aatcgagggc  480
ctgaacgtcg tccactccgc caccgcgtc ttcggctctc tctatcaagc gcagaacaag  540
aggtggtcca acaccagcct gaaagtgatg gacgttgatg ccggtgatcg tgagacggtc  600
catccgcttg tggttacgca cccgggttcc ggccgcaagg gactctacgt gaatcaggtg  660
tactgtcaaa ggattgaggg catgaccgat gctgagtcga agccgctgtt gcaatttctg  720
tacgagcacg caacaagatt cgactttacc tgccgggttc ggtggaagaa ggaccaagtc  780
ttggtgtggg acaatttgtg taccatgcac cgggcagtcc cggattatgc cggtaagttt  840
cgctatctga caagaactac cgtcggcgga gtccggccag ctcgctga               888

SEQ ID NO: 129          moltype = DNA  length = 888
FEATURE                 Location/Qualifiers
source                  1..888
                        mol_type = other DNA
                        organism = synthetic construct
CDS                     1..888
                        protein_id = 126
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHSDSTFLDAPPAAVVMRAIDVPEHGGDTGFLSMYTAWETLSPTMQATIEGLNVV
                         HSATRVFGSLYQAQNKRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 129
atgcatgctg cgttgtcccc tctgagtcaa cgctttgaac gaattgcggt tcagccattg  60
actggggtgt taggagcgga aattacgggc gttgatcttc gtgaaccttt ggacgacagc  120
acgtggaacg aaattcttga cgctttccac acgtaccaag tgatctactt tcccgggcag  180
gcaattacta atgagcagca tattgcattc tcgcgtcgat tcggacccgt cgatcccgtt  240
cctcatctca aatctattga aggctacccg gaagtccaga tgattagaag agaggcaaat  300
gagtcgggag gtgtaatcgg ggacgactgg cactctgact ccacttttct ggatgcaccc  360
cccgcagctg tagtgatgag ggccatagat gtcccggagc atggaggcga tactggtttc  420
ctatcgatgt acactgcgtg ggaaactctt agccccacca tgcaggcgac tattgaggga  480
ctaaatgtag tgcactcggc cacgcgggta ttcggatcct tatatcaagc gcaaaataaa  540
cgatggagta atacaagcct gaaagttatg gatgtagatg ctggagacag ggagactgtg  600
cacccttag ttgttactca tccaggaagt gggcggaagg gcctttatgt taatcaagtg  660
tattgtcaaa gaatcgaagg aatgactgat gccgaatcta agccattgtt gcagttcctg  720
tatgaacacg ccacgcgttt cgatttcaca tgccgggtga gatggaagaa ggaccaggta  780
ttagtgtggg ataacctgtg cacgatgcat cgtgctgtcc ctgactatgc aggcaaattt  840
cgctacctaa ctcgaactac tgtaggaggg gtaagacccg cgaggtga               888

SEQ ID NO: 130          moltype = AA  length = 295
FEATURE                 Location/Qualifiers
source                  1..295
                        mol_type = protein
                        organism = synthetic construct
SEQUENCE: 130
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGGVIGDDW HSDSTFLDAP  120
PAAVVMRAID VPEHGGDTGF LSMYTAWETL SPTMQATIEG LNVVHSATRV FGSLYQAQNM  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 131          moltype = DNA  length = 888
FEATURE                 Location/Qualifiers
source                  1..888
                        mol_type = other DNA
                        organism = synthetic construct
CDS                     1..888
                        protein_id = 130
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHSDSTFLDAPPAAVVMRAIDVPEHGGDTGFLSMYTAWETLSPTMQATIEGLNVV
                         HSATRVFGSLYQAQNMRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 131
atgcatgctg ccctgtctcc tctgtcccag cgtttcgaac gtattgctgt acagccgctg  60
accggtgttc tgggcgcaga aattactggc gtcgatctgc gtgaaccgct ggatgactcc  120
acctggaacg aaatcctgga tgcattccat acttatcagg tcatctattt cccgggccag  180
gcgattacca acgaacagca catcgccttt tctcgccgtt ttggtccggt tgatccggtg  240
ccgcacctga aaagcatcga aggttacccg gaagtgcaga tgatccgtcg tgaagcaaac  300
gaatctggcg gcgtgatcgg tgacgattgg cactctgatt ctaccttcct ggatgctccg  360
ccggcggctg tagttatgcg tgctattgac gttccggaac atggtggtga caccggtttc  420
ctgtccatgt acaccgcttg ggaaacgctg tctccgacca tgcaggccac catcgaaggt  480
ctgaacgtcg tgcacagcgc gactcgtgtg ttcggcagcc tgtatcaagc ccagaacatg  540
```

```
cgctggtcta acaccagcct gaaagtgatg gacgttgacg caggtgaccg tgaaaccgtt  600
catccactgg ttgttaccca tccgggtagc ggtcgcaaag gcctgtacgt aaatcaagtc  660
tactgccagc gcatcgaggg tatgaccgac gcagaatcca aaccgctgct gcagttcctg  720
tacgaacacg cgacccgctt tgatttcacc tgccgtgtac gttggaaaaa ggaccaagta  780
ctggtgtggg acaacctgtg caccatgcac cgtgccgttc cggactacgc aggtaaattc  840
cgttacctga ctcgtactac tgttggtggt gtacgtccgg ctcgttaa              888

SEQ ID NO: 132          moltype = DNA  length = 888
FEATURE                 Location/Qualifiers
source                  1..888
                        mol_type = other DNA
                        organism = synthetic construct
CDS                     1..888
                        protein_id = 130
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHSDSTFLDAPPAAVVMRAIDVPEHGGDTGFLSMYTAWETLSPTMQATIEGLNVV
                         HSATRVFGSLYQAQNMRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 132
atgcatgcgg ccctctcccc actgtcgcaa agatttgaaa gaatcgctgt gcaacccctg  60
acaggcgtgc tgggagctga gattactggg gttgacctcc gggaacccct ggatgactca  120
acctggaatg aaattttgga tgcgttccac acctatcagg tcatctactt cccgggccag  180
gcgattacta atgagcaaca catcgccttt tcacgcaggt ttggaccagt cgaccctgtc  240
cctcacctca aaagcatcga gggataccca gaggttcaaa tgatccggag ggaggccaat  300
gagtctggcg gcgttatcgg cgacgattgg cactcggatt cgactttcct cgatgcgcct  360
ccagccgccg tggtgatgag ggctatcgac gtgcctgagc acgggggcga caccggcttc  420
ctcagcatgt atactgcttg ggagacgctg tcccctacca tgcaggctac tatcgaaggc  480
ctgaacgttg tgcactccgc aacccgcgtt tttgggagcc tgtaccaggc ccagaacatg  540
aggtggagca atacttcact gaaggttatg gatgtcgacg ctggggacag ggagacagtg  600
catccactcg tcgtcacaca tccggggtcg ggccgcaaag gcctttacgt taaccaagtt  660
tactgccaac ggattgaggg catgacggac gccgaatcta agcccctgct tcaattcttg  720
tacgagcacg ctaccaggtt tgactttaca tgccgcgtcc gctggaaaaa ggatcaggtg  780
ctcgtgtggg ataacctttg tacaatgcac cgcgctgtgc cagattacgc aggcaagttc  840
aggtacctca cacgcaccac ggtcggcggg gtgaggccag ccagatga              888

SEQ ID NO: 133          moltype = DNA  length = 888
FEATURE                 Location/Qualifiers
source                  1..888
                        mol_type = other DNA
                        organism = synthetic construct
CDS                     1..888
                        protein_id = 130
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHSDSTFLDAPPAAVVMRAIDVPEHGGDTGFLSMYTAWETLSPTMQATIEGLNVV
                         HSATRVFGSLYQAQNMRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 133
atgcacgcag cgcttagccc attgtcccag cgttttgaga gaatagcagt acagcccttg  60
actggagttc taggcgcaga aatcacaggg gtcgatcttc gcgaaccgct agatgattcc  120
acatggaatg agatcctgga cgcattccac acttatcaag tgatctattt tccgggtcag  180
gcaatcacta acgaacaaca cattgctttt tcgcgtagat ttggcccggt tgatcctgtg  240
ccgcatctca aatctataga aggatacccg gaggttcaga tgattagacg ggaagccaac  300
gagtctggtg gggttattgg ggatgactgg cattctgata gcacctttct ggatgcacct  360
ccagcagcag ttgtaatgcg ggccatagac gtcccggaac acggaggaga tactggtttc  420
ttgtcaatgt acaccgcatg ggaaaccttg tccccaacga tgcaagcgac aattgaaggc  480
ctcaatgtcg ttcactcagc aacaagggtt ttcggttcgc tctaccaggc ccaaaacatg  540
agatggagta acacttcgct taaagtgatg gacgtagacg caggtgaccg ggaaacagta  600
cacccgctgg tcgtcactca tcctgggtca ggtcgtaaag gactgtatgt aaaccaagta  660
tattgccagc gcattgaggg aatgacggat gcagagtcaa agcctctatt acagttttta  720
tacgagcacg cgacacgatt tgacttcact tgtcgagtac gttggaaaaa ggatcaagta  780
ctcgtttggg ataacttatg caccatgcat cgtgcggtcc ctgattatgc cgggaagttt  840
cgctatctaa ctagaaccac tgtcggtgga gttagacctg cgagatga              888

SEQ ID NO: 134          moltype = AA  length = 295
FEATURE                 Location/Qualifiers
source                  1..295
                        mol_type = protein
                        organism = synthetic construct
SEQUENCE: 134
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGGVIGDDW HSDSTFLDAP  120
PAAVVMRAID VPEHGGDTGF LSMYTAWETL SPTMQATIEG LNVVHSATRV FGSLYQAQNW  180
RWSNTSLKVM DVDAGDRETV HPLVVTHPGS GRKGLYVNQV YCQRIEGMTD AESKPLLQFL  240
```

-continued

```
YEHATRFDFT CRVRWKKDQV LVWDNLCTMH RAVPDYAGKF RYLTRTTVGG VRPAR       295

SEQ ID NO: 135         moltype = DNA  length = 888
FEATURE                Location/Qualifiers
source                 1..888
                       mol_type = other DNA
                       organism = synthetic construct
CDS                    1..888
                       protein_id = 134
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHSDSTFLDAPPAAVVMRAIDVPEHGGDTGFLSMYTAWETLSPTMQATIEGLNVV
                        HSATRVFGSLYQAQNWRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 135
atgcatgccg cactgtctcc gctgtctcag cgttttgaac gcattgcggt acagccgctg  60
actggcgtgc tgggtgctga aatcaccggt gttgatctgc gcgaacctct ggacgattcc  120
acctggaacg aaatcctgga cgcgttccac acctaccaag ttatttactt cccgggccag  180
gcaatcacca atgaacagca catcgctttc tctcgtcgct ttggtccggt tgacccggtt  240
ccgcacctga aatccatcga aggctacccg gaggtgcaga tgatccgtcg cgaagcgaac  300
gaatctggtg gtgttatcgg cgatgactgg catagcgata gcacttttct ggatgctcct  360
ccggctgcag tcgttatgcg cgctatcgac gtcccggaac acggtggtga tactggtttc  420
ctgagcatgt acaccgcgtg ggagactctg tctcctacca tgcaggccac catcgaaggc  480
ctgaacgtgg ttcattccgc gacccgtgta tttggttccc tgtaccaggc gcagaactgg  540
cgttggtcca acacttccct gaaagttatg gatgttgatg caggcgaccg tgaaaccgta  600
catccgctgg tggttaccca cccgggttct ggtcgtaaag gtctgtacgt taaccaggtg  660
tattgccagc gcatcgaagg catgactgac gctgaatcca aacctctgct gcagttcctg  720
tatgaacacg cgacccgctt cgattttacc tgccgtgtgc gttggaaaaa ggaccaggta  780
ctggtgtggg acaacctgtg taccatgcac cgtgctgttc cggactatgc gggtaaattc  840
cgttacctga cccgtaccac cgttggcggt gtacgtccag ctcgctaa              888

SEQ ID NO: 136         moltype = DNA  length = 888
FEATURE                Location/Qualifiers
source                 1..888
                       mol_type = other DNA
                       organism = synthetic construct
CDS                    1..888
                       protein_id = 134
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHSDSTFLDAPPAAVVMRAIDVPEHGGDTGFLSMYTAWETLSPTMQATIEGLNVV
                        HSATRVFGSLYQAQNWRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 136
atgcacgctg cactttcacc tctgagccag aggttcgaga gaattgcggt gcaacccctc  60
accggcgtct tgggtgccga gattacgggc gtcgacctta gagaaccact ggatgactct  120
acatggaacg aaatcctgga tgcctttcac acataccagg ttatctattt tccaggacag  180
gcaatcacta acgaacagca catagcgttc tctagacgct tcggccccgt ggacccagtg  240
ccgcatctga agagcataga aggttaccca gaggtgcaga tgattcgccg cgaggctaat  300
gaaagtgggg gcgtgattgg ggacgactgg cattcggatt ccacgttcct ggatgcgcca  360
ccggccgctg tcgtgatgag agcgatagac gtgccagaac acggtggcga cacggggttc  420
ctcagcatgt atacggcttg ggagaccctc agccccacca tgcaggccac gatcgagggc  480
ttgaacgttg tccatagcgc tacacgcgtg ttcggcagtc tctaccaggc gcagaactgg  540
aggtggtcta atacatcact caaggtcatg gatgtcgatg cgggggatcg cgaaacagtg  600
cacccgctcg ttgttaccca tccgggcagc ggtagaaagg gcctgtatgt caaccaagtt  660
tactgccaaa gaatcgaagg aatgacggat gcggaatcca agcctttgct ccagttcctg  720
tacgaacatg ctactcgctt tgactttaca tgccgcgtgc gctggaagaa ggatcaggtg  780
ctcgtctggg ataacctgtg tacgatgcat cgggctgtgc cggattacgc gggcaagttt  840
cgctacctga cgcggactac agtgggcggc gtgcgccctg cgcggtga              888

SEQ ID NO: 137         moltype = DNA  length = 888
FEATURE                Location/Qualifiers
source                 1..888
                       mol_type = other DNA
                       organism = synthetic construct
CDS                    1..888
                       protein_id = 134
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHSDSTFLDAPPAAVVMRAIDVPEHGGDTGFLSMYTAWETLSPTMQATIEGLNVV
                        HSATRVFGSLYQAQNWRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 137
```

-continued

```
atgcatgcgg cccttagtcc attatctcaa cggtttgaaa ggattgcagt acagcctctc  60
acgggcgtac taggggctga gataacaggt gtagatttgc gagagccact cgacgactcc  120
acatggaacg aaatactcga cgcatttcat acatatcaag tgatttattt ccctggtcaa  180
gcgatcacaa acgaacagca tatagctttc tccagacggt tcggcccagt ggacccagtg  240
ccccacttaa agtccattga aggctatccc gaagtccaga tgattagacg cgaggccaat  300
gagtctgggg gagtgatcgg ggatgactgg cattctgact cgacctttct ggacgccccg  360
ccagccgccg ttgtgatgcg tgctatcgat gtccctgaac atggaggcga caccgggttt  420
ctctctatgt atacggcctg ggaaactctg agcccgacga tgcaagcgac aatagaaggg  480
ctaaacgtcg tacactcagc gacaagggtt tttgggtccc tttaccaagc acaaaattgg  540
cgatggtcta ataccagttt aaaagtaatg gatgtcgatg cgggagatcg tgaaacagtc  600
cacccccctgg tggtaactca tcctggcagt ggtagaaaag gcctatatgt gaatcaggtc  660
tactgccaaa gaatagaggg gatgacagat gctgagagca aaccactatt acagttctta  720
tacgaacacg ccacgcgatt cgattttacc tgtcgcgttc gttggaaaaa agatcaggtg  780
ttagtttggg acaacctatg cactatgcac cgtgctgtac cggactatgc cggaaagttt  840
agatatctta cccgcacaac tgtcggagga gttcgtcccg ctcggtga             888

SEQ ID NO: 138          moltype = AA  length = 295
FEATURE                 Location/Qualifiers
source                  1..295
                        mol_type = protein
                        organism = synthetic construct
SEQUENCE: 138
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESLRVIGDDW HTDSTFLDAP  120
PAAVVMRAID VPEHGGDTGF LSMYTAWETL SPTMQATIEG LNVVHSATRV FGSLYQAQNT  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 139          moltype = DNA  length = 888
FEATURE                 Location/Qualifiers
source                  1..888
                        mol_type = other DNA
                        organism = synthetic construct
CDS                     1..888
                        protein_id = 138
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHTDSTFLDAPPAAVVMRAIDVPEHGGDTGFLSMYTAWETLSPTMQATIEGLNVV
                         HSATRVFGSLYQAQNTRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 139
atgcacgctg ctctgagccc tctgtctcag cgttttgaac gcattgcggt gcagccgctg  60
accggtgtcc tgggtgcaga gatcaccggt gtagacctgc gtgaaccact ggatgatagc  120
acctggaatg aaatcctgga tgcgtttcat acctatcagg ttatctactt cccgggtcag  180
gcgatcacta acgaacagca catcgcgttc tctcgccgct tcggcccggt agatccggtc  240
ccgcatctga aatctattga aggctaccct gaggttcaga tgatccgccg tgaagctaac  300
gaaagcctgc gcgtcatcgg tgacgactgg cacaccgatt ccaccttcct ggacgcgcca  360
ccggcggctg tggtaatgcg cgcaattgac gtgccggagc atggtggtga caccggtttc  420
ctgtctatgt acaccgcttg ggaaaccctg agcccgacta tgcaggcaac tatcgaaggt  480
ctgaatgtgg tacatagcgc gactcgtgtg ttcggtagcc tgtaccaggc ccagaacacc  540
cgctggagca acacgtccct gaaagttatg gatgtagacg caggtgaccg tgaaaccgtt  600
cacccgctgg tagtgaccca cccgggctct ggtcgcaagg gtctgtatgt taaccaggtg  660
tactgtcagc gtattgaagg catgaccgat gcggaatcca agccgctgct gcagtttctg  720
tatgaacatg cgacccgttt cgattttacc tgccgtgtcc gttggaaaaa agatcaggtg  780
ctggtttggg acaacctgtg caccatgcac cgtgctgttc cggattacgc tggtaaattc  840
cgttacctga cccgtactac cgtgggcggc gttcgcccgg ctcgctaa             888

SEQ ID NO: 140          moltype = DNA  length = 888
FEATURE                 Location/Qualifiers
source                  1..888
                        mol_type = other DNA
                        organism = synthetic construct
CDS                     1..888
                        protein_id = 138
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHTDSTFLDAPPAAVVMRAIDVPEHGGDTGFLSMYTAWETLSPTMQATIEGLNVV
                         HSATRVFGSLYQAQNTRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 140
atgcatgctg cactgagtcc tctctctcag cgttttgagc gcatcgcggt ccaacccctg  60
accggtgtcc tgggcgcgga gattaccggt gtcgacctgc gcgagcctct tgacgattcc  120
acatggaatg agatcctgga cgctttccat acttaccaag ttatatactt ccctggccag  180
gccatcacta acgagcaaca catcgctttc tcaaggcgct tcggaccagt cgacccggtg  240
ccgcatctga agtccataga ggggtatccg gaggtccaaa tgatcaggcg cgaagctaac  300
```

-continued

```
gagtcgctgc gcgtcatcgg tgacgactgg catacggaca gcaccttcct ggacgccccc  360
ccagccgccg ttgtgatgag ggcaatcgat gtgccagagc acggtggcga taccggtttc  420
ctttcgatgt acacagcatg ggagacgctg tccccgacca tgcaggcgac aatcgaggga  480
ttgaacgtgg tgcactccgc tacaagggtt ttcgggagtc tctaccaggc gcagaataca  540
aggtggtcaa atacgtcatt gaaggtgatg gacgtggacg ctggcgaccg ggagacggtt  600
catcccttgg ttgtcacgca cccaggctcg ggcaggaagg gcctgtacgt gaaccaggtg  660
tactgccaac gcatagaggg catgacagac gccgagtcta agcctctttt gcagtttctg  720
tacgagcacg caactcgttt cgacttcacc tgtcgcgtta ggtggaagaa agatcaggtt  780
ctcgtgtggg acaatctctg taccatgcac cgggctgttc ctgactacgc tgggaagttt  840
aggtatttga cacgtacgac agtcggcggg gtccggcccg ccagatga              888

SEQ ID NO: 141         moltype = DNA  length = 888
FEATURE                Location/Qualifiers
source                 1..888
                       mol_type = other DNA
                       organism = synthetic construct
CDS                    1..888
                       protein_id = 138
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESLRV
                        IGDDWHTDSTFLDAPPAAVVMRAIDVPEHGGDTGFLSMYTAWETLSPTMQATIEGLNVV
                        HSATRVFGSLYQAQNTRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 141
atgcacgctg cgctctcgcc attgagccag cgctttgaaa gaattgctgt acagccacta  60
acgggagtcc tgggggcgga aatcactgga gtagatctaa gagagccatt ggatgactcc  120
acttggaatg aaatattgga cgcgttccac acttaccagg taatttattt tcccggtcag  180
gcaatcacca acgaacaaca tattgctttt agcaggcgct ttggacctgt cgaccctgtt  240
cctcacttaa aatcaattga gggttatcca gaagttcaga tgatacggcg cgaagccaat  300
gaatcactaa gagtaattgg ggacgactgg cataccgaca gtacctttct tgacgcgccg  360
cctgcagccg tagtgatgag agccatcgat gtgccagaac acggtgggga tacgggcttc  420
ttatctatgt atacagcatg ggaaacgtta tcgccgacta tgcaggcgac aattgaaggc  480
cttaacgtgg ttcacagtgc aacacgggtg tttgggagtt tgtaccaagc acagaataca  540
agatggagca atacctcttt aaaggtaatg gatgttgatg ccggtgaccg tgagactgta  600
catccgctcg ttgtaactca ccccggaagt ggacgtaagg gtttatatgt taatcaggta  660
tattgccaac ggatagaagg catgactgat gctgaaagta aaccgctgct tcagttctta  720
tacgagcacg caacgcgttt tgatttcacc tgcagggtgc gttggaagaa agatcaggtc  780
ttggtctggg acaacctatg taccatgcac agagccgtgc ccgactacgc tggtaaattt  840
aggtatctca cgcgcactac tgtgggtgga gtgcgaccag cccgatga              888

SEQ ID NO: 142         moltype = AA  length = 295
FEATURE                Location/Qualifiers
source                 1..295
                       mol_type = protein
                       organism = synthetic construct
SEQUENCE: 142
MHAALSPLSQ RFERIAVQPL TGVLGAEITG VDLREPLDDS TWNEILDAFH TYQVIYFPGQ  60
AITNEQHIAF SRRFGPVDPV PHLKSIEGYP EVQMIRREAN ESGGVIGDDW HSDSTFLDAP  120
PAAVVMRAID VPEHGGDTGF LSMYTAWETL SPTMQATIEG LNVVHSATRV FGSLYQAQNQ  180
RWSNTSLKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 143         moltype = DNA  length = 888
FEATURE                Location/Qualifiers
source                 1..888
                       mol_type = other DNA
                       organism = synthetic construct
CDS                    1..888
                       protein_id = 142
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHSDSTFLDAPPAAVVMRAIDVPEHGGDTGFLSMYTAWETLSPTMQATIEGLNVV
                        HSATRVFGSLYQAQNQRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 143
atgcatgctg cactgagccc gctgtcccaa cgctttgaac gtattgctgt gcagccgctg  60
accggtgttc tgggtgctga gatcaccggt gttgatctgc gtgagcctct ggacgactct  120
acctggaacg aaatcctgga cgcttttcac acttaccaag ttatttactt cccaggtcag  180
gcgattacca acgaacagca catcgcgttc tctcgtcgtt tcggcccggt ggatcctgtt  240
ccgcatctga aatctattga aggttacccg gaggttcaaa tgatccgtcg cgaagccaac  300
gaatctggcg gtgttattgg tgacgattgg cacagcgact ctactttcct ggatgcgccg  360
ccagcagcag tagttatgcg tgctattgac gttccggaac atggtggcga caccggcttc  420
ctgagcatgt ataccgcctg ggaaactctg tctccgacta tgcaggcgac catcgaaggc  480
ctgaacgtgg ttcactctgc cacccgtgtg ttcggctctc tgtaccaggc gcagaaccag  540
cgttggtcca acacttctct gaaagttatg gacgttgacg cgggtgatcg tgaaaccgtt  600
```

```
cacccgctgg ttgtcacgca tccgggttcc ggtcgtaaag gtctgtacgt gaaccaagtt  660
tactgccagc gtatcgaagg tatgaccgac gcggaaagca aaccgctgct gcagtttctg  720
tatgagcacg cgacccgttt cgattttacc tgccgtgtac gttggaaaaa agaccaggtt  780
ctggtttggg acaacctgtg taccatgcac cgtgctgtgc cggattacgc cggcaaattc  840
cgttacctga ctcgtaccac tgttggtggc gttcgcccgg ctcgttaa              888

SEQ ID NO: 144         moltype = DNA  length = 888
FEATURE                Location/Qualifiers
source                 1..888
                       mol_type = other DNA
                       organism = synthetic construct
CDS                    1..888
                       protein_id = 142
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHSDSTFLDAPPAAVVMRAIDVPEHGGDTGFLSMYTAWETLSPTMQATIEGLNVV
                        HSATRVFGSLYQAQNQRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 144
atgcatgcag ccctgtcacc tctctcgcaa aggttcgaaa gaatcgcggt ccaacccctg  60
acaggcgttc tcggtgccga aattacgggc gttgacctgc gcgagccgct ggacgatagc  120
acatggaatg agattcttga tgccttccat acttaccaag tcatctactt cccgggccaa  180
gctatcacca acgaacaaca cattgcattc agtcggcggt tcggcccggt cgaccctgtg  240
ccacacctta agagcattga ggggtacccc gaggtgcaaa tgattcgcag ggaggccaat  300
gagtctgggg gggttatagg ggacgactgg cacagtgact ccaccttcct cgacgcgccg  360
cccgcagccg tggtgatgag ggctattgac gttccggagc acggggggga tacagggttc  420
ctgagcatgt acaccgcgtg ggagaccctg agtcccacga tgcaggccac tatcgagggg  480
ctcaatgtgg ttcactccgc aaccagggtg ttcggatccc tctaccaggc acagaaccag  540
cggtggtcca acacgtcgtt gaaggttatg gacgttgacg ccggcgacag ggaaactgtc  600
catccgttgg tggtcaccca tccgggctcc ggacggaagg gcttgtatgt caaccaggtg  660
tactgccaga ggattgaggg tatgaccgat gcggagtcga aaccacttct tcagttcctt  720
tacgaacacg ccaccaggtt tgactttaca tgtagggtgc gttggaagaa ggaccaagtc  780
ctggtctggg acaacctctg caccatgcac cgtgcagtcc cggactatgc aggcaagttc  840
aggtacctta cgagaacgac agtgggaggg gttagacctg ccaggtga              888

SEQ ID NO: 145         moltype = DNA  length = 888
FEATURE                Location/Qualifiers
source                 1..888
                       mol_type = other DNA
                       organism = synthetic construct
CDS                    1..888
                       protein_id = 142
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHSDSTFLDAPPAAVVMRAIDVPEHGGDTGFLSMYTAWETLSPTMQATIEGLNVV
                        HSATRVFGSLYQAQNQRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 145
atgcatgctg ctctttctcc tctttctcaa agattcgaaa gaattgctgt tcaacctctt  60
actggtgttc ttggtgctga aattactggt gttgatctta gagaacctct tgatgattct  120
acttggaatg aaattcttga tgctttccat acttatcaag ttatttattt ccctggtcaa  180
gctattacta atgaacaaca tattgctttc tctagaagat tcggtcctgt tgatcctgtt  240
cctcatctta agtctattga aggttatcct gaagttcaaa tgattagaag agaagctaat  300
gaatctggtg gtgttattgg tgatgattgg cattctgatt ctactttcct tgatgctcct  360
cctgctgctg ttgttatgag agctattgat gttcctgaac atggtggtga tactggtttc  420
ctttctatgt atactgcttg ggaaactctt tctcctacta tgcaagctac tattgaaggt  480
cttaatgttg ttcattctgc tactagagtt ttcggttctc tttatcaagc tcaaaatcaa  540
agatggtcta atacttctct taaggttatg gatgttgatg ctggtgatag agaaactgtt  600
catcctcttg ttgttactca tcctggttct ggtagaaagg gtctttatgt taatcaagtt  660
tattgtcaaa gaattgaagg tatgactgat gctgaatcta agcctcttct tcaattcctt  720
tatgaacatg ctactagatt cgatttcact tgtagagtta gatggaagaa ggatcaagtt  780
cttgtttggg ataatctttg tactatgcat agagctgttc ctgattatgc tggtaagttc  840
agatatctta ctagaactac tgttggtggt gttagacctg ctagatga              888

SEQ ID NO: 146         moltype = DNA  length = 888
FEATURE                Location/Qualifiers
source                 1..888
                       mol_type = other DNA
                       organism = synthetic construct
CDS                    1..888
                       protein_id = 2
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGRV
                        IGDDWHTDSTFLDAPPAAVVMRAIDVPEHGGDTGFLSMYTAWETLSPTMQATIEGLNVV
```

HSATRVFGSLYQAQNRRFSNTSVKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR

SEQUENCE: 146
```
atgcacgccg cacttagtcc acttagccaa agattcgaga gaatagccgt gcaacccctt  60
actggagtcc ttggtgctga gattacaggt gtcgatttga gagaaccttt ggatgattct  120
acatggaatg agatattgga tgccttccat acctatcagg taatttattt tcctggacag  180
gcaattacca atgagcagca tatagctttt tccagaaggt tcggccccgt tgatcccgtg  240
ccacacctta agtctattga gggttatcca gaagttcaga tgataagaag agaggccaat  300
gaaagtggga gggttatagg cgatgattgg cacactgatt ctacattcct cgatgcacca  360
cccgctgcag tcgttatgag agcaatcgac gttccagagc acgggggaga cacaggattc  420
ctgagcatgt ataccgcatg ggaaacattg tctcccacaa tgcaagccac aatagagggt  480
ttgaacgttg tccattctgc aactagagtg ttcggaagtc tttaccaagc tcaaaatcgc  540
aggttttcta atactagtgt taaagttatg gatgtggacg caggagatag ggaaacagta  600
cacccactcg tggttaccca tccagggtca ggaaggaagg gactttacgt taaccaggtc  660
tactgtcagc gtatcgaggg aatgactgat gcagagtcta agccattgct tcaatttctc  720
tatgagcacg ctactagatt tgattttaca tgtagggtta ggtggaagaa agaccaggtc  780
ttggtgtggg acaacctttg cacaatgcac cgcgcagtgc ctgattatgc tggaaagttc  840
cgctacctta cccgcacaac tgttggaggc gtcaggccag caagatga  888
```

SEQ ID NO: 147 moltype = DNA length = 888
FEATURE Location/Qualifiers
source 1..888
mol_type = other DNA
organism = synthetic construct
CDS 1..888
protein_id = 6
transl_table = 1
translation = MHAALSPLSQRFERIAVQPLTGVLGAEITGVDLREPLDDSTWNEIL
DAFHTYQVIYFPGQAITNEQHIAFSRRFGPVDPVPHLKSIEGYPEVQMIRREANESGRV
IGDDWHTDSTFLDAPPAAVVMRAIDVPEHGGDTGFLSMYTAWETLSPTMQATIEGLNVV
HSATRVFGSLYQAQNRRFSNTSLKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR SEQUENCE: 147
```
atgcacgcag cattgtctcc cctctctcaa aggttcgagc gcattgctgt ccaacccctt  60
acaggggttc tcggtgctga aattacagga gttgacctca gagagccact cgacgacagt  120
acctggaacg aaattctcga tgcctttcat acctatcagg tgatatattt cccaggtcag  180
gcaattacca acgagcagca tattgctttc tctagaaggt tcggaccagt ggatcctgtc  240
ccacatttga agagcattga ggggtaccct gaagttcaga tgatccgccg tgaagccaat  300
gagtcaggca gggtgatcgg tgatgactgg cataccgact caacctttct ggatgcccct  360
ccagctgctg ttgtcatgag agctattgat gtgcctgagc atggcggtga tactggtttt  420
cttagcatgt atactgcctg ggagaccctt tcaccaacca tgcaagctac aatcgaggga  480
cttaacgttg ttcatagtgc cactagggtg ttcggttccc tgtaccaggc acaaaacaga  540
aggttctcta acacatccct gaaagtaatg gatgtggatg caggtgacag agaaactgtg  600
cacccttttgg tggtgacaca tccaggatct ggacgtaagg gactttatgt caatcaagtg  660
tattgccaaa gaatagaagg gatgacagat gccgagagta agcctttgct ccaattcctg  720
tatgaacatg ctacccgttt tgactttaca tgccgtgtcc gttggaagaa ggatcaggtt  780
ttggtgtggg ataatttgtg tacaatgcat cgcgcagttc cagattatgc tggaaaattc  840
aggtatctca ccaggacaac agtaggcggg gttagacctg caaggtga  888
```

SEQ ID NO: 148 moltype = DNA length = 888
FEATURE Location/Qualifiers
source 1..888
mol_type = other DNA
organism = synthetic construct
CDS 1..888
protein_id = 10
transl_table = 1
translation = MHAALSPLSQRFERIAVQPLTGVLGAEITGVDLREPLDDSTWNEIL
DAFHTYQVIYFPGQAITNEQHIAFSRRFGPVDPVPHLKSIEGYPEVQMIRREANESGRV
IGDDWHTDSTFLDAPPAAVVMRAIDVPEHGGDTGFLSMYTAWETLSPTMQATIEGLNVV
HSATRVFGSLYQAQNRRFSNTSMKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR SEQUENCE: 148
```
atgcatgcag ctctttcccc actttcacaa agattcgaaa gaattgcagt tcaaccattg  60
acaggagtgc ttggcgcaga gatcactggt gtggatctta gggaaccact cgatgatagt  120
acctggaacg agattctcga cgccttccat acctaccagg tgatctactt ccccggacag  180
gcaatcacca acgagcaaca catcgctttt agtaggcgct tcggtcctgt cgacccagtc  240
ccccacctca agtcaattga ggggtaccct gaagtgcaga tgatcagaag agaagctaat  300
gaatctggac gtgttattgg tgacgattgg catacagact ctactttcct cgacgcacct  360
cctgccgcag ttgttatgag agctattgat gtacctgagc atggcggaga tactgggttc  420
ctttcaatgt atactgcatg ggaaacactt tctcctacta tgcaggctac tatcgaagga  480
ttgaatgttg ttcatagtgc cactagagtc tttggaagcc tttaccaagc ccaaaacagg  540
cgttttagca acacaagcat gaaggttatg gacgttgatg caggcgatcg cgaaacagtt  600
cacccattgg ttgttacaca tcctgggagc ggaaggaaag gtctctatgt caatcaggtt  660
tactgccaaa ggatcgaagg gatgacagat gcagagtcca agccactgct ccagttcctg  720
tacgagcacg ctacccgctt tgattttacc tgccgcgtta gatggaagaa ggatcaggtg  780
```

-continued

```
cttgtttggg acaatctttg tactatgcac cgcgctgtcc ccgattatgc aggcaagttc  840
agatacctga ctaggactac agttggtggg gtccgccccg ctagatga               888

SEQ ID NO: 149         moltype = DNA  length = 888
FEATURE                Location/Qualifiers
source                 1..888
                       mol_type = other DNA
                       organism = synthetic construct
CDS                    1..888
                       protein_id = 14
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGRV
                        IGDDWHTDSTFLDAPPAAVVMRAIDVPEHGGDTGFLSMYTAWETLSPTMQATIEGLNVV
                        HSATRVFGSLYQAQNRRFSNTSIKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 149
atgcacgctg ccctttctcc actttcacaa aggtttgaac gtattgctgt ccagcctttg  60
actggtgtgt tgggcgctga gattactgga gtcgatctta gggaacctct tgatgacagc  120
acatggaacg aaattttgga tgctttccat acatatcaag ttatctactt cccaggacag  180
gcaataacaa acgagcagca tattgcattt tctagaagat tcggaccagt ggacccagtt  240
cctcatttga aatcaataga ggggtaccca gaggtgcaga tgattaggcg cgaggcaaac  300
gaaagtggta gagttatagg tgacgattgg cacactgact ctacctttct tgacgcacca  360
ccagccgctg tcgtcatgag ggctattgac gtgccagaac acggaggaga tactggattc  420
ttgtctatgt acacagcttg ggagactctt agccccacta tgcaagccac tatcgaagga  480
ctgaacgtcg tgcacagcgc tacaagagtt tttggctccc tttatcaagc ccagaaccgc  540
agattcagta acactagtat taaggtgatg gacgttgatg ctggagatag agaaaccgtg  600
cacccattgg tggtcacaca tccaggaagt ggaaggaagg gactgtacgt aaaccaggtc  660
tattgtcaac gcattgaggg aatgactgat gcagagtcaa agcctctcct tcagtttctc  720
tacgaacacg ccaccaggtt cgatttcact tgtagggttc gctggaaaaa agaccaggtg  780
cttgtgtggg ataacttgtg tacaatgcat agggctgtcc cagattatgc cggtaagttc  840
aggtacctga ctcgcacaac tgttggagga gttaggcctg caagatga               888

SEQ ID NO: 150         moltype = DNA  length = 888
FEATURE                Location/Qualifiers
source                 1..888
                       mol_type = other DNA
                       organism = synthetic construct
CDS                    1..888
                       protein_id = 18
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGAV
                        IGDDWHTDSTFLDAPPAAVVMRAIDVPEHGGDTGFLSMYTAWETLSPTMQATIEGLNVV
                        HSATRVFGSLYQAQNRRFSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 150
atgcacgctg ctcttagccc ccttagtcaa agatttgaaa ggattgcagt tcaacctctc  60
acaggagtgc ttggtgccga gatcacaggt gtagacctca gggaacccct ggatgactct  120
acatggaacg aaatactcga tgccttccat acatatcaag tgatttactt tcctggtcag  180
gcaataacaa atgagcaaca tatagctttt agtaggcgct ttggaccagt ggacccagtg  240
ccacatctca agtccattga gggctaccca gaagtccaga tgataaggag agaggctaac  300
gaatccggag ctgttatagg ggatgactgg catactgata gtacatttct ggatgcacca  360
cccgctgcag ttgttatgag ggccatcgat gtgcctgaac acggcggtga caccgggttc  420
ttgagtatgt atacagcatg ggagactctt tctccaacta tgcaggcaac tatcgaaggg  480
cttaatgtgg ttcatagtgc aactagagtg ttcggatcct tgtatcaagc tcaaaataga  540
cgctttagta acacaagcct caaggttatg gacgtcgatg ccggagatag ggagaccgta  600
cacccactgg tcgtaactca tcccggcagt ggaagaaaag gtctctacgt taaccaagta  660
tactgccagc gtatagaagg aatgactgat gccgaatcaa aacctttgtt gcaattcctt  720
tatgagcacg ctacacgttt cgattttaca tgtagggtga gatggaaaaa agaccaggta  780
cttgtttggg ataacctctg cacaatgcat agagcagttc cagactatgc tgggaaattc  840
aggtacctca ctaggactac cgtcggcggt gtgagacctg ctcgctga               888

SEQ ID NO: 151         moltype = DNA  length = 888
FEATURE                Location/Qualifiers
source                 1..888
                       mol_type = other DNA
                       organism = synthetic construct
CDS                    1..888
                       protein_id = 22
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGDV
                        IGDDWHTDSTFLDAPPAAVVMRAIDVPEHGGDTGFLSMYTAWETLSPTMQATIEGLNVV
                        HSATRVFGSLYQAQNRRFSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
```

```
SEQUENCE: 151
atgcatgctg ctcttagccc actgtcccag aggttcgaaa gaatcgctgt gcagcctctt  60
acaggagttc tcggcgctga aattacaggt gtcgaccttc gtgaacccct tgacgattca  120
acctggaacg agattctcga tgccttccac acctaccagg ttatttactt cccaggtcag  180
gcaatcacta acgaacaaca tatagctttt tccagaagat ttggacccgt ggatccagtg  240
ccacatttga aaagtataga aggttatcca gaggtccaaa tgattaggag ggaagccaac  300
gaatcaggcg atgttattgg agatgactgg cataccgaca gcaccttcct cgacgctcct  360
cctgcagctg ttgtgatgcg cgcaatagat gttccagagc acggaggcga taccggattt  420
ttgtcaatgt acactgcttg ggaaactctg agtcctacca tgcaggcaac cattgagggt  480
ctcaacgtag tgcatagcgc cacccgcgtc tttggttcat tgtaccaagc acaaaatagg  540
aggttctcca acacttcctt gaaggtaatg gatgttgatg ccggtgatcg tgaaaccgtt  600
catcctctcg ttgtgactca tccaggaagt ggacgtaagg gactttacgt caaccaagtt  660
tactgccaga gaattgaagg tatgactgat gctgaatcaa aaccactgct ccagttcttg  720
tacgaacatg ccactagatt tgactttacc tgtcgtgtta gatggaaaaa ggatcaagtg  780
ttggtttggg ataatctctg taccatgcac agggctgtgc cagattatgc cggcaagttt  840
aggtatctga ccagaaccac tgttggtggg gtcagaccag ccagatga              888

SEQ ID NO: 152         moltype = DNA  length = 888
FEATURE                Location/Qualifiers
source                 1..888
                       mol_type = other DNA
                       organism = synthetic construct
CDS                    1..888
                       protein_id = 26
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGLV
                        IGDDWHTDSTFLDAPPAAVVMRAIDVPEHGGDTGFLSMYTAWETLSPTMQATIEGLNVV
                        HSATRVFGSLYQAQNRRFSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 152
atgcacgctg ccctgagccc tctgtcacag aggtttgaaa gaatcgccgt ccaaccactg  60
actggcgttt tgggagctga gattactgga gtggatctga gggaaccact cgatgattca  120
acttggaacg aaattctcga cgcttttcac acttatcagg tcatctactt tccaggtcag  180
gctatcacaa acgagcaaca tattgctttc agcaggagat ttgggcccgt tgatccagtt  240
cctcacctca aatctatcga agggtaccca gaggtccaaa tgattcgcag agaagctaac  300
gaatctggat tggttattgg agatgattgg cacactgata gtacattctt ggatgccccc  360
cctgcagctg ttgtgatgag ggctatcgat gttcccgaac acggaggaga tacagggttc  420
ctttctatgt atacagcctg ggagacattg tctccaacta tgcaggcaac tattgaagga  480
cttaacgtgg tccactctgc cactagggtt ttcggatctc tttatcaggc tcagaatagg  540
agatttagca atacaagtct gaaagtcatg gacgtagatg ctggcgacag agaaacagtt  600
cacccccctgg tggttactca cccaggatct gggcgtaaag gcctttatgt taaccaagta  660
tactgccaga ggattgaggg tatgactgac gcagagtcca aacccctcct tcagttcctt  720
tacgaacatg ctacaagatt cgactttaca tgccgtgttc gctggaaaaa agaccaagtt  780
ttggtgtggg ataacctctg tacaatgcac cgtgcagtgc ctgactacgc cggtaagttc  840
cgctatctta ctagaactac tgtaggaggg gttagacccg ctcgttga              888

SEQ ID NO: 153         moltype = DNA  length = 888
FEATURE                Location/Qualifiers
source                 1..888
                       mol_type = other DNA
                       organism = synthetic construct
CDS                    1..888
                       protein_id = 30
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGRV
                        IGDDWHTDSTFLDAPPAAVVMRAIDVPEHGGDTGFLSMYTAWETLSPTMQATIEGLNVV
                        HSATRVFGSLYQAQNRRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 153
atgcatgctg cattgagtcc cctctctcag aggtttgagc gtattgccgt tcagcctctg  60
actggagtat tgggagctga aattactggc gttgatctcc gtgagcctct tgacgatagt  120
acatggaacg aaatccttga cgcatttcac acataccaag tcatctactt tccaggacag  180
gctattacta acgaacaaca tattgcattt tcaagaagat tcggtccagt tgatccagtt  240
cctcacctga agagcattga gggttacccc gaggttcaga tgatacgcag agaggctaac  300
gagtcaggaa gagttatcgg agatgattgg cacacagata gcacttttct tgatgcccca  360
ccagctgctg tcgtaatgag agccattgat gttcctgaac acggcggcga cactggtttc  420
ctctccatgt atactgcatg ggaaaccctt agcccaacta tgcaagcaac tatcgaagga  480
ctcaatgtcg tgcacagtgc aactagagtg tttggctccc tctatcaagc acagaaccgc  540
agatggagta atacctcttt gaaggtcatg gatgtggacg ctggagatag ggaaacagtg  600
catcctctcg ttgttactca tccagggagc ggtagaaaag gattgtacgt gaaccaagtt  660
tactgtcagc gcattgaagg tatgaccgac gcagaatcta agcctctgtt gcaatttctc  720
tatgagcacg caaccagatt tgatttcaca tgtagagtga ggtggaagaa agatcaagtt  780
cttgtctggg acaacctttg tacaatgcac agagccgtgc cagattacgc cggaaaattc  840
agatatctca ctagaactac tgtcgggggc gtgagacctg caaggtga              888
```

```
SEQ ID NO: 154          moltype = DNA  length = 888
FEATURE                 Location/Qualifiers
source                  1..888
                        mol_type = other DNA
                        organism = synthetic construct
CDS                     1..888
                        protein_id = 34
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHTDSTFLDAPPAAVVMRAIDVPEHGGDTGFLSMYTAWETLSPTMQATIEGLNVV
                         HSATRVFGSLYQAQNRRFSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 154
atgcatgcag ccctttctcc cctttcacag cgctttgaga ggatagctgt tcaaccactc  60
accggcgtat tgggcgctga gataaccgga gtggacctca gggagccact tgatgattct  120
acctggaacg aaatactcga tgccttccat acctaccaag tgatctactt cccagggcaa  180
gctatcacca atgagcagca cattgctttt tcccgtcgtt tcgggccagt ggatccagtt  240
cctcatctta agtctatcga aggatatccc gaagttcaga tgataagaag ggaggcaaac  300
gaatcattga gagttatcgg agatgactgg cataccgact ccacttttct tgatgcacca  360
cctgccgcag tggtcatgag ggcaatcgat gtacccgaac atggaggaga tacaggtttc  420
ctctctatgt ataccgcctg ggaaactttg tctccaacaa tgcaagctac catcgagggg  480
ctcaatgtcg ttcacagtgc aacacgtgtg tttggtagcc tctatcaagc ccagaatcgc  540
agattttcta acacttcttt gaaggtgatg gatgtggacg caggcgacag ggagaccgtg  600
catccactgg ttgtcaccca tcctgggtca ggtaggaaag ggctttatgt taatcaggtg  660
tactgtcaaa ggattgaagg tatgacagat gcagagagca aacctcttct gcaatttctc  720
tacgaacatg ctacaagatt cgatttcaca tgccgtgtta gatggaaaaa agatcaagta  780
ctcgtgtggg acaacctgtg tactatgcac agggctgtac ccgactatgc cggaaaattt  840
agatatctca caaggaccac agtcggtggt gtcagacctg ccaggtga              888

SEQ ID NO: 155          moltype = DNA  length = 888
FEATURE                 Location/Qualifiers
source                  1..888
                        mol_type = other DNA
                        organism = synthetic construct
CDS                     1..888
                        protein_id = 38
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 155
atgcacgctg ccttgagccc tctgtcacag agattcgaaa gaatcgcagt tcaaccactt  60
actggagtcc tgggtgctga gattactggt gtcgatctta gagagccact cgatgactcc  120
acttggaacg agattttgga tgctttccat acttatcaag ttatatattt tccaggccag  180
gccataacaa acgagcagca tattgccttc tctcgtagat tcggaccagt ggatcccgtt  240
cctcacctga aatcaatcga gggctatcca gaggtccaaa tgatccgcag agaggcaaac  300
gagtcaggcg gtgttatcgg cgatgactgg cacaccgact ccactttctt ggatgctccc  360
ccagcagcag ttgttatgag agctattgac gtgcccgaac acggtggaga tacaggattt  420
ctctccatgt atacagcctg ggagacactt tcccccacaa tgcaagcaac cattgagggt  480
ttgaatgtgg tacattctgc aacccgtgtc tttggaagtc tgtatcaggc acagaacaga  540
aggtggtcca atacatcttt gaaggtcatg gatgtggatg ccggagatag agaaaccgtt  600
catcctctcg tggtgacaca tcccgggtca gggcgcaagg gtctctacgt taatcaagtt  660
tactgccagc gtattgaagg gatgacagat gcagaaagta agcccttgct tcagttcttg  720
tatgaacacg caactaggtt cgactttacc tgtcgtgtta gatggaagaa agatcaggtt  780
cttgtgtggg acaacctttg cactatgcat agagctgtgc ccgattacgc cggaaagttt  840
agatatctta ctaggactac cgtaggcgga gtaaggcccg caagatga              888

SEQ ID NO: 156          moltype = DNA  length = 888
FEATURE                 Location/Qualifiers
source                  1..888
                        mol_type = other DNA
                        organism = synthetic construct
CDS                     1..888
                        protein_id = 42
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 156
atgcatgctg cattgagtcc cttgtcccaa aggttcgaaa gaatcgccgt gcaacctctt  60
actggagtgc ttggagctga aattaccggt gtcgatttgc gtgaaccact tgatgactct  120
```

```
acctggaatg agatcttgga cgcatttcac acataccaag tgatatactt tcctggtcaa  180
gccatcacta acgagcagca tattgccttc agcaggaggt ttggcccagt tgatccagtg  240
ccccacttga aatctataga gggttaccca gaagttcaga tgatcagaag ggaagctaac  300
gagtctctcc gcgtcatagg agatgattgg catactgact ccacatttct cgacgcacct  360
cccgcagccg tcgtaatgcg cgccattgac gtgcctgagc atgggggtga taccggtttc  420
ctctcaatgt atacagcatg ggagactctt tcacctacta tgcaggccac tattgaggga  480
ctcaacgttg tgcatagcgc tacacgcgtt tttggttcac tgtatcaggc tcaaaataga  540
aggtggtcta acacctccct taaggttatg gatgtggatg ccggtgacag agaaacagta  600
catcctcttg ttgtgacaca tccagggtcc ggtcgcaagg gactttacgt taaccaagtg  660
tactgccaaa ggattgaagg aatgactgac gcagagtcaa agcccctcct ccaatttttg  720
tacgaacatg ctacaagatt tgattttact tgtagagtgc gctggaaaaa ggatcaagtt  780
ttggtttggg ataatttgtg caccatgcat cgcgcagtcc ctgattatgc cggcaaattc  840
aggtatctta caagaacaac cgtgggtgga gtccgccctg ctcgctga              888

SEQ ID NO: 157         moltype = DNA  length = 888
FEATURE                Location/Qualifiers
source                 1..888
                       mol_type = other DNA
                       organism = synthetic construct
CDS                    1..888
                       protein_id = 46
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHSDSTFLDAPPAAVVMRAIDVPEHGGDTGFLSMYTAWETLSPTMQATIEGLNVV
                        HSATRVFGSLYQAQNRRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 157
atgcatgctg ccttgtcccc tttgagccaa cgctttgaaa gaatagctgt gcaacccttg  60
acaggtgtgt tgggggccga gatcaccggt gtggacttgc gtgagcccct cgatgattcc  120
acttggaatg agattctgga cgccttccac acttaccaag ttatttattt ccctggtcag  180
gccatcacaa acgagcaaca cattgcattc tctcgccgtt tcggaccagt tgatcccgtc  240
ccccacttga aatctattga ggggtaccct gaagttcaaa tgataagacg tgaggcaaat  300
gagtctggag ggttattgg cgatgactgg cattccgatt ctacttttct cgatgcacct  360
cctgccgcag tggtgatgag ggccattgat gtgccagaac atggcgggga taccggattt  420
ctttccatgt ataccgcatg ggagaccctt tcaccaacaa tgcaagctac aatagaaggt  480
cttaacgtgg ttcatagtgc aacaagagtt ttcgggagtc tctaccaagc acaaaatcgt  540
aggtggagca atacctcttt gaaggtgatg gacgtcgatg caggggatag ggaaaccgtg  600
catccacttg tagttacaca cccagggtct ggtaggaagg ggttgtatgt taatcaagtc  660
tactgccaga gaattgaggg aatgactgat gctgagagta agcccctcct gcagtttctt  720
tatgagcatg ccactaggtt tgactttaca tgcagagtga gatggaagaa ggaccaagtg  780
ctcgtctggg acaacctgtg taccatgcat agggccgtcc cagattatgc aggcaagttt  840
agatatctga ctagaacaac cgtaggtggt gttcgccccg ctaggtga              888

SEQ ID NO: 158         moltype = DNA  length = 888
FEATURE                Location/Qualifiers
source                 1..888
                       mol_type = other DNA
                       organism = synthetic construct
CDS                    1..888
                       protein_id = 50
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPTPHLKSIEGYPEVQMIRREANESGGV
                        IGDDWHTDSTFLDAPPAAVVMRAIDVPEHGGDTGFLSMYTAWETLSPTMQATIEGLNVV
                        HSATRVFGSLYQAQNRRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 158
atgcacgcag ccttgtcacc actttctcaa cgctttgaga gaatcgcagt acaacctctt  60
actggggttc ttggagccga aataacagga gttgacctga gggaaccact tgacgattct  120
acctggaatg agatacttga tgcttttcat acctatcaag tcatttattt cccagggcaa  180
gccattacta acgaacagca catagctttt tcaaggaggt ttggaccagt ggatccacc   240
cctcatttga agtcaattga gggctaccct gaggttcaaa tgatccgtcg tgaggcaaat  300
gagtccggcg gtgtaattgg tgatgattgg cacactgata gcacattctt ggatgcacca  360
ccagctgcag ttgttatgag ggcaatcgat gtcccagaac acgggggaga cactggattt  420
ctctctatgt acacagcttg ggaaaccctg tctccaacta tgcaagctac cattgaagga  480
ctgaatgttg ttcattctgc cactcgtgtg ttcggtagtt tgtatcaggc acaaaataga  540
aggtggagta acacaagttt gaaagtgatg gacgtcgatg ctggtgatag ggagacagtt  600
catcccctgg tggttactca tcctggttcc ggacgtaaag gtctgtatgt taaccaggtt  660
tactgtcaaa ggattgaggg gatgactgat gctgagagca aaccattgct tcaattcttg  720
tatgagcatg caacaagatt tgattttact tgtcgtgtca gatggaagaa ggatcaagtt  780
ttggtgtggg ataacctttg cacaatgcac agagcagtcc ctgattatgc tggcaaattt  840
aggtatttga ctaggacaac cgtgggagga gttagaccag ccagatga              888

SEQ ID NO: 159         moltype = DNA  length = 888
FEATURE                Location/Qualifiers
source                 1..888
```

```
                        mol_type = other DNA
                        organism = synthetic construct
CDS                     1..888
                        protein_id = 54
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNWRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 159
atgcatgccg cactcagtcc actctcccag agattcgaga gaattgcagt ccagccactg  60
actggagttc ttggtgctga gattactggc gttgatctca gggaaccctt ggatgattca  120
acttggaatg agatacttga cgctttccat acttaccagg ttatatactt ccctggccaa  180
gccattacaa atgagcaaca catcgctttt tcccgcagat tcggccctgt cgacccagtt  240
ccacacttga aatcaataga aggttacccc gaggtccaaa tgataagaag agaagctaac  300
gagtctggcg gtgtcattgg tgatgactgg cacaccgatt caacatttct ggacgcaccc  360
cctgctgctg tcgtgatgag agctattgat gttccagagc acggaggtga tacagggttc  420
ttgtccatgt atacagcctg ggagactttg tccccaacaa tgcaggcaac tatagaagga  480
ttgaatgtgg ttcacagtgc aaccagggtt tttgggagcc tgtaccaagc ccagaactgg  540
cgctggtcta acacaagtct caaggttatg gatgtggatg ctggcgatag agaaacagtt  600
caccctctcg tggttactca tcctggttca ggtaggaagg gcctgtacgt taatcaagtt  660
tactgccaaa ggatcgaagg catgacagac gctgagtcaa aacctctgct tcaatttttg  720
tacgaacacg caactagatt tgactttacc tgtcgcgtga ggtggaagaa agaccaagtt  780
ttggtatggg ataatctttg cactatgcat agggctgtgc ctgattacgc aggaaagttc  840
aggtacctga ctagaaccac cgtcggggga gtgaggccag caagatga              888

SEQ ID NO: 160          moltype = DNA  length = 888
FEATURE                 Location/Qualifiers
source                  1..888
                        mol_type = other DNA
                        organism = synthetic construct
CDS                     1..888
                        protein_id = 58
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNMRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 160
atgcacgcag ctttgtcccc tctgtcacaa aggttcgaga gaatcgctgt tcagcccctt  60
actggtgttc ttggtgccga gattacaggt gttgacttga gggagcctct tgatgacagt  120
acctggaatg agattcttga cgcttttcac acctaccaag ttatctactt tcccgggcaa  180
gcaattacta atgaacaaca catagccttc tctagaagat ttggccctgt tgaccctgtg  240
cctcatttga aaagtatcga aggatatccc gaggttcaaa tgattagaag ggaggctaat  300
gaatccggag gtgtgatagg agatgattgg cataccgata gcactttcct ggatgcacct  360
cctgcagctg ttgttatgcg tgctattgat gtgccagagc atggagggga tactggtttt  420
ttgagtatgt acaccgcttg ggagacattg tcaccaacta tgcaagcaac cattgaggga  480
ctcaatgttg ttcactctgc taccagggtc tttggttctc tttaccaggc acaaaacatg  540
agatggtcca acaccagtct taaggtaatg gacgtggatg ccggagaccg tgaaaccgtc  600
catccacttg tcgttacaca tcctggaagc ggaaggaaag gtctctatgt taatcaggtt  660
tattgccaac gcattgaggg aatgacagat gccgaatcca aaccattgct gcaatttctt  720
tacgaacatg caacacgctt tgatttcacc tgcagggtta gatggaagaa ggatcaggta  780
cttgtgtggg ataatctttg tactatgcac agggccgtcc ctgattatgc cggaaagttc  840
agatatttga caagaaccac cgtgggagga gtaaggccag ccaggtga              888

SEQ ID NO: 161          moltype = DNA  length = 888
FEATURE                 Location/Qualifiers
source                  1..888
                        mol_type = other DNA
                        organism = synthetic construct
CDS                     1..888
                        protein_id = 62
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGCDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 161
atgcatgccg ctctttcccc actgagtcaa cgcttcgaga ggattgctgt gcagcccttg  60
acaggagttc tcggagctga gattaccggg gttgacctta gggaacctct cgacgattct  120
acctggaatg agatcttgga tgctttccat acttaccagg tgatatactt ccctggacag  180
gcaattacta acgagcaaca catcgctttt agcagaaggt tcggaccagt cgatcccgtg  240
ccacatctta agagcataga gggctatcct gaagtacaaa tgataagaag agaggccaat  300
```

-continued

```
gagtcaggcg gtgtcattgg ctgcgattgg catactgact ccaccttcct ggacgcacct  360
cctgccgcag ttgtcatgag ggccatagat gtgcctgagc atggaggaga tacaggattc  420
ttgtcaatgt atactgcatg ggagaccctt tcccccacca tgcaggccac aattgagggc  480
ttgaacgtgg tccattctgc tacccgcgta tttggatcat tgtaccaggc acagaataga  540
aggtggtcaa atacaagctt gaaggttatg gatgttgatg caggagacag agagacagtg  600
caccctctcg ttgtgacaca tcctggaagt ggcagaaagg ggttgtacgt gaatcaggtg  660
tactgtcaaa gaatagaagg catgactgac gctgagagca aacccttgct ccagttcctt  720
tacgaacatg caaccaggtt tgatttcaca tgcagagtta ggtggaaaaa agaccaagta  780
ttggtgtggg acaatctttg tacaatgcat agggctgtac cagattacgc tgggaagttc  840
cgctacttga ctaggacaac cgtgggaggt gtgcgccccg ccaggtga              888

SEQ ID NO: 162          moltype = DNA  length = 888
FEATURE                 Location/Qualifiers
source                  1..888
                        mol_type = other DNA
                        organism = synthetic construct
CDS                     1..888
                        protein_id = 66
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDEWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 162
atgcatgctg ccctttctcc actttcacaa agatttgaga ggattgctgt ccaaccactt  60
accggtgtgc tcggtgctga gattacagga gttgatctca gagaaccact ggacgactct  120
acatggaacg agatccttga cgctttccac acttaccagg taatctattt ccctggccag  180
gccattacaa atgagcaaca tatcgcattc tcacgccgtt tcggacctgt tgatcctgtt  240
ccccatctca agtcaataga aggttatcct gaggtgcaaa tgattcgtag agaagcaaac  300
gagtccgggg gggtgatagg ggacgaatgg cataccgatt ccacatttct tgatgcccca  360
cctgccgcag ttgttatgcg tgcaattgat gtacccgagc atggcggtga caccggattt  420
ttgagtatgt acaccgcatg ggaaactctt tccccaacaa tgcaagccac tattgaagga  480
ctcaacgtgg ttcacagcgc aacaagggtt ttcggttctc tgtaccaggc tcaaaacaga  540
cgttggtcta atacaagcct taaagtcatg gacgttgatg caggagatag ggaaaccgta  600
catccactcg tggtgacaca tccaggcagt ggaaggaagg gactttacgt taatcaagtt  660
tactgtcaac gtattgaagg aatgacagat gccgaatcta aacctttgct gcaattcctg  720
tatgaacacg ctaccagatt tgatttcact tgcagggtta gatggaaaaa ggatcaggtc  780
ctggtgtggg acaacttgtg cactatgcat cgtgctgtcc cagattacgc cggaaagttc  840
cgctacttga ctcgcactac tgtcggtgga gtcaggcccg ctcgctga              888

SEQ ID NO: 163          moltype = DNA  length = 888
FEATURE                 Location/Qualifiers
source                  1..888
                        mol_type = other DNA
                        organism = synthetic construct
CDS                     1..888
                        protein_id = 70
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNCVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 163
atgcatgctg cattgtctcc attgtcccag cgctttgaga gaatcgccgt tcagcctctt  60
acaggtgttc tgggagcaga gattaccggg gttgacttga gagagccttt ggacgattca  120
acatggaatg agatcctgga cgctttccac acttaccaag taatctattt ccctggacaa  180
gccatcacaa acgaacagca catagcattt tccaggagat ttgggcctgt agatccagtt  240
ccccatctta agtcaattga gggctatcct gaagtacaga tgatcagacg tgaagcaaat  300
gagtcagggg gcgtgatagg tgacgattgg cacactgact caacatttct cgatgcaccc  360
cctgccgcag ttgttatgag agctattgat gtccctgaac atggtggcga tacaggcttt  420
cttagtatgt ataccgcctg ggagaccctt tcacctacca tgcaagctac aatcgaagga  480
ttgaatgttg tccacagtgc tactagagtt tttggttcat tgtatcaggc acagaacaga  540
aggtggtcca acacaagctt gaaggtcatg gatgtagacg caggagatag agagacagtg  600
cacccactcg tggtgacaca tcccggttcc ggtaggaaag gactctacgt aaactgcgtt  660
tactgccagc gtatagaagg tatgaccgat gccgaatcaa aacctttgtt gcagtttctg  720
tatgagcacg ctactagatt tgattttacc tgcagggtca ggtggaaaaa agatcaggtg  780
ctcgtgtggg acaatctgtg cactatgcat cgcgcagtgc ccgactatgc tgggaagttt  840
agatacttga ctagaaccac agtcggtggc gtgcgccctg ccagatga              888

SEQ ID NO: 164          moltype = DNA  length = 888
FEATURE                 Location/Qualifiers
source                  1..888
                        mol_type = other DNA
                        organism = synthetic construct
CDS                     1..888
```

```
                        protein_id = 74
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNPVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 164
atgcatgctg cccttagtcc actgagccaa aggtttgagc gtattgctgt ccaaccactt  60
accggcgtcc ttggcgcaga aattacaggg gtggacctta gagagccatt ggatgatagt  120
acctggaatg aaattcttga tgctttccac acttatcaag tcatctattt tccagggcag  180
gccattacaa acgagcaaca tatcgccttc tctcgtaggt ttggaccagt tgatcctgta  240
ccacatctca agtctattga gggatatcct gaggtccaaa tgataagaag ggaggccaat  300
gagagtggtg gcgttatcgg cgatgactgg catactgact ctacattctt ggatgcccct  360
cccgcagccg ttgtaatgcg tgctattgat gtgccagaac acgggggaga tactggcttt  420
ctcagtatgt ataccgcatg ggaaaccctc tcacctacca tgcaagctac aattgagggc  480
ctgaacgtag tacactcagc cacaagggtg ttcggaagtc tgtatcaggc ccaaaacaga  540
cgttggtcca acaccagctt gaaagttatg gacgttgatg caggagacag agagacagtt  600
catccattgg tcgtcacaca tccaggcagt ggccgtaagg ggctctacgt gaacccagtg  660
tactgccagc gtatagaagg gatgactgac gccgagtcaa aacccttgct tcaattcttg  720
tatgagcacg ctacaagatt cgatttcact tgcagagttc gctggaaaaa ggaccaggtc  780
ctcgtttggg acaatttgtg tacaatgcat agagcagttc cagattatgc aggcaagttt  840
aggtacctca ctcgcaccac cgttggaggt gtgagacctg cacgttga              888

SEQ ID NO: 165          moltype = DNA  length = 888
FEATURE                 Location/Qualifiers
source                  1..888
                        mol_type = other DNA
                        organism = synthetic construct
CDS                     1..888
                        protein_id = 78
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHTDSTFLDAPPAAVVMRAIDVPEHGGDTGFLSMYTAWETLSPTMQATIEGLNVV
                         HSATRVFGSLYQAQNDRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 165
atgcatgcag cattgagtcc tctcagccaa aggtttgagc gtatagccgt gcaaccactc  60
actggagtcc tgggcgcaga aattactgga gtggatttga gggaaccttt ggatgattct  120
acatggaacg agatcctcga cgcatttcat acctaccagg ttatttattt tccaggccag  180
gccattacca acgaacaaca catagcattt tctaggagat ttggtccagt ggacccagta  240
ccacacctga agtccataga gggataccct gaggtgcaga tgattcgcag ggaggctaac  300
gaatccctcc gtgttatagg ggatgattgg cacacagatt ctaccttttt ggatgcacca  360
cctgctgctg ttgttatgag agcaatagat gtgcccgagc atggaggaga tactggcttc  420
ttgtctatgt atacagcatg ggagaccctt tccccaacta tgcaagcaac tattgaagga  480
cttaacgttg ttcactctgc tactagggtt tttggatctt tgtatcaggc acaaaatgac  540
agatggtcta acactagtct taaagtgatg gatgtggatg ctggtgacag agaaactgtt  600
catccactcg tcgtgaccca cccagggtct ggaagaaaag gactctatgt caaccaagtg  660
tactgtcaaa gaatagaagg gatgaccgac gcagagagca agccacttct tcaatttttg  720
tatgagcacg ccacccgctt tgattttacc tgtagggtga gatggaaaaa agaccaggtc  780
cttgtatggg ataatctgtg cactatgcac aggcgtgttc ctgattatgc aggtaaattt  840
aggtacttga caagaacaac cgtcggagga gttaggcccg ctagatga              888

SEQ ID NO: 166          moltype = DNA  length = 888
FEATURE                 Location/Qualifiers
source                  1..888
                        mol_type = other DNA
                        organism = synthetic construct
CDS                     1..888
                        protein_id = 82
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHTDSTFLDAPPAAVVMRAIDVPEHGGDTGFLSMYTAWETLSPTMQATIEGLNVV
                         HSATRVFGSLYQAQNERWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 166
atgcatgcag cactgagtcc tcttagtcaa aggtttgaga gaattgctgt tcagcctctg  60
acaggggtcc ttggtgccga gataacaggt gttgatctta gggagcctct cgatgatagc  120
acatggaacg agattttgga tgccttccac acctatcaag ttatttactt tcctggtcaa  180
gccatcacta acgaacaaca tattgccttc agcaggagat ttggtccagt tgacccagtc  240
ccacatctga agagtattga ggggtatccc gaggttcaga tgattaggag ggaagctaac  300
gaatcattga gggtcattgg agatgactgg catacagata gtactttcct ggacgctcca  360
ccagcagctg tagttatgag agccatagat gttcccgaac atggaggtga tactgggttc  420
ttgtccatgt acaccgcctg ggaaacactg agccccacta tgcaagctac tattgaagga  480
```

-continued

```
cttaatgtag tccattcagc cacccgtgtc tttggtagcc tctaccaagc acaaaatgag  540
agatggagta atacaagcct taaagttatg gatgttgatg ccggggatcg tgagaccgtg  600
caccctttgg tcgtgaccca tccaggtagc ggaaggaagg gcttgtacgt taatcaagtg  660
tactgtcaga ggattgaggg tatgacagat gctgaatcca agccacttct gcaattcttg  720
tacgaacatg caactcgctt cgattttact tgtagagtca ggtggaaaaa agatcaagtt  780
ttggtctggg acaacttgtg cacaatgcac cgcgcagtcc ctgattatgc aggcaagttt  840
aggtatttga caaggactac cgtaggaggg gtgaggcctg ctagatga              888

SEQ ID NO: 167          moltype = DNA  length = 888
FEATURE                 Location/Qualifiers
source                  1..888
                        mol_type = other DNA
                        organism = synthetic construct
CDS                     1..888
                        protein_id = 86
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHTDSTFLDAPPAAVVMRAIDVPEHGGDTGFLSMYTAWETLSPTMQATIEGLNVV
                         HSATRVFGSLYQAQNSRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 167
atgcatgctg cactgtctcc acttagccaa aggttcgaga gaatagctgt ccaaccattg  60
accggcgtcc ttggggctga aataactggc gtcgatctca gagagccatt ggatgatagc  120
acttggaacg aaattttgga tgccttccac acataccaag tcatctattt tccaggtcaa  180
gcaatcacaa acgagcagca catagccttt tctcgtcgtt ttggtccagt tgatccagtg  240
ccacatttga aatcaataga aggttaccct gaggtccaga tgattagacg tgaggccaat  300
gaaagtcttc gtgtgatagg tgatgattgg cataccgact caacctttct ggacgctcca  360
cccgcagctg ttgtcatgcg cgctattgat gtgccagagc acggcggaga caccggattt  420
ttgtccatgt acaccgcctg ggagactttg tccccaacaa tgcaggcaac catagagggg  480
ttgaacgtcg tgcactcagc tactcgcgtc tttggaagcc tctaccaagc tcaaaattct  540
cgttggagta acacctcatt gaaagtgatg gatgttgatg caggtgatag agaaacagtt  600
catcctctcg tggtgactca cccaggttct ggtcgcaagg ggctgtatgt taatcaggtt  660
tattgccaga gaatcgaggg tatgacagat gcagaaagca agcctttgtt gcagtttctt  720
tatgaacatg ccacaagatt cgactttaca tgtagggttc gttggaaaaa ggatcaagta  780
ttggtctggg ataatctttg tacaatgcac agagccgtcc ccgactacgc tggcaagttt  840
cgttacttga caagaacaac agttggtgga gttaggccag ctcgctga              888

SEQ ID NO: 168          moltype = DNA  length = 888
FEATURE                 Location/Qualifiers
source                  1..888
                        mol_type = other DNA
                        organism = synthetic construct
CDS                     1..888
                        protein_id = 90
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHTDSTFLDAPPAAVVMRAIDVPEHGGDTGFLSMYTAWETLSPTMQATIEGLNVV
                         HSATRVFGSLYQAQNLRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 168
atgcacgcag cactttcccc tctttctcaa agattcgaaa gaattgcagt gcaacccctc  60
accggggttc ttggtgctga aatcacagga gtagatttga gagaacccct cgatgattcc  120
acttggaacg aaattttgga tgcttttcac acttatcaag tgatctattt tcctggtcag  180
gccatcacta acgaacagca cattgctttt tctagaaggt ttggaccagt tgatcctgtt  240
ccacacttga aaagcatcga agggtaccct gaagttcaga tgataagaag agaggcaaat  300
gaaagcctca gggtcatcgg ggatgactgg cacactgatt caacattcct tgacgccccc  360
ccagcagccg tagtcatgag agctattgat gtgcccgaac atggtggaga cactggcttt  420
ctttccatgt ataccgcatg ggagactctc tctccaacaa tgcaagccac aatagagggc  480
cttaatgtcg ttcactctgc cacacgcgtg ttcggttcct tgtaccaagc tcaaaacctg  540
aggtggagta acacttccct taaggttatg gatgttgatg ccggtgacag ggaaacagtg  600
cacccactgg ttgtgaccca tccagggtcc ggcaggaagg gactctatgt gaaccaagtc  660
tattgtcaac gcatagaagg catgactgat gcagaaagta agccacttct tcagtttctt  720
tacgagcacg ccactcgctt cgattttacc tgccgcgtta ggtggaagaa agatcaagtt  780
ctggtctggg ataacctttg cacaatgcac agggctgtgc ccgactatgc aggcaaattt  840
agatatctca ctcgcaccac tgtcggtgga gtgagacctg ctaggtga              888

SEQ ID NO: 169          moltype = DNA  length = 888
FEATURE                 Location/Qualifiers
source                  1..888
                        mol_type = other DNA
                        organism = synthetic construct
CDS                     1..888
                        protein_id = 94
                        transl_table = 1
                        translation = MHAALSPLSQRFERIAVQPLTGVLGAEITGVDLREPLDDSTWNEIL
```

-continued

DAFHTYQVIYFPGQAITNEQHIAFSRRFGPVDPVPHLKSIEGYPEVQMIRREANESLRV
IGDDWHTDSTFLDAPPAAVVMRAIDVPEHGGDTGFLSMYTAWETLSPTMQATIEGLNVV
HSATRVFGSLYQAQNWRWSNTSLKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR

SEQUENCE: 169
atgcacgcag ccctttcccc tctgagtcaa aggttcgagc gtattgctgt gcaacccctc 60
actggcgttt tgggcgcaga aattactggt gttgaccttc gcgaaccatt ggacgacagc 120
acttggaacg agatccttga tgctttccat acctatcaag ttatctactt tcctggccaa 180
gctatcacta acgagcaaca tattgctttc agtcgtagat tcggtccagt ggatccagta 240
ccccatttga aaagcattga gggataccca gaagtacaga tgattaggag ggaggcaaac 300
gagagccttc gcgtcatagg cgatgattgg cataccgata gcacttttct ggacgcccca 360
cctgctgctg ttgtaatgag ggctatcgat gtacctgagc acggaggtga taccgggttt 420
cttagtatgt acaccgcctg ggagacactc agtccaacaa tgcaagctac tatcgagggt 480
ctgaatgtcg ttcacagtgc caccagagtt ttcggatccc tttatcaagc tcagaactgg 540
agatggtcca atacatccct taaagtcatg gatgtggatg ctggtgatag agaaacagtc 600
catcctctcg tcgtgactca tccaggaagt ggaagaaagg ggctttatgt gaatcaggtc 660
tattgtcaac gcatcgaggg catgactgac gctgaaagta agccacttct tcaattcctt 720
tacgagcacg ccactagatt tgattttaca tgtagagtta gatggaaaaa agaccaggtg 780
cttgtttggg acaacctctg tacaatgcat cgtgcagtgc ccgactatgc tggtaagttc 840
aggtacctca ccagaacaac cgttggaggt gttagacccg ctagatga 888

SEQ ID NO: 170 moltype = DNA length = 888
FEATURE Location/Qualifiers
source 1..888
mol_type = other DNA
organism = synthetic construct
CDS 1..888
protein_id = 98
transl_table = 1
translation = MHAALSPLSQRFERIAVQPLTGVLGAEITGVDLREPLDDSTWNEIL
DAFHTYQVIYFPGQAITNEQHIAFSRRFGPVDPTPHLKSIEGYPEVQMIRREANESLRV
IGDDWHTDSTFLDAPPAAVVMRAIDVPEHGGDTGFLSMYTAWETLSPTMQATIEGLNVV
HSATRVFGSLYQAQNRRWSNTSLKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR SEQUENCE: 170
atgcatgccg ctctcagtcc attgtctcaa aggttcgaga gaatcgctgt tcaacccctt 60
actggtgttc ttggagccga aataactggt gtagacctgc gcgagccact ggatgatagc 120
acatggaacg agattcttga cgctttccat acctaccagg tgatttactt tcctggtcag 180
gctattacaa acgagcagca tatcgctttc agtcgtcgct tcggccctgt tgacccaact 240
ccccatttga aatccattga gggttaccca gaagttcaaa tgattagacg tgaggcaaac 300
gaatcattga gagtcattgg agatgattgg catacagatt caacttttct ggatgcacca 360
cctgcagctg ttgtgatgcg cgcaattgac gttccagagc acggtggtga tacagggttc 420
ctttctatgt atactgcttg ggaaacactt tctcccacca tgcaagctac catagaggga 480
ctcaatgttg tacattccgc aaccagggtt ttcggcagcc tttaccaagc tcagaaccgc 540
agatggtcaa acacctctct gaaagttatg gacgtagacg ctggtgaccg cgagactgtg 600
catcctcttg ttgtcactca tcctggaagc ggcagaaaag gtctttatgt taatcaggtt 660
tattgccagc gtatcgaagg aatgactgac gcagagtcta agcccttgct gcaatttttg 720
tacgaacatg caactaggtt tgacttcacc tgtcgcgtta ggtggaagaa agatcaggtc 780
cttgtttggg ataacttgtg cactatgcat agggcagtgc cagattacgc agggaagttt 840
aggtatctta ccaggaccac cgttggtggg gtgaggccag cacgctga 888

SEQ ID NO: 171 moltype = DNA length = 888
FEATURE Location/Qualifiers
source 1..888
mol_type = other DNA
organism = synthetic construct
CDS 1..888
protein_id = 102
transl_table = 1
translation = MHAALSPLSQRFERIAVQPLTGVLGAEITGVDLREPLDDSTWNEIL
DAFHTYQVIYFPGQAITNEQHIAFSRRFGPVDPVPHLKSIEGYPEVQMIRREANESLRV
IGDDWHADSTFLDAPPAAVVMRAIDVPEHGGDTGFLSMYTAWETLSPTMQATIEGLNVV
HSATRVFGSLYQAQNRRWSNTSLKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR SEQUENCE: 171
atgcatgccg ctctttcccc tttgtctcag aggttcgaac gtattgctgt gcaaccactt 60
acaggtgttc ttggagcaga aattactgga gtcgatttga gggagcccct ggatgactcc 120
acatggaatg agattctcga cgccttccat acttatcagg ttatctactt tcccggacag 180
gctataacaa acgagcaaca cattgctttt tctcgccgtt ttggccctgt ggaccctgtt 240
ccacatttga agagtataga gggttatcca gaggtgcaaa tgattagaag agaagctaat 300
gagtccttga gagttatagg tgatgattgg catgcagata gcacttttct tgatgcacca 360
ccagcagcag tggttatgag ggccattgat gtcccagagc atggaggtga tacaggtttt 420
ctgtcaatgt atacagcctg ggaaactttg agcccaacaa tgcaagccac cattgagggt 480
ttgaatgtcg ttcattccgc cacaagggtg tttggctctc tttatcaagc acaaaacaga 540
agatggtcaa atacaagcct caaagtcatg gatgtggatg ccggtgacag ggaaactgtg 600
catccccttg tggtgactca tccaggatca ggtaggaaag ggttgtatgt aaatcaggta 660

-continued

```
tattgccaaa gaatagaagg gatgactgat gctgaatcca aacctctgct gcaatttttg  720
tatgaacacg ctaccaggtt cgatttcaca tgtagagttc gctggaagaa agatcaagtc  780
ttggtttggg acaacctgtg caccatgcac cgcgccgtgc ccgattatgc tggtaagttt  840
agatatttga cccgcaccac cgtgggcgga gtacgcccag caagatga              888

SEQ ID NO: 172          moltype = DNA  length = 888
FEATURE                 Location/Qualifiers
source                  1..888
                        mol_type = other DNA
                        organism = synthetic construct
CDS                     1..888
                        protein_id = 106
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHSDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 172
atgcatgcag ccctttcacc tctctctcaa aggtttgaac gtatcgctgt ccagcccctg  60
actggcgtgc tgggtgcaga gataaccgga gtagacttga gggaaccact tgatgactca  120
acttggaatg agattctcga cgctttccat acataccagg ttatttactt tccaggacag  180
gcaattacta acgaacagca tatagctttc tccagaagat ttggaccagt tgacccagtt  240
ccacatctta agtccataga gggatatcca gaggttcaga tgataaggag agaagcaaac  300
gagagcttga gagtcatcgg tgacgattgg cactctgata gcactttcct cgatgcacct  360
ccagccgctg ttgtgatgcg cgctattgat gttcctgagc acggcggtga tacaggattc  420
ctctccatgt atacagcatg ggagactttg tcaccaacaa tgcaggccac catcgaagga  480
cttaatgtcg ttcacagcgc aacacgtgtt ttcggcagct tgtaccaagc acagaatcgc  540
agatggagta acacatctct gaaggtgatg gatgtggacg ccggcgatcg tgaaacagtc  600
cacccactcg ttgttaccca tcctggatcc ggccgcaaag gtctttacgt gaaccaggtt  660
tactgtcaga ggatcgaagg tatgaccgac gccgagtcaa aacctctcct tcagtttctc  720
tatgagcatg ccaccaggtt tgattttacc tgtagggtta gatggaaaaa ggatcaagtt  780
cttgtgtggg acaatttgtg tacaatgcat agggcagttc ccgattatgc agggaaattc  840
agatatttga ctagaactac cgttggcggt gttcgtccag ccagatga              888

SEQ ID NO: 173          moltype = DNA  length = 888
FEATURE                 Location/Qualifiers
source                  1..888
                        mol_type = other DNA
                        organism = synthetic construct
CDS                     1..888
                        protein_id = 110
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHMDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 173
atgcatgcag ctttgtcacc actctcacag cgtttcgaaa ggattgcagt gcaacccctt  60
accggtgtgt tgggggctga aattacaggg gtggaccttc gtgaaccttt ggatgattca  120
acttggaacg aaatccttga tgcatttcat acctaccaag ttatttactt tcctggtcaa  180
gctatcacca atgagcagca tatcgctttc agcaggaggt tcgggcccgt tgatcccgtg  240
ccacacttga agtctattga aggataccca gaagtgcaaa tgataagaag ggaggctaac  300
gagtcattgc gcgttatcgg ggacgactgg catatggatt ctaccttttt ggacgctcca  360
cctgccgctg tcgtgatgag agcaatcgac gtacctgaac atggtggaga tactggattc  420
ttgtccatgt acacagcttg ggagaccttg agcccaacta tgcaggcaac tatcgaggga  480
ctcaatgttg tgcacagcgc tacacgcgtg tttggttctc tttaccaggc acaaaataga  540
cgttggagta acacatctct taaggtgatg gatgttgatg ctggcgatag agaaaccgtg  600
catcctctgg tggttacaca tccaggctcc ggacgcaagg gactctacgt caatcaagtc  660
tattgtcaac gtatcgaagg aatgacagat gctgaatcta aacccttgct gcagtttttg  720
tatgagcacg caactagatt tgactttacc tgtagagtta ggtggaagaa agaccaggtg  780
cttgtgtggg ataatctgtg tacaatgcat agggcagttc cagattatgc tggaaagttt  840
aggtacctta ctagaactac tgtcggtgga gttagaccag ccagatga              888

SEQ ID NO: 174          moltype = DNA  length = 888
FEATURE                 Location/Qualifiers
source                  1..888
                        mol_type = other DNA
                        organism = synthetic construct
CDS                     1..888
                        protein_id = 114
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHTDSTFLDAPPAAVVMRAIDVPEHGGDTGFLSMYTAWETLSPTMQATIEGLNVV
                         HSATRVFGSLYQAQNRRWSNTSLKVMDVDAGDRETVHPLVVTHPGSGRKGLYVNQVYCQ
```

-continued

RIEGMTDAESKPLLQFLYEHATRYDFTCRVRWKKDQVLVWDNLCTMHRAVPDYAGKFRY
LTRTTVGGVRPAR

SEQUENCE: 174
atgcacgctg cactttcacc tttgtcacag aggttcgaac gcatcgccgt tcaacccctc 60
acaggggtcc ttggagctga aatcactggg gtggatttgc gcgagccact tgatgatagc 120
acatggaatg agatcttgga cgcttttcat acctatcagg taatctattt ccctggacaa 180
gctatcacca atgaacagca cattgcattt tctaggagat tcggaccagt ggaccccgta 240
ccacacctga aatccattga gggctacccc gaggtgcaga tgataagaag ggaggcaaat 300
gaaagcctta gggttatcgg ggatgattgg cataccgact caactttcct cgacgcccca 360
cctgctgctg ttgtcatgag ggcaatagat gtgcctgaac atggcggcga caccggcttc 420
ctgtccatgt acaccgcctg ggaaaccctc agcccaacca tgcaggctac tatagaggga 480
cttaacgtgg tacacagtgc caccagagtt ttcggatctc tctaccaggc tcagaataga 540
aggtggtcaa acactagcct caaagtcatg gatgtcgatg caggagatcg tgaaactgtg 600
catcctctgg ttgtcactca cccagggtca ggccgcaagg ggttgtatgt taatcaagtc 660
tactgccaga ggattgaggg aatgacagac gctgagtcca agcctcttct gcaattcctt 720
tatgaacatg caactagata cgatttcaca tgtagagtgc gctggaaaaa agaccaagta 780
cttgtgtggg ataacttgtg cacaatgcat agggccgtgc ctgattacgc agggaagttc 840
aggtatttga caaggaccac tgtgggaggc gttcgtcccg cacgttga 888

SEQ ID NO: 175 moltype = DNA length = 888
FEATURE Location/Qualifiers
source 1..888
mol_type = other DNA
organism = synthetic construct
CDS 1..888
protein_id = 118
transl_table = 1
translation = MHAALSPLSQRFERIAVQPLTGVLGAEITGVDLREPLDDSTWNEIL
DAFHTYQVIYFPGQAITNEQHIAFSRRFGPIDPVPHLKSIEGYPEVQMIRREANESGGV
IGDDWHTDSTFLDAPPAAVVMRAIDVPEHGGDTGFLSMYTAWETLSPTMQATIEGLNVV
HSATRVFGSLYQAQNRRWSNTSLKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR SEQUENCE: 175
atgcatgccg cacttagccc actctcccaa cgttttgagc gcattgctgt gcagccactt 60
actggggtat tgggtgctga gataaccgga gtcgatcttc gtgagccttt ggatgattca 120
acctggaacg aaatccttga tgcttttcac acttatcaag tgatctattt tccaggacaa 180
gctataacta atgagcagca cattgcattc agcagaagat tcggaccaat tgacccagtc 240
cctcatctta agtctattga aggataccccc gaagtccaaa tgatcaggcg tgaggccaat 300
gaaagcctta gggtgattgg agacgattgg cacacagact ccaccttcct cgatgcacca 360
cccgcagcag ttgttatgag agctatcgat gttccagagc atgggggcga tactggattc 420
ctttcaatgt atactgcttg ggagacactc agtcctacaa tgcaagccac tatagaagga 480
cttaacgtag tgcattccgc cacaagagtt tttggttctc tttaccaagc acagaacaga 540
aggtggagta atactagcct caaggtcatg gatgtcgacg ctggagaccg cgaaaccgtc 600
caccctcttg tggtcaccca tcctgggtct ggcagaaagg ggttgtatgt taaccaggtt 660
tactgtcaac gtatcgaagg aatgacagac gctgaaagca aaccacttct tcagttcctt 720
tatgaacacg caaccagatt tgactttacc tgtagagtac gttggaagaa agaccaggtg 780
ttggtttggg acaacctgtg taccatgcat agggctgtgc ccgattatgc aggaaagttc 840
aggtacctga ccaggaccac tgtgggtggt gttaggcctg ctcgttga 888

SEQ ID NO: 176 moltype = DNA length = 888
FEATURE Location/Qualifiers
source 1..888
mol_type = other DNA
organism = synthetic construct
CDS 1..888
protein_id = 122
transl_table = 1
translation = MHAALSPLSQRFERIAVQPLTGVLGAEITGVDLREPLDDSTWNEIL
DAFHTYQVIYFPGQAITNEQHIAFSRRFGPVDPVPHLKSIEGYPEVQMIRREANESLGY
IGDDWHTDSTFLDAPPAAVVMRAIDVPEHGGDTGFLSMYTAWETLSPTMQATIEGLNVV
HSATRVFGSLYQAQNRRWSNTSLKVMDVDAGDRETVHPLVVTHPGSGRKGLYVNQVYCQ
RIEGMTDAESKPLLQFLYEHATRFDFTCRVRWKKDQVLVWDNLCTMHRAVPDYAGKFRY
LTRTTVGGVRPAR SEQUENCE: 176
atgcacgcag ctttgagtcc cttgtcccaa aggttcgagc gtatcgcagt tcagcctctt 60
acaggagttc ttggcgccga aatcacagga gtggatctca gggaaccctt ggacgactct 120
acatggaatg agatcttgga tgcttttcat acataccaag tgatatactt tcctggacag 180
gccattacta atgagcagca cattgctttt tcaagacgtt ttggacccgt tgatcctgtg 240
cctcatctca agagcataga gggctatcct gaagttcaga tgataaggcg tgaggctaac 300
gaaagcttgg gttatattgg cgacgattgg cacaccgata gtacttttct ggacgccccc 360
cctgccgctg tcgtcatgag ggctatagac gtgcctgaac atggcgggga taccggattt 420
ttgtctatgt acactgcctg ggagacattg agtcctacta tgcaggccac catagaggga 480
cttaatgtcg tgcactcagc aaccagggtg ttcggaagct tgtaccaagc tcagaataga 540
aggtggtcca acacttcatt gaaggttatg gacgttgacg caggagacag agaaactgtg 600
catcctttgg tggttactca cccaggaagt ggccgcaaag ggctgtatgt taatcaagtc 660
tactgtcagc gtattgaggg aatgaccgat gccgaaagca agcctttgct tcagttcctt 720
tatgaacatg caacacgctt cgattttact tgcagagtta gatggaaaaa ggatcaagtt 780
cttgtttggg ataatttgtg cactatgcat cgtgctgttc ccgactatgc tggaaaattc 840

```
agatatctta cacgcactac agttggtgga gtacgtcctg cacgttga              888

SEQ ID NO: 177         moltype = DNA  length = 888
FEATURE                Location/Qualifiers
source                 1..888
                       mol_type = other DNA
                       organism = synthetic construct
CDS                    1..888
                       protein_id = 126
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHSDSTFLDAPPAAVVMRAIDVPEHGGDTGFLSMYTAWETLSPTMQATIEGLNVV
                        HSATRVFGSLYQAQNKRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 177
atgcacgctg ctttgtcccc tctttcacaa agattcgaac gcatcgccgt tcagcccctc  60
accggggtac tcggagcaga aattacagga gttgatcttc gcgagcccct cgatgattca  120
acttggaatg aaatcttgga cgcattccat acatatcagg taatctactt tcctggacaa  180
gctattacta acgaacagca tatcgctttt tcaagaagat tcggcccagt ggatccagtc  240
ccacatctta aaagcataga gggatatcca gaggtccaga tgatcagaag ggaggcaaac  300
gagtccggcg gtgtgatcgg agatgactgg cattctgatt ctaccttctt ggatgcccct  360
ccagccgccg tagtcatgag agcaatcgat gtccctgaac atggaggtga tactgggttt  420
ctctctatgt acaccgcatg ggaaacactc tcacccacta tgcaagctac aattgaaggt  480
cttaacgtgg ttcatagtgc taccagggtg ttcggcagtt tgtaccaggc tcagaacaag  540
aggtggtcta acacctcttt gaaggtgatg gatgtagacg ccggggacag agaaaccgtt  600
catcctttgg ttgttactca tccaggaagt ggcagaaaag ggctctacgt caatcaagtt  660
tattgtcagc gcattgaggg tatgactgac gccgaatcaa aacctctttt gcaattcctg  720
tatgaacatg ccacaaggtt cgactttaca tgtagagttc gctggaagaa ggatcaagtg  780
cttgtgtggg ataatctttg tacaatgcat agggctgtac cagattatgc cggcaagttc  840
cgctacttga ccagaacaac tgtaggtggg gtgcgccctg ctaggtga              888

SEQ ID NO: 178         moltype = DNA  length = 888
FEATURE                Location/Qualifiers
source                 1..888
                       mol_type = other DNA
                       organism = synthetic construct
CDS                    1..888
                       protein_id = 130
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHSDSTFLDAPPAAVVMRAIDVPEHGGDTGFLSMYTAWETLSPTMQATIEGLNVV
                        HSATRVFGSLYQAQNMRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 178
atgcatgccg cccttagtcc tctcagccag aggtttgagc gtatagcagt gcaacctttg  60
accggggttc ttggagccga gatcactggc gttgacttgc gcgagccact tgatgactcc  120
acttggaatg agatcttgga cgcttttcac acatatcagg tgatttattt tccaggacaa  180
gccataacca acgaacaaca cattgcattc agtagaaggt tcggaccagt tgacccagtt  240
cctcacttga agtcaataga aggttatcct gaagtgcaaa tgattagaag agaggctaac  300
gagagtgggg gtgtgatcgg cgatgattgg catagcgatt caactttcct tgatgctccc  360
ccagcagccg tggtcatgag agcaatcgac gtgccagaac atggaggcga tacaggtttt  420
ctttccatgt atactgcatg ggaaaccctc tctcctacca tgcaggccac aattgaagga  480
ctgaatgttg tgcatagcgc tactagggtg tttggctctc tctatcaggc acaaaacatg  540
cgctggagca atacatcact taaggtaatg gatgtagatg ctggcgatag agaaaccgtg  600
catccattgg tggttactca tccaggctca ggacgtaagg gtttgtacgt caatcaagtt  660
tactgccaga gaatagaggg gatgactgac gctgaatcta agcctcttct ccaatttttg  720
tacgagcacg ctacaagatt cgacttcaca tgccgtgttc gctggaaaaa ggaccaggtt  780
cttgtctggg ataacctttg cactatgcat agggctgttc cagattacgc tggaaaattt  840
aggtacttga ctaggactac agtcggtggc gttagacctg ctcgctga              888

SEQ ID NO: 179         moltype = DNA  length = 888
FEATURE                Location/Qualifiers
source                 1..888
                       mol_type = other DNA
                       organism = synthetic construct
CDS                    1..888
                       protein_id = 134
                       transl_table = 1
                       translation = MHAALSPLSQRFERIAVQPLTGVLGAEITGVDLREPLDDSTWNEIL
                        DAFHTYQVIYFPGQAITNEQHIAFSRRFGPVDPVPHLKSIEGYPEVQMIRREANESGGV
                        IGDDWHSDSTFLDAPPAAVVMRAIDVPEHGGDTGFLSMYTAWETLSPTMQATIEGLNVV
                        HSATRVFGSLYQAQNWRWSNTSLKVMDVDAGDRETVHPLVVTHPGSGRKGLYVNQVYCQ
                        RIEGMTDAESKPLLQFLYEHATRFDFTCRVRWKKDQVLVWDNLCTMHRAVPDYAGKFRY
                        LTRTTVGGVRPAR
SEQUENCE: 179
```

-continued

```
atgcatgctg ccctctcacc actgagccaa aggttcgagc gtattgcagt ccaaccactg  60
accggtgttc tcggagctga gattactggt gtggatctca gggagccact cgacgactcc  120
acttggaatg aaattcttga tgcttttcat acctaccaag tcatctactt tcctggtcaa  180
gctattacta acgaacagca tattgcattc tcaaggagat tcggaccagt ggaccctgtt  240
cctcatctca agagcatcga aggatatcca gaagtccaga tgattcgtcg tgaggcaaac  300
gagtcaggtg gagtcattgg ggatgattgg cattccgaca gtactttctt ggatgcacca  360
ccagcagctg ttgttatgag ggctattgat gttcctgaac atggagggga tacagggttc  420
ctctccatgt acacagcttg ggaaactttg tctcccacca tgcaggcaac aattgagggg  480
cttaatgtgg ttcatagcgc tacacgtgtt tttgggagtc tctatcaagc ccaaaattgg  540
aggtggtcaa acacatcatt gaaggtgatg gatgtggatg ctggggatag agagacagtg  600
catcctctcg tcgtcactca cccaggaagc ggaagaaagg ggctttatgt taatcaggtt  660
tattgccaga gaatcgaagg aatgaccgat gcagaatcta aacccctgct tcagtttctg  720
tatgaacatg caactaggtt tgacttcact tgtagggtta gatggaagaa ggatcaggtt  780
ttggtttggg acaacctttg taccatgcac cgtgctgtcc ctgactacgc tggcaagttt  840
agatatctta caagaactac tgtcggaggt gttcgccctg cccgctga              888
```

```
SEQ ID NO: 180          moltype = DNA  length = 888
FEATURE                 Location/Qualifiers
source                  1..888
                        mol_type = other DNA
                        organism = synthetic construct
CDS                     1..888
                        protein_id = 138
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESLRV
                         IGDDWHTDSTFLDAPPAAVVMRAIDVPEHGGDTGFLSMYTAWETLSPTMQATIEGLNVV
                         HSATRVFGSLYQAQNTRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 180
atgcacgctg ctctctcccc tctttcccaa agatttgagc gtattgccgt acaaccattg  60
accggagtcc tcggggcaga gattaccggg gtcgatttga gggaacctct ggacgacagc  120
acttggaatg aaatattgga tgcttttcac acctatcaag tcatatactt ccctgggcag  180
gctatcacaa atgaacaaca tattgcattt agcaggagat tcggtcctgt tgatccagtt  240
cctcacctca agtctataga agggtacccc gaagttcaaa tgattcgccg cgaggccaac  300
gaaagtctta gagtgatcgg tgatgattgg cataccgata gcactttctt ggacgcccca  360
cccgctgctg tagttatgcg cgcaatcgac gttccagaac atggtggcga tactggattc  420
ctttctatgt ataccgcatg ggaaaccctc tccccaacca tgcaggcaac catagaaggc  480
ctcaacgtcg tgcactcagc aacaagggtt tttgggagcc tttatcaagc acagaatacc  540
aggtggtcaa acacaagcct taaggttatg gatgtagatg caggtgatcg cgagacagta  600
catcccctcg ttgttactca ccccggttca gggaggaagg gactttacgt taatcaagtc  660
tactgccaaa gaatcgaagg gatgactgat gcagaatcta agcccttgct tcaatttttg  720
tatgagcacg ccaccagatt cgatttttact tgcagggtga ggtggaaaaa agaccaggta  780
ctggtgtggg acaatctgtg taccatgcat cgtgcagtcc ctgattatgc cggtaagttt  840
agatatctca cacgcacaac agtgggtggt gttcgtcccg caagatga              888
```

```
SEQ ID NO: 181          moltype = DNA  length = 888
FEATURE                 Location/Qualifiers
source                  1..888
                        mol_type = other DNA
                        organism = synthetic construct
CDS                     1..888
                        protein_id = 142
                        transl_table = 1
                        translation = MHAALSPLSQRFERIAVQPLTGVLGAEITGVDLREPLDDSTWNEIL
                         DAFHTYQVIYFPGQAITNEQHIAFSRRFGPVDPVPHLKSIEGYPEVQMIRREANESGGV
                         IGDDWHSDSTFLDAPPAAVVMRAIDVPEHGGDTGFLSMYTAWETLSPTMQATIEGLNVV
                         HSATRVFGSLYQAQNQRWSNTSLKVMDVDAGDRETVHPLVVTHPGSGRKGLYVNQVYCQ
                         RIEGMTDAESKPLLQFLYEHATRFDFTCRVRWKKDQVLVWDNLCTMHRAVPDYAGKFRY
                         LTRTTVGGVRPAR
SEQUENCE: 181
atgcatgctg ctctcagccc acttagtcag agattcgaga gaatagcagt gcaacccttg  60
actggagtcc tgggtgcaga gattaccgga gtcgatttga gagaacctct cgatgattcc  120
acctggaatg aaatcttgga cgctttccac acttaccaag ttatttattt ccctggacaa  180
gctatcacca acgaacaaca cattgctttt tctcgtaggt tcggaccagt tgacccagtc  240
ccacacttga agagtatcga aggatacccc gaagtccaaa tgatcagaag ggaggctaat  300
gaatcaggtg gggtgatcgg tgacgactgg cacagcgatt ctacttttct ggatgcacca  360
ccagcagcag ttgtcatgcg cgctatcgac gtgccagagc acggggggga tactggtttc  420
ctctccatgt acactgcctg ggaaaccctg tcaccaacaa tgcaggccac tattgaaggc  480
ctcaatgttg tgcatagcgc tacaagggtt ttcggctctt tgtatcaagc ccaaaaccag  540
aggtggtcaa atacttcact gaaggttatg gacgttgatg ctggtgacag agagaccgtc  600
catccacttg tagtcaccca tcccggttcc ggcaggaaag gattgtatgt taatcaggta  660
tactgtcaaa ggatcgaggg tatgaccgat gcagaatcaa aacctctttt gcagttcctg  720
tatgaacatg caacaagatt tgatttttact tgtagggtgc gttggaagaa ggaccaggtg  780
ctcgtttggg ataacttgtg tacaatgcac cgcgcagtgc cagactatgc tggtaagttt  840
cgttacctca ccagaaccac tgtaggcggc gttagacccg cacgttga              888
```

HERBICIDE-TOLERANT GENES AND METHOD FOR USING SAME

CROSS-REFERENCE TO RELATED APPLICATIONS

This patent application is a U.S. National Stage of International Patent Application No. PCT/CN2023/074624, filed Feb. 6, 2024, which claims the benefit of Chinese Patent Application No. 202210180516.3, filed Feb. 25, 2022.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 435,883 Byte XML file named "771660_XML," created on Aug. 13, 2024.

TECHNICAL FIELD

The present invention generally relates to the field of biotechnology. More specifically, the present invention relates to a recombinant DNA molecule encoding an enzyme that degrades herbicides. The present invention also relates to a transgenic plant, part, seed, cell and plant part containing the recombinant DNA molecule and the method of use thereof.

BACKGROUND OF THE INVENTION

Transgenic traits created by biotechnological methods are commonly used in agricultural crop production. A heterologous gene (also referred to as a transgene) is introduced into a plant to generate a transgenic trait. Expression of the transgene in the plant confers a desirable trait, such as herbicide tolerance, on the plant. Examples of transgenic herbicide-tolerant traits include glyphosate tolerance, glufosinate tolerance, and dicamba tolerance. With the increase of weed species that are resistant to the most commonly used herbicides, new herbicide-tolerant traits are needed in the field. Herbicides of particular interest are the pyridinyloxy acid herbicides. Pyridinyloxy acid herbicides provide control of a range of glyphosate-resistant weeds, thus resulting in a trait conferring herbicide tolerance that is particularly used in combination with other herbicide tolerance trait(s) in a cropping system.

The *Sphingobium herbicidovorans* strain MH isolated from a dichlorprop-degrading soil sample was identified as being capable of cleaving the ether bond of various phyenoxyalkanoic acid herbicides, thereby utilizing this as the sole source of carbon and energy for its growth (HPE Kohler, Journal of Industrial Microbiology & Biotechnology (1999) 23:336-340). Catabolism of the herbicides is carried out by two different enantioselective α-ketoglutarate-dependent dioxygenases, RdpA (R-dichlorprop dioxygenase) and SdpA (S-dichlorprop dioxygenase). (A Westendorf, et al., Microbiological Research (2002) 157:317-322; Westendorf, et al., ActaBiotechnologica (2003) 23 (1): 3-17). RdpA has been isolated from *Sphingobium herbicidovorans* (GenBank accessions AF516752 (DNA) and AAM90965 (protein)) and Delftia *acidovorans* (GenBank accessions NG-036924 (DNA) and YP-009083283 (protein)) (TA Mueller, et al., Applied and Environmental Microbiology (2004) 70 (10): 6066-6075). The RdpA and SdpA genes have been used for plant transformation to confer herbicide tolerance to crops (T R Wright, et al., Proceedings of the National Academy of Sciences USA, (2010) 107 (47): 20240-5). Improving the activity of the RdpA enzyme using protein engineering techniques to create a protein for use in transgenic plants would allow higher rates of herbicide application, thereby improving the safety of transgenic crops and weed control measures.

BRIEF SUMMARY OF THE INVENTION

The present invention provides a recombinant DNA molecule comprising a nucleic acid sequence encoding a polypeptide, as compared with the amino acid sequence of RdpA as set forth in SEQ ID NO: 1, the amino acid sequence of the polypeptide has the following mutation: the amino acid at position 82 is mutated from leucine into histidine. In one embodiment, the amino acid sequence of the polypeptide also has one or more mutation(s) selected from the following groups: the amino acid at position 187 is mutated from valine into leucine, methionine or isoleucine; the amino acid at position 187 is mutated from valine into leucine, and the amino acid at position 104 is mutated from arginine into alanine, aspartic acid or leucine; the amino acid at position 187 is mutated from valine into leucine, and the amino acid at position 182 is mutated from phenylalanine into tryptophan; the amino acid at position 187 is mutated from valine into leucine, and the amino acid at position 103 is mutated from glycine into leucine; the amino acid at position 187 is mutated from valine into leucine, the amino acid at position 182 is mutated from phenylalanine into tryptophan, and the amino acid at position 104 is mutated from arginine into glycine; the amino acid at position 187 is mutated from valine into leucine, the amino acid at position 182 is mutated from phenylalanine into tryptophan, and the amino acid at position 103 is mutated from glycine into leucine; the amino acid at position 187 is mutated from valine into leucine, the amino acid at position 182 is mutated from phenylalanine into tryptophan, the amino acid at position 104 is mutated from arginine into glycine, and the amino acid at position 112 is mutated from threonine into serine; the amino acid at position 187 is mutated from valine into leucine, the amino acid at position 182 is mutated from phenylalanine into tryptophan, the amino acid at position 104 is mutated from arginine into glycine, and the amino acid at position 80 is mutated from valine into threonine; the amino acid at position 187 is mutated from valine into leucine, the amino acid at position 182 is mutated from phenylalanine into tryptophan, the amino acid at position 104 is mutated from arginine into glycine, and the amino acid at position 180 is mutated from arginine into tryptophan or methionine; the amino acid at position 187 is mutated from valine into leucine, the amino acid at position 182 is mutated from phenylalanine into tryptophan, the amino acid at position 104 is mutated from arginine into glycine, and the amino acid at position 108 is mutated from aspartic acid into cysteine; the amino acid at position 187 is mutated from valine into leucine, the amino acid at position 182 is mutated from phenylalanine into tryptophan, the amino acid at position 104 is mutated from arginine into glycine, and the amino acid at position 109 is mutated from aspartic acid into glutamic acid; the amino acid at position 187 is mutated from valine into leucine, the amino acid at position 182 is mutated from phenylalanine into tryptophan, the amino acid at position 104 is mutated from arginine into glycine, and the amino acid at position 219 is mutated from glutamine into cysteine or proline; the amino acid at position 187 is mutated from valine into leucine, the amino acid at position 182 is mutated from phenylalanine into tryptophan, the amino acid at position 103 is mutated from glycine into leucine, and the amino acid at position 180 is mutated from arginine into aspartic acid, glutamic acid, serine, leucine, tryptophan or threonine; the amino acid at position 187 is mutated from valine into leucine, the amino acid at position 182 is mutated from phenylalanine into tryptophan, the amino acid at position 103 is mutated from glycine into leucine, and the amino acid at position 80 is mutated from valine into threonine; the amino acid at position 187 is mutated from valine into leucine, the amino acid at position 182 is mutated from phenylalanine into tryptophan, the amino acid at position 103 is mutated from glycine into leucine, and the amino acid at position 112 is mutated from threonine into alanine, serine or methionine; the amino acid at position 187 is mutated from valine into leucine, the amino acid at position 182 is mutated from phenylalanine into tryptophan, the amino acid at position 103 is mutated from glycine into leucine, and the amino acid at position 247 is mutated from phenylalanine into tyrosine; the amino acid at position 187 is mutated from valine into leucine, the amino acid at position 182 is mutated from phenylalanine into tryptophan, the amino acid at position 104 is mutated from arginine into glycine, and the amino acid at position 77 is mutated from valine into isoleucine; the amino acid at position 187 is mutated from valine into leucine, the amino acid at position 182 is mutated from phenylalanine into tryptophan, the amino acid at position 104 is mutated from arginine into glycine, the amino acid at position 112 is mutated from threonine into serine, and the amino acid at position 180 is mutated from arginine into lysine, methionine, tryptophan or glutamine; and/or the amino acid at position 187 is mutated from valine into leucine, the amino acid at position 182 is mutated from phenylalanine into tryptophan, the amino acid at position 103 is mutated from glycine into leucine, the amino acid at position 104 is mutated from arginine into glycine, and the amino acid at position 105 is mutated from valine into tyrosine. In another embodiment, the amino acid sequence of the polypeptide further has at least 80%, at least 85%, at least 90%, at least 95%, at least 96%, at least 97%, at least 98%, at least 99% sequence identity to the amino acid sequence of RdpA as set forth in SEQ ID NO: 1.

The present invention also provides a recombinant DNA molecule comprising a nucleic acid sequence encoding a polypeptide that has at least about 92% sequence identity to an amino acid sequence selected from the group consisting of SEQ ID NO: 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138 and 142. In another embodiment, the recombinant DNA molecule comprises a nucleic acid sequence selected from the group consisting of SEQ ID NO: 3, 4, 5, 7, 8, 9, 11, 12, 13, 15, 16, 17, 19, 20, 21, 23, 24, 25, 27, 28, 29, 31, 32, 33, 35, 36, 37, 39, 40, 41, 43, 44, 45, 47, 48, 49, 51, 52, 53, 55, 56, 57, 59, 60, 61, 63, 64, 65, 67, 68, 69, 71, 72, 73, 75, 76, 77, 79, 80, 81, 83, 84, 85, 87, 88, 89, 91, 92, 93, 95, 96, 97, 99, 100, 101, 103, 104, 105, 107, 108, 109, 111, 112, 113, 115, 116, 117, 119, 120, 121, 123, 124, 125, 127, 128, 129, 131, 132, 133, 135, 136, 137, 139, 140, 141 and 143-181, and a nucleic acid sequence encoding the same amino acid sequence as the sequence shown due to degeneracy of genetic code. In another embodiment, the recombinant DNA molecule encodes a polypeptide having oxygenase activity against at least one herbicide selected from the group consisting of pyridinyloxy acid herbicides. In another embodiment, the recombinant DNA molecule is operably linked to a heterologous promoter functional in a plant cell. In another embodiment, the recombinant DNA molecule is operably linked to a DNA molecule encoding a chloroplast transit peptide (CTP) that functions to localize an operably linked polypeptide within a cell.

The present invention provides a DNA construct comprising a heterologous promoter functional in a plant cell, and the heterologous promoter is operably linked to the recombinant DNA molecule of the present invention. In an embodiment, the recombinant DNA molecule is operably linked to a DNA molecule encoding a chloroplast transit peptide (CTP) that functions to localize an operably linked polypeptide within a cell. In another embodiment, the expression of the polypeptide in a transgenic plant encoded by the recombinant DNA molecule confers herbicide tolerance to the plant. In another embodiment, the DNA construct is present in the genome of a transgenic plant.

The present invention provides a transgenic plant, seed, cell or plant part comprising a recombinant DNA molecule of the present invention. In one embodiment, the transgenic plant, seed, cell or plant part comprises a transgenic trait for tolerance to at least one herbicide selected from the group consisting of pyridinyloxy acid herbicides. In another embodiment, the transgenic plant, seed, cell or plant part comprises a DNA construct of the present invention. In another embodiment, the transgenic plant, seed, cell or plant part comprises a polypeptide of the present invention.

The present invention provides a polypeptide, the amino acid sequence of which has the following mutation compared with the amino acid sequence of RdpA as set forth in SEQ ID NO: 1: the amino acid at position 82 is mutated from leucine into histidine. In one embodiment, the amino acid sequence of the polypeptide also has one or more mutation (s) as mentioned above. In another embodiment, the amino acid sequence of the polypeptide further has at least 80%, at least 85%, at least 90%, at least 95%, at least 96%, at least 97%, at least 98%, at least 99% sequence identity to the amino acid sequence of RdpA as set forth in SEQ ID NO: 1.

The present invention provides a polypeptide that has at least about 92% sequence identity to an amino acid sequence selected from the group consisting of SEQ ID NO: 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138 and 142. In one embodiment, the polypeptide has oxygenase activity against at least one herbicide selected from the group consisting of pyridinyloxy acid herbicides.

The present invention provides a method for conferring herbicide tolerance to a plant, seed, cell or plant part comprising expressing a polypeptide of the present invention in the plant, seed, cell or plant part. In one embodiment, the method for conferring herbicide tolerance is used in combination with a transgenic plant, seed, cell or plant part that comprises a transgenic trait comprising a recombinant DNA molecule of the present invention. In one embodiment, the method for conferring herbicide tolerance is used in combination with a herbicide selected from the group consisting of pyridinyloxy acid herbicides.

The present invention provides a method of plant transformation comprising introducing a recombinant DNA molecule or DNA construct of the present invention into a plant cell or tissue, and regenerating a plant therefrom that comprises the recombinant DNA molecule or DNA construct and is tolerant to at least one herbicide selected from the group consisting of pyridinyloxy acid herbicides. In an embodiment, the method of plant transformation includes crossing the regenerated plant with itself or with a second plant and collecting seed from the cross.

The present invention provides a method for controlling weeds in a plant growing area by exposing a plant growing area comprising a transgenic plant or seed of the invention to at least one herbicide selected from the group consisting of pyridinyloxy acid herbicides, wherein the transgenic plant or seed is tolerant to the herbicide.

BRIEF DESCRIPTION OF THE SEVERAL VIEWS OF THE DRAWING(S)

FIG. 1 shows control Jinjing 818 plants and transgenic Jinjing 818 plants comprising the protein-coding gene of SEQ ID NO: 42 after adding 0.5 μM and 1 μM compound B to medium for 19 days (variations in growth among plants that express the same protein may be resulted from changes in construct design or insertion position of the transgene, the same hereinafter).

FIG. 3 shows wild-type control and T2 generation *Arabidopsis thaliana* plant seeds comprising the protein-coding gene of SEQ ID NO: 46 after adding 0.15 μM compound A to medium for 11 days of screening.

FIG. 4 shows wild-type control *Arabidopsis thaliana* plants transformed with RdpA gene and *Arabidopsis thaliana* plants comprising the protein-coding gene of SEQ ID NO: 42, after plants being foliage-sprayed with 40 g/mu compound B for 12 days.

FIG. 5 shows control Jinjing 818 plants and transgenic Jinjing 818 plants comprising the protein-coding genes of SEQ ID NO: 138/86 after adding 1 μM compound B to medium for 17 days.

Figure 1:
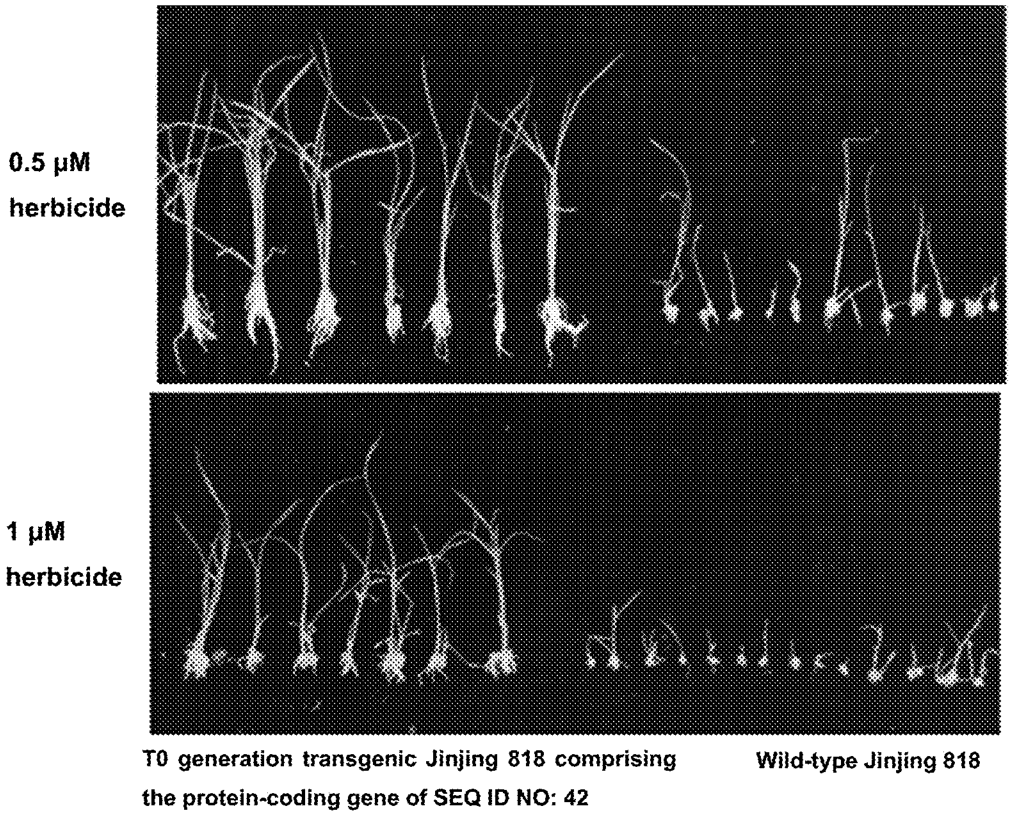

| | |
|---|---|
| SEQ ID NO: 1 | Amino acid sequence of RdpA |
| SEQ ID NO: 2 | Amino acid sequence of RdpA mutant L82H |
| SEQ ID NO: 3 | *E. Coli* codon optimized RdpA mutant L82H |
| SEQ ID NO: 4 | Maize codon optimized RdpA mutant L82H |
| SEQ ID NO: 5 | Cotton codon optimized RdpA mutant L82H |
| SEQ ID NO: 6 | Amino acid sequence of RdpA mutant L82H + V187L |
| SEQ ID NO: 7 | *E. Coli* codon optimized RdpA mutant L82H + V187L |
| SEQ ID NO: 8 | Maize codon optimized RdpA mutant L82H + V187L |
| SEQ ID NO: 9 | Cotton codon optimized RdpA mutant L82H + V187L |
| SEQ ID NO: 10 | Amino acid sequence of RdpA mutant L82H + V187M |
| SEQ ID NO: 11 | *E. Coli* codon optimized RdpA mutant L82H + V187M |
| SEQ ID NO: 12 | Maize codon optimized RdpA mutant L82H + V187M |
| SEQ ID NO: 13 | Cotton codon optimized RdpA mutant L82H + V187M |
| SEQ ID NO: 14 | Amino acid sequence of RdpA mutant L82H + V187I |
| SEQ ID NO: 15 | *E. Coli* codon optimized RdpA mutant L82H + V187I |
| SEQ ID NO: 16 | Maize codon optimized RdpA mutant L82H + V187I |
| SEQ ID NO: 17 | Cotton codon optimized RdpA mutant L82H + V187I |
| SEQ ID NO: 18 | Amino acid sequence of RdpA mutant L82H + V187L + R104A |
| SEQ ID NO: 19 | *E. Coli* codon optimized RdpA mutant L82H + V187L + R104A |
| SEQ ID NO: 20 | Maize codon optimized RdpA mutant L82H + V187L + R104A |
| SEQ ID NO: 21 | Cotton codon optimized RdpA mutant L82H + V187L + R104A |
| SEQ ID NO: 22 | Amino acid sequence of RdpA mutant L82H + V187L + R104D |
| SEQ ID NO: 23 | *E. Coli* codon optimized RdpA mutant L82H + V187L + R104D |
| SEQ ID NO: 24 | Maize codon optimized RdpA mutant L82H + V187L + R104D |
| SEQ ID NO: 25 | Cotton codon optimized RdpA mutant L82H + V187L + R104D |
| SEQ ID NO: 26 | Amino acid sequence of RdpA mutant L82H + V187L + R104L |
| SEQ ID NO: 27 | *E. Coli* codon optimized RdpA mutant L82H + V187L + R104L |
| SEQ ID NO: 28 | Maize codon optimized RdpA mutant L82H + V187L + R104L |
| SEQ ID NO: 29 | Cotton codon optimized RdpA mutant L82H + V187L + R104L |
| SEQ ID NO: 30 | Amino acid sequence of RdpA mutant L82H + V187L + F182W |
| SEQ ID NO: 31 | *E. Coli* codon optimized RdpA mutant L82H + V187L + F182W |
| SEQ ID NO: 32 | Maize codon optimized RdpA mutant L82H + V187L + F182W |
| SEQ ID NO: 33 | Cotton codon optimized RdpA mutant L82H + V187L + F182W |
| SEQ ID NO: 34 | Amino acid sequence of RdpA mutant L82H + V187L + G103L |
| SEQ ID NO: 35 | *E. Coli* codon optimized RdpA mutant L82H + V187L + G103L |
| SEQ ID NO: 36 | Maize codon optimized RdpA mutant L82H + V187L + G103L |
| SEQ ID NO: 37 | Cotton codon optimized RdpA mutant L82H + V187L + G103L |
| SEQ ID NO: 38 | Amino acid sequence of RdpA mutant L82H + V187L + F182W + R104G |
| SEQ ID NO: 39 | *E. Coli* codon optimized RdpA mutant L82H + V187L + F182W + R104G |
| SEQ ID NO: 40 | Maize codon optimized RdpA mutant L82H + V187L + F182W + R104G |
| SEQ ID NO: 41 | Cotton codon optimized RdpA mutant L82H + V187L + F182W + R104G |
| SEQ ID NO: 42 | Amino acid sequence of RdpA mutant L82H + V187L + F182W + G103L |
| SEQ ID NO: 43 | *E. Coli* codon optimized RdpA mutant L82H + V187L + F182W + G103L |
| SEQ ID NO: 44 | Maize codon optimized RdpA mutant L82H + V187L + F182W + G103L |
| SEQ ID NO: 45 | Cotton codon optimized RdpA mutant L82H + V187L + F182W + G103L |
| SEQ ID NO: 46 | Amino acid sequence of RdpA mutant L82H + V187L + F182W + R104G + T112S |
| SEQ ID NO: 47 | *E. Coli* codon optimized RdpA mutant L82H + V187L + F182W + R104G + T112S |
| SEQ ID NO: 48 | Maize codon optimized RdpA mutant L82H + V187L + F182W + R104G + T112S |
| SEQ ID NO: 49 | Cotton codon optimized RdpA mutant L82H + V187L + F182W + R104G + T112S |
| SEQ ID NO: 50 | Amino acid sequence of RdpA mutant L82H + V187L + F182W + R104G + V80T |
| SEQ ID NO: 51 | *E. Coli* codon optimized RdpA mutant L82H + V187L + F182W + R104G + V80T |
| SEQ ID NO: 52 | Maize codon optimized RdpA mutant L82H + V187L + F182W + R104G + V80T |
| SEQ ID NO: 53 | Cotton codon optimized RdpA mutant L82H + V187L + F182W + R104G + V80T |
| SEQ ID NO: 54 | Amino acid sequence of RdpA mutant L82H + V187L + F182W + R104G + R180W |
| SEQ ID NO: 55 | *E. Coli* codon optimized RdpA mutant L82H + V187L + F182W + R104G + R180W |
| SEQ ID NO: 56 | Maize codon optimized RdpA mutant L82H + V187L + F182W + R104G + R180W |
| SEQ ID NO: 57 | Cotton codon optimized RdpA mutant L82H + V187L + F182W + R104G + R180W |
| SEQ ID NO: 58 | Amino acid sequence of RdpA mutant L82H + V187L + F182W + R104G + R180M |
| SEQ ID NO: 59 | *E. Coli* codon optimized RdpA mutant L82H + V187L + F182W + R104G + R180M |
| SEQ ID NO: 60 | Maize codon optimized RdpA mutant L82H + V187L + F182W + R104G + R180M |
| SEQ ID NO: 61 | Cotton codon optimized RdpA mutant L82H + V187L + F182W + R104G + R180M |
| SEQ ID NO: 62 | Amino acid sequence of RdpA mutant L82H + V187L + F182W + R104G + D108C |
| SEQ ID NO: 63 | *E. Coli* codon optimized RdpA mutant L82H + V187L + F182W + R104G + D108C |
| SEQ ID NO: 64 | Maize codon optimized RdpA mutant L82H + V187L + F182W + R104G + D108C |
| SEQ ID NO: 65 | Cotton codon optimized RdpA mutant L82H + V187L + F182W + R104G + D108C |
| SEQ ID NO: 66 | Amino acid sequence of RdpA mutant L82H + V187L + F182W + R104G + D109E |
| SEQ ID NO: 67 | *E. Coli* codon optimized RdpA mutant L82H + V187L + F182W + R104G + D109E |
| SEQ ID NO: 68 | Maize codon optimized RdpA mutant L82H + V187L + F182W + R104G + D109E |
| SEQ ID NO: 69 | Cotton codon optimized RdpA mutant L82H + V187L + F182W + R104G + D109E |
| SEQ ID NO: 70 | Amino acid sequence of RdpA mutant L82H + V187L + F182W + R104G + Q219C |
| SEQ ID NO: 71 | *E. Coli* codon optimized RdpA mutant L82H + V187L + F182W + R104G + Q219C |
| SEQ ID NO: 72 | Maize codon optimized RdpA mutant L82H + V187L + F182W + R104G + Q219C |
| SEQ ID NO: 73 | Cotton codon optimized RdpA mutant L82H + V187L + F182W + R104G + Q219C |
| SEQ ID NO: 74 | Amino acid sequence of RdpA mutant L82H + V187L + F182W + R104G + Q219P |
| SEQ ID NO: 75 | *E. Coli* codon optimized RdpA mutant L82H + V187L + F182W + R104G + Q219P |
| SEQ ID NO: 76 | Maize codon optimized RdpA mutant L82H + V187L + F182W + R104G + Q219P |
| SEQ ID NO: 77 | Cotton codon optimized RdpA mutant L82H + V187L + F182W + R104G + Q219P |
| SEQ ID NO: 78 | Amino acid sequence of RdpA mutant L82H + V187L + F182W + G103L + R180D |
| SEQ ID NO: 79 | *E. Coli* codon optimized RdpA mutant L82H + V187L + F182W + G103L + R180D |
| SEQ ID NO: 80 | Maize codon optimized RdpA mutant L82H + V187L + F182W + G103L + R180D |
| SEQ ID NO: 81 | Cotton codon optimized RdpA mutant L82H + V187L + F182W + G103L + R180D |

-continued

| | |
|---|---|
| SEQ ID NO: 82 | Amino acid sequence of RdpA mutant L82H + V187L + F182W + G103L + R180E |
| SEQ ID NO: 83 | *E. Coli* codon optimized RdpA mutant L82H + V187L + F182W + G103L + R180E |
| SEQ ID NO: 84 | Maize codon optimized RdpA mutant L82H + V187L + F182W + G103L + R180E |
| SEQ ID NO: 85 | Cotton codon optimized RdpA mutant L82H + V187L + F182W + G103L + R180E |
| SEQ ID NO: 86 | Amino acid sequence of RdpA mutant L82H + V187L + F182W + G103L + R180S |
| SEQ ID NO: 87 | *E. Coli* codon optimized RdpA mutant L82H + V187L + F182W + G103L + R180S |
| SEQ ID NO: 88 | Maize codon optimized RdpA mutant L82H + V187L + F182W + G103L + R180S |
| SEQ ID NO: 89 | Cotton codon optimized RdpA mutant L82H + V187L + F182W + G103L + R180S |
| SEQ ID NO: 90 | Amino acid sequence of RdpA mutant L82H + V187L + F182W + G103L + R180L |
| SEQ ID NO: 91 | *E. Coli* codon optimized RdpA mutant L82H + V187L + F182W + G103L + R180L |
| SEQ ID NO: 92 | Maize codon optimized RdpA mutant L82H + V187L + F182W + G103L + R180L |
| SEQ ID NO: 93 | Cotton codon optimized RdpA mutant L82H + V187L + F182W + G103L + R180L |
| SEQ ID NO: 94 | Amino acid sequence of RdpA mutant L82H + V187L + F182W + G103L + R180W |
| SEQ ID NO: 95 | *E. Coli* codon optimized RdpA mutant L82H + V187L + F182W + G103L + R180W |
| SEQ ID NO: 96 | Maize codon optimized RdpA mutant L82H + V187L + F182W + G103L + R180W |
| SEQ ID NO: 97 | Cotton codon optimized RdpA mutant L82H + V187L + F182W + G103L + R180W |
| SEQ ID NO: 98 | Amino acid sequence of RdpA mutant L82H + V187L + F182W + G103L + V80T |
| SEQ ID NO: 99 | *E. Coli* codon optimized RdpA mutant L82H + V187L + F182W + G103L + V80T |
| SEQ ID NO: 100 | Maize codon optimized RdpA mutant L82H + V187L + F182W + G103L + V80T |
| SEQ ID NO: 101 | Cotton codon optimized RdpA mutant L82H + V187L + F182W + G103L + V80T |
| SEQ ID NO: 102 | Amino acid sequence of RdpA mutant L82H + V187L + F182W + G103L + T112A |
| SEQ ID NO: 103 | *E. Coli* codon optimized RdpA mutant L82H + V187L + F182W + G103L + T112A |
| SEQ ID NO: 104 | Maize codon optimized RdpA mutant L82H + V187L + F182W + G103L + T112A |
| SEQ ID NO: 105 | Cotton codon optimized RdpA mutant L82H + V187L + F182W + G103L + T112A |
| SEQ ID NO: 106 | Amino acid sequence of RdpA mutant L82H + V187L + F182W + G103L + T112S |
| SEQ ID NO: 107 | *E. Coli* codon optimized RdpA mutant L82H + V187L + F182W + G103L + T112S |
| SEQ ID NO: 108 | Maize codon optimized RdpA mutant L82H + V187L + F182W + G103L + T112S |
| SEQ ID NO: 109 | Cotton codon optimized RdpA mutant L82H + V187L + F182W + G103L + T112S |
| SEQ ID NO: 110 | Amino acid sequence of RdpA mutant L82H + V187L + F182W + G103L + T112M |
| SEQ ID NO: 111 | *E. Coli* codon optimized RdpA mutant L82H + V187L + F182W + G103L + T112M |
| SEQ ID NO: 112 | Maize codon optimized RdpA mutant L82H + V187L + F182W + G103L + T112M |
| SEQ ID NO: 113 | Cotton codon optimized RdpA mutant L82H + V187L + F182W + G103L + T112M |
| SEQ ID NO: 114 | Amino acid sequence of RdpA mutant L82H + V187L + F182W + G103L + F247Y |
| SEQ ID NO: 115 | *E. Coli* codon optimized RdpA mutant L82H + V187L + F182W + G103L + F247Y |
| SEQ ID NO: 116 | Maize codon optimized RdpA mutant L82H + V187L + F182W + G103L + F247Y |
| SEQ ID NO: 117 | Cotton codon optimized RdpA mutant L82H + V187L + F182W + G103L + F247Y |
| SEQ ID NO: 118 | Amino acid sequence of RdpA mutant L82H + V187L + F182W + R104G + V77I |
| SEQ ID NO: 119 | *E. Coli* codon optimized RdpA mutant L82H + V187L + F182W + R104G + V77I |
| SEQ ID NO: 120 | Maize codon optimized RdpA mutant L82H + V187L + F182W + R104G + V77I |
| SEQ ID NO: 121 | Cotton codon optimized RdpA mutant L82H + V187L + F182W + R104G + V77I |
| SEQ ID NO: 122 | Amino acid sequence of RdpA mutant L82H + V187L + F182W + G103L + R104G + V105Y |
| SEQ ID NO: 123 | *E. Coli* codon optimized RdpA mutant L82H + V187L + F182W + G103L + R104G + V105Y |
| SEQ ID NO: 124 | Maize codon optimized RdpA mutant L82H + V187L + F182W + G103L + R104G + V105Y |
| SEQ ID NO: 125 | Cotton codon optimized RdpA mutant L82H + V187L + F182W + G103L + R104G + V105Y |
| SEQ ID NO: 126 | Amino acid sequence of RdpA mutant L82H + V187L + F182W + R104G + T112S + R180K |
| SEQ ID NO: 127 | *E. Coli* codon optimized RdpA mutant L82H + V187L + F182W + R104G + T112S + R180K |
| SEQ ID NO: 128 | Maize codon optimized RdpA mutant L82H + V187L + F182W + R104G + T112S + R180K |
| SEQ ID NO: 129 | Cotton codon optimized RdpA mutant L82H + V187L + F182W + R104G + T112S + R180K |
| SEQ ID NO: 130 | Amino acid sequence of RdpA mutant L82H + V187L + F182W + R104G + T112S + R180M |
| SEQ ID NO: 131 | *E. Coli* codon optimized RdpA mutant L82H + V187L + F182W + R104G + T112S + R180M |
| SEQ ID NO: 132 | Maize codon optimized RdpA mutant L82H + V187L + F182W + R104G + T112S + R180M |
| SEQ ID NO: 133 | Cotton codon optimized RdpA mutant L82H + V187L + F182W + R104G + T112S + R180M |
| SEQ ID NO: 134 | Amino acid sequence of RdpA mutant L82H + V187L + F182W + R104G + T112S + R180W |
| SEQ ID NO: 135 | *E. Coli* codon optimized RdpA mutant L82H + V187L + F182W + R104G + T112S + R180W |
| SEQ ID NO: 136 | Maize codon optimized RdpA mutant L82H + V187L + F182W + R104G + T112S + R180W |
| SEQ ID NO: 137 | Cotton codon optimized RdpA mutant L82H + V187L + F182W + R104G + T112S + R180W |
| SEQ ID NO: 138 | Amino acid sequence of RdpA mutant L82H + V187L + F182W + G103L + R180T |
| SEQ ID NO: 139 | *E. Coli* codon optimized RdpA mutant L82H + V187L + F182W + G103L + R180T |
| SEQ ID NO: 140 | Maize codon optimized RdpA mutant L82H + V187L + F182W + G103L + R180T |
| SEQ ID NO: 141 | Cotton codon optimized RdpA mutant L82H + V187L + F182W + G103L + R180T |
| SEQ ID NO: 142 | Amino acid sequence of RdpA mutant L82H + V187L + F182W + R104G + T112S + R180Q |
| SEQ ID NO: 143 | *E. Coli* codon optimized RdpA mutant L82H + V187L + F182W + R104G + T112S + R180Q |
| SEQ ID NO: 144 | Maize codon optimized RdpA mutant L82H + V187L + F182W + R104G + T112S + R180Q |
| SEQ ID NO: 145 | Cotton codon optimized RdpA mutant L82H + V187L + F182W + R104G + T112S + R180Q |
| SEQ ID NO: 146 | Soybean codon optimized RdpA mutant L82H |
| SEQ ID NO: 147 | Soybean codon optimized RdpA mutant L82H + V187L |
| SEQ ID NO: 148 | Soybean codon optimized RdpA mutant L82H + V187M |
| SEQ ID NO: 149 | Soybean codon optimized RdpA mutant L82H + V187I |
| SEQ ID NO: 150 | Soybean codon optimized RdpA mutant L82H + V187L + R104A |
| SEQ ID NO: 151 | Soybean codon optimized RdpA mutant L82H + V187L + R104D |
| SEQ ID NO: 152 | Soybean codon optimized RdpA mutant L82H + V187L + R104L |
| SEQ ID NO: 153 | Soybean codon optimized RdpA mutant L82H + V187L + F182W |
| SEQ ID NO: 154 | Soybean codon optimized RdpA mutant L82H + V187L + G103L |
| SEQ ID NO: 155 | Soybean codon optimized RdpA mutant L82H + V187L + F182W + R104G |
| SEQ ID NO: 156 | Soybean codon optimized RdpA mutant L82H + V187L + F182W + G103L |
| SEQ ID NO: 157 | Soybean codon optimized RdpA mutant L82H + V187L + F182W + R104G + T112S |
| SEQ ID NO: 158 | Soybean codon optimized RdpA mutant L82H + V187L + F182W + R104G + V80T |
| SEQ ID NO: 159 | Soybean codon optimized RdpA mutant L82H + V187L + F182W + R104G + R180W |
| SEQ ID NO: 160 | Soybean codon optimized RdpA mutant L82H + V187L + F182W + R104G + R180M |

-continued

| | |
|---|---|
| SEQ ID NO: 161 | Soybean codon optimized RdpA mutant L82H + V187L + F182W + R104G + D108C |
| SEQ ID NO: 162 | Soybean codon optimized RdpA mutant L82H + V187L + F182W + R104G + D109E |
| SEQ ID NO: 163 | Soybean codon optimized RdpA mutant L82H + V187L + F182W + R104G + Q219C |
| SEQ ID NO: 164 | Soybean codon optimized RdpA mutant L82H + V187L + F182W + R104G + Q219P |
| SEQ ID NO: 165 | Soybean codon optimized RdpA mutant L82H + V187L + F182W + G103L + R180D |
| SEQ ID NO: 166 | Soybean codon optimized RdpA mutant L82H + V187L + F182W + G103L + R180E |
| SEQ ID NO: 167 | Soybean codon optimized RdpA mutant L82H + V187L + F182W + G103L + R180S |
| SEQ ID NO: 168 | Soybean codon optimized RdpA mutant L82H + V187L + F182W + G103L + R180L |
| SEQ ID NO: 169 | Soybean codon optimized RdpA mutant L82H + V187L + F182W + G103L + R180W |
| SEQ ID NO: 170 | Soybean codon optimized RdpA mutant L82H + V187L + F182W + G103L + V80T |
| SEQ ID NO: 171 | Soybean codon optimized RdpA mutant L82H + V187L + F182W + G103L + T112A |
| SEQ ID NO: 172 | Soybean codon optimized RdpA mutant L82H + V187L + F182W + G103L + T112S |
| SEQ ID NO: 173 | Soybean codon optimized RdpA mutant L82H + V187L + F182W + G103L + T112M |
| SEQ ID NO: 174 | Soybean codon optimized RdpA mutant L82H + V187L + F182W + G103L + F247Y |
| SEQ ID NO: 175 | Soybean codon optimized RdpA mutant L82H + V187L + F182W + R104G + V77I |
| SEQ ID NO: 176 | Soybean codon optimized RdpA mutant L82H + V187L + F182W + G103L + R104G + V105Y |
| SEQ ID NO: 177 | Soybean codon optimized RdpA mutant L82H + V187L + F182W + R104G + T112S + R180K |
| SEQ ID NO: 178 | Soybean codon optimized RdpA mutant L82H + V187L + F182W + R104G + T112S + R180M |
| SEQ ID NO: 179 | Soybean codon optimized RdpA mutant L82H + V187L + F182W + R104G + T112S + R180W |
| SEQ ID NO: 180 | Soybean codon optimized RdpA mutant L82H + V187L + F182W + G103L + R180T |
| SEQ ID NO: 181 | Soybean codon optimized RdpA mutant L82H + V187L + F182W + R104G + T112S + R180Q |

DETAILED DESCRIPTION OF THE INVENTION

The following definitions and methods are provided to better define the invention and to guide those of ordinary skill in the art in the practice of the invention. Unless otherwise noted, terms are to be understood according to conventional usage by those of ordinary skill in the relevant art.

Engineered Proteins and Recombinant DNA Molecules

The present invention provides novel engineered proteins and the recombinant DNA molecules that encode them. As used herein, the term "engineered" refers to a non-natural DNA, protein or organism that would not normally be found in nature and is created by human intervention. An "engineered protein" is a protein, of which the polypeptide sequence is conceived of and created in laboratory using one or more of the techniques of protein engineering, such as protein design using site-directed mutagenesis and directed evolution using random mutagenesis and DNA shuffling. For example, an engineered protein may have one or more deletion(s), insertion(s) or substitution(s) compared with the coding sequence of the wild-type protein, and each deletion, insertion or substitution may consist of one or more amino acid(s). Examples of engineered proteins are provided herein as SEQ ID NO: 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138 and 142.

Engineered proteins provided by the present invention are enzymes with oxygenase activity. As used herein, the term "oxygenase activity" refers to the ability to oxidize a substrate by transferring the oxygen from molecular oxygen to the substrate, byproduct or an intermediate. The oxygenase activity of the engineered proteins provided by the present invention may inactivate one or more of pyridinyloxy acid herbicides.

As used herein, "wild-type" means naturally occurring. As used herein, a "wild-type DNA molecule", "wild-type polypeptide" or "wild-type protein" is a naturally occurring DNA molecule, polypeptide or protein, i.e., a DNA molecule, polypeptide or protein pre-existing in nature. A wild-type pattern of a polypeptide, protein or DNA molecule may be used for comparison with an engineered protein or gene. A wild-type pattern of a protein or DNA molecule may be used as a control in an experiment.

As used herein, a "control" means an experimental control designed for comparison purposes. For example, a control plant in a transgenic plant analysis is a plant of the same type as the experimental plant (i.e., the plant to be tested) but does not contain the transgenic insert, recombinant DNA molecule, or DNA construct of the experimental plant. An example of a control plant useful for comparison with transgenic maize plants is the non-transgenic LH244 maize (U.S. Pat. No. 6,252,148), and with transgenic soy plants is the non-transgenic A3555 soybean (U.S. Pat. No. 7,700,846).

As used herein, the term "recombinant" refers to a non-natural DNA, polypeptide or protein that is the result of genetic engineering and as such would not normally be found in nature and is created by human intervention. A "recombinant DNA molecule" is a DNA molecule comprising a DNA sequence that does not naturally occur and as such is the result of human intervention, for example, a DNA molecule that encodes an engineered protein. Another example is a DNA molecule comprised of a combination of at least two DNA molecules heterologous to each other, such as a protein-coding DNA molecule and an operably linked heterologous promoter. An example of a recombinant DNA molecule is a DNA molecule comprising at least one sequence selected from SEQ ID NO: 3, 4, 5, 7, 8, 9, 11, 12, 13, 15, 16, 17, 19, 20, 21, 23, 24, 25, 27, 28, 29, 31, 32, 33, 35, 36, 37, 39, 40, 41, 43, 44, 45, 47, 48, 49, 51, 52, 53, 55, 56, 57, 59, 60, 61, 63, 64, 65, 67, 68, 69, 71, 72, 73, 75, 76, 77, 79, 80, 81, 83, 84, 85, 87, 88, 89, 91, 92, 93, 95, 96, 97, 99, 100, 101, 103, 104, 105, 107, 108, 109, 111, 112, 113, 115, 116, 117, 119, 120, 121, 123, 124, 125, 127, 128, 129, 131, 132, 133, 135, 136, 137, 139, 140, 141 and 143-181. A "recombinant polypeptide" or "recombinant protein" is a polypeptide or protein comprising an amino acid sequence that does not naturally occur and as such is the result of human intervention, for example, an engineered protein.

The term "transgene" refers to a DNA molecule artificially incorporated into the genome of an organism as a result of human intervention, such as by plant transformation methods. As used herein, the term "transgenic" means comprising a transgene, for example, a "transgenic plant" refers to a plant comprising a transgene in its genome and a "transgenic trait" refers to a characteristic or phenotype conveyed or conferred by the presence of a transgene incorporated into the plant genome. As a result of such genomic alteration, the transgenic plant is something distinctly different from the related wild-type plant and the transgenic trait is a trait not naturally found in the wild-type plant. Transgenic plants of the present invention comprise the recombinant DNA molecules and engineered proteins provided by the invention.

As used herein, the term "heterologous" refers to the relationship between two or more things derived from different sources and thus not normally associated in nature. For example, a protein-coding recombinant DNA molecule is heterologous with respect to an operably linked promoter if such a combination is not normally found in nature. In addition, a particular recombinant DNA molecule may be heterologous with respect to a cell or organism into which it is inserted when it would not naturally occur in that particular cell or organism.

As used herein, the term "protein-coding DNA molecule" or "polypeptide-coding DNA molecule" refers to a DNA molecule comprising a nucleotide sequence that encodes a protein or polypeptide. A "protein-coding sequence" or "polypeptide-coding sequence" means a DNA sequence that encodes a protein or polypeptide. A "sequence" means a sequential arrangement of nucleotides or amino acids. The boundaries of a protein-coding sequence or polypeptide-coding sequence are usually determined by a translation start codon at the 5'-terminus and a translation stop codon at the 3'-terminus. A protein-coding molecule or polypeptide-coding molecule may comprise a DNA sequence encoding a protein or polypeptide sequence. As used herein, "transgene expression", "expressing a transgene", "protein expression", "polypeptide expression", "expressing a protein", and "expressing a polypeptide" mean the production of a protein or polypeptide through the process of transcribing a DNA molecule into messenger RNA (mRNA) and translating the mRNA into polypeptide chains, which may be ultimately folded into proteins. A protein-coding DNA molecule or polypeptide-coding DNA molecule may be operably linked to a heterologous promoter in a DNA construct for use in expressing the protein or polypeptide in a cell transformed with the recombinant DNA molecule. As used herein, "operably linked" means two DNA molecules linked in manner so that one may affect the function of the other. Operably-linked DNA molecules may be part of a single contiguous molecule and may or may not be adjacent. For example, a promoter is operably linked with a protein-coding DNA molecule or polypeptide-coding DNA molecule in a DNA construct where the two DNA molecules are so arranged that the promoter may affect the expression of the transgene.

As used herein, a "DNA construct" is a recombinant DNA molecule comprising two or more heterologous DNA sequences. DNA constructs are useful for transgene expression and may be comprised in vectors and plasmids. DNA constructs may be used in vectors for the purpose of transformation, that is the introduction of heterologous DNA into a host cell, in order to produce transgenic plants and cells, and as such may also be contained in the plasmid DNA or genomic DNA of a transgenic plant, seed, cell or plant part. As used herein, a "vector" means any recombinant DNA molecule that may be used for the purpose of plant transformation. Recombinant DNA molecules as set forth in the sequence listing can, for example, be inserted into a vector as part of a construct having the recombinant DNA molecule operably linked to a promoter that functions in a plant to drive expression of the engineered protein encoded by the recombinant DNA molecule. Methods for constructing DNA constructs and vectors are well known in the art. The components for a DNA construct, or a vector comprising a DNA construct, generally include, but are not limited to, one or more of the following: a suitable promoter for the expression of an operably linked DNA, an operably linked non-human protein-coding DNA molecule, and a 3' untranslated region (3'-UTR). Promoters useful in practicing the present invention include those that function in a plant for expression of an operably linked polynucleotide. Such promoters are varied and well known in the art and include those that are inducible, viral, synthetic, constitutive, temporally regulated, spatially regulated, and/or spatio-temporally regulated. Additional optional components include, but are not limited to, one or more of the following elements: 5'-UTR, enhancer, leader sequence, cis-acting element, intron, chloroplast transit peptides (CTP), and one or more selectable marker transgene(s).

The DNA constructs of the invention may include a CTP molecule operably linked to the protein-coding DNA molecules provided by the invention. A CTP useful in practicing the present invention includes those that function to facilitate localization of the engineered protein molecule within the cell. By facilitating protein localization within the cell, the CTP may increase the accumulation of engineered protein, protect it from proteolytic degradation, enhance the level of herbicide tolerance, and thereby reduce levels of injury after herbicide application. CTP molecules used in the present invention are known in the art and include, but are not limited to the *Arabidopsis thaliana* EPSPS CTP (Klee et al., 1987), the *Petunia hybrida* EPSPS CTP (della-Cioppa et al., 1986), the maize cab-m7 signal sequence (Becker et al., 1992; PCT WO 97/41228) and the pea glutathione reductase signal sequence (Creissen et al., 1991; PCT WO 97/41228).

Recombinant DNA molecules of the present invention may be synthesized and modified by methods known in the art, either completely or in part, especially where it is desirable to provide sequences useful for DNA manipulation (such as restriction enzyme recognition sites or recombination-based cloning sites), plant-preferred sequences (such as plant-codon usage or Kozak consensus sequences), or sequences useful for DNA construct design (such as spacer or linker sequences). The present invention includes recombinant DNA molecules and engineered proteins having at least about 80% (percent) sequence identity, about 85% sequence identity, about 90% sequence identity, about 91% sequence identity, about 92% sequence identity, about 93% sequence identity, about 94% sequence identity, about 95% sequence identity, about 96% sequence identity, about 97% sequence identity, about 98% sequence identity, and about 99% sequence identity to any of the recombinant DNA molecule or engineered protein sequences provided herein, for instance, to a recombinant DNA molecule comprising a sequence selected from the group consisting of SEQ ID NO: 3, 4, 5, 7, 8, 9, 11, 12, 13, 15, 16, 17, 19, 20, 21, 23, 24, 25, 27, 28, 29, 31, 32, 33, 35, 36, 37, 39, 40, 41, 43, 44, 45, 47, 48, 49, 51, 52, 53, 55, 56, 57, 59, 60, 61, 63, 64, 65, 67, 68, 69, 71, 72, 73, 75, 76, 77, 79, 80, 81, 83, 84, 85, 87, 88, 89, 91, 92, 93, 95, 96, 97, 99, 100, 101, 103, 104, 105, 107, 108, 109, 111, 112, 113, 115, 116, 117, 119, 120, 121, 123, 124, 125, 127, 128, 129, 131, 132, 133, 135, 136, 137, 139, 140, 141 and 143-181. As used herein, the term "percent sequence identity" or "% sequence identity" refers to the percentage of identical nucleotides or amino acids in a linear polynucleotide or polypeptide sequence of a reference ("query") sequence (or its complementary strand) as compared to a test ("subject") sequence (or its complementary strand) when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and by computerized implementations of these algorithms such as GAP, BESTFIT, FASTA, and TFASTA available as part of the GCG® Wisconsin Package® (Accelrys Inc., San Diego, CA), MEGAlign (DNAStar, Inc., 1228S. Park St., Madison, Wis. 53715), and MUSCLE (version 3.6) (RCEdgar, Nucleic Acids Research (2004) 32 (5): 1792-1797) with default parameters. An "identity fraction" for aligned segments of a test sequence and a reference sequence is the number of identical components which are shared by the two aligned sequences divided by the total number of components in the reference sequence segment, that is, the entire reference sequence or a smaller defined part of the reference sequence. Percent sequence identity is represented as the identity fraction multiplied by 100. The comparison of one or more sequence(s) may be to a full-length sequence or a portion thereof, or to a longer sequence.

Engineered proteins may be produced by changing (i.e., modifying) a wild-type protein to produce a new protein with a novel combination of useful protein characteristics, such as altered $V_{max}$, $K_m$, substrate specificity, substrate selectivity, and protein stability. Modifications may be made at specific amino acid positions in a protein and may be a substitution of the amino acid found at that position in nature (i.e., in the wild-type protein) with a different amino acid. The amino acid sequence of the wild-type RdpA protein useful for protein engineering is shown in SEQ ID NO: 1. An engineered protein can be designed that has at least about 92% sequence identity to an amino acid sequence selected from the group consisting of SEQ ID NO: 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138 and 142, and comprises at least one of these amino acid mutations. Engineered proteins provided by the invention thus provide a new protein with one or more altered protein characteristic(s) relative to the wild-type protein found in nature. In one embodiment of the present invention, an engineered protein has altered protein characteristics such as improved or decreased activity against one or more herbicide(s) or improved protein stability as compared to a similar wild-type protein or any combination of such characteristics. In one embodiment, the present invention provides an engineered protein and the recombinant DNA molecule encoding it, having at least about 80% sequence identity, about 85% sequence identity, about 90% sequence identity, about 91% sequence identity, about 92% sequence identity, about 93% sequence identity, about 94% sequence identity, about 95% sequence identity, about 96% sequence identity, about 97% sequence identity, about 98% sequence identity, and about 99% sequence identity to an engineered protein sequence selected from the group consisting of SEQ ID NO: 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138 and 142. Amino acid mutations may be made as a single amino acid substitution in the protein or in combination with one or more other mutation(s), such as one or more other amino acid substitution(s), deletion(s), or addition(s). Mutations may be made as described herein or by any other method known to those of skill in the art.

Transgenic Plants

An aspect of the invention includes transgenic plant cells, transgenic plant tissues, transgenic plants, and transgenic seeds that comprise the recombinant DNA molecules and engineered proteins provided by the invention. These cells, tissues, plants, and seeds comprising the recombinant DNA molecules and engineered proteins exhibit herbicide tolerance to one or more of pyridinyloxy acid herbicides.

Suitable methods for transforming host plant cells for use in the present invention include virtually any method by which DNA can be introduced into a cell (for example, where a recombinant DNA construct is stably integrated into a plant chromosome) and are well known in the art. An exemplary and widely used method for introducing a recombinant DNA construct into a plant is the *Agrobacterium* transformation system, which is well known to those of skill in the art. A transgenic plant can be regenerated from a transformed plant cell by the methods of plant cell culture. A transgenic plant homozygous with respect to a transgene (i.e., two allelic copies of the transgene) can be obtained by self-pollinating (selfing) a transgenic plant that contains a single transgene allele with itself, for example an R0 plant, to produce R1 seed. One fourth of the R1 seed produced will be homozygous with respect to the transgene. Plants grown from germinating R1 seed can be tested for zygosity, typically using a SNP assay, DNA sequencing, or a thermal amplification assay that allows for the distinction between heterozygotes and homozygotes, referred to as a zygosity assay.

Plants, seeds, plant parts, plant tissues and cells provided by the present invention exhibit herbicide tolerance to one or more of pyridinyloxy acid herbicides. The pyridinyloxy acid herbicides are synthetic auxins similar to the plant growth hormone indoleacetic acid (IAA). Broad-leaf plants are sensitive to these herbicides, which induce rapid and uncontrolled growth, eventually killing the plant.

Examples of pyridinyloxy acid herbicides include, but are not limited to, the chemical compounds as shown in Formula I, and salt and ester derivatives thereof,

I

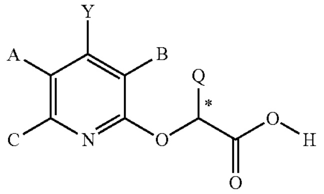

wherein, A and B independently represent halogen, C1-C6 alkyl, halo C1-C6 alkyl, C3-C6 cycloalkyl;

C represents hydrogen, halogen, C1-C6 alkyl, halo C1-C6 alkyl;

Q represents C1-C6 alkyl, halo C1-C6 alkyl, C3-C6 cycloalkyl, C2-C6 alkenyl, C2-C6 alkynyl, halogen, cyano, amino, nitro, formyl, C1-C6 alkoxy, C1-C6 alkylthio, C1-C6 alkoxycarbonyl, hydroxyl C1-C6 alkyl, C1-C6 alkoxy C1-C2 alkyl, cyano C1-C2 alkyl, C1-C6 alkylamino C1-C2 alkyl, benzyl, naphthyl, furyl, thienyl, thiazolyl, pyridinyl, pyrimidinyl, and

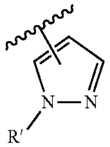

that is unsubstituted or substituted by C1-C6 alkyl, phenyl that is unsubstituted or substituted by at least one group of C1-C6 alkyl, halo C1-C6 alkyl, halogen and C1-C6 alkoxy;

Y represents amino, C1-C6 alkylamino, C1-C6 alkylcarbonylamino, phenylcarbonylamino, benzylamino, furylmethyleneamino that is unsubstituted or substituted by halo C1-C6 alkyl;

The salts are metal salt, ammonium salt $NH_4^+$, primary amine salt $RNH_2^+$, secondary amine salt $(R)_2NH^+$, tertiary ammonium salt $(R)_3N^+$, quaternary ammonium salt $(R)_4N^+$, morpholine salt, piperidine salt, pyridine salt, aminopropylmorpholine salt, Jeff amine D-230 salt, the salt of 2,4,6-tris (dimethylaminomethyl) phenol and sodium hydroxide, C1-C14 alkyl sulfonium salt, C1-C14 alkyl sulfoxonium salt, C1-C14 alkyl phosphonium salt, C1-C14 alkanol phosphonium salt;

wherein, R independently represents unsubstituted C1-C14 alkyl, C2-C12 alkenyl, C2-C12 alkynyl, C3-C12 cycloalkyl or phenyl, and C1-C14 alkyl optionally substituted by any one or more of the following group(s): halogen, hydroxyl, C1-C6 alkoxy, C1-C6 alkylthio, hydroxyl C1-C6 alkoxy, amino, C1-C6 alkylamino, amino C1-C6 alkylamino, phenyl;

The ester is

I-1

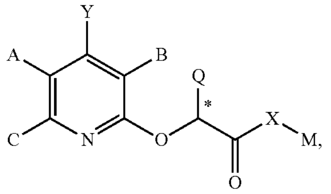

wherein, X represents O or S;

M represents C1-C18 alkyl, halo C1-C8 alkyl, C3-C6 cycloalkyl, C2-C6 alkenyl, halo C2-C6 alkenyl, C2-C6 alkynyl, C1-C6 alkoxy, C1-C6 alkoxycarbonyl, C1-C6 alkylsulfonyl, cyano C1-C2 alkyl, nitro C1-C2 alkyl, C1-C6 alkoxy C1-C2 alkyl, C1-C6 alkoxycarbonyl C1-C2 alkyl, C2-C6 allyloxycarbonyl C1-C2 alkyl, —(C1-C2 alkyl)-Z,

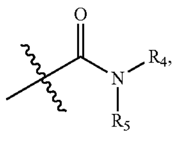 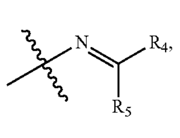 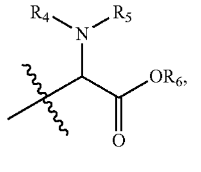

tetrahydrofuranyl, pyridinyl, naphthyl, furyl, thienyl,

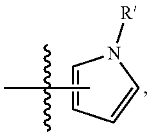, 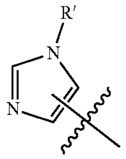, and 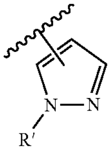

that is unsubstituted or substituted by C1-C6 alkyl, phenyl that is unsubstituted or substituted by C1-C6 alkyl, halo C1-C6 alkyl, C1-C6 alkylamino, halogen or C1-C6 alkoxy;

Z represents

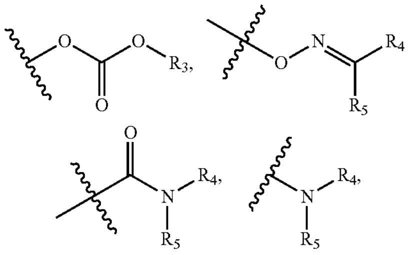

tetrahydrofuranyl, pyridinyl,

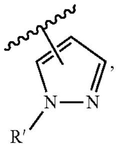

thienyl, furyl, naphthyl, and phenyl that is unsubstituted or substituted by at least one group of C1-C6 alkyl, C1-C6 alkoxy, halo C1-C6 alkyl, cyano and halogen;

$R_3$ independently represents C1-C6 alkyl;

$R_4$, $R_5$, $R_6$ independently represent hydrogen, C1-C6 alkyl, C1-C6 alkoxycarbonyl;

R' represents hydrogen, C1-C6 alkyl, halo C1-C6 alkyl.

In one embodiment, the compounds of general formula I and I-1 are both in R configuration (the carbon atoms at * are chiral centers). In another embodiment, in the compound of general formula I, A represents chlorine, B represents chlorine, C represents fluorine, Y represents amino, Q represents methyl, and the compound is in R configuration (the carbon atom at * is the chiral center) (i.e., compound A); in the compound of general formula I-1, A represents chlorine, B represents chlorine, C represents fluorine, Y represents amino, Q represents methyl, X represents O, M represents methyl, and the compound is in R configuration (the carbon atom at * is the chiral center) (i.e., compound B); or in the compound of general formula I-1, A represents chlorine, B represents chlorine, C represents fluorine, Y represents amino, Q represents methyl, X represents O, M represents (tetrahydrofuran-2-yl)methyl

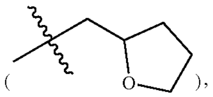

and the compound is in R configuration (i.e., compound C) (the carbon atom at * is the chiral center).

Herbicides may be applied to a plant growing area comprising the plants and seeds provided by the invention as a method for controlling weeds. Plants and seeds provided by the invention comprise a herbicide tolerance trait and as such are tolerant to the application of one or more pyridinyloxyl acid herbicide(s). The plant growing area may or may not comprise weed plants at the time of herbicide application.

The herbicide application may be sequentially or tank mixed with one, two, or a combination of several pyridinyloxy acid herbicides, or any other compatible herbicide. Multiple applications of one herbicide or of two or more herbicides, in combination or alone, may be used over a growing season to an area comprising transgenic plants of the invention to control a broad spectrum of dicot weeds, monocot weeds, or both, for example, two applications (such as a pre-planting application and a post-emergence application, or a pre-emergence application and a post-emergence application) or three applications (such as a pre-planting application, a pre-emergence application, and a post-emergence application, or a pre-emergence application and two post-emergence applications).

As used herein, "tolerance" or "herbicide tolerance" means a plant, seed, plant tissue, plant part or cell's ability to resist the toxic effects of one or more herbicide(s). The herbicide tolerance of a plant, seed, plant tissue, plant part or cell may be measured by comparing the plant, seed, plant tissue, plant part or cell to a suitable control. For example, the herbicide tolerance may be measured by applying a herbicide to a plant comprising a recombinant DNA molecule encoding a protein capable of conferring herbicide tolerance (the test plant) and a plant not comprising the recombinant DNA molecule encoding the protein capable of conferring herbicide tolerance (the control plant) and then comparing the plant injury of the two plants, wherein herbicide tolerance of the test plant is indicated by a reduced injury rate as compared to the injury rate of the control plant. A herbicide-tolerant plant, seed, plant tissue, plant part or cell exhibits a decreased response to the toxic effects of a herbicide when compared to a control plant, seed, plant tissue, plant part or cell. As used herein, an "herbicide tolerance trait" is a transgenic trait imparting improved herbicide tolerance to a plant as compared to a wild-type plant or control plant.

The transgenic plants, progeny, seeds, plant cells, and plant parts of the invention may also contain one or more additional transgenic trait(s). Additional transgenic traits may be introduced by crossing a plant containing a transgene comprising the recombinant DNA molecules provided by the invention with another plant containing an additional transgenic trait(s). As used herein, "crossing" means breeding two individual plants to produce a progeny plant. Two transgenic plants may thus be crossed to produce a progeny that contains the transgenic traits. As used herein, "progeny" means the offspring of any generation of a parent plant, and transgenic progeny comprises a DNA construct provided by the invention and inherited from at least one parent plant. Alternatively, the additional transgenic trait may be introduced by co-transforming the DNA constructs of the additional transgenic trait with a DNA construct comprising a recombinant DNA molecules provided by the invention (e.g., wherein all of the DNA constructs present as part of the same vector used for plant transformation) or by inserting the additional trait into a transgenic plant comprising a DNA construct provided by the invention or vice versa (for example, by using any of the methods of plant transformation on a transgenic plant or plant cell). Such additional transgenic traits include, but are not limited to, increased insect resistance, increased water use efficiency, increased yield performance, increased drought resistance, increased seed quality, improved nutritional quality, hybrid seed production, and herbicide tolerance, in which the trait is measured with respect to a wild-type plant or control plant. Such additional transgenic traits are known to one skilled in the art; for example, a list of such traits is provided by Animal and Plant Health Inspection Service (APHIS), the United States Department of Agriculture (USDA) and can be found on their website at www.aphis.usda.gov.

Transgenic plants and progeny that contain a transgenic trait provided by the invention may be used with any breeding methods that are commonly known in the art. In plant lines comprising two or more transgenic traits, the transgenic traits may be independently segregating, linked, or a combination of both in plant lines comprising three or more transgenic traits. Back-crossing to a parent plant and out-crossing with a non-transgenic plant as well as vegetative propagation are also contemplated. Descriptions of breeding methods that are commonly used for different traits and crops are well known to those of skill in the art. To confirm the presence of the transgene(s) in a particular plant or seed, a variety of assays may be performed. Such assays include, for example, molecular biology assays, such as Southern and Northern blotting, PCR and DNA sequencing; biochemical assays, such as detecting the presence of a protein product, for example, by immunological means (ELISAs and Western blotting) or by enzymatic function; plant part assays, such as leaf or root assays; and also, by analyzing the phenotype of a whole plant.

Introgression of a transgenic trait into a plant genotype is achieved as the result of the process of backcross conversion. A plant genotype into which a transgenic trait that has been introgressed may be referred to as a backcross converted genotype, line, inbred, or hybrid. Similarly, a plant genotype lacking the desired transgenic trait may be referred to as an unconverted genotype, line, inbred, or hybrid.

As used herein, the term "comprising" means "including but not limited to".

The following embodiments are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein with the same or similar result achieved. All such similar substitutes and modifications apparent to those skilled in the art are deemed to be within the spirit, scope, and concept of the invention as defined by the appended claims.

Example 1

Initial Protein Engineering and Enzyme Analysis

By performing homology modeling, molecular docking of RdpA protein, and combining sequence alignment results, the candidate sites were mutated using techniques known to those of skill in the art, such as Alanine-Scanning Mutations, Homology-Scanning Mutations, Pro/Gly Scanning Mutations, Region Swaps or Mutations, and combinations of these various techniques (See M Lehmann and M Wyss, Current Opinion in Biotechnology (2001) 12 (4): 371-375; B Van den Burg and VGH Eijsink, Current Opinion in Biotechnology (2002) 13 (4): 333-337; and Weiss et al., Proc Natl Acad Sci USA (2000) 97 (16): 8950-8954).

The high-throughput bacterial protein expression was achieved by cloning the synthesized gene that encodes each engineered protein into a bacterial expression vector with a C-terminal histidine tag (His-tag). The vectors were transformed into *Escherichia coli* (*E. coli*), and expression of the engineered proteins was induced. *E. coli* cultures were selected and cultured in centrifuge tubes overnight, meanwhile, added with substrates and IPTG, and the cultures were centrifuged to pellet the bacteria the next day. Alternatively, *E. coli* cultures were selected and cultured in centrifuge tubes overnight, and centrifuged to pellet the bacteria after adding substrates for reaction the next day. The supernatant of reaction solution was pipetted into a 96-well plate and the absorbance at 510 nm from 4-aminoantipyrine and potassium ferricyanide was measured by an endpoint colorimetric method to detect phenol products. Substrate reduction and product yield were measured by high performance liquid chromatography (HPLC) to detect the oxygenase activity (i.e., enzymatic activity) of the engineered proteins, and the activities of the proteins were compared by calculating conversion rates. The results are shown in Table 1.

Conversion rate=(Peak area of initial substrate−Peak area of substrate after reaction)/Peak area of initial substrate*100%

TABLE 1

Conversion rate of each mutant

| Sequence No. | Mutation site | Conversion rate | Reaction condition |
|---|---|---|---|
| SEQ ID NO: 1 | RdpA-wild type | 0.06% | 1 |
| SEQ ID NO: 1 | RdpA-wild type | 0.06% | 2 |
| SEQ ID NO: 2 | L82H | 67.5% | 1 |
| SEQ ID NO: 6 | L82H + V187L | 95.2% | 1 |
| SEQ ID NO: 10 | L82H + V187M | 94.1% | 1 |
| SEQ ID NO: 14 | L82H + V187I | 76.8% | 1 |
| SEQ ID NO: 18 | L82H + V187L + R104A | 92.1% | 1 |
| SEQ ID NO: 22 | L82H + V187L + R104D | 95.5% | 1 |
| SEQ ID NO: 26 | L82H + V187L + R104L | 96.8% | 1 |
| SEQ ID NO: 30 | L82H + V187L + F182W | 96.5% | 1 |
| SEQ ID NO: 34 | L82H + V187L + G103L | 90% | 1 |
| SEQ ID NO: 38 | L82H + V187L + F182W + R104G | 96.9% | 1 |
| SEQ ID NO: 42 | L82H + V187L + F182W + G103L | 96.6% | 1 |
| SEQ ID NO: 46 | L82H + V187L + F182W + R104G + T112S | 97% | 1 |
| SEQ ID NO: 50 | L82H + V187L + F182W + R104G + V80T | 97.2% | 1 |
| SEQ ID NO: 54 | L82H + V187L + F182W + R104G + R180W | 92.5% | 1 |
| SEQ ID NO: 58 | L82H + V187L + F182W + R104G + R180M | 90% | 1 |
| SEQ ID NO: 62 | L82H + V187L + F182W + R104G + D108C | 90% | 1 |
| SEQ ID NO: 66 | L82H + V187L + F182W + R104G + D109E | 94% | 1 |
| SEQ ID NO: 70 | L82H + V187L + F182W + R104G + Q219C | 94% | 1 |
| SEQ ID NO: 74 | L82H + V187L + F182W + R104G + Q219P | 97.2% | 1 |
| SEQ ID NO: 78 | L82H + V187L + F182W + G103L + R180D | 79% | 2 |
| SEQ ID NO: 82 | L82H + V187L + F182W + G103L + R180E | 71.6% | 2 |
| SEQ ID NO: 86 | L82H + V187L + F182W + G103L + R180S | 76.8% | 2 |
| SEQ ID NO: 90 | L82H + V187L + F182W + G103L + R180L | 57.5% | 2 |
| SEQ ID NO: 94 | L82H + V187L + F182W + G103L + R180W | 63.2% | 2 |
| SEQ ID NO: 98 | L82H + V187L + F182W + G103L + V80T | 81% | 2 |
| SEQ ID NO: 102 | L82H + V187L + F182W + G103L + T112A | 93.2% | 2 |
| SEQ ID NO: 106 | L82H + V187L + F182W + G103L + T112S | 86.3% | 2 |
| SEQ ID NO: 110 | L82H + V187L + F182W + G103L + T112M | 54.6% | 2 |
| SEQ ID NO: 114 | L82H + V187L + F182W + G103L + F247Y | 53% | 2 |
| SEQ ID NO: 118 | L82H + V187L + F182W + R104G + V77I | 95.8% | 1 |
| SEQ ID NO: 122 | L82H + V187L + F182W + G103L + R104G + V105Y | 94.3% | 1 |
| SEQ ID NO: 126 | L82H + V187L + F182W + R104G + T112S + R180K | 92.6% | 2 |
| SEQ ID NO: 130 | L82H + V187L + F182W + R104G + T112S + R180M | 88.3% | 2 |
| SEQ ID NO: 134 | L82H + V187L + F182W + R104G + T112S + R180W | 77.6% | 2 |
| SEQ ID NO: 138 | L82H + V187L + F182W + G103L + R180T | 54.6% | 2 |
| SEQ ID NO: 142 | L82H + V187L + F182W + R104G + T112S + R180Q | 67% | 2 |

Note:

Reaction condition 1: The bacteria were cultured overnight, and substrate compound A and IPTG were added to react overnight; Reaction condition 2: The bacteria were cultured overnight, and 8 times dose of substrate compound A in Reaction condition 1 were added to react for 3 hours the next day.

Figure 2:
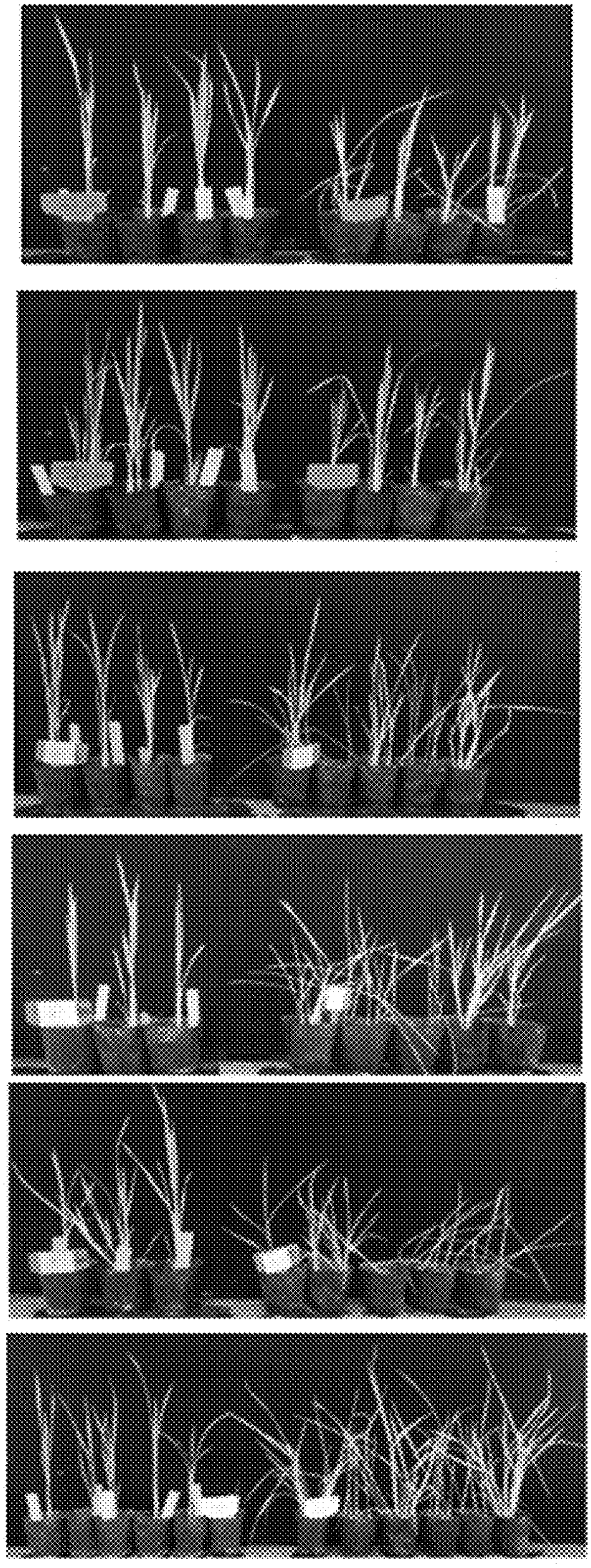
FIG. 2 shows control Jinjing 818 plants and transgenic Jinjing 818 plants comprising the protein-coding gene of SEQ ID NO: 42 after applying 20 g, 40 g, 60 g, 80 g, 100 g, 120 g/mu compound B for corresponding days (DAT).
Figure 6:
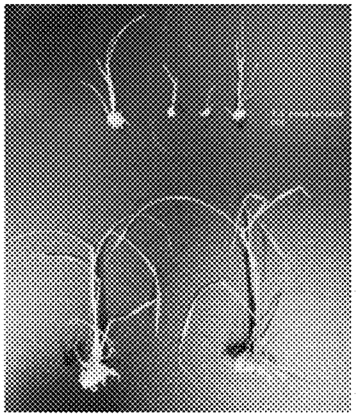
FIG. 6 shows control Jinjing 818 plants and transgenic Jinjing 818 plants comprising the protein-coding gene of SEQ ID NO: 102 after adding 1 μM compound B to medium for 22 days.
Figure 7:
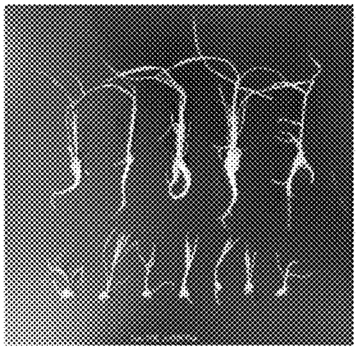
FIG. 7 shows control Jinjing 818 plants and transgenic Jinjing 818 plants comprising the protein-coding gene of SEQ ID NO: 82 after adding 1 μM compound B to medium for 17 days.
Figure 8:
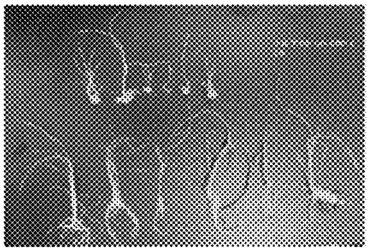
FIG. 8 shows control Jinjing 818 plants and transgenic Jinjing 818 plants comprising the protein-coding gene of SEQ ID NO: 106 after adding 1 μM compound B to medium for 22 days.
Figure 9:
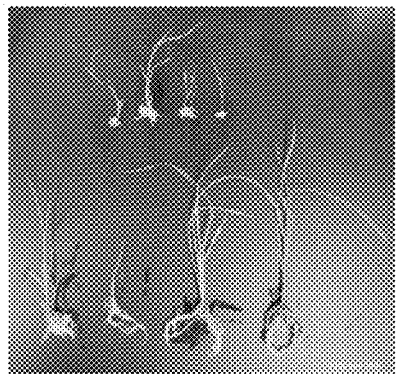
FIG. 9 shows control Jinjing 818 plants and transgenic Jinjing 818 plants comprising the protein-coding gene of SEQ ID NO: 126 after adding 1 μM compound B to medium for 26 days.
Figure 10:
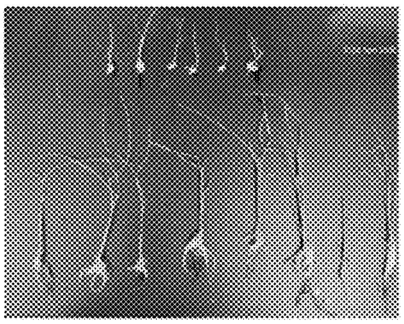
FIG. 10 shows control Jinjing 818 plants and transgenic Jinjing 818 plants comprising the protein-coding gene of SEQ ID NO: 142 after adding 1 μM compound B to medium for 26 days.
Figure 11:
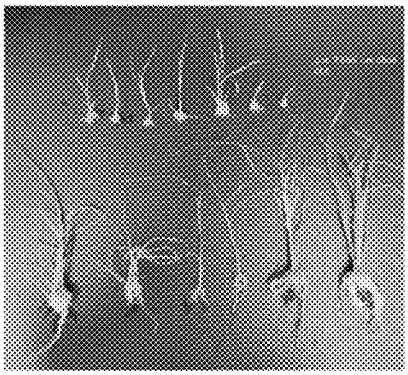
FIG. 11 shows control Jinjing 818 plants and transgenic Jinjing 818 plants comprising the protein-coding gene of SEQ ID NO: 38 after adding 1 μM compound B to medium for 22 days.

Based on the results of HPLC, representative engineered proteins were selected for protein purification. Further protein characterization, such as $K_m$, $V_{max}$ and $K_{cat}$, was performed on the 8 engineered proteins from Table 2. Conventional Ni column affinity chromatography was used for protein purification and protein extract purity was assessed by SDS-PAGE analysis. After determining protein concentration by BCA method, enzyme activity was determined. The controls were purified wild-type enzyme, and the enzymatic kinetic measurements of the proteins were performed using 0, 5, 10, 20, 50, 200, 500 or 1000 μM of compound A. Table 2 shows the $K_m$, $V_{max}$, $K_{cat}$ and $K_{cat}/K_m$ measured for the 8 proteins with compound A as substrates. The enzymatic kinetic parameters of these 8 engineered proteins demonstrated that the enzymatic activity, i.e., $K_m$ and $K_{cat}$, of the proteins could be significantly improved through protein engineering.

levels of plants were recorded and evaluated after spraying treatment, wherein, the test results of control Jinjing 818 plants and transgenic Jinjing 818 plants comprising the protein-coding gene of SEQ ID NO: 42 after applying 20 g, 40 g, 60 g, 80 g, 100 g, 120 g/mu (1 mu=1/15 ha) compound B for corresponding days (DAT) are shown in FIG. 2. Compared with wild-type plants, Jinjing 818 plants comprising the protein-coding gene of SEQ ID NO: 42 exhibited better drug resistance, which demonstrated that plants expressing the engineered protein exhibited tolerance to compound B herbicide when foliage-sprayed with at least 120 g/mu of compound B.

In summary, in the medicated medium test and the greenhouse spraying test for TO generation, the plants comprising the recombinant DNA molecule encoding the engineered protein (SEQ ID NO: 42/38/82/86/102/106/126/138/142) all exhibited apparent tolerance compared with the wild types.

TABLE 2

Determination results of engineered proteins

| Sequence No. | Mutation site | $V_{max}$ | $K_m$ (μm) | $K_{cat}$ ($S^{-1}$) | $K_{cat}/K_m$ ($M^{-1}*S^{-1}*10^3$) |
|---|---|---|---|---|---|
| SEQ ID NO: 1 | RdpA-wild type | | | N/D | |
| SEQ ID NO: 38 | L82H + V187L + F182W + R104G | 49.9 | 54.6 | 0.43 | 7.86 |
| SEQ ID NO: 42 | L82H + V187L + F182W + G103L | 99.6 | 81.3 | 0.86 | 10.54 |
| SEQ ID NO: 46 | L82H + V187L + F182W + R104G + T112S | 35.2 | 17.5 | 0.15 | 8.65 |
| SEQ ID NO: 50 | L82H + V187L + F182W + R104G + V80T | 15.7 | 24.9 | 0.07 | 2.71 |
| SEQ ID NO: 54 | L82H + V187L + F182W + R104G + R180W | 81 | 96.9 | 0.35 | 3.59 |
| SEQ ID NO: 58 | L82H + V187L + F182W + R104G + R180M | 12.3 | 28.3 | 0.05 | 1.87 |
| SEQ ID NO: 118 | L82H + V187L + F182W + R104G + V77I | 99.5 | 83.7 | 0.43 | 5.11 |
| SEQ ID NO: 122 | L82H + V187L + F182W + G103L + R104G + V105Y | 127.9 | 96.4 | 1.1 | 11.41 |

Note:
N/D represented the enzymatic activity is too low to determine its enzymatic kinetic parameters.

Example 2

Expression of Engineered Proteins in Rice

Plant transformation vectors were constructed, each comprising a recombinant DNA molecule encoding an engineered protein (SEQ ID NO: 42/38/82/86/102/106/126/138/142) with the protein-coding sequence optimized for monocot expression, and rice (Jinjing 818) calli were transformed with these vectors using *Agrobacterium tumifaciens* and standard methods known in the art. Different concentrations of hormone herbicide compound B were added at the rooting phase of the rice seedlings to test hormone resistance, wherein, the test results of control Jinjing 818 plants and transgenic Jinjing 818 plants comprising the protein-coding gene of SEQ ID NO: 42 after adding 0.5 μM and 1 μM compound B to medium for 19 days are shown in FIG. 1. The test results of control Jinjing 818 plants and transgenic Jinjing 818 plants comprising the protein-coding genes of SEQ ID NO: 38/82/86/102/106/126/138/142 after adding 1 μM compound B to medium are shown in FIG. 5-11. Compared with wild-type plants, Jinjing 818 plants comprising the protein-coding gene of SEQ ID NO: 42/38/82/86/102/106/126/138/142 exhibited better drug resistance, which demonstrated that plants expressing the engineered protein exhibited tolerance to compound B herbicide when screened with at least 1 μM of compound B medium.

Then, the obtained regenerated TO generation transgenic plantlets grew in the greenhouse, and were sprayed with compound B at the growth stage when approximately two leaves unfolded and the third one just appearing. Resistance levels of plants were recorded and evaluated after spraying treatment, wherein, the test results of control Jinjing 818 plants and transgenic Jinjing 818 plants comprising the protein-coding gene of SEQ ID NO: 42 after applying 20 g, 40 g, 60 g, 80 g, 100 g, 120 g/mu (1 mu=1/15 ha) compound B for corresponding days (DAT) are shown in FIG. 2.

Figure 12:
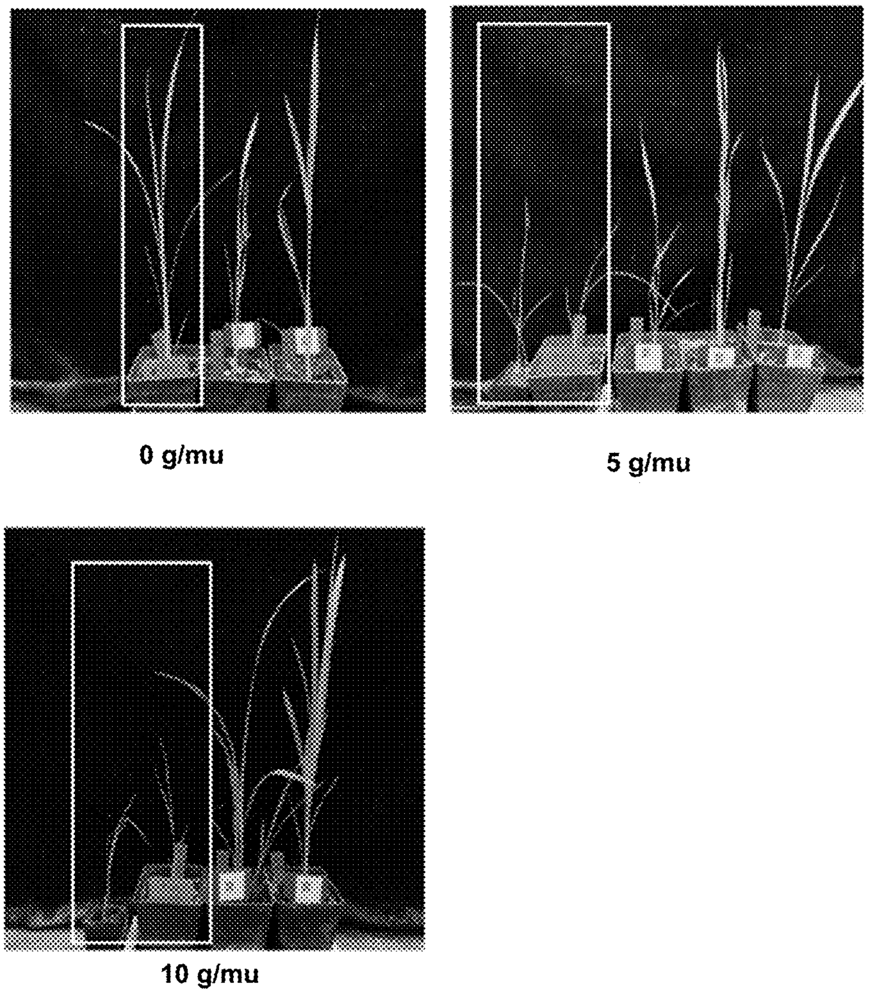
FIG. 12 shows test results of control Jinjing 818 plants and transgenic Jinjing 818 plants comprising the protein-coding gene of SEQ ID NO: 46 after applying 0 g, 5 g, 10 g/mu compound quizalofop-P-ethyl for 20 DAT (framed ones in the picture are wild-type Jinjing 818 control plants, the rest are transgenic Jinjing 818 plants comprising the protein-coding gene of SEQ ID NO: 46).

The obtained regenerated TO generation transgenic plantlets grew in the greenhouse, and were sprayed with compound quizalofop-P-ethyl at the growth stage when approximately two leaves unfolded and the third one just appearing. Resistance levels of plants were recorded and evaluated after spraying treatment, wherein, the test results of control Jinjing 818 plants and transgenic Jinjing 818 plants comprising the protein-coding gene of SEQ ID NO: 46 after applying 0 g, 5 g, 10 g/mu compound quizalofop-P-ethyl for 20 DAT are shown in FIG. 12. Compared with wild-type plants, Jinjing 818 plants comprising the protein-coding gene of SEQ ID NO: 46 exhibited better drug resistance, which demonstrated that plants expressing the engineered protein exhibited tolerance to compound quizalofop-P-ethyl herbicide when foliage-sprayed with at least 10 g/mu of compound quizalofop-P-ethyl.

Figure 13:
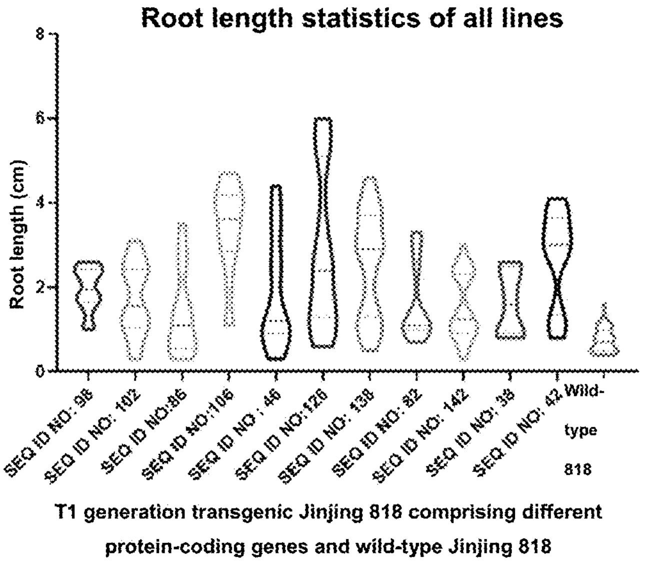
FIG. 13 shows the root length comparison of T1 generation transgenic Jinjing 818 seeds comprising different protein-coding genes compared with wild-type Jinjing 818 after adding 0.3 μM compound B and soaking seeds for 20 days.
Figure 14:
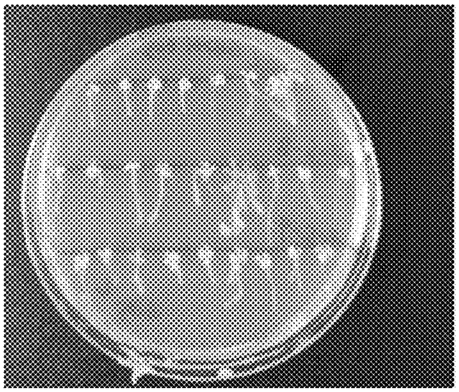
FIG. 14 shows the emergence comparison between T2 generation transgenic *Arabidopsis thaliana* seeds comprising the protein-coding gene of SEQ ID NO: 42 and wild-type *Arabidopsis thaliana* (the first line), after adding 0.15 μM compound A for 20-day screening.
Figure 15:
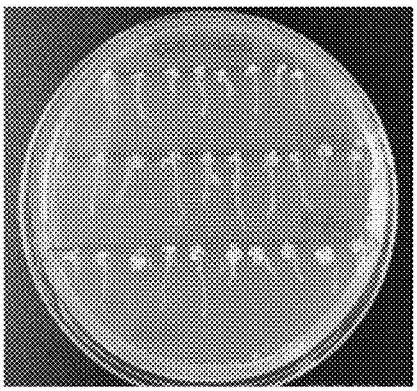
FIG. 15 shows the emergence comparison between T2 generation transgenic *Arabidopsis thaliana* seeds comprising the protein-coding gene of SEQ ID NO: 78 and wild-type *Arabidopsis thaliana* (the first line), after adding 0.15 μM compound A for 19-day screening.
Figure 16:
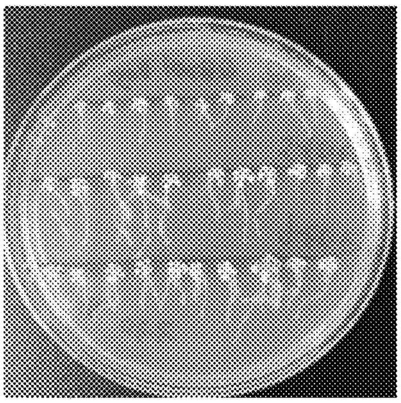
FIG. 16 shows the emergence comparison between T2 generation transgenic *Arabidopsis thaliana* seeds comprising the protein-coding gene of SEQ ID NO: 82 and wild-type *Arabidopsis thaliana* (the first line), after adding 0.15 μM compound A for 24-day screening.
Figure 17:
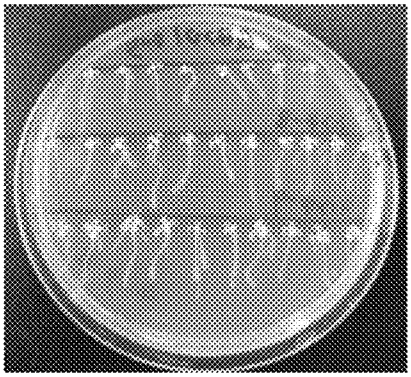
FIG. 17 shows the emergence comparison between T2 generation transgenic *Arabidopsis thaliana* seeds comprising the protein-coding gene of SEQ ID NO: 86 and wild-type *Arabidopsis thaliana* (the first line), after adding 0.15 μM compound A for 21-day screening.
Figure 18:
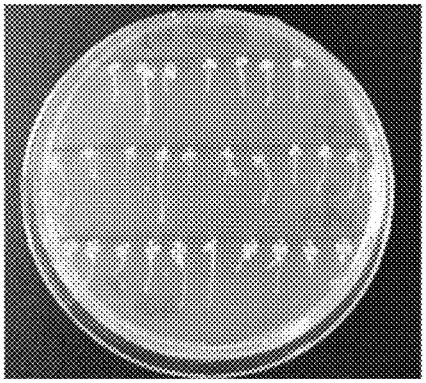
FIG. 18 shows the emergence comparison between T2 generation transgenic *Arabidopsis thaliana* seeds comprising the protein-coding gene of SEQ ID NO: 98 and wild-type *Arabidopsis thaliana* (the first line), after adding 0.15 μM compound A for 19-day screening.
Figure 19:
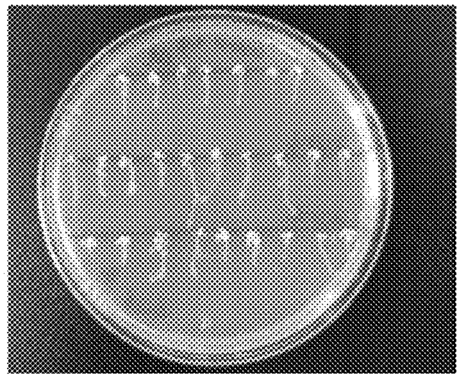
FIG. 19 shows the emergence comparison between T2 generation transgenic *Arabidopsis thaliana* seeds comprising the protein-coding gene of SEQ ID NO: 102 and wild-type *Arabidopsis thaliana* (the first line), after adding 0.15 μM compound A for 19-day screening.
Figure 20:
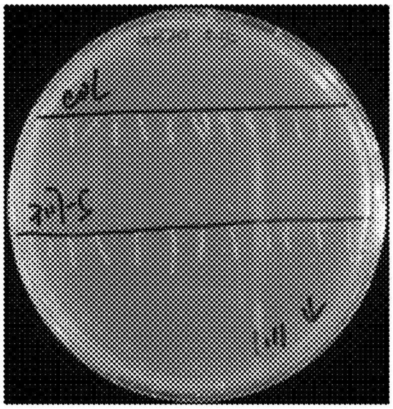
FIG. 20 shows the emergence comparison between T2 generation transgenic *Arabidopsis thaliana* seeds comprising the protein-coding gene of SEQ ID NO: 126 and wild-type *Arabidopsis thaliana* (the first line), after adding 0.15 μM compound A for 20-day screening.
Figure 21:
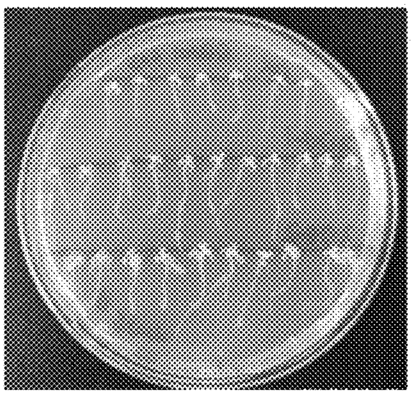
FIG. 21 shows the emergence comparison between T2 generation transgenic *Arabidopsis thaliana* seeds comprising the protein-coding gene of SEQ ID NO: 138 and wild-type *Arabidopsis thaliana* (the first line), after adding 0.15 μM compound A for 19-day screening.
Figure 22:
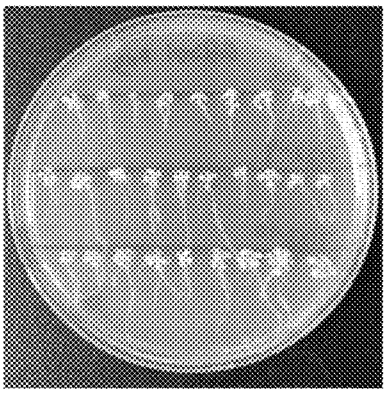
FIG. 22 shows the emergence comparison between T2 generation transgenic *Arabidopsis thaliana* seeds comprising the protein-coding gene of SEQ ID NO: 142 and wild-type *Arabidopsis thaliana* (the first line), after adding 0.15 μM compound A for 24-day screening.

The transformed T0 transgenic plants grew in the greenhouse. T1 generation rice plant seeds produced by transformation of all constructs were collected. The resistance level of each construct was tested and compared by adding 0.3 μM compound B to the liquid of T1 generation and soaking seeds. Comparisons were made by measuring the root length of each construct. As shown in FIG. 13, after adding 0.3 μM compound B and soaking seeds for 20 days, T1 generation transgenic Jinjing 818 seeds comprising different protein-coding genes all exhibited better drug resistance compared with wild-type Jinjing 818, presenting as longer roots, which demonstrated that plants expressing engineered proteins exhibited tolerance to compound B herbicide when screened by hydroponics and seed soaking with 0.3 μM compound B.

Example 3

Expression of Engineered Proteins in *Arabidopsis thaliana*

Engineered proteins were selected for *Arabidopsis thaliana* transformation and plant analysis. DNA constructs were transformed into *Arabidopsis thaliana* using *Agrobacterium tumifaciens* and standard methods known in the art.

The transformed T0 transgenic plantlets grew in the greenhouse. T1 generation *Arabidopsis thaliana* plant seeds produced by transformation of all constructs were collected after approximately 60 days of growth. Transgenic T1 generation *Arabidopsis thaliana* plants were screened by adding HYG to medium for T1 generation. T1 plants were selfed to produce seeds of T2 generation *Arabidopsis thaliana* plants. Wherein, compound A was added to medium to screen and test T2 generation *Arabidopsis thaliana* plant seeds, that were produced by all constructs, comprising unique events screened by T1 generation. As shown in FIGS. 3, 14-22, after adding 0.15 μM compound A to medium for corresponding days of screening, the transgenic T2 *Arabidopsis thaliana* seeds comprising the protein-coding gene of SEQ ID NO: 46/42/78/82/86/98/102/126/138/142 exhibited better drug resistance compared with the wild-type *Arabidopsis thaliana*, presenting as longer roots and larger leaves. It demonstrated that plants expressing the engineered protein exhibited tolerance to compound A herbicide when screened with 0.15 μM of compound A medium.

In addition, compound B was sprayed to test T2 generation *Arabidopsis thaliana* plants, that were produced by some of the constructs, comprising unique events screened by T1 generation, wherein, the test results of the wild-type *Arabidopsis thaliana* control plants transformed with RdpA gene and *Arabidopsis thaliana* plants comprising the protein-coding gene of SEQ ID NO: 42 after being foliage-sprayed with 40 g/mu compound B for 12 days are shown in FIG. 4. Compared with the wild-type plants transformed with RdpA gene, *Arabidopsis thaliana* plants comprising the protein-coding gene of SEQ ID NO: 42 exhibited better drug resistance, which demonstrated that plants expressing the engineered protein exhibited tolerance to compound B herbicide when foliage-sprayed with 40 g/mu of compound B.

Example 4

Expression of Engineered Proteins in Soybeans

Engineered proteins were selected for soybean transformation and plant analysis. DNA constructs were transformed into soybeans using *Agrobacterium tumifaciens* and standard methods known in the art.

Figure 23:
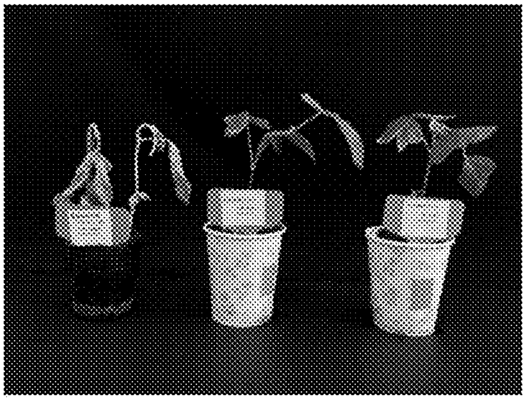
FIG. 23 shows the resistance comparison between TO generation transgenic soybeans comprising the protein-coding gene of SEQ ID NO: 46 and a wild-type soybean (10 g compound C).
Figure 24:
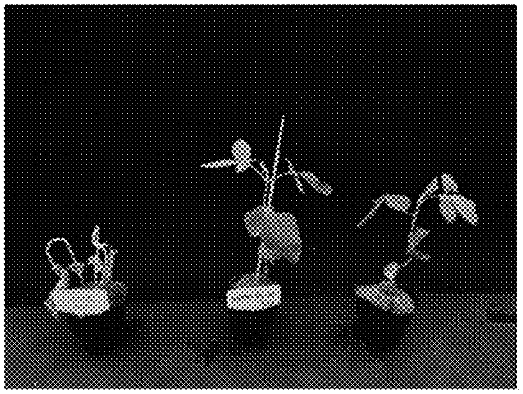
FIG. 24 shows the resistance comparison between T1 generation transgenic soybeans comprising the protein-coding gene of SEQ ID NO: 46 and a wild-type soybean (10 g compound C).
Figure 25:
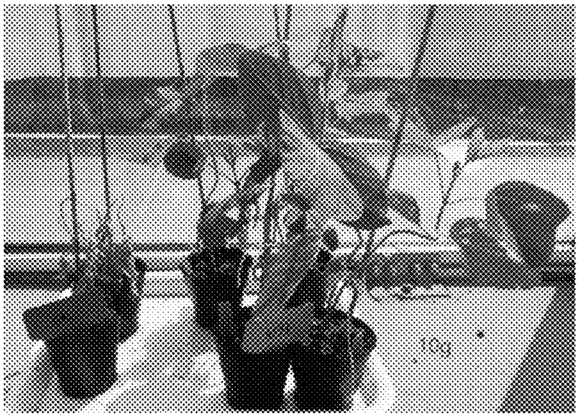
FIG. 25 shows the resistance comparison between T1 generation transgenic soybeans comprising the protein-coding gene of SEQ ID NO: 42 and wild-type soybeans (10 g compound C).
Figure 26:
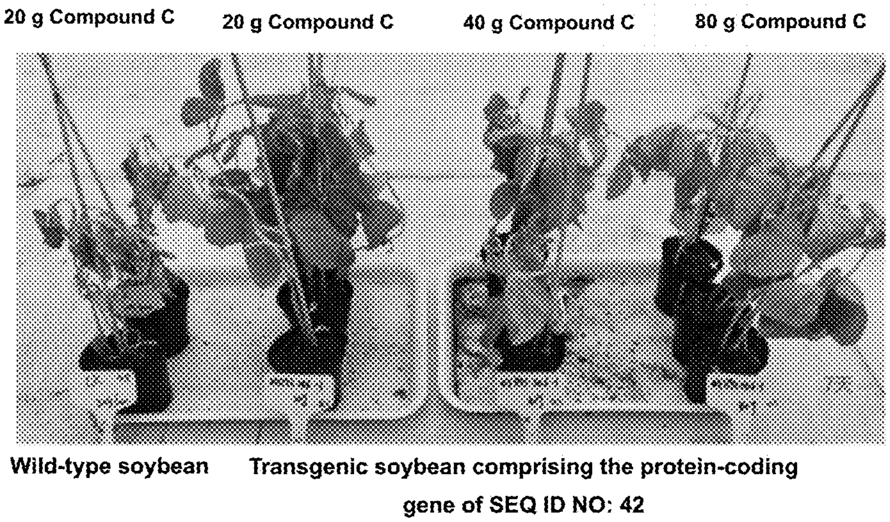
FIG. 26 shows the resistance comparison between T1 generation transgenic soybeans comprising the protein-coding gene of SEQ ID NO: 42 and wild-type soybeans (20 g, 40 g, 80 g compound C).

The transformed T0 transgenic plantlets grew in the greenhouse. TO generation transgenic plantlets were tested by spraying 10 g compound C. As shown in FIG. 23, the transgenic soybeans comprising the protein-coding gene of SEQ ID NO: 46 exhibited apparent resistance compared with the wild-type soybean. T1 generation soybean plant seeds produced by transformation of all constructs were collected, and T1 generation seedlings were tested by spraying 10 g compound C. As shown in FIG. 24, the transgenic soybeans comprising the protein-coding gene of SEQ ID NO: 46 exhibited apparent resistance compared with the wild-type soybean. T1 generation transgenic plantlets produced by some of the constructs were sprayed with 10 g, 20 g, 40 g, 80 g compound C, and as shown in FIG. 25-26, the transgenic soybeans comprising the protein-coding gene of SEQ ID NO: 42 exhibited better drug resistance compared with the wild-type soybeans when applying at least 40 g compound C.

Example 5

Expression of Engineered Proteins in Maizes

Engineered proteins were selected for maize transformation and plant analysis. DNA constructs were transformed into maizes using *Agrobacterium tumifaciens* and standard methods known in the art.

Figure 27:
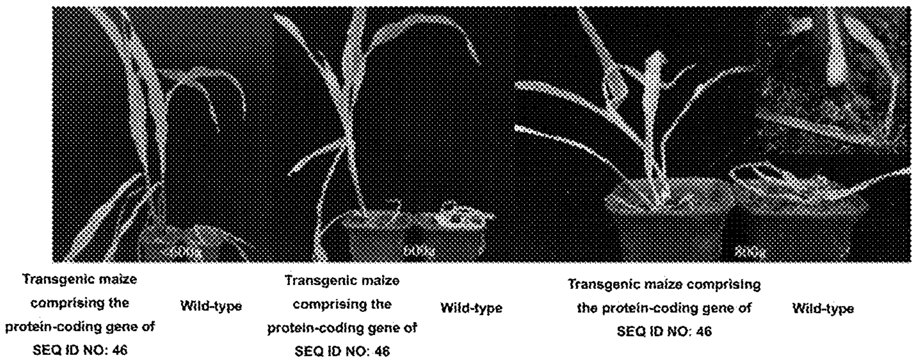
FIG. 27 shows test results of TO generation transgenic maize plantlets sprayed with 150 g, 250 g, 400 g, 600 g, 800 g of 30% glyphosate compound C (25+5) ME.

The transformed T0 transgenic plantlets grew in the greenhouse. TO generation transgenic plantlets were tested by spraying with 150 g, 250 g, 400 g, 600 g, 800 g of 30% glyphosate compound C (25+5) ME. As shown in FIG. 27, the wild types treated by each concentration all died, and the transgenic plantlets had no apparent phytotoxicity reaction when treated at a concentration below 600 g (representative image of the data below 600 g as shown on the far left in FIG. 27). At a concentration of 600 g, the stem base was slightly enlarged, the whole plant growth was obviously inhibited, and the plant was in normal condition. At a concentration of 800 g, the stem base was significantly enlarged, inhibition on the whole plant growth was further intensified, and the leaf color became lighter and lusterless. Thus it may be concluded that the transgenic maize comprising the protein-coding gene of SEQ ID NO: 46 had better drug resistance compared with the wild-type maize when applying 600 g 30% glyphosate compound C (25+5) ME.

Meanwhile, it was found after many tests that, the introduction of the recombinant DNA molecule of the present invention into model plants, such as *Arabidopsis thaliana*, Brachypodium distachyon, etc., resulted in corresponding increases in drug resistance to pyridinyloxy acid herbicides. Thus, it may be known that transforming it into other plants, such as food crops, legume crops, oil crops, fiber crops, fruit crops, root crops, vegetable crops, flower crops, medicine crops, raw material crops, pasture crops, sugar crops, beverage crops, lawn plants, forest crops, nut crops, etc. would also produce corresponding resistance traits, which have good industrial value.

The invention claimed is:

1. A recombinant DNA molecule, comprising a nucleic acid sequence encoding a polypeptide, as compared with the amino acid sequence of RdpA as set forth in SEQ ID NO: 1, the amino acid sequence of the polypeptide has the following mutation: the amino acid at position 82 is mutated from leucine into histidine;

wherein, the amino acid sequence of the polypeptide further has at least 80% sequence identity to the amino acid sequence of RdpA as set forth in SEQ ID NO: 1.

2. The recombinant DNA molecule according to claim 1, wherein the amino acid sequence of the polypeptide also has one or more mutation(s) selected from the following groups:

the amino acid at position 187 is mutated from valine into leucine, methionine or isoleucine;

the amino acid at position 187 is mutated from valine into leucine, and the amino acid at position 104 is mutated from arginine into alanine, aspartic acid or leucine;

the amino acid at position 187 is mutated from valine into leucine, and the amino acid at position 182 is mutated from phenylalanine into tryptophan;

the amino acid at position 187 is mutated from valine into leucine, and the amino acid at position 103 is mutated from glycine into leucine;

the amino acid at position 187 is mutated from valine into leucine, the amino acid at position 182 is mutated from phenylalanine into tryptophan, and the amino acid at position 104 is mutated from arginine into glycine;

the amino acid at position 187 is mutated from valine into leucine, the amino acid at position 182 is mutated from phenylalanine into tryptophan, and the amino acid at position 103 is mutated from glycine into leucine;

the amino acid at position 187 is mutated from valine into leucine, the amino acid at position 182 is mutated from phenylalanine into tryptophan, the amino acid at position 104 is mutated from arginine into glycine, and the amino acid at position 112 is mutated from threonine into serine;

the amino acid at position 187 is mutated from valine into leucine, the amino acid at position 182 is mutated from phenylalanine into tryptophan, the amino acid at position 104 is mutated from arginine into glycine, and the amino acid at position 80 is mutated from valine into threonine;

the amino acid at position 187 is mutated from valine into leucine, the amino acid at position 182 is mutated from phenylalanine into tryptophan, the amino acid at position 104 is mutated from arginine into glycine, and the amino acid at position 180 is mutated from arginine into tryptophan or methionine;

the amino acid at position 187 is mutated from valine into leucine, the amino acid at position 182 is mutated from phenylalanine into tryptophan, the amino acid at position 104 is mutated from arginine into glycine, and the amino acid at position 108 is mutated from aspartic acid into cysteine;

the amino acid at position 187 is mutated from valine into leucine, the amino acid at position 182 is mutated from phenylalanine into tryptophan, the amino acid at position 104 is mutated from arginine into glycine, and the amino acid at position 109 is mutated from aspartic acid into glutamic acid;

the amino acid at position 187 is mutated from valine into leucine, the amino acid at position 182 is mutated from phenylalanine into tryptophan, the amino acid at position 104 is mutated from arginine into glycine, and the amino acid at position 219 is mutated from glutamine into cysteine or proline;

the amino acid at position 187 is mutated from valine into leucine, the amino acid at position 182 is mutated from phenylalanine into tryptophan, the amino acid at position 103 is mutated from glycine into leucine, and the amino acid at position 180 is mutated from arginine into aspartic acid, glutamic acid, serine, leucine, tryptophan or threonine;

the amino acid at position 187 is mutated from valine into leucine, the amino acid at position 182 is mutated from phenylalanine into tryptophan, the amino acid at position 103 is mutated from glycine into leucine, and the amino acid at position 80 is mutated from valine into threonine;

the amino acid at position 187 is mutated from valine into leucine, the amino acid at position 182 is mutated from phenylalanine into tryptophan, the amino acid at position 103 is mutated from glycine into leucine, and the amino acid at position 112 is mutated from threonine into alanine, serine or methionine;

the amino acid at position 187 is mutated from valine into leucine, the amino acid at position 182 is mutated from phenylalanine into tryptophan, the amino acid at position 103 is mutated from glycine into leucine, and the amino acid at position 247 is mutated from phenylalanine into tyrosine;

the amino acid at position 187 is mutated from valine into leucine, the amino acid at position 182 is mutated from phenylalanine into tryptophan, the amino acid at position 104 is mutated from arginine into glycine, and the amino acid at position 77 is mutated from valine into isoleucine;

the amino acid at position 187 is mutated from valine into leucine, the amino acid at position 182 is mutated from phenylalanine into tryptophan, the amino acid at position 104 is mutated from arginine into glycine, the amino acid at position 112 is mutated from threonine into serine, and the amino acid at position 180 is mutated from arginine into lysine, methionine, tryptophan or glutamine; and/or the amino acid at position 187 is mutated from valine into leucine, the amino acid at position 182 is mutated from phenylalanine into tryptophan, the amino acid at position 103 is mutated from glycine into leucine, the amino acid at position 104 is mutated from arginine into glycine, and the amino acid at position 105 is mutated from valine into tyrosine.

3. The recombinant DNA molecule according to claim 1, wherein the recombinant DNA molecule has one or more characteristics selected from the following:

(1) the amino acid sequence of the polypeptide has at least 92%, at least 95%, at least 96%, at least 97%, at least 98%, at least 99% or 100% sequence identity to an amino acid sequence selected from the group consisting of SEQ ID NO: 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138 and 142;

(2) the nucleic acid sequence is selected from the group consisting of SEQ ID NO: 3, 4, 5, 7, 8, 9, 11, 12, 13, 15, 16, 17, 19, 20, 21, 23, 24, 25, 27, 28, 29, 31, 32, 33, 35, 36, 37, 39, 40, 41, 43, 44, 45, 47, 48, 49, 51, 52, 53, 55, 56, 57, 59, 60, 61, 63, 64, 65, 67, 68, 69, 71, 72, 73, 75, 76, 77, 79, 80, 81, 83, 84, 85, 87, 88, 89, 91, 92, 93, 95, 96, 97, 99, 100, 101, 103, 104, 105, 107, 108, 109, 111, 112, 113, 115, 116, 117, 119, 120, 121, 123, 124, 125, 127, 128, 129, 131, 132, 133, 135, 136, 137, 139, 140, 141 and 143-181, and a nucleic acid sequence encoding the same amino acid sequence as the sequence shown due to degeneracy of genetic code.

4. The recombinant DNA molecule according to claim 1, wherein the recombinant DNA molecule is operably linked to a heterologous promoter functional in a plant cell.

5. The recombinant DNA molecule according to claim 4, wherein the recombinant DNA molecule is further operably linked to a DNA molecule encoding a chloroplast transit peptide.

6. A DNA construct comprising a heterologous promoter functional in a plant cell operably linked to the recombinant DNA molecule according to claim 1.

7. The DNA construct according to claim 6, further comprising a DNA molecule encoding a chloroplast transit peptide operably linked to the recombinant DNA molecule.

8. The DNA construct according to claim 6, wherein the DNA construct exists in the genome of a transgenic plant.

9. A plant, seed, plant tissue, plant part or cell, comprising the recombinant DNA molecule according to claim 6.

10. The plant, seed, plant tissue, plant part or cell according to claim 9, wherein the plant, seed, plant tissue, plant part or cell comprises tolerance to at least one herbicide selected from the group consisting of pyridinyloxy acid herbicides.

11. A plant, seed, plant tissue, plant part or cell, comprising the DNA construct according to claim 6.

12. A plant, seed, plant tissue, plant part or cell, comprising the polypeptide encoded by the recombinant DNA molecule according to claim 1.

13. A polypeptide, of which the amino acid sequence having the following mutation compared with the amino acid sequence of RdpA as set forth in SEQ ID NO: 1: the amino acid at position 82 is mutated from leucine into histidine; optionally, also having one or more mutation(s) selected from the following groups:

the amino acid at position 187 is mutated from valine into leucine, methionine or isoleucine;

the amino acid at position 187 is mutated from valine into leucine, and the amino acid at position 104 is mutated from arginine into alanine, aspartic acid or leucine;

the amino acid at position 187 is mutated from valine into leucine, and the amino acid at position 182 is mutated from phenylalanine into tryptophan;

the amino acid at position 187 is mutated from valine into leucine, and the amino acid at position 103 is mutated from glycine into leucine;

the amino acid at position 187 is mutated from valine into leucine, the amino acid at position 182 is mutated from phenylalanine into tryptophan, and the amino acid at position 104 is mutated from arginine into glycine;

the amino acid at position 187 is mutated from valine into leucine, the amino acid at position 182 is mutated from phenylalanine into tryptophan, and the amino acid at position 103 is mutated from glycine into leucine;

the amino acid at position 187 is mutated from valine into leucine, the amino acid at position 182 is mutated from phenylalanine into tryptophan, the amino acid at position 104 is mutated from arginine into glycine, and the amino acid at position 112 is mutated from threonine into serine;

the amino acid at position 187 is mutated from valine into leucine, the amino acid at position 182 is mutated from phenylalanine into tryptophan, the amino acid at position 104 is mutated from arginine into glycine, and the amino acid at position 80 is mutated from valine into threonine;

the amino acid at position 187 is mutated from valine into leucine, the amino acid at position 182 is mutated from phenylalanine into tryptophan, the amino acid at position 104 is mutated from arginine into glycine, and the amino acid at position 180 is mutated from arginine into tryptophan or methionine;

the amino acid at position 187 is mutated from valine into leucine, the amino acid at position 182 is mutated from phenylalanine into tryptophan, the amino acid at position 104 is mutated from arginine into glycine, and the amino acid at position 108 is mutated from aspartic acid into cysteine;

the amino acid at position 187 is mutated from valine into leucine, the amino acid at position 182 is mutated from phenylalanine into tryptophan, the amino acid at position 104 is mutated from arginine into glycine, and the amino acid at position 109 is mutated from aspartic acid into glutamic acid;

the amino acid at position 187 is mutated from valine into leucine, the amino acid at position 182 is mutated from phenylalanine into tryptophan, the amino acid at position 104 is mutated from arginine into glycine, and the amino acid at position 219 is mutated from glutamine into cysteine or proline;

the amino acid at position 187 is mutated from valine into leucine, the amino acid at position 182 is mutated from phenylalanine into tryptophan, the amino acid at position 103 is mutated from glycine into leucine, and the amino acid at position 180 is mutated from arginine into aspartic acid, glutamic acid, serine, leucine, tryptophan or threonine;

the amino acid at position 187 is mutated from valine into leucine, the amino acid at position 182 is mutated from phenylalanine into tryptophan, the amino acid at position 103 is mutated from glycine into leucine, and the amino acid at position 80 is mutated from valine into threonine;

the amino acid at position 187 is mutated from valine into leucine, the amino acid at position 182 is mutated from phenylalanine into tryptophan, the amino acid at position 103 is mutated from glycine into leucine, and the amino acid at position 112 is mutated from threonine into alanine, serine or methionine;

the amino acid at position 187 is mutated from valine into leucine, the amino acid at position 182 is mutated from phenylalanine into tryptophan, the amino acid at position 103 is mutated from glycine into leucine, and the amino acid at position 247 is mutated from phenylalanine into tyrosine;

the amino acid at position 187 is mutated from valine into leucine, the amino acid at position 182 is mutated from phenylalanine into tryptophan, the amino acid at position 104 is mutated from arginine into glycine, and the amino acid at position 77 is mutated from valine into isoleucine;

the amino acid at position 187 is mutated from valine into leucine, the amino acid at position 182 is mutated from phenylalanine into tryptophan, the amino acid at position 104 is mutated from arginine into glycine, the amino acid at position 112 is mutated from threonine into serine, and the amino acid at position 180 is mutated from arginine into lysine, methionine, tryptophan or glutamine; and/or the amino acid at position 187 is mutated from valine into leucine, the amino acid at position 182 is mutated from phenylalanine into tryptophan, the amino acid at position 103 is mutated from glycine into leucine, the amino acid at position 104 is mutated from arginine into glycine, and the amino acid at position 105 is mutated from valine into tyrosine;

wherein, the amino acid sequence of the polypeptide further has at least 80% sequence identity to the amino acid sequence of RdpA as set forth in SEQ ID NO: 1.

14. The polypeptide according to claim 13, wherein the polypeptide has one or more characteristics selected from the following:

(1) the amino acid sequence of the polypeptide has at least 92%, at least 95%, at least 96%, at least 97%, at least 98%, at least 99% or 100% sequence identity to an amino acid sequence selected from the group consisting of SEQ ID NO: 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138 and 142;

(2) the polypeptide has oxygenase activity against at least one herbicide selected from the group consisting of pyridinyloxy acid herbicides.

15. A method for conferring herbicide tolerance to a plant, seed, cell or plant part, comprising expressing the polypeptide according to claim 13, in the plant, seed, cell or plant part.

16. The method according to claim 15, wherein, the plant, seed, cell or plant part comprises a DNA construct, the DNA construct comprises a heterologous promoter functional in a plant cell operably linked to a recombinant DNA molecule, the recombinant DNA molecule comprises the nucleic acid sequence encoding the polypeptide according to claim 13.

17. The method according to claim 13, wherein the plant, seed, cell or plant part comprises tolerance to at least one herbicide selected from the group consisting of pyridinyloxy acid herbicides.

18. A method for producing a herbicide tolerant transgenic plant comprising transforming a plant cell or tissue with the recombinant DNA molecule according to claim 6 or a DNA construct comprising the recombinant DNA molecule, and regenerating a herbicide tolerant transgenic plant from the transformed plant cell or tissue.

19. The method according to claim 18, wherein the herbicide tolerant transgenic plant comprises tolerance to at least one herbicide selected from the group consisting of pyridinyloxy acid herbicides.

20. A method for controlling weeds in a plant growing area, comprising exposing a plant growing area that comprises a plant or seed to at least one herbicide selected from the group consisting of pyridinyloxy acid herbicides, wherein the plant or seed comprises the recombinant DNA molecule according to claim 1 and is tolerant to at least one of the herbicides.

* * * * *